(12) United States Patent
Butler et al.

(10) Patent No.: US 8,013,153 B2
(45) Date of Patent: Sep. 6, 2011

(54) SUBSTITUTED PYRIMIDINE KINASE INHIBITORS

(75) Inventors: Jeannene Butler, Washington, NJ (US); Peter J. Connolly, New Providence, NJ (US); Angel R. Fuentes-Pesquera, New Brunswick, NJ (US); Lee M. Greenberger, Montclair, NJ (US); Shenlin Huang, San Diego, CA (US); Kenneth R. LaMontagne, Jr., Morristown, NJ (US); Ronghua Li, Bridgewater, NJ (US); Guozhang Xu, Bensalem, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 790 days.

(21) Appl. No.: 11/690,305

(22) Filed: Mar. 23, 2007

(65) Prior Publication Data

US 2007/0254896 A1 Nov. 1, 2007

Related U.S. Application Data

(60) Provisional application No. 60/785,127, filed on Mar. 23, 2006, provisional application No. 60/787,627, filed on Mar. 30, 2006, provisional application No. 60/831,702, filed on Jul. 18, 2006.

(51) Int. Cl.
C07D 403/12 (2006.01)
C07D 403/14 (2006.01)
A61K 31/506 (2006.01)
A61P 19/02 (2006.01)

(52) U.S. Cl. ........ 544/298; 514/269; 544/321; 544/320; 544/319

(58) Field of Classification Search .................. 544/298, 544/321; 514/269
See application file for complete search history.

(56) References Cited

U.S. PATENT DOCUMENTS

| | | | |
|---|---|---|---|
| 6,080,750 | A | 6/2000 | Hisaki et al. |
| 6,107,301 | A | 8/2000 | Aldrich et al. |
| 6,833,378 | B2 | 12/2004 | Chen |
| 7,253,174 | B2 | 8/2007 | Ahmed et al. |
| 2003/0060466 | A1 | 3/2003 | Binggeli et al. |
| 2003/0139435 | A1 | 7/2003 | Ahmed et al. |
| 2005/0256111 | A1 | 11/2005 | Kath et al. |
| 2005/0261313 | A1 | 11/2005 | Askew et al. |
| 2005/0277652 | A1 | 12/2005 | Matsushima et al. |
| 2006/0052604 | A1 | 3/2006 | Newton et al. |
| 2007/0270425 | A1 | 11/2007 | Xu et al. |
| 2008/0249304 | A1 | 10/2008 | Chen et al. |

OTHER PUBLICATIONS

Cecil Textbook of Medicine, edited by Bennet, J.C., and Plum F., 20th edition,vol. 1, 1004-1010, 1996.*
Cohen et al., Current Opinion in Chemical Biology, 3,459-465, 1999.*
Dermer et al., Bio/Technology, 1994, 12:320.*
Freshney et al.,Culture of Animal Cells, A Manual of Basic Technique, Alan R. Liss, Inc., 1983, New York, p. 4.*
Golub et al., Science, 286, 531-537, 1999.*
Powell et al., British Journal of Dermatology, 141: 802-810, 1999.*
Mass, R. D., Int. J. Radiation Oncology Bio. Phys. vol. 58(3): 932-940, 2004.*
Fabbro et al. Pharmacology & therapeutics 93, 79-98, 2002.*
Noble et al., Science, 303, 1800-1805, 2004.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Bertino, J., et al. "Horizons in Cancer Therapeutics: From Bench to Bedside, Signal Transduction Inhibitors", 2001, 2(2), ISSN 1532-3048.
Boyden S. J., "The Chemotactic Effect of Mixtures of Antibody and Anatigen on Polymorphonuclear Lleuocytes", Exp. Med., 1962.
Brooks, E. et al., CVT-313, "Specific and Potent Inhibitor of CDK2 That Prevents Neointimal Proliferation", J. Biol. Chem. 1997, 272(46):29207-29211).
Bundgaard, "Design of Prodrugs", Title Page, Table of Contents 1985.
Cas Registry No. 109831-69-8) and N,N'-dimethyl-5-[(methylimino)methyl]-4,6-pyrimidinediamine, Heterocycles, 1987, 25 (10, 343-345.
Cas Registry No. 14160-97-5) and described in Heterocycles, 1987, 25(1), 343-5.
Cross, F., et al., "Simple and Complex Cell Cycles", Annual Rev. Cell Biol. 1989, 5 pp. 341-396.
Davis S.T. et al., "Prevention of chemotherapy-induced Alcopecia in rats by CDK Inhibitors", Science 2001 (Jan. 5), 291, 5501, 25-6.
Del Sal et al., "Cell Cycle and Cancer: Critical Events at the G1 Restriction Point", Critical Rev. Oncogenesis, vol. 71 (1996), p. 127-142.

(Continued)

Primary Examiner — Venkataraman Balasubramanian
(74) Attorney, Agent, or Firm — Rajiv Shah, Esquire; Johnson & Johnson

(57) ABSTRACT

The present invention is directed to substituted pyrimidine compounds of formula (I):

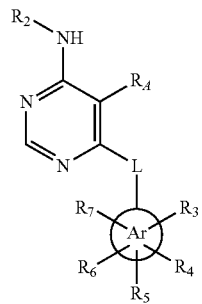

and forms thereof, their synthesis and use for treating a chronic or acute protein kinase mediated disease, disorder or condition.

18 Claims, No Drawings

OTHER PUBLICATIONS

Draetta, G., "Cell Cycle Control im Eurkaryote: Molecular Mechanisms of cdc2 Activation", Trends in Biochem. Science, 1990, 15 pp. 378-382.

Eckstrand, A.J. "Amplified and rearranged epidermal growth factor receptor genes in human glioblastomas reveal deletions of sequences encoding portions of the N-and/or C-terminal tails", Proc. Acad. Natl. Sci. USA, 1992, 89, 4309-4313.

Edgar, B, "Developmemtal Control of Cell Cycle Regulators: A Fly's Perspective", Science, 1996, 274, p. 1646.

Elledge, S., "Cell Cycle Checkpoints: Preventing an Identiy Crisis", Science 1996, 274, p. 1664.

Emanuel, S., et al. "A Vascular Endothelial Growth Factor Receptor-2 Kinase Inhibitor Potentiates the Activity of the conventional Chemotherapeutic Agents Paclitaxel and Doxorubicin in Tumor Xenograft Models", Mol. Pharmacol., 2004, 66:635-647.

Gerber, H, et al. "Vascular Endothelial Growth Factor Regulates Endothelial Cell Survival Through the Phosphaatidylinisitol 3-Kinase/Akt Signal Transduction Pathway", (1998) J Biol Chem 273: 30336-30343.

Greene, Title Page, Table of Contents, 3$^{rd}$ Edition, John Wiley & Sons, 1999.

Grossi, P. et al. "Efficacy of intracerebral microinfusion of trastuzumab in an athymic rat model of intracerebral metastatic breast cancer", Clin. Can. Res., 2003, 9, 5514-5520.

Hall et al, "Genetic Alterations of Cyclins, Cyclin-Dependent Kinases and CDK Inhibitors in Human Cancer", Adv. Cancer Res., vol. 68 (1996), p. 67-108.

Harper, "Cyclin Dependent Kinase Inhibitors, Cancer Surv.", vol. 29 (1997), p. 91-107.

Hetzel, D.J., et al. "A major prognostic factor in endometrial cancer" Gynecol. Oncol., 1992, 47, 179-85.

Hunt, T. "Maturation Promoting Factor, Chyclin and the Control of M-phase", Current Opinion Cell Biol. 1980, 1, pp. 2690274.

Kamb et al., "A Cell Cycle Regulator Potentially Involved in Genesis of Many Tumor Types", Science, vol. 264 (1994), p. 436-440.

Kenyon, B., et al. "A model of angiogenesis in the mouse cornea", Invest. Opthalmol. Vis. Sci., 1996, 37:1625-1632.

King, R., et al. "How Proteolysis Drives the Cell Cycle", Science 1996, 274, p. 1652.

Kirsch, D. et al. "Targeting HER-2 in brain metastases from breast cancer" Clin. Can. Res., 2003, 9, 5435-5436.

Kitamura, T., et al. (2004) "Combined Effcts of Cycloxygenase-1 and Cyclooxytenase-2 Selective Inhibitors on Intestinal Tumorigenesis in Adenomatous Polyposis Coli Gene Knockout Mice", Int J Cancer 109: 576-580.

Klijn J. et al. "The clinical significance of epidermal growth factor receptor (EGF-R) in human breast cancer: a review on 5232 patients" Endocr. Rev., 1992, 13, 3-17.

Koprivica, V., et al, EGFR activation mediates inhibition of axon regeneration by myelin and chondroitin sulfate proteoglycans, Science, 2005, 310, 106.

La Montagne, K., "Antagonism of sphingosine-1-phosphate receptors by FTY720 inhibits angiogenesis and tumor vascularization" Cancer Res., 2006, 66:221-31.

Liu, B, ,et al. "Melanoma Cell Lines Express VEGF Receptor KDR and Respond to Exogenously Added VEGF", Biochem Biophys Res Commun 1995 217: 721-727.

Loda et al., "Increased Proteasome-dependent Degragadion of the Cyclin-Dependent of the Cyclin-Dependent Kinase Inhibitor" p. 27 in "Aggressive Colorectal Carcinomas", Nature Medicine, vol. 3 (1997), p. 231-234.

Lukas et al., "Cyclin E-induced S. Phase without activation of the pRb/E2F Pathway", Genes and Dev., vol. 11 (1997), p. 1479-1492.

Mc Omie, J.F.W., Protective Groups in Organic Chemistry, ed., Plenum Press, 1973.

Morgan, D. et al. "Cyclin-Dependent Kinases: Engines, Clocks, and Microprocessors", Ann. Rev. Cell Dev. Biol., vol. 13 (1977), p. 261-291.

Nasmyth, K. "Viewpoint: Putting the Cell Cycle in Order", Science, vol. 274 (1996), p. 1643-1677.

Nobori, T., "Deletions of the Cyclln-Dependent Kinases-4 Inhibitor Gene in Multiple Human Cancers", Letters to Nature, 368, 1994, pp. 753.

Nurse, P., "Universal Control Mechanism Regulating Onset of M-Phase", Nature, 1990, 344, pp. 503.

Okada, F., et al. "Impact of Oncogenes in Tumor Angiogenesis: Mutant K-ras up-regulations of Vascular Endothelial Growth Factor/ Vascular Permeaability Factor is necessary, but not sufficient for tumorigenicity of Human Colorectal Carcinoma Cells", (1998) Proc Natl Acad Sci USA 95: 3609-3614.

Ross, R., "The Pathogenesis of Atherosclerosis: A Perspective fo rthe 1990s", Nature, 1993, 362, 801-809.

Rousseua, S., et al. "Integrating the VEGF Signals Lelading to Actin-Basead Motility on Vascular Endothelial Cells", (2000) Trends Cardiovasc Med 10: 321-327.

Salomon D, et al. "The erbB family of receptors and their ligands: Multiple targets for therapy", Signal, 2001, 2, 4-11.

Schueneman, A. J. et al "SSU11248 Maintenance Therapy Prevents Tumor Regrowth after Fractionated Irradiation of Murine Tumor Models", Cancer Res 63 4009-4016 , 2003.

Sherr, C., "Mamamalian G Cyclins", Cell, 73, 1993, p. 1059.

Sherr, C., "Cancer Cell Cycles", Science 1996, 274, p. 1672.

Slamon D. et al. "Studies of the HER-2/neu proto-oncogene in human breast and ovarian cancer", Science, 1989, 244, 707-712.

Slamon, D. et al. Human breast cancer: Correlation of relapse and survival with amplification of HER-2/neu oncogene, Science, 1987, 235, 177-82.

Stillman, B., "Cell Cycle Control for DNA Replication", Science 1996, 274, p. 1659.

Viloria-Petit, A. "Acquired Resistance to the Antitumor Effect of Epidermal Growth Factor Receptor-blocking Antibodies in Vivo: A Role for Altered Tumor Angiogenesis", (2001) Cancer Res 61: 5090-5101.

Wei, G.L. et al., "Temporally and spatially Coordinated Expression of Cell Cycle Regulatory Factors After Angioplasty", Circ. Res. 1997, 80, 318-426).

Wickstrand, C. et al. "Monoclonal antibodies against EGFRvIII are tumor specific and react with breast and lung carcinomas and malignant gliomas", Cancer Res., 1995, 55, 3140-3148.

Yang, K., et. al. "A mouse model of human familial adenomatous polyposis" J. Exp Zool. 1997 15;277(3):245-54.

In the U.S. Patent and Trademark Office U.S. Appl. No. 11/609,450 Non-Final Office Action dated Feb. 1, 2011, 5 pages.

In the U.S. Patent and Trademark Office U.S. Appl. No. 11/609,450 Final Office Action dated Oct. 22, 2010, 15 pages.

In the U.S. Patent and Trademark Office U.S. Appl. No. 11/609,450 Non-Final Office Action dated May 20, 2010, 19 pages.

In the U.S. Patent and Trademark Office U.S. Appl. No. 11/609,450 Non-Final Office Action dated Aug. 31, 2009, 25 pages.

In the U.S. Patent and Trademark Office U.S. Appl. No. 11/766,257 Final Office Action dated Oct, 14, 2010, 11pages.

In the U.S. Patent and Trademark Office U.S. Appl. No. 11/766,257 Non-Final Office Action dated Apr. 7, 2010, 9 pages.

Abdel-Razik, et al., "Synthesis of Some New 2,6-Diamino-4-(P-Arylazo) Anilinopyrimidine and Some Related 5-Arylazopyrimidine Derivates for Dyeing Synthetic Fibres", Heterocyclic Communications, 7(3):263-270, 2001.

Barillari, et al., "Solid Phase Synthesis of Diamino-Substituted Pyrimidines", Eur. J. Org. Chem., 4737-4741, 2001.

Chapman, et al., "Nucleophilic Displacement Reactions in Aromatic Systems. Part III. Kinetics of the Reactions of Chloronitropyridines and Chloropyrimidines with Piperidine, Morpholine, Pyridine, and Aniline", J. Chem. Soc., 1190-1196, 1954.

W. G. Dunphy, et al., The Xenopus cdc2 Protein Is a Component of MPF, a Cytoplasmic Regulator of Mitosis, Cell 54(3):423-431, 1988.

J. Gautier, et al., Purified Maturation-Promoting Factor Contains the Product of a Xenopus Homolog of the Fission Yeast Cell Cycle Control Gene cdc2, Cell, 54(3):433-439, 1988.

Gomtsyan, et al., "Design, Synthesis, and Structure-Activity Relationship of 6-Alkynylpyrimidines as Potent Adenosine Kinase Inhibitors", J. Med. Chem., 45:3639-3648.

Hartung, et al., "Efficient Microwave-Assisted Synthesis of Highly Functionalized Pyrimidine Derivatives", *Tetrahedron*, 62:10055-10064, 2006.

M. Lee et al., Cell Cycle Control Genes in Fission Yeast and Mammalian Cells *Trends Genet.*, 4(10):287-90, 1988.

Maggiolo, et al., "The Reaction of Alkylamines With Chloroheterocyclic Compounds II. 2-Amino-4-Chloro-6-Methylpyrimdine", *J. Am. Chem. Soc.*, 376-382, 1950.

Maggiolo, et al., "Synthesis of 2-Methyl-4-Amino-6-Substituted Aminopyrimidines", *J. Am. Chem. Soc.*, 73:106-107, 1951.

O'Brien, et al., "Pyrimidines, VII. 2-Amino-4-(Substituted Anilino) Pyrimidines", *J. of Organic Chemistry*, 27(3):1104-1107, 1962.

Taylor et al, A Novel "Ring-Switching" Amination: Conversion of 4-Amino-5-Cyanopyrimidine to 4, 6 Diamino-5-Cyanopyrimdine, *Heterocycles*, 25: 343-345, 1987.

Kasprzyk, et al., Therapy of an Animal Model of Human Gastric Cancer Using a Combination of AntierbB-2 Monoclonal Antibodies, *Cancer Research*, 52:2771-2776, 1992.

Giard et al., In Vitro Cultivation of Human Tumors: Establishment of Cell Lines Derived From a Series of Solid Tumors, *Journal of the National Cancer Institute*, 5l(5):1417-1423, 1973.

Kawamoto, et al, Growth Stimulation of A431 Cells by Epidermal Growth Factor: Identification of High Affinity Receptors for Epidermal Growth Factor by an Anti-Receptor Monoclonal Antibody, *Proc. Natl. Acad. Sci. USA*, 80:1337-1341, 1983.

Rabindran, et al., Antitumor Activity of HKI-272, an Orally Active, Irreversible Inhibitor of the HER-2 Tyrosine Kinase, *Cancer Research*, 64:3958-3965, 2004.

Horizons in Cancer Therapeutics: From Bench to Bedside, Signal Transduction Inhibitors 2(2), 2001.

International Search Report rom PCT/US06/61890 dated Oct. 3, 2007 1 page.

\* cited by examiner

US 8,013,153 B2

SUBSTITUTED PYRIMIDINE KINASE INHIBITORS

CROSS-REFERENCE TO RELATED APPLICATIONS

This present application claims benefit of U.S. Provisional Patent Application Ser. No. 60/785,127, filed Mar. 23, 2006; U.S. Provisional Patent Application Ser. No. 60/787,627, filed Mar. 30, 2006; and, U.S. Provisional Patent Application Ser. No. 60/831,702, filed Jul. 18, 2006, which are incorporated herein by reference in their entirety and for all purposes.

FIELD OF THE INVENTION

The present invention is in the area of substituted pyrimidine compounds and forms thereof and methods of preparation and use thereof as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-1 or c-MET), PDGFR ($\alpha$ and $\beta$), Tie-1, Tie-2 (also Tek-1 or Tek), VEGFRI (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (I-IV), CamKK, Chk1 and 2 (Checkpoint kinases), CK1, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 ($\alpha$ and $\beta$), PKA, P38, Erk (1-3), PKB (including all PKB subtypes) (also AKT-1, AKT-2, AKT-3 or AKT3-1), IRAK1, FRK, SGK, TAK1 or Tpl-2 (also COT).

Protein kinases play very important roles in the normal regulation of cell growth. However, as a result of dysregulation of the tyrosine kinases (receptor or non-receptor) or the ligands of the receptor tyrosine kinases, signaling can become deregulated, resulting in uncontrolled cell proliferation leading to cancer or a related disease, disorder or syndrome.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Defective control of protein phosphorylation due to unregulated cellular mitosis, unregulated cell proliferation and upregulated kinase activity has been implicated in a number of diseases and disease conditions, such as osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohns disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, occular diseases, viral infections, heart disease, lung or pulmonary diseases or kidney or renal diseases. Therefore, kinase inhibitors have potential use as therapeutic agents.

The term "myasthenia gravis" means a disease having the characteristic feature of easy fatigue of certain voluntary muscle groups on repeated use. Muscles of the face or upper trunk are especially likely to be affected. In most and perhaps all cases, the disease is due to the development of autoantibodies against the acetylcholine receptor in neuromuscular junctions. Immunization of animals with this receptor protein leads to a disease with the features of myasthenia gravis.

In reference to "synovial pannus invasion in arthritis," the term "pannus" means a disease whereby vascularised granulation tissue rich in fibroblasts, lymphocytes and macrophages, derived from synovial tissue, overgrows the bearing surface of the joint in rheumatoid arthritis and is associated with the breakdown of the articular surface.

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

Cyclin dependent kinases (CDK) constitute a class of enzymes that play critical roles in regulating the transitions between different phases of the cell cycle, such as the progression from a quiescent stage in $G_1$ (the gap between mitosis and the onset of DNA replication for a new round of cell division) to S (the period of DNA synthesis), or the progression from $G_2$ to M phase, in which active mitosis and cell-division occur. See, e.g., the articles compiled in *Science*, vol. 274 (1996), p. 1643-1677; and *Ann. Rev. Cell Dev. Biol*, vol. 13 (1997), pp. 261-291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The D cyclins are sensitive to extracellular growth signals and become activated in response to mitogens during the $G_1$ phase of the cell cycle. CDK4/cyclin D plays an important role in cell cycle progression by phosphorylating, and thereby inactivating, the retinoblastoma protein (Rb). Hypophosphorylated Rb binds to a family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the $G_1$ phase, whereupon sensitivity to extracellular growth or inhibitory signals is lost and the cell is committed to cell division. During late $G_1$, Rb is also phosphorylated and inactivated by CDK2/cyclin E, and recent evidence indicates that CDK2/cyclin E can also regulate progression into S phase through a parallel pathway that is independent of Rb phosphorylation (see Lukas et al., "Cyclin E-induced S Phase Without Activation of the pRb/E2F Pathway," *Genes and Dev.*, vol. 11 (1997), pp. 1479-1492).

The progression from $G_1$ to S phase, accomplished by the action of CDK4/cyclin D and CDK2/cyclin E, is subject to a variety of growth regulatory mechanisms, both negative and positive. Growth stimuli, such as mitogens, caused increased synthesis of cyclin D1 and thus increased functional CDK4. By contrast, cell growth can be "reined in," in response to DNA damage or negative growth stimuli, by the induction of endogenous inhibitory proteins. These naturally occurring protein inhibitors include $p21^{WAF1/CIP1}$, $p27^{KIP1}$, and the $p16^{INK4}$ family, the latter of which inhibit CDK4 exclusively (see Harper, "Cyclin Dependent Kinase Inhibitors," *Cancer Surv.*, vol. 29 (1997), pp. 91-107). Aberrations in this control system, particularly those that affect the function of CDK4 and CKD2, are implicated in the advancement of cells to the highly proliferative state characteristic of malignancies, such as familial melanomas, esophageal carcinomas, and pancreatic cancers (see, e.g., Hall and Peters, "Genetic Alterations of Cyclins, Cyclin-Dependent Kinases, and CDK Inhibitors in Human Cancer," *Adv. Cancer Res.*, vol. 68 (1996), pp. 67-108; and Kamb et al., "A Cell Cycle Regulator Potentially Involved in Genesis of Many Tumor Types," *Science*, vol. 264 (1994), pp. 436-440). Over-expression of cyclin D1 is linked to esophageal, breast, and squamous cell carcinomas (see, e.g., DelSal et al., "Cell Cycle and Cancer: Critical Events at the $G_1$ Restriction Point," *Critical Rev. Oncogenesis*, vol. 71 (1996), pp. 127-142). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., "Deletions of the Cyclin-Dependent Kinase-4 Inhibitor Gene in Multiple Human Cancers," *Nature*, vol. 368 (1994), pp. 753-756). Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the state of disease (see Loda et al., "Increased Proteasome-dependent Degradation of the Cyclin-Dependent Kinase Inhibitor p27 in Aggressive Colorectal Carcinomas," *Nature Medicine*, vol. 3 (1997), pp. 231-234). The p21 protein also appear to transmit the p53 tumor-suppression signal to the CDKs; thus, the mutation of p53 in approximately 50% of all human cancers may indirectly result in deregulation of CDK activity.

In the eukaryotic cell cycle a key role is played by the cyclin dependent kinases. CDK complexes are formed via the association of a regulatory cyclin subunit and a catalytic kinase subunit. In mammalian cells, the combination of the kinase subunits (such as CDK1, CDK2, CDK4 or CDK6) with a variety of cyclin subunits (such as cyclin A, B, D1, D2, D3 or E) results in the assembly of functionally distinct kinase complexes. The coordinated activation of these complexes drives the cells through the cell cycle and ensures the fidelity of the process (Draetta, G., *Trends Biochem. Sci.*, 1990, 15:378-382; Sherr, C. J., Cell, 1993, 73:1059-1065). Each step in the cell cycle is regulated by a distinct and specific cyclin-dependent kinase. Regulation occurs at the boundaries of the G1/S and G2/M phases, two major transition points of the cell cycle. For example, complexes of CDK4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the CDK1/cyclin B complex controls the entry into M-phase (Sherr, 1993). A key regulator of these transitions is CDK1 kinase, a universal intracellular factor which triggers the G2/M transition of the cell cycle in all organisms. Both biochemical and genetic evidence have shown that CDK1 is the primary activity required for a cell to enter mitosis in all eukaryotic cells. In late G2, it is present as an inactive complex of CDK1 and cyclin B. In M phase, it is activated and thereafter displays kinase activity. CDK1 is known to phosphorylate a number of proteins including histone H1, DNA polymerase alpha, RNA polymerase II, retinoblastoma tumor suppressor protein (RB), p53, nucleolin, cAb1 and lamin A. The kinase activity of CDK1 is required for entry of cells into mitosis, i.e., for passage from the G2 phase of the cell cycle into the M phase (Lee M. and Nurse P., *Trends Genet.*, 1988, 4:289-90; Dunphy W. G., Brizuela L., Beach D. and Newport J., *Cell*, 1988, 54:423-431; Gautier J., Norbury C., Lohka M., Nurse P. and Maller J., *Cell*, 1988, 54:433-439; Cross F., Roberts J. and Weintraub H., *Ann. Rev. Cell Biol.*, 1989, 5:341-395; Hunt, T. and Sherr, C., *Curr. Opinion Cell Biol.*, 1989, 1:268-274; and, Nurse, P., *Nature*, 1990, 344:503-508). Therefore, using cyclin dependent kinase inhibitors for tumor therapy has the potential for inhibiting tumor growth or controlling unregulated cell proliferation.

Many conventional cytotoxic cancer therapies destroy the rapidly dividing epithelium of the hair follicle and induce alopecia (hair loss). Inhibition of cyclin dependent kinases during conventional chemotherapy may represent a therapeutic strategy for prevention of chemotherapy-induced alopecia by arresting the cell cycle and reducing the sensitivity of epithelial cells to antitumor agents (Davis S. T., et al., Prevention of chemotherapy-induced alopecia in rats by CDK inhibitors, *Science*, 2001, (January 5), 291, 5501, 25-6). Accordingly, to be useful in a method for the prevention of chemotherapy-induced alopecia, a CDK inhibitor compound would have to be cytostatic rather than cytotoxic and be able to hold the cell in a stationary growth phase, thus protecting a hair follicle from the cytotoxic activity of a conventional chemotherapeutic agent being administered at the same time. In this way, topical application of non-apoptotic CDK inhibitors represents a potentially useful approach for the prevention of chemotherapy-induced alopecia in cancer patients.

A second protein target that can facilitate elimination of a tumor is the tyrosine kinase vascular endothelial growth factor (VEGF) receptor. This protein is associated with both normal and pathological angiogenesis. The VEGF receptors are tripartite, consisting of an extracellular ligand-binding domain, a transmembrane domain and an intracellular tyrosine kinase domain. Presently there are two known VEGF receptors: (1) VEGF-R2 (KDR/Flk1/VEGF-R2), a receptor that mediates the biological activities of mitogenesis and proliferation of endothelial cells; and (2) VEGF-R1 (Flt1/VEGF-R1), a receptor that mediates functions such as endothelial cell adhesion. Inhibition of VEGF-R2 signalling has been shown to inhibit the process of angiogenesis. Inhibitors of this receptor are likely useful in controlling or limiting angiogenesis.

Many conventional cytotoxic cancer therapies destroy the rapidly dividing epithelium of the hair follicle and induce alopecia (hair loss). Inhibition of cyclin dependent kinases during conventional chemotherapy may represent a therapeutic strategy for prevention of chemotherapy-induced alopecia by arresting the cell cycle and reducing the sensitivity of epithelial cells to antitumor agents (Davis S. T., et al., Prevention of chemotherapy-induced alopecia in rats by CDK inhibitors, *Science,* 2001, (January 5), 291, 5501, 25-6). Accordingly, to be useful for such an application, a CDK inhibitor compound would have to be cytostatic, rather than cytotoxic and be able to hold the cell in a stationary growth phase which would protect it from the cytotoxic activity of a conventional chemotherapeutic agent being administered at the same time. In this way, topical application of non-apoptotic CDK inhibitors represents a potentially useful approach for the prevention of chemotherapy-induced alopecia in cancer patients.

Although coronary angioplasty is a highly effective procedure used to reduce the severity of coronary occlusion, its long-term success is limited by a high rate of restenosis. Vascular smooth muscle cell activation, migration and proliferation is largely responsible for restenosis following angioplasty (Ross, R., *Nature,* 1993, 362, 801-809). Recent studies have shown that CDK2 is activated very early after endothelial denudation in a rat carotid artery model of restenosis (Wei, G. L., et al., *Circ. Res.,* 1997, 80, 418-426). Therefore, antiproliferative therapies targeted to cyclin dependent kinases or other components of the cell cycle machinery may be a suitable approach to treat these disorders. One aspect for use of the compounds of the present invention is a method for the treatment of restenosis wherein a CDK inhibitor is impregnated on the surface of an angioplasty balloon or stent, thus targeting drug delivery to the local environment where endothelial and smooth muscle cell proliferation are the leading cause of vascular occlusion following an initial angioplasty and restenosis in the area of a stent's implantation (Eric E. Brooks, Nathanael S. Gray, Alison Joly, Suresh S. Kerwar, Robert Lum, Richard L. Mackman, Thea C. Norman, Jose Rosete, Michael Rowe, Steven R. Schow, Peter G. Schultz, Xingbo Wang, Michael M. Wick and Dov Shiffman, CVT-313, a Specific and Potent Inhibitor of CDK2 That Prevents Neointimal Proliferation, *J. Biol. Chem.,* 1997, 272(46): 29207-29211).

The epidermal growth factor receptor (EGFR) tyrosine-kinase family includes the receptors EGFR (also referred to as EGFR-1 or Erb-B1), HER-2 (or neu), EGFR3 and EGFR4. Epidermal Growth Factor (EGF), Transforming Growth Factor-α (TGF-α) and the HER-2 ligand heregulin are three of the ligands that bind to the EGFR receptors.

For example, EGFR overexpression or mutation of one or more EGFR kinase family members has been commonly involved in cancer and other diseases characterized by uncontrolled or abnormal cell growth. Diseases associated with increased EGFR expression include proliferative glomerulonephritis, diabetes-induced renal disease and chronic pancreatitis. Deregulation of EGFR has also been associated with epidermoid tumors, head and neck tumors, breast tumors and tumors involving other major organs, such as the lungs and gastrointestinal tract. The clinically prevalent cancers related to EGFR include lung, gastric and head and neck cancer (Klijn JG, Berns PM, Schmitz P I and Foekens JA; The clinical significance of epidermal growth factor receptor (EGF-R) in human breast cancer: a review on 5232 patients, *Endocr. Rev.,* 1992, 13, 3-17; Salomon D and Gullick W; The erbB family of receptors and their ligands: Multiple targets for therapy, *Signal,* 2001, 2, 4-11).

In treating cancers of the head such as brain cancers and the like, the ability of small molecule EGFR inhibitors to penetrate the blood brain barrier could have therapeutic advantages since EGFR is often overexpressed in primary brain tumors and also in breast and non-small cell lung carcinomas that frequently metastasize to the brain (Eckstrand AJ, Sugawa N, James CD and Collins VP; Amplified and rearranged epidermal growth factor receptor genes in human glioblastomas reveal deletions of sequences encoding portions of the N- and/or C-terminal tails, *Proc. Acad. Natl. Sci. USA,* 1992, 89, 4309-4313; and, Wickstrand CJ, Hale LP, Batra SK, Hill ML, Humphrey PA, Kurpad SN, McLendon RE, Moscatello D, Pegram CN, Reist CJ, Traweek ST, Wong AJ, Zalutsky MR and Bigner, DD; Monoclonal antibodies against EGFRvIII are tumor specific and react with breast and lung carcinomas and malignant gliomas, *Cancer Res.,* 1995, 55, 3140-3148).

EGFR inhibitors tested in neurite outgrowth assays have activity in promoting neurite outgrowth in both cerebellar granule cells and dorsal root ganglion neurons, likely by acting directly on neurons to block neuronal inhibitory responses to myelin inhibitors, and thus an EGFR inhibitor may have potential use for promoting axon regeneration after brain and spinal cord injury (V. Koprivica, et al., EGFR activation mediates inhibition of axon regeneration by myelin and chondroitin sulfate proteoglycans, *Science,* 2005, 310, 106).

HER1 and HER2 overexpression has been implicated in a variety of cancers, such as bladder, breast, colorectal, endometrial, esophageal, gastric(stomach), glioma head and neck, lung (non-small cell lung cancer), ovarian, pancreatic, renal and prostate cancer.

Comparing the overexpression of HER1 and HER2 in tumors, according to order of prevalence, HER1 overexpression is found in breast, renal cell, lung, colorectal, head and neck, ovarian, pancreatic, glioma, bladder, esophageal, gastric, endometrial and cervical cancer tumors; in contrast, HER2 overexpression is found in esophageal, head and neck, lung, gastric, renal cell, breast, bladder, ovarian and colorectal, prostate and endometrial cancer tumors (Horizons in Cancer Therapeutics: From Bench to Bedside, Signal Transduction Inhibitors, 2001, 2(2), ISSN 1532-3048).

While the degree of HER2 overexpression in breast and ovarian cancer is not as great as in some other cancers, HER2 has been found to be responsible for these clinically prevalent cancers (Slamon DJ, Clark GM, Wong SG, Levin WJ, Ullrich A and McGuire WL; Human breast cancer: Correlation of relapse and survival with amplification of HER-2/neu oncogene, *Science,* 1987, 235, 177-82; Slamon DJ, Godolphin W, Jones LA, Holt JA, Wong SG, Keith DE, et al.; Studies of the HER-2/neu proto-oncogene in human breast and ovarian cancer, *Science,* 1989, 244, 707-712; Hetzel DJ, Wilson TO, Keeney GL, Roche PC, Cha SS and Podrantz KC; HER-2/neu expression: A major prognostic factor in endometrial cancer, *Gynecol. Oncol.,* 1992, 47, 179-85).

Furthermore, patients with HER-2 overexpressing breast cancer frequently experience metastases to the brain (Kirsch DG and Hochberg FH; Targeting HER-2 in brain metastases from breast cancer, *Clin. Can. Res.,* 2003, 9, 5435-5436). These patients have an extremely poor prognosis and intracerebral tumors are often the cause of death. Autopsy revealed that 20-30% of patients who die of breast cancer have brain metastases (Grossi PM, Ochiai H, Archer GE, McLendon RE, Zalutsky MR, Friedman AH, Friedman HS, Bigner DD and Sampson JH; Efficacy of intracerebral microinfusion of trastuzumab in an athymic rat model of intracerebral metastatic breast cancer, *Clin. Can. Res.,* 2003, 9, 5514-5520).

Aurora kinases (Aurora-A, Aurora-B and Aurora-C) are highly conserved tyrosine kinases found in all organisms where they function to regulate microtubule dynamics during the M phase of the cell cycle and are essential for mitotic progression. Aurora-A kinase associates with the centrosome around the pericentriolar material, as well as the microtubules at the bipolar mitotic-spindle poles and the midbody microtubules and plays a role in spindle formation and organization of the centrosome. Aurora-B regulates chromosomal movement and cytokinesis and Aurora-C's biological function is not yet understood. The Aurora-A kinase is involved in centrosome separation, duplication and maturation as well as in bipolar spindle assembly and stability. Aurora-A is overexpressed in a number of different human cancers and tumor cell lines. Overexpression of Aurora is sufficient to induce growth in soft agar and transforms cells making them tumorigenic. Inhibition of Aurora activity results in centrosome/chromosome segregation defects leading to monopolar spindles and polyploidy which induces cell apoptosis in a variety of cancer cell lines and has suppressed tumor growth in vivo.

Certain oxime substituted pyrimidines are registered by the Chemical Abstracts Society (CAS) such as 4,6-diamino-5-pyrimidinecarboxaldehyde oxime (CAS Registry No.: 109831-69-8) and N,N'-dimethyl-5-[(methylimino)methyl]-4,6-pyrimidinediamine (CAS Registry No.: 14160-97-5) and described in *Heterocycles,* 1987, 25(1), 343-5. Certain references describe substituted pyrimidine compounds such as U.S. patents: U.S. Pat. No. 6,080,750, 6,107,301 and 6,833,378.

There is a need for potent small-molecule kinase inhibitors of one or more of the CDK, EGFR (pan-HER), VEGF, Aurora-A or RET kinase proteins and the like possessing anti-tumor cell proliferation activity, and as such are useful for treating a CDK, EGFR, VEGF, Aurora-A or RET kinase receptor mediated, angiogenesis-mediated or hyperproliferative disorders.

SUMMARY OF THE INVENTION

The present invention is directed to a compound of formula (I):

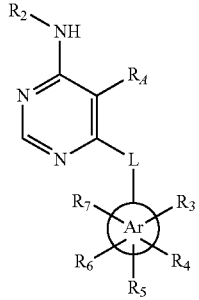

and forms thereof, wherein L, $R_4$, $R_2$, $R_3$, $R_4$, $R_5$, $R_6$, $R_7$ and Ar are as defined herein.

An example of the present invention includes a compound of formula (I) and forms thereof as a protein kinase inhibitor.

An example of the present invention includes a prodrug form of a compound of formula (I) and forms thereof as a protein kinase inhibitor.

An example of the present invention includes a metabolite form of a compound of formula (I) and forms thereof as a protein kinase inhibitor.

An example of the present invention includes use of a compound of formula (I) and forms thereof as an inhibitor of a protein kinase such as CDK, EGFR (pan-HER), VEGF, Aurora-A or RET and the like comprising contacting the protein kinase domain or receptor with the compound.

An example of the present invention includes the use of a compound of formula (I) and forms thereof as a pharmaceutical composition, medicine or medicament for treating a kinase mediated disease, disorder or condition.

An example of the present invention includes the use of a compound of formula (I) and forms thereof in the manufacture of a medicament for treating a kinase mediated disease, disorder or condition.

An example of the present invention includes the use of a prodrug of a compound of formula (I) and forms thereof as a pharmaceutical composition, medicine or medicament for treating a kinase mediated disease, disorder or condition.

An example of the present invention includes the use of a prodrug of a compound of formula (I) and forms thereof in the manufacture of a medicament for treating a kinase mediated disease, disorder or condition.

The present invention is further directed to a method for treating a chronic or acute protein kinase mediated disease, disorder or condition in a subject in need thereof comprising administering to the subject an effective amount of a compound of formula (I) and forms thereof.

An example of the present invention includes a method for treating a chronic or acute protein kinase mediated disease, disorder or condition in a subject in need thereof comprising administering to the subject an effective amount of a prodrug of a compound of formula (I) and forms thereof.

These and other aspects and advantages of the invention, which will become apparent in light of the detailed description below, are achieved through use of the compounds of this invention.

DETAILED DESCRIPTION OF THE INVENTION

The present invention is directed to a compound of formula (I):

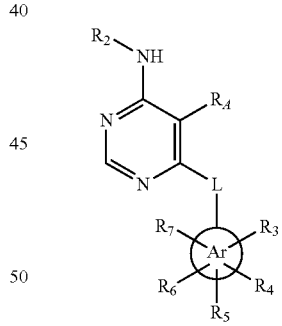

and forms thereof, wherein

L is selected from the group consisting of 0 and O—CH$_2$, wherein the O atom portion of O—CH$_2$ is attached to the pyrimidine ring of formula (I);

Ar is selected from the group consisting of aryl, heteroaryl, benzofused-heterocyclyl and benzofused-C$_{3-12}$cycloalkyl, wherein the benzene ring portion of the benzofused ring system is attached to the L group of formula (I);

$R_A$ is selected from the group consisting of C=N—O—R$_1$ and cyano;

$R_1$ is selected from the group consisting of hydrogen, C$_{1-8}$alkyl, C$_{2-8}$alkenyl, C$_{2-8}$alkynyl, C$_{1-8}$alkoxy-C$_{1-8}$alkyl, hydroxy-C$_{1-8}$alkyl, amino-C$_{1-8}$alkyl, C$_{1-8}$alkyl-amino-C$_{1-8}$alkyl, C$_{1-8}$alkoxy-C$_{1-8}$alkyl-amino-C$_{1-8}$alkyl, $C_{1-8}$alkyl-sulfonyl-$C_{1-8}$alkyl, $C_{1-8}$alkyl-sulfonyl-oxy-$C_{1-8}$alkyl, $C_{3-12}$cycloalkyl, $C_{3-12}$cycloalkyl-$C_{1-8}$alkyl, aryl, aryl-$C_{1-8}$alkyl, aryl-oxy-$C_{1-8}$alkyl, heterocyclyl, heterocyclyl-$C_{1-8}$alkyl, heterocyclyl-carbonyl-$C_{1-8}$alkyl, heteroaryl and heteroaryl-$C_{1-8}$alkyl, wherein aryl and aryl-$C_{1-8}$alkyl are each optionally substituted on aryl with one, two, three, four or five substituents each selected from the group consisting of hydroxy, $C_{1-8}$alkyl, $C_{1-8}$alkoxy, amino, $C_{1-8}$alkyl-amino and $C_{1-8}$alkoxy-carbonyl, and wherein heterocyclyl, heterocyclyl-$C_{1-8}$alkyl and heterocyclyl-carbonyl-$C_{1-8}$alkyl are each optionally substituted on heterocyclyl with one, two, three or four substituents each selected from the group consisting of hydroxy, $C_{1-8}$alkyl, $C_{1-8}$alkoxy, amino, $C_{1-8}$alkyl-amino, $C_{1-8}$alkyl-carbonyl, $C_{1-8}$alkoxy-carbonyl, $C_{1-8}$alkyl-sulfonyl and $C_{1-8}$alkyl-sulfonyl-$C_{1-8}$alkyl;

$R_2$ is selected from the group consisting of hydrogen, $C_{1-8}$alkyl and $C_{1-8}$alkoxy; and $R_3$, $R_4$, $R_5$, $R_6$ and $R_7$ is each selected from the group consisting of hydrogen, cyano, halogen, hydroxy, carboxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$alkyl, $C_{1-8}$alkoxy, $C_{1-8}$alkoxy-carbonyl, $C_{1-8}$alkoxy-carbonyl-amino, $C_{1-8}$alkoxy-$C_{1-8}$alkyl, $C_{1-8}$alkoxy-$C_{1-8}$alkyl-carbonyl, $C_{1-8}$alkoxy-$C_{1-8}$alkyl-carbonyl-amino, hydroxy-$C_{1-8}$alkyl, hydroxy-$C_{1-8}$alkyl-amino-carbonyl, hydroxy-$C_{1-8}$alkyl-amino-carbonyl-amino, halo-$C_{1-8}$alkyl, hydroxy-$C_{1-8}$alkoxy, halo-$C_{1-8}$alkoxy, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, amino, $C_{1-8}$alkyl-amino, amino-carbonyl, $C_{1-8}$alkyl-amino-carbonyl, $C_{2-8}$alkenyl-amino-carbonyl, $C_{2-8}$alkynyl-amino-carbonyl, amino-carbonyl-$C_{1-8}$alkyl, $C_{1-8}$alkyl-amino-carbonyl-$C_{1-8}$alkyl, $C_{2-8}$alkenyl-amino-carbonyl-$C_{1-8}$alkyl, $C_{2-8}$-alkynyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, $C_{2-8}$alkenyl-amino-carbonyl-oxy, $C_{2-8}$alkynyl-amino-carbonyl-oxy, amino-$C_{1-8}$alkyl, $C_{1-8}$alkyl-amino-$C_{1-8}$alkyl, amino-$C_{1-8}$alkyl-amino-carbonyl, $C_{1-8}$alkyl-amino-$C_{1-8}$alkyl-amino-carbonyl, amino-$C_{1-8}$alkyl-amino-carbonyl-amino, $C_{1-8}$alkyl-amino-$C_{1-8}$alkyl-amino-carbonyl-amino, $C_{3-12}$cycloalkyl, $C_{3-12}$cycloalkyl-$C_{1-8}$alkyl, $C_{3-12}$cycloalkyl-$C_{1-8}$alkoxy, $C_{3-12}$cycloalkyl-amino-carbonyl, $C_{3-12}$cycloalkyl-amino-carbonyl-amino, $C_{3-12}$cycloalkyl-$C_{1-8}$alkyl-amino-carbonyl, $C_{3-12}$cycloalkyl-$C_{1-8}$alkyl-amino-carbonyl-amino, $C_{3-12}$cycloalkyl-amino-carbonyl-$C_{1-8}$alkyl, aryl, aryl-oxy, aryl-$C_{1-8}$alkyl, aryl-$C_{1-8}$alkoxy, aryl-carbonyl, aryl-amino, aryl-amino-carbonyl, aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy, heteroaryl, heteroaryl-oxy, heteroaryl-$C_{1-8}$alkoxy, heteroaryl-amino-carbonyl, heteroaryl-amino-carbonyl-amino, heteroaryl-$C_{1-8}$alkyl-amino-carbonyl, heteroaryl-$C_{1-8}$alkyl-amino-carbonyl-amino, heteroaryl-amino-carbonyl-$C_{1-8}$alkyl, heterocyclyl, heterocyclyl-$C_{1-8}$alkyl, heterocyclyl-$C_{1-8}$alkyl-amino-carbonyl, heterocyclyl-$C_{1-8}$alkyl-amino-carbonyl-amino and heterocyclyl-amino-carbonyl-$C_{1-8}$alkyl, wherein aryl, aryl-oxy, aryl-$C_{1-8}$alkyl, aryl-$C_{1-8}$alkoxy, aryl-carbonyl, aryl-amino, aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy, heteroaryl and heteroaryl-amino-carbonyl-amino are each optionally substituted on aryl and heteroaryl with one, two, three, four or five substituents each selected from the group consisting of cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl and $C_{1-8}$alkoxy-carbonyl.

An example of a compound of formula (I) and forms thereof includes a compound wherein Ar is selected from the group consisting of aryl and heteroaryl.

An example of a compound of formula (I) and forms thereof includes a compound wherein Ar is selected from the group consisting of benzofused-heterocyclyl and benzofused-$C_{3-12}$cycloalkyl, wherein the benzene ring portion of the benzofused ring system is attached to the L group of formula (I).

An example of a compound of formula (I) and forms thereof includes a compound wherein Ar is selected from the group consisting of phenyl, naphthalenyl, indolyl, quinolinyl, isoquinolinyl, benzo[1,3]dioxolyl, indanyl and 5,6,7,8-tetrahydro-naphthalenyl.

An example of a compound of formula (I) and forms thereof includes a compound wherein $R_4$ is $C=N-O-R_1$.

An example of a compound of formula (I) and forms thereof includes a compound wherein $R_1$ is selected from the group consisting of hydrogen, $C_{1-8}$alkyl, $C_{2-8}$alkenyl, $C_{2-8}$alkynyl, $C_{1-8}$alkoxy-$C_{1-8}$alkyl, hydroxy-$C_{1-8}$alkyl, amino-$C_{1-8}$alkyl, $C_{1-8}$alkyl-amino-$C_{1-8}$alkyl, $C_{3-12}$cycloalkyl, $C_{3-12}$cycloalkyl-$C_{1-8}$alkyl, aryl, aryl-$C_{1-8}$alkyl, heterocyclyl, heterocyclyl-$C_{1-8}$alkyl, heteroaryl and heteroaryl-$C_{1-8}$alkyl, wherein heterocyclyl and heterocyclyl-$C_{1-8}$alkyl are each optionally substituted on heterocyclyl with one, two, three or four substituents each selected from the group consisting of hydroxy, $C_{1-8}$alkyl, $C_{1-8}$alkoxy, amino, $C_{1-8}$alkyl-amino, $C_{1-8}$alkyl-carbonyl, $C_{1-8}$alkoxy-carbonyl and $C_{1-8}$alkyl-sulfonyl.

An example of a compound of formula (I) and forms thereof includes a compound wherein $R_1$ is selected from the group consisting of hydrogen, $C_{1-8}$alkyl, $C_{2-8}$alkenyl, $C_{2-8}$alkynyl, $C_{1-8}$alkoxy-$C_{1-8}$alkyl, hydroxy-$C_{1-8}$alkyl, $C_{1-8}$alkyl-amino-$C_{1-8}$alkyl, $C_{3-12}$cycloalkyl-$C_{1-8}$alkyl, aryl-$C_{1-8}$alkyl and heterocyclyl-$C_{1-8}$alkyl, wherein heterocyclyl-$C_{1-8}$alkyl is optionally substituted on heterocyclyl with $C_{1-8}$alkyl-carbonyl or $C_{1-8}$alkyl-sulfonyl.

An example of a compound of formula (I) and forms thereof includes a compound wherein $R_1$ is selected from the group consisting of hydrogen, $C_{1-4}$alkyl, $C_{2-8}$alkenyl, $C_{2-8}$alkynyl, $C_{1-8}$alkoxy-$C_{1-8}$alkyl, hydroxy-$C_{1-8}$alkyl, $C_{1-8}$alkyl-amino-$C_{1-8}$alkyl, cyclopropyl-$C_{1-8}$alkyl, cyclohexyl-$C_{1-8}$alkyl, phenyl-$C_{1-8}$alkyl, pyrrolidinyl-$C_{1-8}$alkyl, morpholinyl-$C_{1-8}$alkyl, piperidinyl-$C_{1-8}$alkyl and piperazinyl-$C_{1-8}$alkyl, wherein piperazinyl-$C_{1-8}$alkyl is optionally substituted on piperazinyl with $C_{1-8}$alkyl-carbonyl or $C_{1-8}$alkyl-sulfonyl.

An example of a compound of formula (I) and forms thereof includes a compound wherein $R_2$ is hydrogen.

An example of a compound of formula (I) and forms thereof includes a compound wherein $R_2$ is $C_{1-8}$alkyl.

An example of a compound of formula (I) and forms thereof includes a compound wherein $R_2$ is $C_{1-8}$alkoxy.

An example of a compound of formula (I) and forms thereof includes a compound wherein $R_3$, $R_4$, $R_5$, $R_6$ and $R_7$ is each selected from the group consisting of hydrogen, cyano, halogen, hydroxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$alkyl, $C_{1-8}$alkoxy, $C_{1-8}$alkoxy-carbonyl, $C_{1-8}$alkoxy-carbonyl-amino, $C_{1-8}$alkoxy-$C_{1-8}$alkyl, hydroxy-$C_{1-8}$alkyl, hydroxy-$C_{1-8}$alkyl-amino-carbonyl, hydroxy-$C_{1-8}$ alkyl-amino-carbonyl-amino, halo-$C_{1-8}$alkyl, hydroxy-$C_{1-8}$ alkoxy, halo-$C_{1-8}$alkoxy, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, amino, $C_{1-8}$alkyl-amino, amino-carbonyl, $C_{1-8}$alkyl-amino-carbonyl, $C_{2-8}$alkenyl-amino-carbonyl, $C_{2-8}$alkynyl-amino-carbonyl, amino-carbonyl-$C_{1-8}$alkyl, $C_{1-8}$alkyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, amino-$C_{1-8}$alkyl, $C_{1-8}$alkyl-amino-$C_{1-8}$alkyl, amino-$C_{1-8}$alkyl-amino-carbonyl, $C_{1-8}$alkyl-amino-$C_{1-8}$alkyl-amino-carbonyl, amino-$C_{1-8}$alkyl-amino-carbonyl-amino, $C_{1-8}$alkyl-amino-$C_{1-8}$alkyl-amino-carbonyl-amino, $C_{3-12}$cycloalkyl, $C_{3-12}$cycloalkyl-amino-carbonyl, $C_{3-12}$cycloalkyl-amino-carbonyl-amino, $C_{3-12}$cycloalkyl-$C_{1-8}$alkyl-amino-carbonyl, $C_{3-12}$cycloalkyl-$C_{1-8}$alkyl-amino-carbonyl-amino, $C_{3-12}$cycloalkyl-amino-carbonyl-$C_{1-8}$alkyl, aryl, aryl-$C_{1-8}$alkyl, aryl-$C_{1-8}$alkoxy, aryl-carbonyl, aryl-amino, aryl-amino-carbonyl, aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy, heteroaryl, heteroaryl-amino-carbonyl, heteroaryl-amino-carbonyl-amino, heteroaryl-$C_{1-8}$alkyl-amino-carbonyl, heteroaryl-$C_{1-8}$alkyl-amino-carbonyl-amino, heteroaryl-amino-carbonyl-$C_{1-8}$alkyl, heterocyclyl, heterocyclyl-$C_{1-8}$alkyl, heterocyclyl-$C_{1-8}$alkyl-amino-carbonyl, heterocyclyl-$C_{1-8}$alkyl-amino-carbonyl-amino and heterocyclyl-amino-carbonyl-$C_{1-8}$alkyl, wherein aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy and heteroaryl-amino-carbonyl-amino are each optionally substituted on aryl and heteroaryl with one, two, three, four or five substituents each selected from the group consisting of cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl and $C_{1-8}$alkoxy-carbonyl.

An example of a compound of formula (I) and forms thereof includes a compound wherein $R_3$, $R_4$, $R_5$, $R_6$ and $R_7$ is each selected from the group consisting of hydrogen, cyano, halogen, hydroxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$ alkyl, $C_{1-8}$alkoxy, $C_{1-8}$alkoxy-carbonyl, $C_{1-8}$alkoxy-carbonyl-amino, hydroxy-$C_{1-8}$alkyl-amino-carbonyl, hydroxy-$C_{1-8}$alkyl-amino-carbonyl-amino, halo-$C_{1-8}$alkyl, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, $C_{1-8}$alkyl-amino-carbonyl, $C_{2-8}$alkynyl-amino-carbonyl, $C_{1-8}$alkyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, $C_{1-8}$alkyl-amino-$C_{1-8}$alkyl-amino-carbonyl, $C_{1-8}$alkyl-amino-$C_{1-8}$alkyl-amino-carbonyl-amino, cyclopropyl-amino-carbonyl, cyclohexyl-amino-carbonyl-amino, cyclopropyl-amino-carbonyl-amino, phenyl-$C_{1-8}$alkyl, phenyl-$C_{1-8}$alkoxy, phenyl-carbonyl, phenyl-amino, phenyl-amino-carbonyl-amino, phenyl-$C_{1-8}$alkyl-amino-carbonyl, phenyl-$C_{1-8}$alkyl-amino-carbonyl-amino, phenyl-amino-carbonyl-$C_{1-8}$alkyl, phenyl-amino-carbonyl-oxy, [1,2,4]triazolyl, pyridinyl-amino-carbonyl-amino, thiazolyl-amino-carbonyl-amino, isoxazolyl-amino-carbonyl-amino, morpholinyl-$C_{1-8}$alkyl, pyrrolidinyl-$C_{1-8}$alkyl-amino-carbonyl and pyrrolidinyl-$C_{1-8}$alkyl-amino-carbonyl-amino, wherein phenyl-amino-carbonyl-amino, phenyl-$C_{1-8}$alkyl-amino-carbonyl, phenyl-$C_{1-8}$alkyl-amino-carbonyl-amino, phenyl-amino-carbonyl-$C_{1-8}$alkyl, phenyl-amino-carbonyl-oxy and thiazolyl-amino-carbonyl-amino isoxazolyl-amino-carbonyl-amino is each optionally substituted on phenyl, thiazolyl and isoxazolyl with one or two substituents each selected from the group consisting of halogen, $C_{1-8}$alkyl and $C_{1-8}$alkoxy.

An example of a compound of formula (I) and forms thereof includes a compound wherein L is selected from the group consisting of O and O—$CH_2$, wherein the O atom portion of O—$CH_2$ is attached to the pyrimidine ring of formula (I);

Ar is selected from the group consisting of aryl, heteroaryl, benzofused-heterocyclyl and benzofused-$C_{3-12}$cycloalkyl, wherein the benzene ring portion of the benzofused ring system is attached to the L group of formula (I);

$R_A$ is C=N—O—$R_1$;

$R_1$ is selected from the group consisting of hydrogen, $C_{1-8}$alkyl, $C_{2-8}$alkenyl, $C_{2-8}$alkynyl, $C_{1-8}$alkoxy-$C_{1-8}$alkyl, hydroxy-$C_{1-8}$alkyl, $C_{1-8}$alkyl-amino-$C_{1-8}$alkyl, $C_{3-12}$cycloalkyl-$C_{1-8}$alkyl, aryl-$C_{1-8}$alkyl and heterocyclyl-$C_{1-8}$alkyl, wherein heterocyclyl-$C_{1-8}$alkyl is optionally substituted on heterocyclyl with $C_{1-8}$alkyl-carbonyl or $C_{1-8}$alkyl-sulfonyl;

$R_2$ is selected from the group consisting of hydrogen, $C_{1-8}$alkyl and $C_{1-8}$alkoxy; and $R_3$, $R_4$, $R_5$, $R_6$ and $R_7$ is each selected from the group consisting of hydrogen, cyano, halogen, hydroxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$ alkyl, $C_{1-8}$alkoxy, $C_{1-8}$alkoxy-carbonyl, $C_{1-8}$alkoxy-carbonyl-amino, hydroxy-$C_{1-8}$alkyl-amino-carbonyl, hydroxy-$C_{1-8}$alkyl-amino-carbonyl-amino, halo-$C_{1-8}$alkyl, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, $C_{1-8}$alkyl-aminocarbonyl, $C_{2-8}$alkynyl-amino-carbonyl, $C_{1-8}$alkyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, $C_{1-8}$alkyl-amino-$C_{1-8}$alkyl-amino-carbonyl, $C_{1-8}$alkyl-amino-$C_{1-8}$alkyl-amino-carbonyl-amino, $C_{3-12}$cycloalkyl-amino-carbonyl, $C_{3-12}$cycloalkyl-amino-carbonyl-amino, aryl-$C_{1-8}$alkyl, aryl-$C_{1-8}$alkoxy, aryl-carbonyl, aryl-amino, aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy, heteroaryl, heteroaryl-amino-carbonyl-amino, heterocyclyl-$C_{1-8}$alkyl, heterocyclyl-$C_{1-8}$alkyl-amino-carbonyl and heterocyclyl-$C_{1-8}$alkyl-amino-carbonyl-amino, wherein aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy and heteroaryl-amino-carbonyl-amino are each optionally substituted on aryl and heteroaryl with one or two substituents each selected from the group consisting of halogen, $C_{1-8}$alkyl and $C_{1-8}$alkoxy.

Examples of a compound of Formula (I) include compounds selected from the group consisting of:

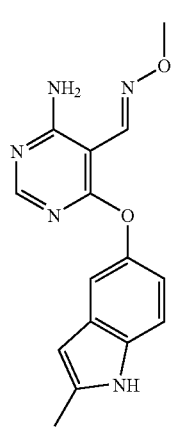

Cpd 1

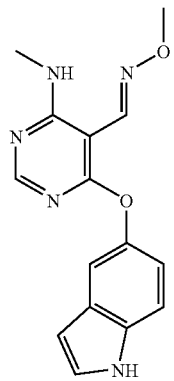

Cpd 2

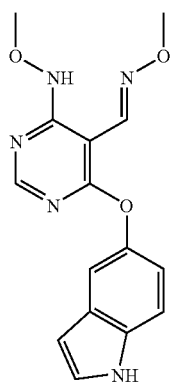

Cpd 3

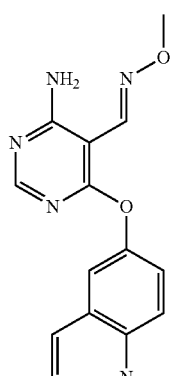

Cpd 4

Cpd 5

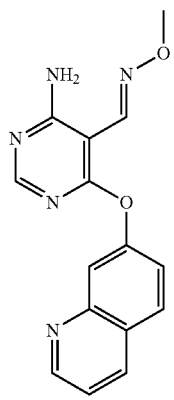

Cpd 6

Cpd 7
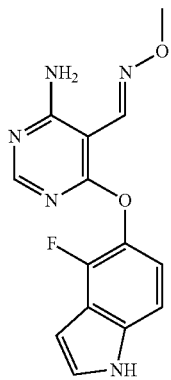
Cpd 11
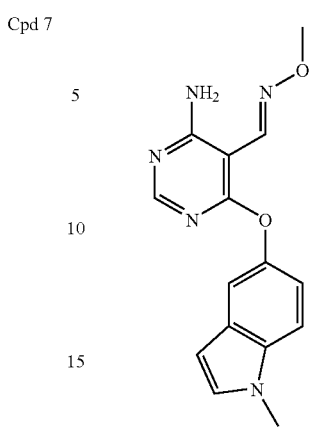
Cpd 8
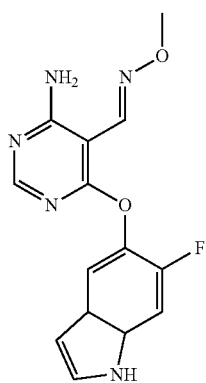
Cpd 12
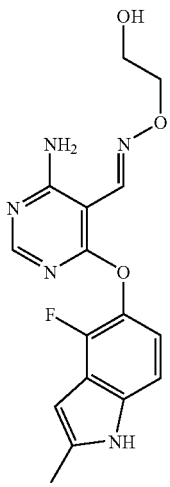
Cpd 9
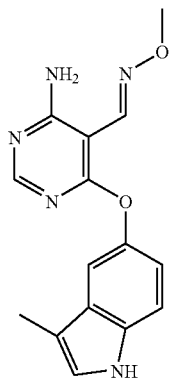
Cpd 13
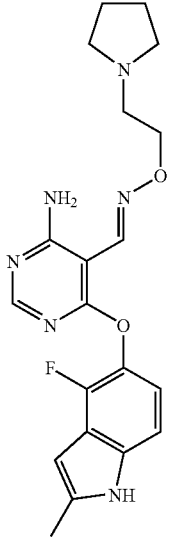
Cpd 10

Cpd 14
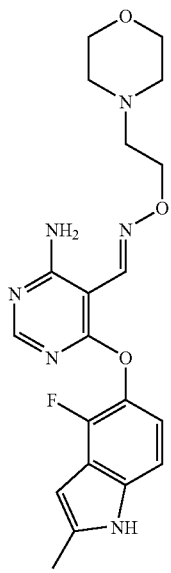
Cpd 15
Cpd 16
Cpd 17
Cpd 18
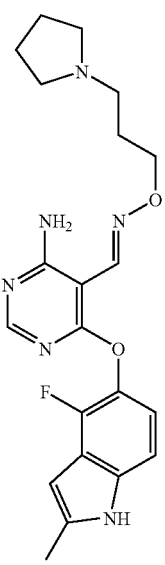
Cpd 19
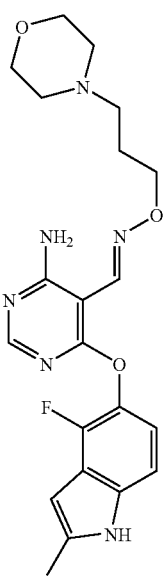

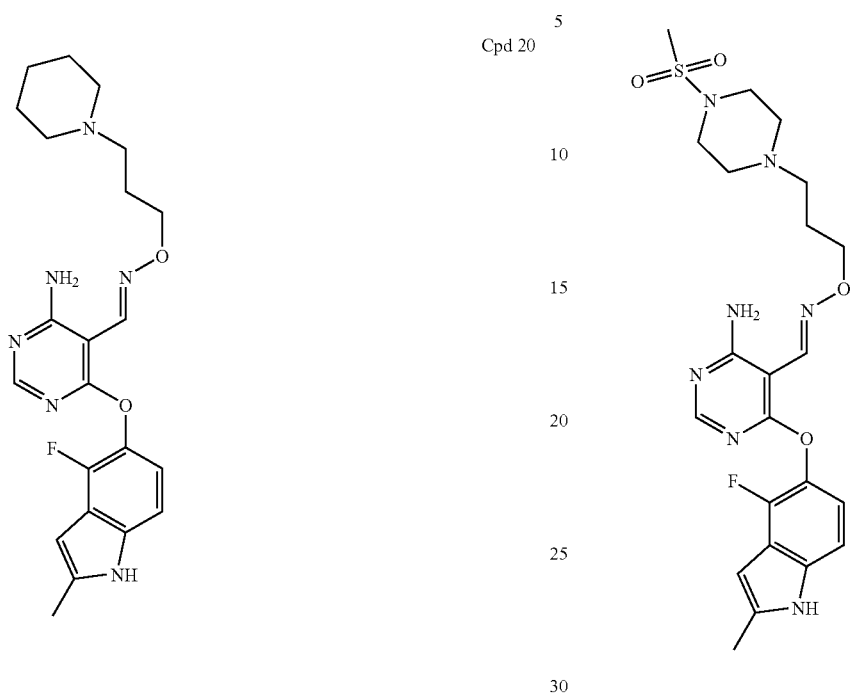
Cpd 20
Cpd 21
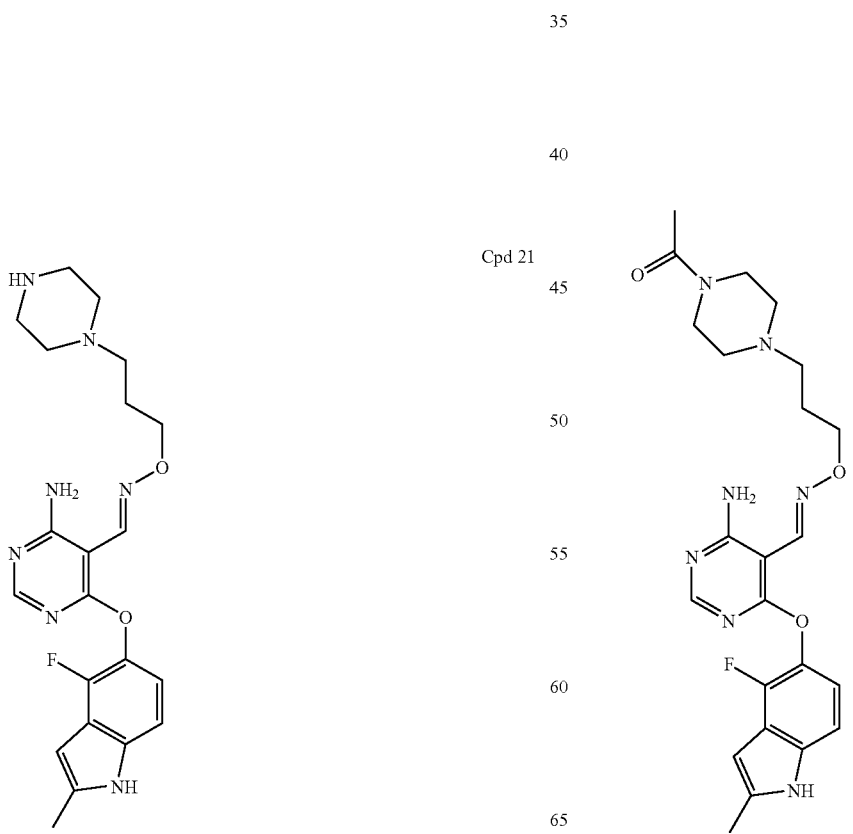
Cpd 22
Cpd 23

Cpd 24
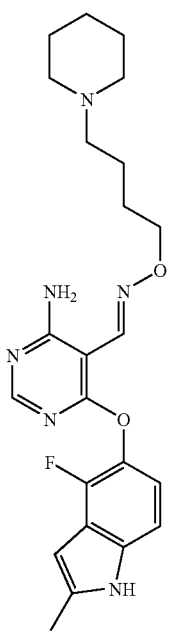
Cpd 26
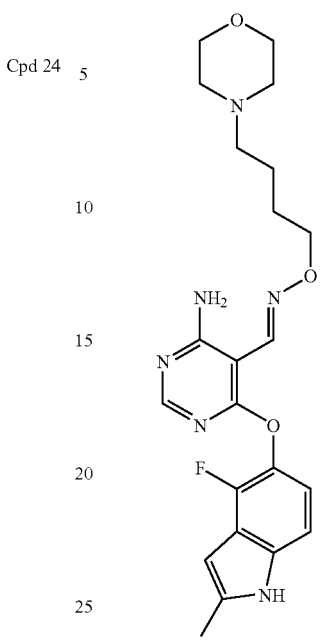
Cpd 25
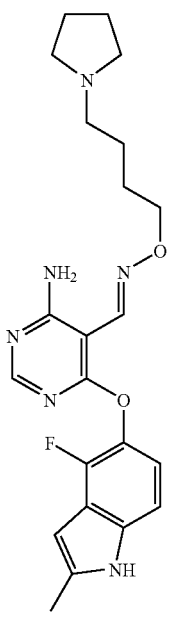
Cpd 27
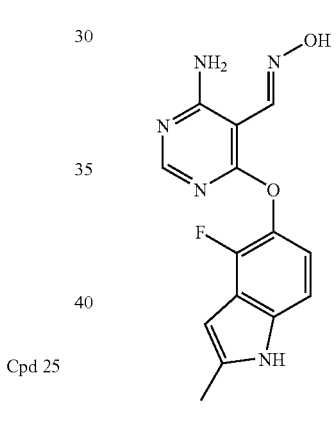
Cpd 28

Cpd 29
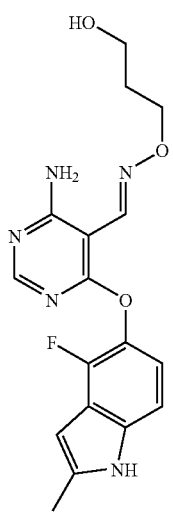
Cpd 30
Cpd 31
Cpd 32
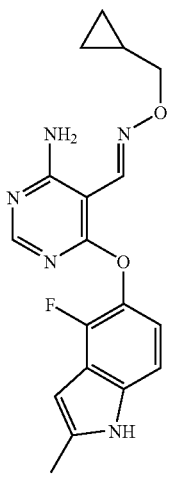
Cpd 33
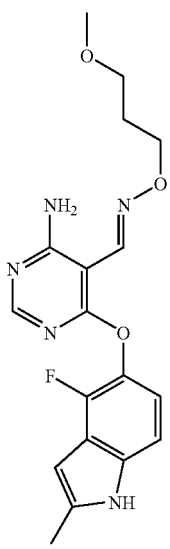
Cpd 34
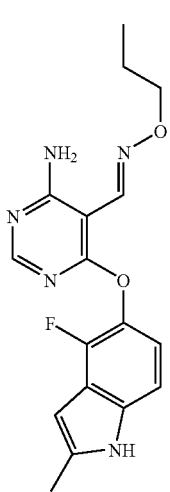

Cpd 35
Cpd 36
Cpd 37
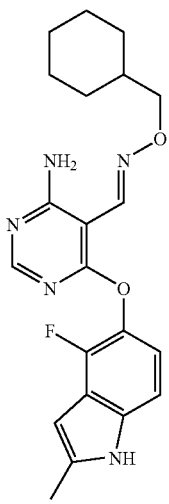
Cpd 38
Cpd 39
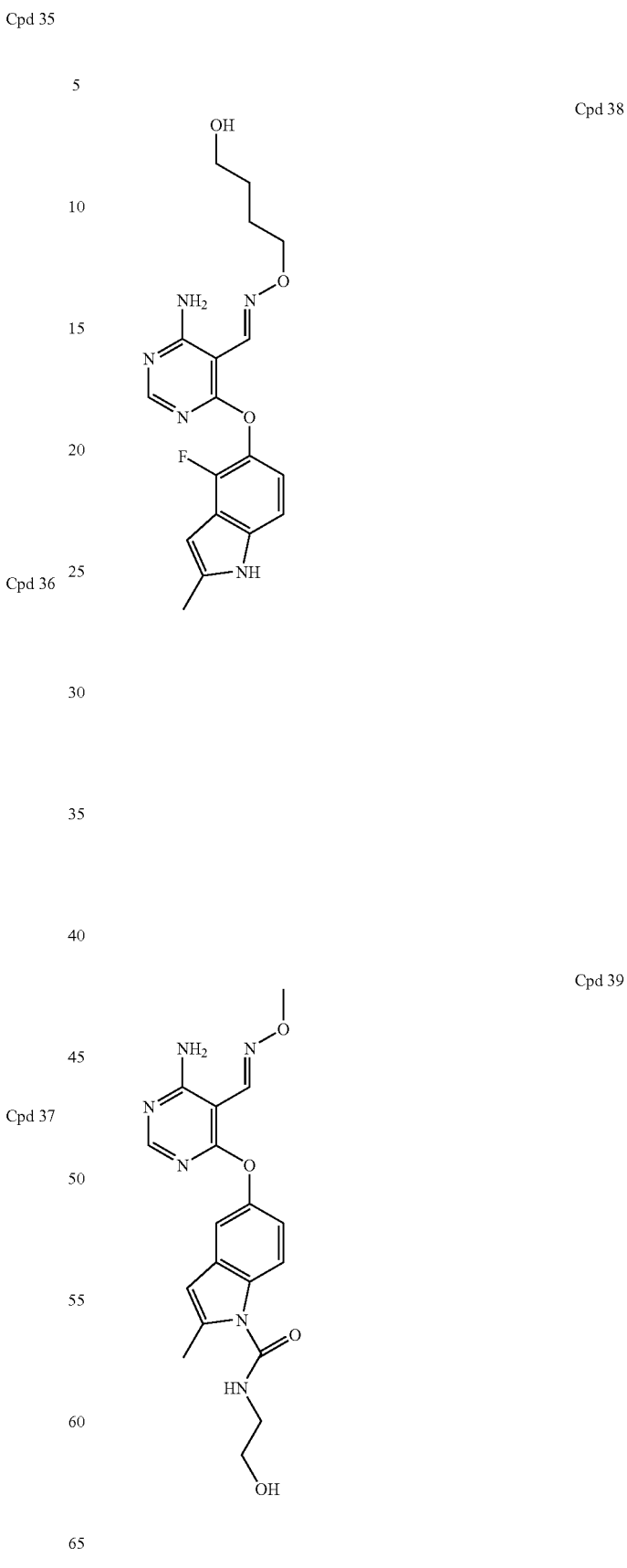

Cpd 40
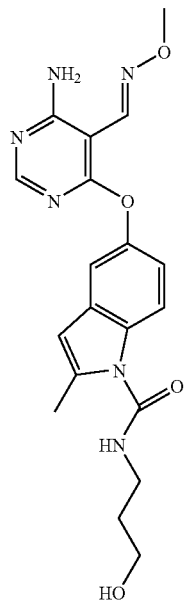
Cpd 41
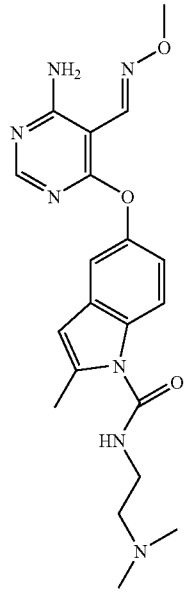
Cpd 42
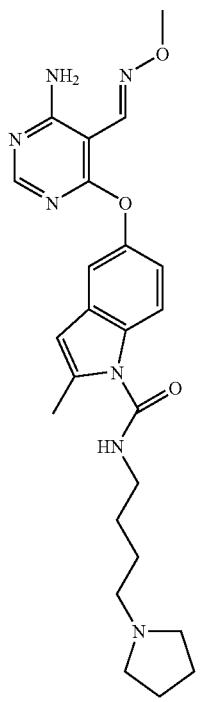
Cpd 43
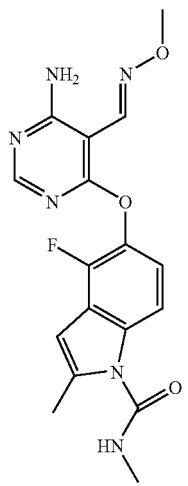

Cpd 44
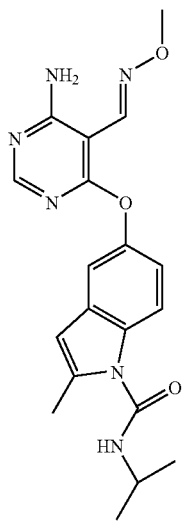
Cpd 45
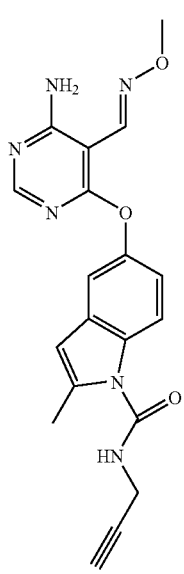
Cpd 46
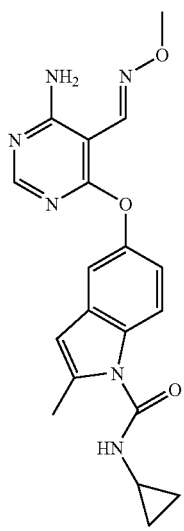
Cpd 47
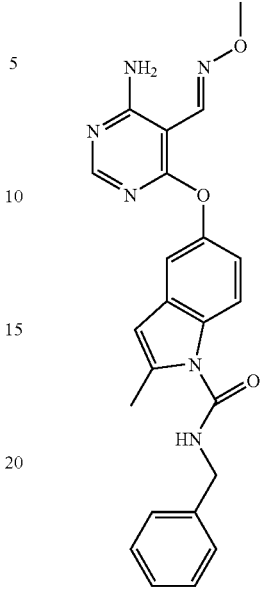
Cpd 48
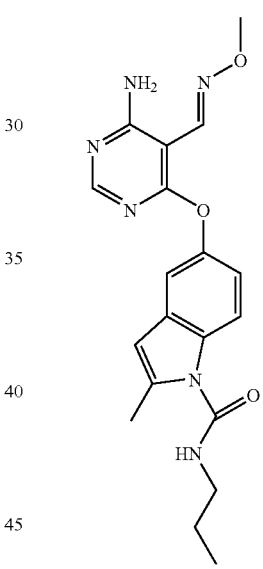
Cpd 49
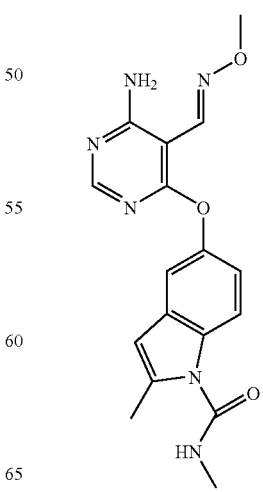

Cpd 50
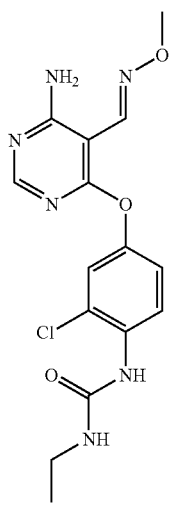
Cpd 53
Cpd 51
Cpd 54
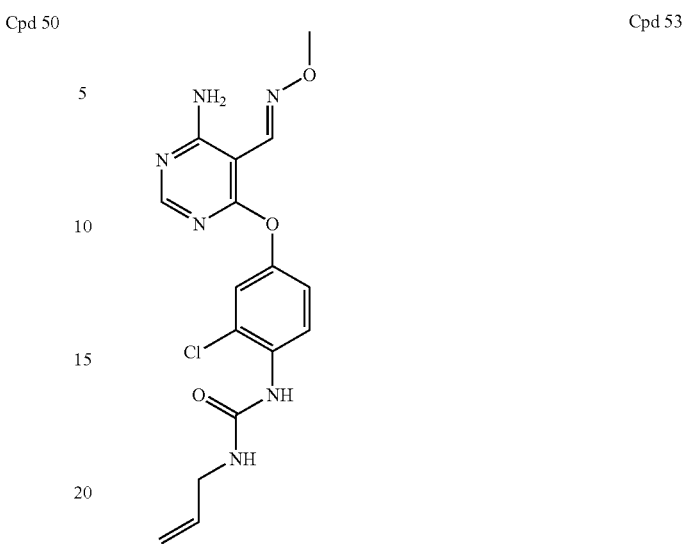
Cpd 52
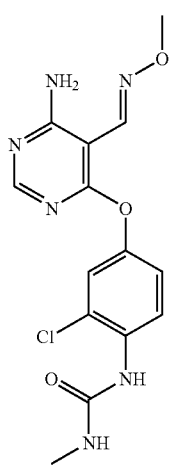
Cpd 55
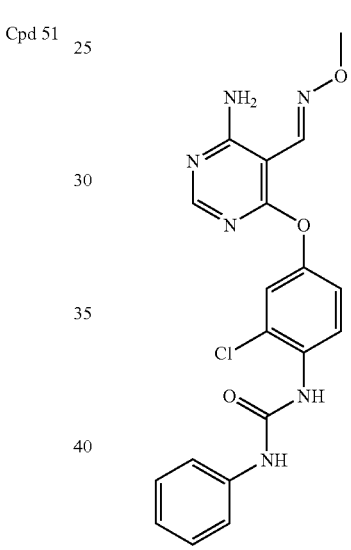
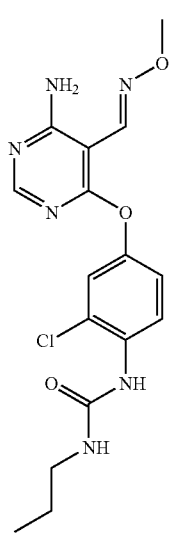
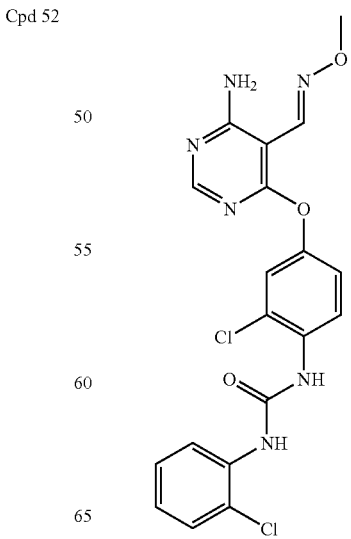

Cpd 56
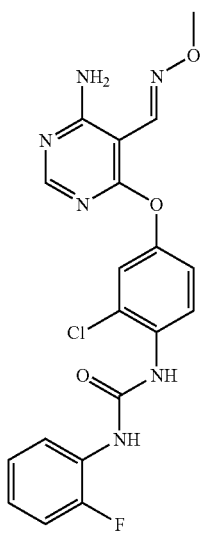
Cpd 57
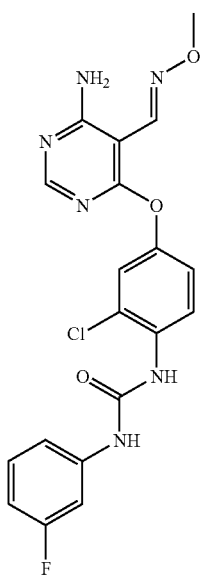
Cpd 58
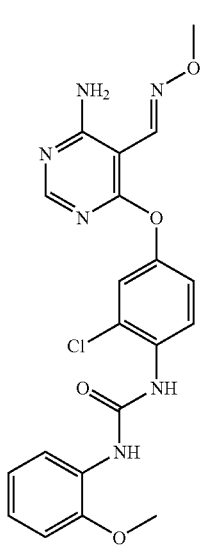
Cpd 59
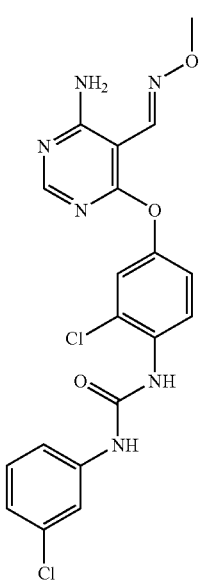
Cpd 60
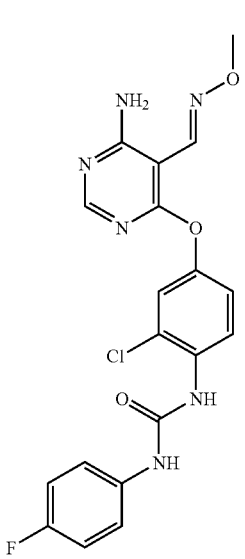
Cpd 61
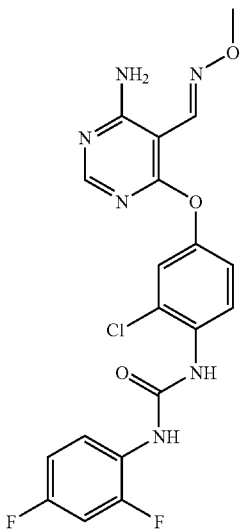

Cpd 62
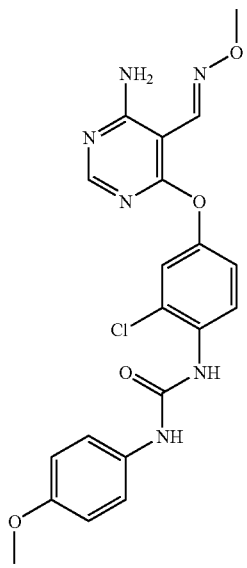
Cpd 63
Cpd 64
Cpd 65
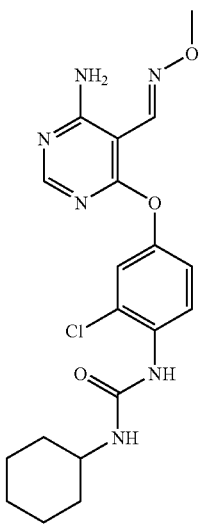
Cpd 66
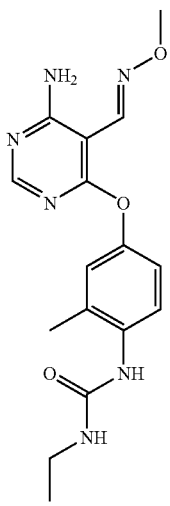
Cpd 67
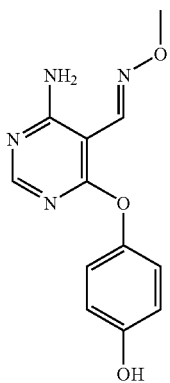

Cpd 68
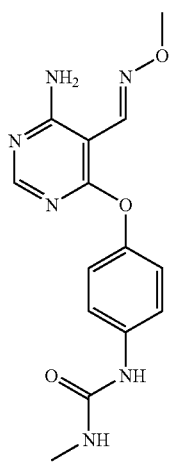
Cpd 69
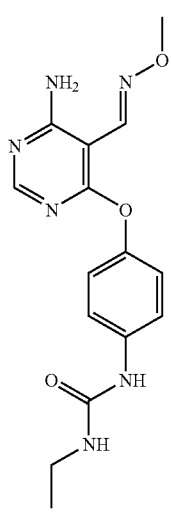
CPd70
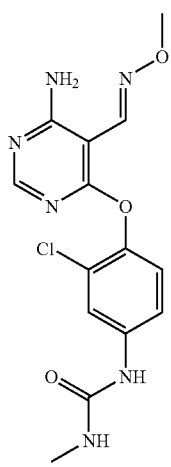
Cpd 71
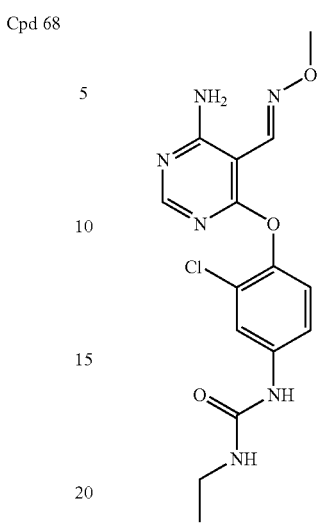
Cpd 72
Cpd 73

Cpd 74
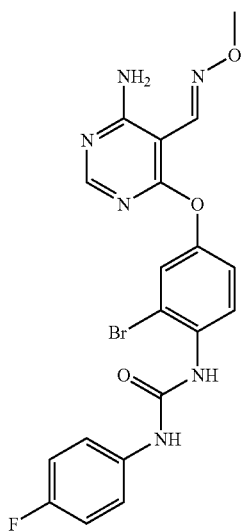
Cpd 75
Cpd 76
Cpd 77
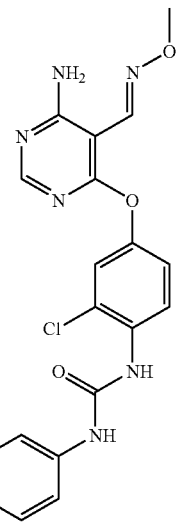
Cpd 78
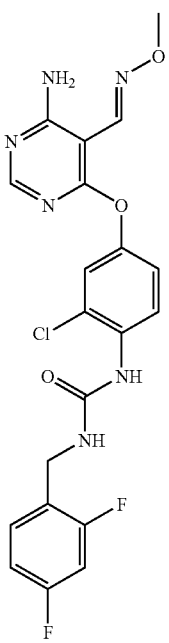

Cpd 79
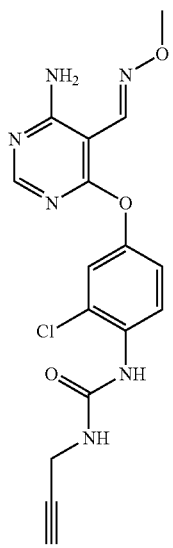
Cpd 80
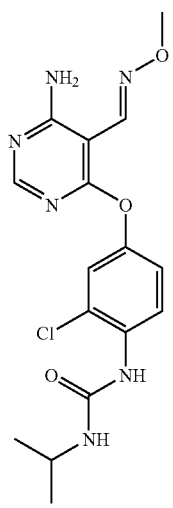
Cpd 81
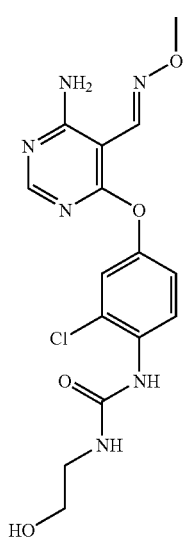
Cpd 82
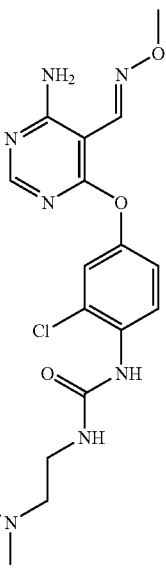
Cpd 83
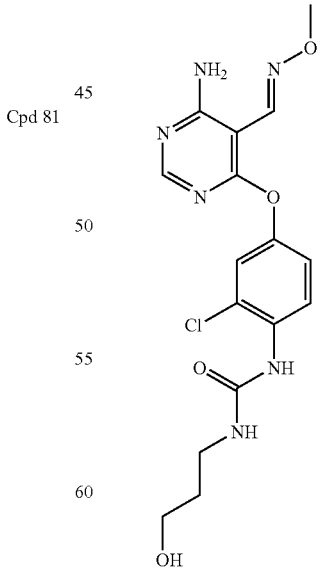

Cpd 84
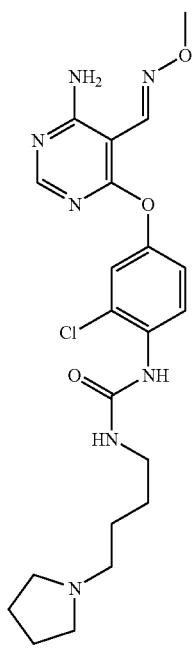
Cpd 85
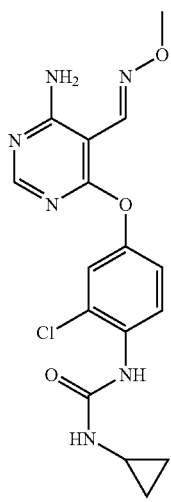
Cpd 86
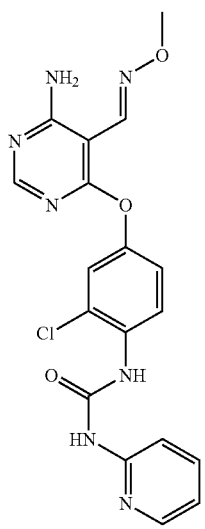
Cpd 87
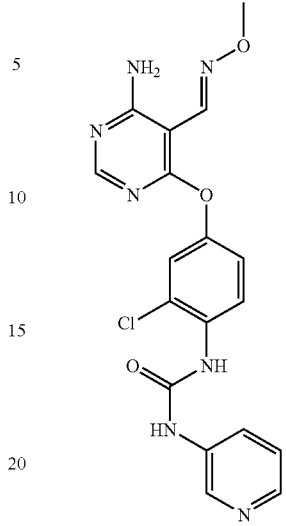
Cpd 88
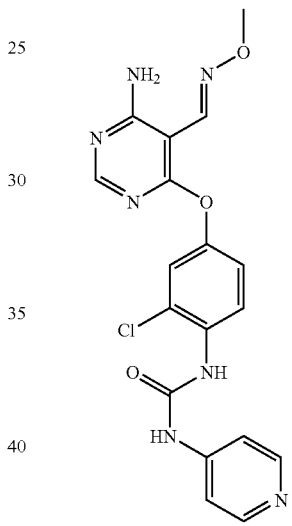
Cpd 89
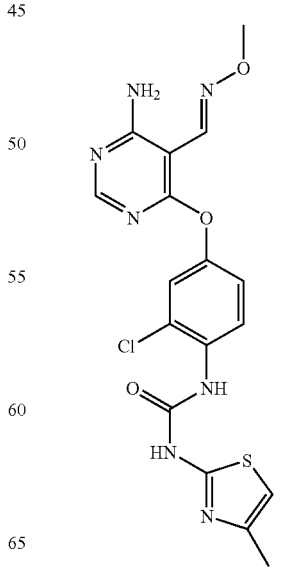

Cpd 90
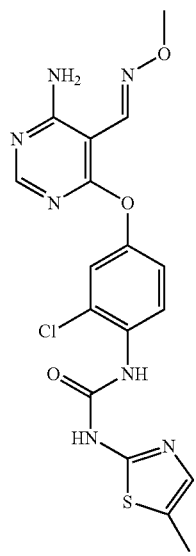
Cpd 93
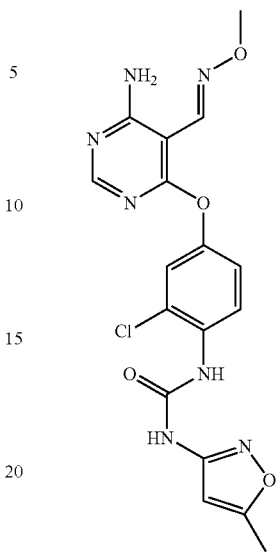
Cpd 91
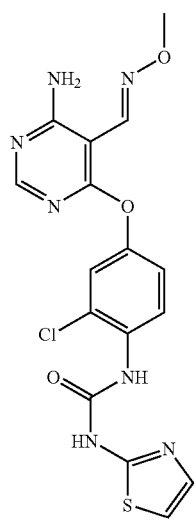
Cpd 94
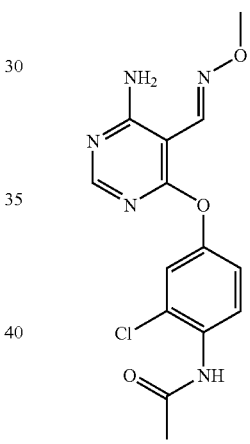
Cpd 92
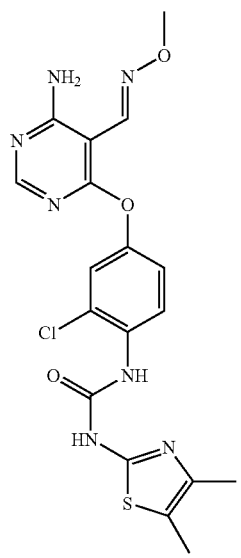
Cpd 95
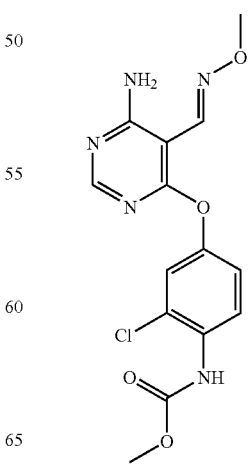

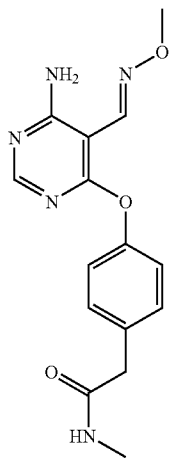
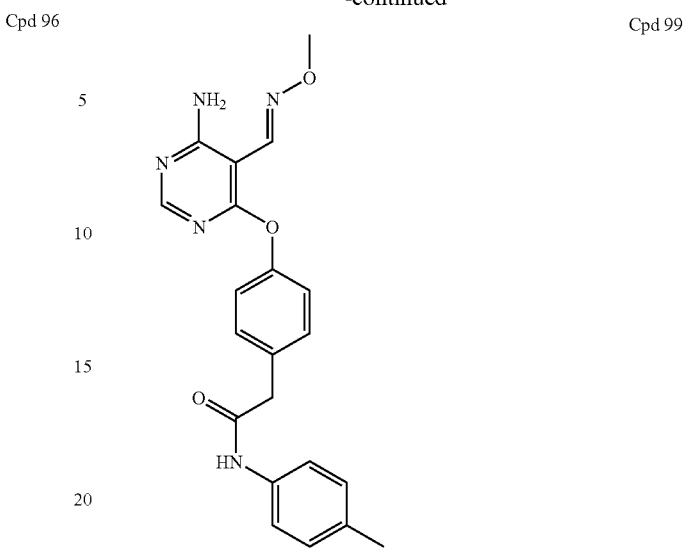

Cpd 102
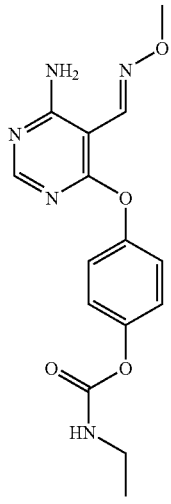
Cpd 103
Cpd 104
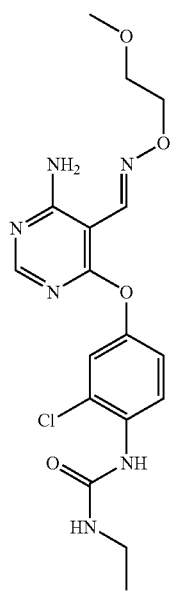
Cpd 105
Cpd 106

Cpd 107
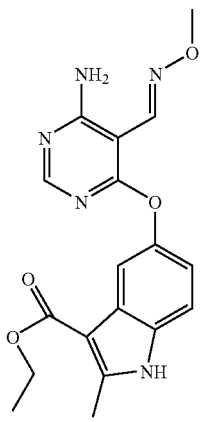
Cpd 110
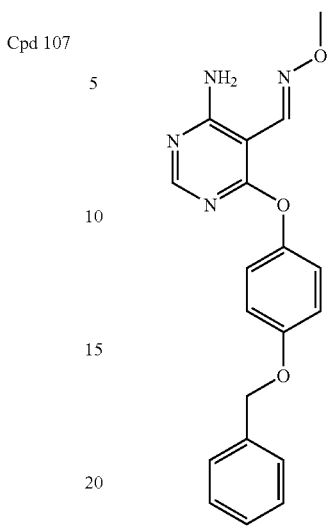
Cpd 108
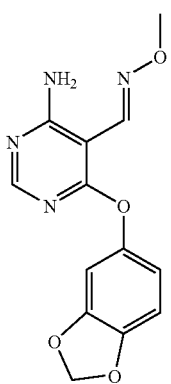
Cpd 111
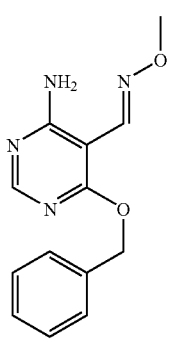
Cpd 112
Cpd 109
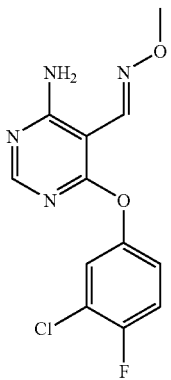
Cpd 113
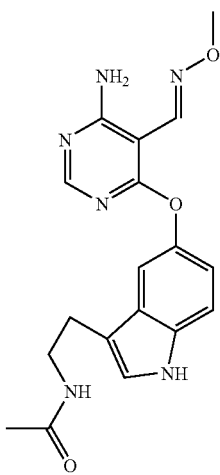

Cpd 114
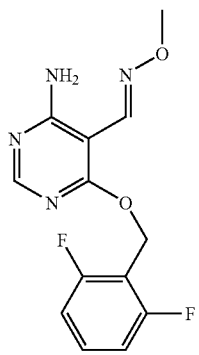
Cpd 115
Cpd 116
Cpd 117
Cpd 118
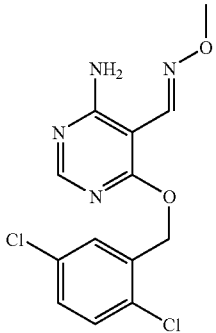
Cpd 119
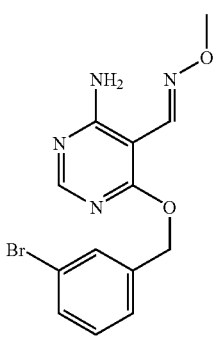
Cpd 120
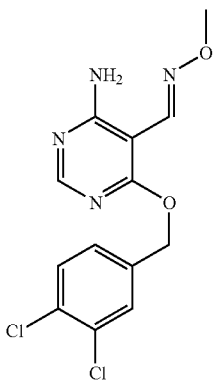
Cpd 121
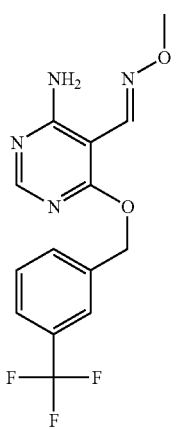

Cpd 122
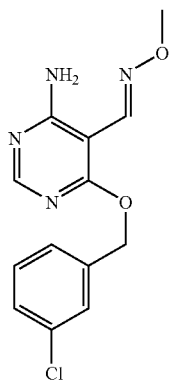
Cpd 123
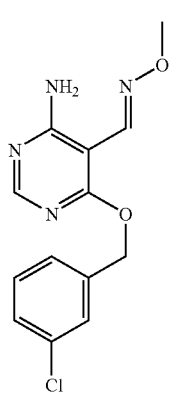
Cpd 124
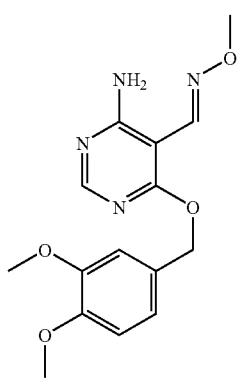
Cpd 125
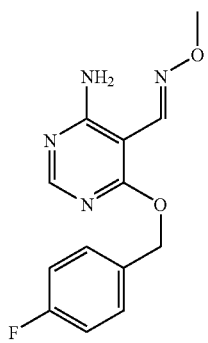
Cpd 126
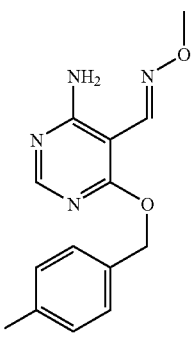
Cpd 127
Cpd 128
Cpd 129
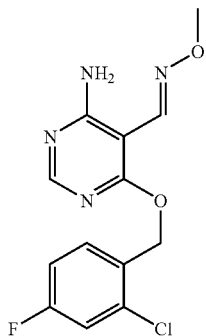

Cpd 130
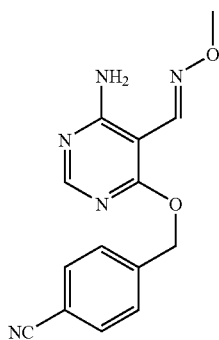
Cpd 131
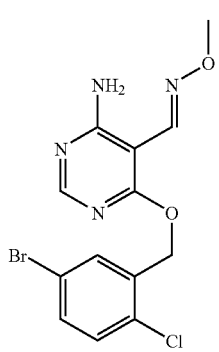
Cpd 132
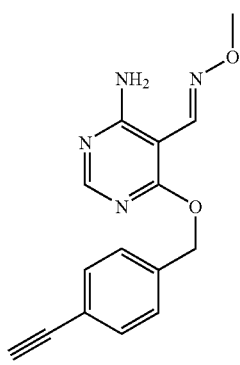
Cpd 133
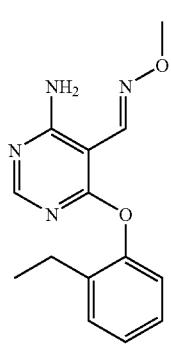
Cpd 134
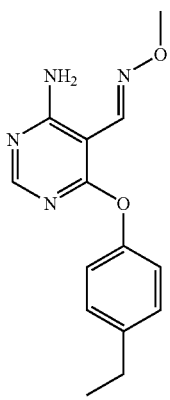
Cpd 135
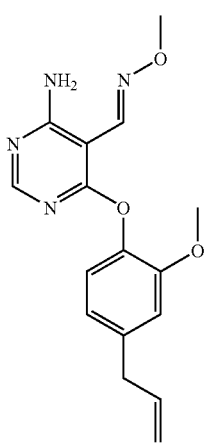
Cpd 136
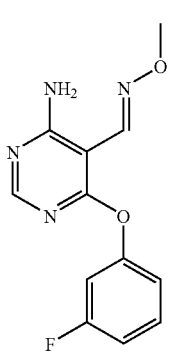
Cpd 137
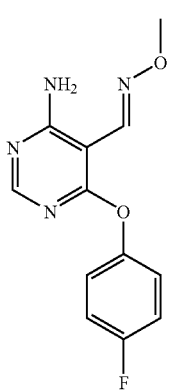

-continued
Cpd 138
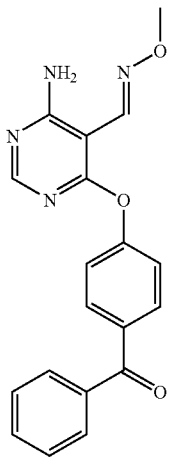
Cpd 139
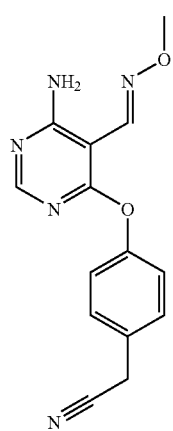
Cpd 140
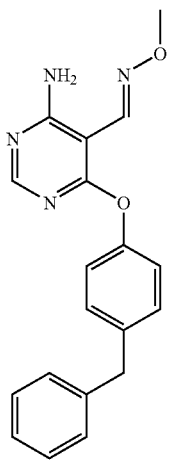
-continued
Cpd 141
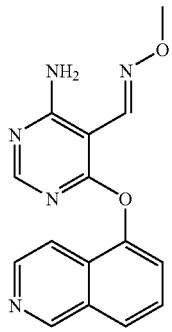
Cpd 142
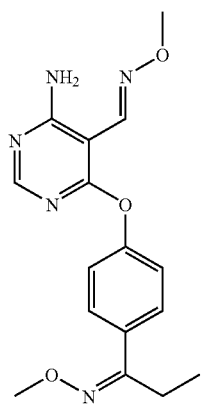
Cpd 143
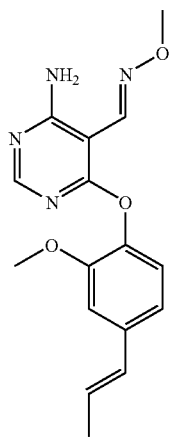
Cpd 144

Cpd 145
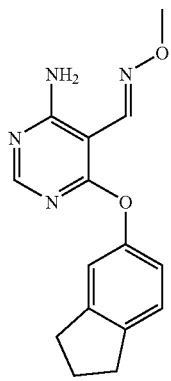
Cpd 146
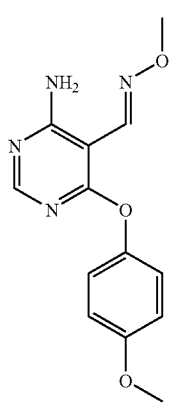
Cpd 147
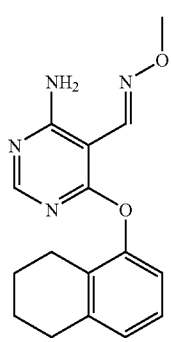
Cpd 148
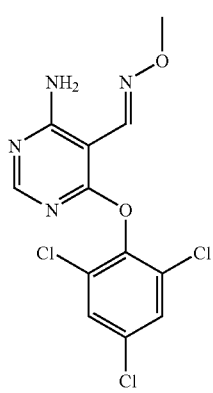
Cpd 149
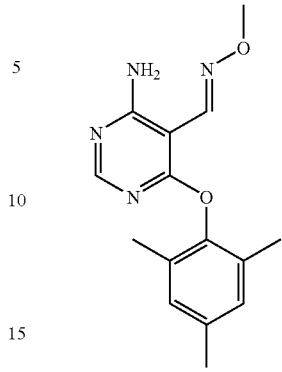
Cpd 150
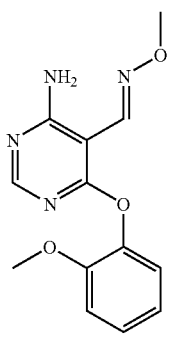
Cpd 151
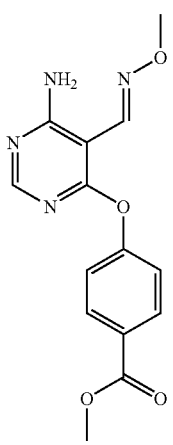
Cpd 152
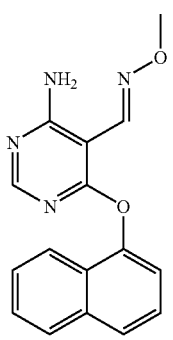

Cpd 153 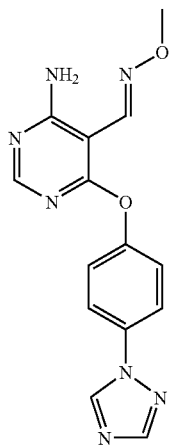 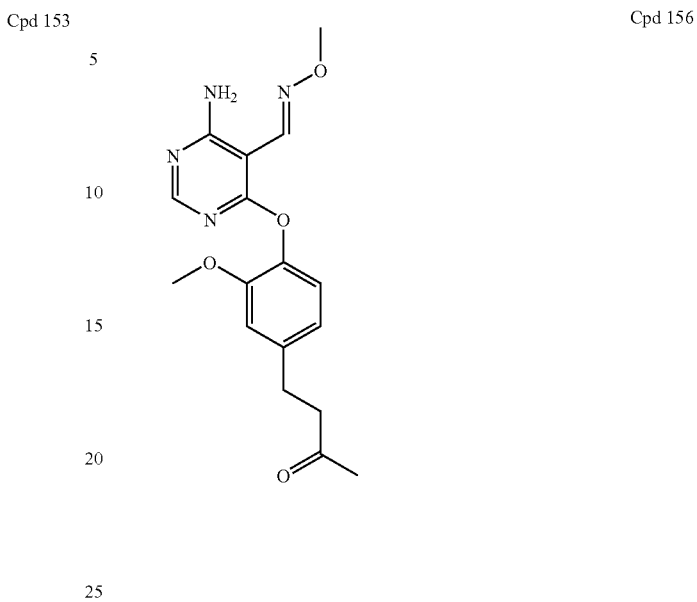 Cpd 156
Cpd 154 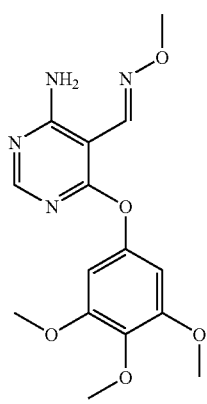 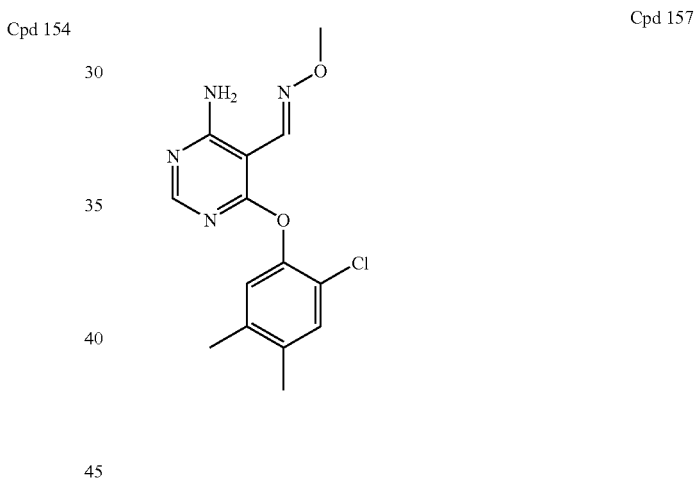 Cpd 157
Cpd 155 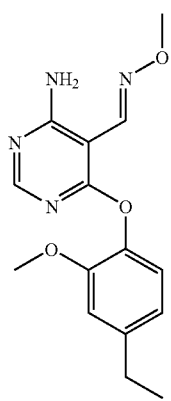 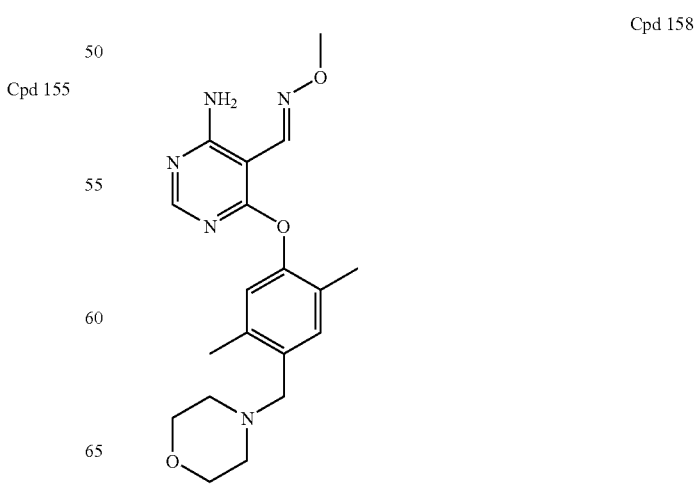 Cpd 158

Cpd 159
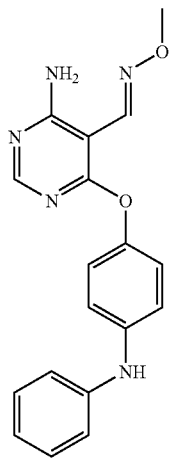

Cpd 160
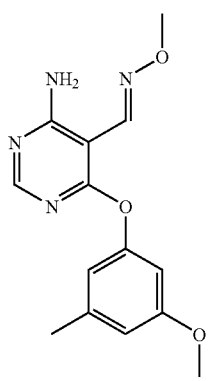

Cpd 161
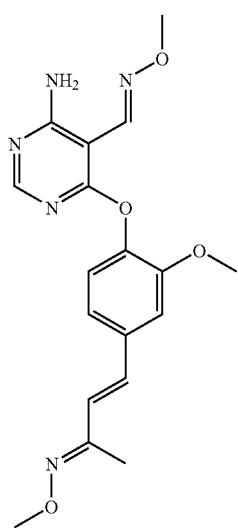

Cpd 162
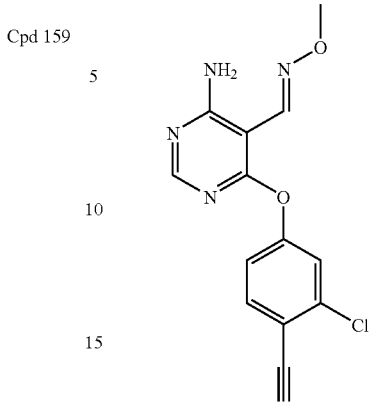

Cpd 163
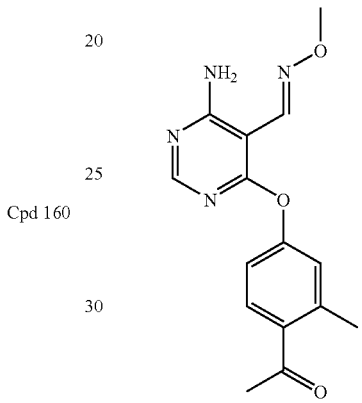

Cpd 164
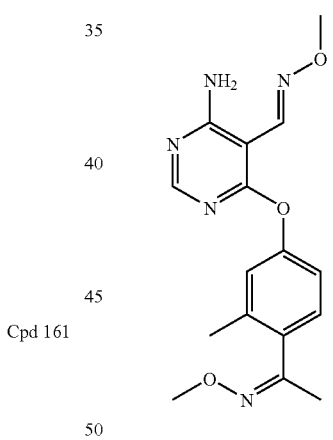

Chemical Definitions & Nomenclature

Bond lines drawn into a ring system from a substituent variable indicate that the substituent may be attached to any of the substitutable ring atoms.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$alkyl" means a saturated aliphatic branched or straight-chain hydrocarbon radical or linking group having from 1 up to 8 carbon atoms in a linear or branched arrangement, wherein the radical is derived by the removal of one hydrogen atom from a carbon atom and the linking group is derived by the removal of one hydrogen atom from each of two carbon atoms in the chain. The term "$C_{1-8}$alkyl" also includes a "$C_{1-6}$alkyl" and "$C_{1-4}$alkyl" radical or linking group having from 1 up to 6 carbon atoms and 1 up to 4 carbon atoms respectively, such as methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Alkyl radicals may be attached to a core molecule and further substituted on any atom when allowed by available valences.

The term "$C_{2-8}$alkenyl" means an alkyl radical or linking group having from 2 up to 8 carbon atoms in a linear or branched arrangement having at least one carbon-carbon double bond. The term "$C_{2-8}$alkenyl" also includes a "$C_{2-4}$alkenyl" radical or linking group having from 2 up to 4 carbon atoms, such as ethenyl (also referred to as vinyl), iso-propenyl, allyl (also referred to as propenyl), propylidene and the like. Alkenyl radicals may be attached to a core molecule and further substituted on any atom when allowed by available valences.

The term "$C_{2-8}$alkynyl" means an alkyl radical or linking group having from 2 up to 8 carbon atoms in a linear or branched arrangement having at least one carbon-carbon triple bond. The term "$C_{2-8}$alkynyl" also includes a "$C_{2-4}$alkynyl" radical or linking group having from 2 up to 4 carbon atoms, such as ethynyl, propynyl and the like. Alkynyl radicals may be attached to a core molecule and further substituted on any atom when allowed by available valences.

The term "$C_{1-8}$alkoxy" means an alkyl radical or linking group having from 1 up to 8 carbon atoms in a linear or branched arrangement, wherein the radical or linking group is attached through an oxygen linking atom, as in the formula: —O—$C_{1-8}$alkyl. The term "$C_{1-8}$alkoxy" also includes a "$C_{1-6}$alkoxy" and "$C_{1-4}$alkoxy" radical or linking group having from 1 up to 6 carbon atoms and from 1 up to 4 carbon atoms respectively, such as methoxy, ethoxy, propoxy, butoxy and the like. An alkoxy radical may be attached to a core molecule and further substituted on any atom when allowed by available valences.

The term "$C_{3-12}$cycloalkyl" means a saturated or partially unsaturated cyclic hydrocarbon ring system radical. The term "$C_{3-12}$cycloalkyl" also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-12}$cycloalkyl or benzofused-$C_{3-12}$cycloalkyl ring system radical and the like, such as cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, 5,6,7,8-tetrahydro-naphthalenyl acenaphthenyl, adamantanyl and the like. A $C_{3-12}$cycloalkyl radical may be attached to a core molecule and further substituted on any atom when allowed by available valences.

The term "benzofused-$C_{3-12}$cycloalkyl" means a $C_{3-12}$cycloalkyl ring system radical having a benzene ring fused on the ring system on adjacent carbons. A benzofused-$C_{3-12}$cycloalkyl radical may be attached to a core molecule and further substituted on any atom when allowed by available valences.

The term "aryl" means an unsaturated aromatic hydrocarbon ring system radical. Aryl ring systems include phenyl, naphthalenyl, azulenyl, anthracenyl and the like. An aryl radical may be attached to a core molecule and further substituted on any atom when allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heterocyclyl" means a saturated or partially unsaturated "hetero" ring system radical. Heterocyclyl ring systems include azetidinyl, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azepanyl, hexahydro-1,4-diazepinyl, hexahydro-1,4-oxazepanyl, tetrahydro-furanyl, tetrahydrothienyl, tetrahydro-pyranyl, tetrahydro-pyridazinyl and the like. The term "heterocyclyl" also includes a benzofused-heterocyclyl ring system radical and the like, such as indolinyl (also referred to as 2,3-dihydro-indolyl), benzo[1,3]dioxolyl, 2,3-dihydro-1,4-benzodioxinyl, 2,3-dihydrobenzofuranyl, 1,2-dihydro-phthalazinyl and the like. A heterocyclyl radical may be attached to a core molecule and further substituted on any atom when allowed by available valences.

The term "benzofused-heterocyclyl" means a heterocyclyl ring system radical having a benzene ring fused on the ring system on adjacent carbons. A benzofused-heterocyclyl radical may be attached to a core molecule and further substituted on any atom when allowed by available valences.

The term "heteroaryl" means a monovalent, unsaturated aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like. The term "heteroaryl" also includes a benzofused-heteroaryl ring system radical and the like, such as indolizinyl, indolyl, azaindolyl, isoindolyl, benzofuranyl, benzothienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like. A heteroaryl radical may be attached to a core molecule and further substituted on any atom when allowed by available valences.

The term "benzofused-heteroaryl" means a heteroaryl ring system radical having a benzene ring fused on the ring system on adjacent carbons. Examples of benzofused-heteroaryl in compounds representative of the present invention include indolyl and quinolinyl. A benzofused-heteroaryl radical may be attached to a core molecule and further substituted on any atom when allowed by available valences.

The term "$C_{1-8}$alkoxy-$C_{1-8}$alkyl" means a radical of the formula: —$C_{1-8}$alkyl-O—$C_{1-8}$alkyl, wherein $C_{1-8}$alkyl is optionally further substituted.

The term "$C_{1-8}$alkoxy-$C_{1-8}$alkyl-amino-$C_{1-8}$alkyl" means a radical of the formula: —$C_{1-8}$alkyl-NH—$C_{1-8}$alkyl-O—$C_{1-8}$alkyl or —$C_{1-8}$alkyl-N($C_{1-8}$alkyl-O—$C_{1-8}$alkyl)$_2$, wherein $C_{1-8}$alkyl is optionally further substituted.

The term "$C_{1-8}$alkoxy-carbonyl" means a radical of the formula: —C(O)—O—$C_{1-8}$alkyl, wherein $C_{1-8}$alkyl is optionally further substituted.

The term "$C_{1-8}$alkoxy-carbonyl-amino" means a radical of the formula: —NH—C(O)—O—$C_{1-8}$alkyl or —N[C(O)—O—$C_{1-8}$alkyl]$_2$, wherein $C_{1-8}$alkyl is optionally further substituted.

The term "$C_{1-8}$alkoxy-$C_{1-8}$alkyl-carbonyl" means a radical of the formula: —C(O)—$C_{1-8}$alkyl-O—$C_{1-8}$alkyl, wherein $C_{1-8}$alkyl is optionally further substituted.

The term "$C_{1-8}$alkoxy-$C_{1-8}$alkyl-carbonyl-amino" means a radical of the formula: —NH—C(O)—$C_{1-8}$alkyl-O—$C_{1-8}$alkyl or —N[C(O)—$C_{1-8}$alkyl-O—$C_{1-8}$alkyl]$_2$, wherein $C_{1-8}$alkyl is optionally further substituted.

The term "$C_{1-8}$alkoxy-imino-$C_{1-8}$alkyl" means a radical of the formula: —$C_{1-8}$alkyl=N—O—$C_{1-8}$alkyl, wherein $C_{1-8}$alkyl is optionally further substituted.

The term "$C_{1-8}$alkoxy-imino-$C_{2-8}$alkenyl" means a radical of the formula: —$C_{2-8}$alkenyl=N—O—$C_{1-8}$alkyl, wherein $C_{1-8}$alkyl is optionally further substituted and the imino portion is attached to $C_{2-8}$alkenyl where allowed by available valences.

The term "$C_{1-8}$alkyl-amino" means a radical of the formula: —NH—$C_{1-8}$alkyl or —N($C_{1-8}$alkyl)$_2$, wherein $C_{1-8}$alkyl is optionally further substituted.

The term "$C_{1-8}$alkyl-amino-$C_{1-8}$alkyl" means a radical of the formula: —$C_{1-8}$alkyl-NH—$C_{1-8}$alkyl or —$C_{1-8}$alkyl-N($C_{1-8}$alkyl)$_2$, wherein $C_{1-8}$alkyl is optionally further substituted.

The term "$C_{1-8}$alkyl-amino-carbonyl" means a radical of the formula: —C(O)—NH—$C_{1-8}$alkyl or —C(O)—N($C_{1-8}$alkyl)$_2$, wherein $C_{1-8}$alkyl is optionally further substituted.

The term "$C_{1-8}$alkyl-amino-carbonyl-$C_{1-8}$alkyl" means a radical of the formula: —$C_{1-8}$alkyl-C(O)—NH—$C_{1-8}$alkyl or —$C_{1-8}$alkyl-C(O)—N($C_{1-8}$alkyl)$_2$, wherein $C_{1-8}$alkyl is optionally further substituted.

The term "$C_{1-8}$alkyl-amino-$C_{1-8}$alkyl-amino-carbonyl" means a radical of the formula: —C(O)—NH—$C_{1-8}$alkyl-NH—$C_{1-8}$alkyl, —C(O)—NH—$C_{1-8}$alkyl-N($C_{1-8}$alkyl)$_2$, —C(O)—N($C_{1-8}$alkyl-NH—$C_{1-8}$alkyl) or —C(O)—N[$C_{1-8}$alkyl-N($C_{1-8}$alkyl)$_2$]$_2$, wherein $C_{1-8}$alkyl is optionally further substituted.

The term "$C_{1-8}$alkyl-amino-$C_{1-8}$alkyl-amino-carbonyl-amino" means a radical of the formula: —NH—C(O)—NH—$C_{1-8}$alkyl-NH—$C_{1-8}$alkyl, —NH—C(O)—NH—$C_{1-8}$alkyl-N($C_{1-8}$alkyl)$_2$, —NH—C(O)—N($C_{1-8}$alkyl-NH—$C_{1-8}$alkyl) or —NH—C(O)—N[$C_{1-8}$alkyl-N($C_{1-8}$alkyl)$_2$]$_2$, wherein $C_{1-8}$alkyl is optionally further substituted.

The term "$C_{1-8}$alkyl-amino-carbonyl-amino" means a radical of the formula: —NH—C(O)—NH—$C_{1-8}$alkyl or —NH—C(O)—N($C_{1-8}$alkyl)$_2$, wherein $C_{1-8}$alkyl is optionally further substituted.

The term "$C_{1-8}$alkyl-amino-carbonyl-oxy" means a radical of the formula: —O—C(O)—NH—$C_{1-8}$alkyl or —O—C(O)—N($C_{1-8}$alkyl)$_2$, wherein $C_{1-8}$alkyl is optionally further substituted.

The term "$C_{2-8}$alkenyl-amino-carbonyl" means a radical of the formula: —C(O)—NH—$C_{2-8}$-alkenyl or —C(O)—N($C_{2-8}$alkenyl)$_2$, wherein $C_{2-8}$alkenyl is optionally further substituted.

The term "$C_{2-8}$alkenyl-amino-carbonyl-$C_{1-8}$alkyl" means a radical of the formula: —$C_{1-8}$alkyl-C(O)—NH—$C_{2-8}$-alkenyl or —$C_{1-8}$alkyl-C(O)—N($C_{2-8}$alkenyl)$_2$, wherein $C_{2-8}$alkenyl is optionally further substituted.

The term "$C_{2-8}$alkenyl-amino-carbonyl-amino" means a radical of the formula: —NH—C(O)—NH—$C_{2-8}$alkenyl or —NH—C(O)—N($C_{2-8}$alkenyl)$_2$, wherein $C_{2-8}$alkenyl is optionally further substituted.

The term "$C_{2-8}$alkenyl-amino-carbonyl-oxy" means a radical of the formula: —O—C(O)—NH—$C_{2-8}$alkenyl or —O—C(O)—N($C_{2-8}$alkenyl)$_2$, wherein $C_{2-8}$alkenyl is optionally further substituted.

The term "$C_{2-8}$alkynyl-amino-carbonyl" means a radical of the formula: —C(O)—NH—$C_{2-8}$alkynyl or —C(O)—N($C_{2-8}$alkynyl)$_2$, wherein $C_{2-8}$alkynyl is optionally further substituted.

The term "$C_{2-8}$alkynyl-amino-carbonyl-$C_{1-8}$alkyl" means a radical of the formula: —$C_{1-8}$alkyl-C(O)—NH—$C_{2-8}$alkynyl or —$C_{1-8}$alkyl-C(O)—N($C_{2-8}$alkynyl)$_2$, wherein $C_{2-8}$alkynyl is optionally further substituted.

The term "$C_{2-8}$alkynyl-amino-carbonyl-amino" means a radical of the formula: —NH—C(O)—NH—$C_{2-8}$alkynyl or —NH—C(O)—N($C_{2-8}$alkynyl)$_2$, wherein $C_{2-8}$alkynyl is optionally further substituted.

The term "$C_{2-8}$alkynyl-amino-carbonyl-oxy" means a radical of the formula: —O—C(O)—NH—$C_{2-8}$alkynyl or —O—C(O)—N($C_{2-8}$alkynyl)$_2$, wherein $C_{2-8}$alkynyl is optionally further substituted.

The term "$C_{1-8}$alkyl-carbonyl" means a radical of the formula: —C(O)—$C_{1-8}$alkyl, wherein $C_{1-8}$alkyl is optionally further substituted.

The term "$C_{1-8}$alkyl-carbonyl-$C_{1-8}$alkyl" means a radical of the formula: —$C_{1-8}$alkyl-C(O)—$C_{1-8}$alkyl, wherein $C_{1-8}$alkyl is optionally further substituted.

The term "$C_{1-8}$alkyl-carbonyl-amino" means a radical of the formula: —NH—C(O)—$C_{1-8}$alkyl or —N[C(O)—$C_{1-8}$alkyl]$_2$, wherein $C_{1-8}$alkyl is optionally further substituted.

The term "$C_{1-8}$alkyl-carbonyl-amino-$C_{1-8}$alkyl" means a radical of the formula: —$C_{1-8}$alkyl-NH—C(O)—$C_{1-8}$alkyl, wherein $C_{1-8}$alkyl is optionally further substituted.

The term "$C_{1-8}$alkyl-sulfonyl-$C_{1-8}$alkyl" means a radical of the formula: —$C_{1-8}$alkyl-SO$_2$—$C_{1-8}$alkyl, wherein $C_{1-8}$alkyl is optionally further substituted.

The term "$C_{1-8}$alkyl-sulfonyl-oxy-$C_{1-8}$alkyl" means a radical of the formula: —$C_{1-8}$alkyl-SO$_2$—O—$C_{1-8}$alkyl, wherein $C_{1-8}$alkyl is optionally further substituted.

The term "amino" means a radical of the formula: —NH$_2$.

The term "amino-$C_{1-8}$alkyl" means a radical of the formula: —$C_{1-8}$alkyl-NH$_2$.

The term "amino-carbonyl-$C_{1-8}$alkyl" means a radical of the formula: —$C_{1-8}$alkyl-C(O)—NH$_2$.

The term "amino-$C_{1-8}$alkyl-amino-carbonyl" means a radical of the formula: —C(O)—NH—$C_{1-8}$alkyl-NH$_2$ or —C(O)—N($C_{1-8}$alkyl-NH$_2$)$_2$.

The term "amino-$C_{1-8}$alkyl-amino-carbonyl-amino" means a radical of the formula: —NH—C(O)—NH—$C_{1-8}$alkyl-NH$_2$ or —NH—C(O)—N($C_{1-8}$alkyl-NH$_2$)$_2$.

The term "$C_{3-8}$cycloalkyl-$C_{1-8}$alkoxy" means a radical of the formula: —O—$C_{1-8}$alkyl-$C_{3-8}$cycloalkyl.

The term "$C_{3-8}$cycloalkyl-$C_{1-8}$alkyl" means a radical of the formula: —$C_{1-8}$alkyl-$C_{3-8}$cycloalkyl.

The term "$C_{3-8}$cycloalkyl-$C_{1-8}$alkyl-amino-carbonyl" means a radical of the formula: —C(O)—NH—$C_{1-8}$alkyl-$C_{3-8}$cycloalkyl or —C(O)—N($C_{1-8}$alkyl-$C_{3-8}$cycloalkyl)$_2$.

The term "$C_{3-8}$cycloalkyl-$C_{1-8}$alkyl-amino-carbonyl-amino" means a radical of the formula: —NH—C(O)—NH—$C_{1-8}$alkyl-$C_{3-8}$cycloalkyl or —NH—C(O)—N($C_{1-8}$alkyl-$C_{3-8}$cycloalkyl)$_2$.

The term "$C_{3-8}$cycloalkyl-amino-carbonyl" means a radical of the formula: —C(O)—NH—$C_{3-8}$cycloalkyl or —C(O)—N($C_{3-8}$cycloalkyl)$_2$.

The term "$C_{3-8}$cycloalkyl-amino-carbonyl-amino" means a radical of the formula: —NH—C(O)—NH—$C_{3-8}$cycloalkyl or —NH—C(O)—N($C_{3-8}$cycloalkyl)$_2$.

The term "$C_{3-8}$cycloalkyl-amino-carbonyl-$C_{1-8}$alkyl" means a radical of the formula: —$C_{1-8}$alkyl-C(O)—NH—$C_{3-8}$cycloalkyl or —$C_{1-8}$alkyl-C(O)—N($C_{3-8}$cycloalkyl)$_2$.

The term "halogen" or "halo" means the group chloro, bromo, fluoro or iodo.

The term "halo-$C_{1-8}$alkoxy" means a radical of the formula: —O—$C_{1-8}$alkyl-(halo)$_n$, wherein one or more halogen atoms may be substituted on $C_{1-8}$alkyl when allowed by available valences (wherein n represents that amount of available valences based on the number of carbon atoms in the chain), and includes monofluoromethoxy, difluoromethoxy, trifluoromethoxy, trifluoroethoxy and the like.

The term "halo-$C_{1-8}$alkyl" means a radical of the formula: —$C_{1-8}$alkyl-(halo)$_n$, wherein one or more halogen atoms may be substituted on $C_{1-8}$alkyl when allowed by available valences (wherein n represents that amount of available valences based on the number of carbon atoms in the chain), and includes monofluoromethyl, difluoromethyl, trifluoromethyl, trifluoroethyl and the like.

The term "aryl-oxy" means a radical of the formula: —O-aryl.

The term "aryl-oxy-$C_{1-8}$alkyl" means a radical of the formula: —$C_{1-8}$alkyl-O-aryl.

The term "aryl-$C_{1-8}$alkoxy" means a radical of the formula: —O—$C_{1-8}$alkyl-aryl.

The term "aryl-$C_{1-8}$alkyl" means a radical of the formula: —$C_{1-8}$alkyl-aryl.

The term "aryl-amino" means a radical of the formula: —NH-aryl.

The term "aryl-carbonyl" means a radical of the formula: —C(O)-aryl.

The term "aryl-$C_{1-8}$alkyl-amino-carbonyl" means a radical of the formula: —C(O)—NH—$C_{1-8}$alkyl-aryl or —C(O)—N($C_{1-8}$alkyl-aryl)$_2$.

The term "aryl-$C_{1-8}$alkyl-amino-carbonyl-amino" means a radical of the formula: —NH—C(O)—NH—$C_{1-8}$alkyl-aryl or —NH—C(O)—N($C_{1-8}$alkyl-aryl)$_2$.

The term "aryl-amino-carbonyl" means a radical of the formula: —C(O)—NH-aryl or —C(O)—N(aryl)$_2$.

The term "aryl-amino-carbonyl-$C_{1-8}$alkyl" means a radical of the formula: —$C_{1-8}$alkyl-C(O)—NH-aryl or —$C_{1-8}$alkyl-C(O)—N(aryl)$_2$.

The term "aryl-amino-carbonyl-amino" means a radical of the formula: —NH—C(O)—NH-aryl or —NH—C(O)—N(aryl)$_2$.

The term "heteroaryl-oxy" means a radical of the formula: —O-heteroaryl.

The term "heteroaryl-$C_{1-8}$alkoxy" means a radical of the formula: —O—$C_{1-8}$alkyl-heteroaryl.

The term "heteroaryl-$C_{1-8}$alkyl" means a radical of the formula: —$C_{1-8}$alkyl-heteroaryl.

The term "heteroaryl-amino-carbonyl" means a radical of the formula: —C(O)—NH-heteroaryl or —C(O)—N(heteroaryl)$_2$.

The term "heteroaryl-amino-carbonyl-$C_{1-8}$alkyl" means a radical of the formula: —$C_{1-8}$alkyl-C(O)—NH-heteroaryl or —$C_{1-8}$alkyl-C(O)—N(heteroaryl)$_2$.

The term "heteroaryl-amino-carbonyl-amino" means a radical of the formula: —NH—C(O)—NH-heteroaryl or —NH—C(O)—N(heteroaryl)$_2$.

The term "heteroaryl-$C_{1-8}$alkyl-amino-carbonyl" means a radical of the formula: —C(O)—NH—$C_{1-8}$alkyl-heteroaryl or —C(O)—N($C_{1-8}$alkyl-heteroaryl)$_2$.

The term "heteroaryl-$C_{1-8}$alkyl-amino-carbonyl-amino" means a radical of the formula: —NH—C(O)—NH—$C_{1-8}$alkyl-heteroaryl or —NH—C(O)—N($C_{1-8}$alkyl-heteroaryl)$_2$.

The term "heterocyclyl-$C_{1-8}$alkyl-amino-carbonyl" means a radical of the formula: —C(O)—NH—$C_{1-8}$alkyl-heterocyclyl or —C(O)—N($C_{1-8}$alkyl-heterocyclyl)$_2$.

The term "heterocyclyl-$C_{1-8}$alkyl-amino-carbonyl-amino" means a radical of the formula: —NH—C(O)—NH—$C_{1-8}$alkyl-heterocyclyl or —NH—C(O)—N($C_{1-8}$alkyl-heterocyclyl)$_2$.

The term "heterocyclyl-$C_{1-8}$alkyl" means a radical of the formula: —$C_{1-8}$alkyl-heterocyclyl.

The term "heterocyclyl-carbonyl-$C_{1-8}$alkyl" means a radical of the formula: —$C_{1-8}$alkyl-C(O)-heterocyclyl.

The term "heterocyclyl-amino-carbonyl-$C_{1-8}$alkyl" means a radical of the formula: —$C_{1-8}$alkyl-C(O)—NH-heterocyclyl or —$C_{1-8}$alkyl-C(O)—N(heterocyclyl)$_2$.

The term "hydroxy-$C_{1-8}$alkoxy" means a radical of the formula: —O—$C_{1-8}$alkyl-hydroxy, wherein $C_{1-8}$alkyl is substituted on one or more available carbon chain atoms with one or more hydroxy radicals when allowed by available valences.

The term "hydroxy-$C_{1-8}$alkyl" means a radical of the formula: —$C_{1-8}$alkyl-hydroxy, wherein $C_{1-8}$alkyl is substituted on one or more available carbon chain atoms with one or more hydroxy radicals when allowed by available valences.

The term "hydroxy-$C_{1-8}$alkyl-amino-carbonyl" means a radical of the formula: —C(O)—NH—$C_{1-8}$alkyl-hydroxy or —C(O)—N($C_{1-8}$alkyl-hydroxy)$_2$, wherein $C_{1-8}$alkyl is substituted on one or more available carbon chain atoms with one or more hydroxy radicals when allowed by available valences.

The term "hydroxy-$C_{1-8}$alkyl-amino-carbonyl-amino" means a radical of the formula: —NH—C(O)—NH—$C_{1-8}$alkyl-hydroxy or —NH—C(O)—N($C_{1-8}$alkyl-hydroxy)$_2$, wherein $C_{1-8}$alkyl is substituted on one or more available carbon chain atoms with one or more hydroxy radicals when allowed by available valences.

The term "substituted" means the independent replacement of one or more hydrogen atoms within a radical with that amount of substitutents allowed by available valences.

The term "dependently selected" means that the structure variables are specified in an indicated combination.

In general, IUPAC nomenclature rules are used herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J.F.W. McOmie, Plenum Press, 1973; and T.W. Greene & P.G.M. Wuts, *Protective Groups in Organic Synthesis*, $3^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to a isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\%levorotatory = \frac{(mass\ levorotatory)}{(mass\ dextrorotatory) + (mass\ levorotatory)} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\%dextrorotatory = \frac{(mass\ dextrorotatory)}{(mass\ dextrorotatory) + (mass\ levorotatory)} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond. As illustrated by certain compounds of the present invention, the orientation of substituent atoms in relationship to the carbon-carbon double bond are not designated either E or Z. Accordingly, the illustrated bond lines and orientation are non-limiting and are intended to include both the E or Z configuration.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

Methods of Use

The compounds of formula (I) are inhibitors of a protein kinase such as CDK, EGFR (pan-HER), VEGF, Aurora-A or RET and the like, having an $IC_{50}$ (50% inhibition concentration) or an $EC_{50}$ (50% effective concentration) in a range of about 50 µM or less, of about 25 µM or less, of about 15 µM or less, of about 10 µM or less, of about 5 µM or less, of about 1 µM or less, of about 0.5 µM or less, of about 0.25 µM or less or of about 0.1 µM or less.

The present invention includes a compound of formula (I) and forms thereof as a protein kinase inhibitor, wherein the CDK protein kinase is CDK-1, the EGFR protein kinase is HER-2 and the VEGF protein kinase is VEGF-R2.

The present invention includes a prodrug form of a compound of formula (I) and forms thereof as a protein kinase inhibitor.

The present invention includes a metabolite form of a compound of formula (I) and forms thereof as a protein kinase inhibitor.

The present invention includes an isolated form of a compound of formula (I) and forms thereof as a protein kinase inhibitor.

The present invention includes a compound of formula (I) or a form thereof, wherein the compound is labeled with a ligand for use as a marker, and wherein the ligand is a radio-ligand selected from deuterium, tritium and the like.

The present invention includes use of a compound of formula (I) and forms thereof as an inhibitor of a protein kinase such as CDK (CDK-1), EGFR (HER-2), VEGF (VEGF-R2), Aurora-A or RET and the like comprising contacting the protein kinase domain or receptor with the compound.

The present invention includes the use of a compound of formula (I) and forms thereof as a pharmaceutical composition, medicine or medicament for treating a kinase mediated disease, disorder or condition.

The present invention includes the use of a compound of formula (I) and forms thereof as a medicament.

The present invention includes the use of a prodrug of a compound of formula (I) and forms thereof as a pharmaceutical composition, medicine or medicament for treating a kinase mediated disease, disorder or condition.

The present invention includes the use of a prodrug of a compound of formula (I) and forms thereof as a medicament.

The present invention is directed to a method for treating a chronic or acute protein kinase mediated disease, disorder or condition in a subject in need thereof comprising administering to the subject an effective amount of a compound of formula (I) and forms thereof.

The method of the present invention further comprises administering to the subject an effective amount of a prodrug of a compound of formula (I) and forms thereof.

The method of the present invention further comprises treating a chronic or acute CDK (CDK-1), EGFR (HER-2), VEGF (VEGF-R2), Aurora-A or RET mediated disease, disorder or condition.

The method of the present invention wherein the disease, disorder or condition is associated with increased or unregulated protein kinase activity, expression or signaling and the like in the subject.

The method of the present invention further comprises administering to the subject an effective amount of a compound of formula (I) as a pharmaceutical composition, medicine or medicament thereof.

The method of the present invention wherein the disease, disorder or condition is an EGFR kinase mediated head or brain cancer in the subject, and wherein the compound penetrates the blood brain barrier.

The method of the present invention further comprises treating nerve damage and promoting axon regeneration subsequent to a brain or spinal cord injury in the subject, wherein the compound is an EGFR inhibitor.

The method of the present invention further comprises treating viral infection by an EGFR kinase mediated cytomegalovirus in the subject.

The term "chronic or acute protein kinase mediated disease, disorder or condition" as used herein, includes, and is not limited to diseases, disorders or conditions associated with unregulated kinase activity and conditions that accompany such activity.

The term "unregulated protein kinase activity, expression or signaling" refers to 1) increased or unregulated kinase expression or signaling, 2) increased kinase expression leading to unregulated cell proliferation, 3) increased kinase signalling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that a compound of formula (I) or a form thereof is useful for treating diseases, disorders or conditions such as, without limitation, osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohns disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, occular diseases, viral infections, heart disease, lung or pulmonary diseases or kidney or renal diseases.

Certain diseases, disorders or conditions further include, without limitation, acute or chronic cancer selected from bladder cancer, brain, head or neck cancer, breast cancer, colorectal cancer, endometrial cancer, epidermoid cancer, esophageal cancer, gastric cancer, glioma cancer, lung cancer, ovarian cancer, pancreatic cancer, prostate cancer, renal cell cancer, Kaposi's sarcoma, leukemia, lymphoma or papillocarcinoma; and, cancer-associated pathologies selected from abnormal cell proliferation, unregulated cell proliferation, tumor growth, tumor angiopathy, tumor angiogenesis, tumor vascularization or metastatic cancer cell invasion and migration.

Certain diseases, disorders or conditions further include, without limitation, fibroproliferative and differentiative skin diseases or disorders selected from papilloma formation, psoriasis, dermatitis, eczema, seborrhea or chemotherapy-induced alopecia; central nervous system diseases selected from Alzheimer's disease, Parkinson's disease or depression; occular diseases selected from macular degeneration, diseases of the cornea or glaucoma; viral infections selected from mycotic infection, autoimmune disease or cytomegalovirus; heart disease selected from atherosclerosis, neointima formation or transplantation-induced vasculopathies such as arterial restenosis; lung or pulmonary diseases selected from allergic-asthma, lung fibrosis, pulmonary fibrosis or chronic obstructive pulmonary disorder; and, kidney or renal diseases selected from acute, subacute or chronic forms of glomerulonephritis or membranoproliferative glomerulonephritis, glomerulosclerosis, congenital multicystic renal dysplasia or kidney fibrosis.

Certain HER2 kinase mediated cancer includes, without limitation, bladder cancer, brain, head or neck cancer, breast cancer, colorectal cancer, gastric cancer, endometrial cancer, esophageal cancer, lung cancer, ovarian cancer, prostate cancer or renal cell cancer.

The term "administering," with respect to the methods of the present invention, refers to a means for treating a disease, disorder or syndrome as described herein with a compound of formula (I) or a form thereof, which would obviously be included within the scope of the invention albeit not specifically disclosed for certain of said compounds.

Such methods include therapeutically or prophylactically administering an effective amount of compound of formula (I) or a form thereof at different times during the course of a therapy or concurrently in a combination form. Such methods further include administering an effective amount of said compound with one or more agents at different times during the course of a therapy or concurrently in a combination form.

The term "prodrug" means a compound of formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions.

Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "*Design of Prodrugs*", ed. H. Bundgaard, Elsevier, 1985.

The term "metabolite" means a prodrug form of a compound of formula (I) or a form thereof converted by in vivo metabolism or a metabolic process to a relatively less active functional derivative of said compound.

The term "subject" as used herein, refers to a patient, such as an animal, a mammal or a human, who has been the object of treatment, observation or experiment and is at risk of (or susceptible to) developing a disease or disorder or having a disease or disorder related to unregulated kinase activity.

The term "effective amount" refers to that amount of a compound of formula (I) or a form, pharmaceutical composition, medicine or medicament thereof that elicits the biological or medicinal response (such as inhibiting activation of unregulated kinase activity) in a tissue system, animal or human, that is being sought by a researcher, veterinarian, medical doctor, or other clinician, which includes alleviation of the symptoms of the disease or disorder being treated.

The effective amount of said compound is from about 0.001 mg/kg/day to about 300 mg/kg/day.

The term "pharmaceutical composition" refers to a product containing a compound of formula (I) or a form thereof, such as a product comprising the specified ingredients in the specified amounts, as well as any product which results, directly or indirectly, from such combinations of the specified ingredients in the specified amounts.

The term "medicament" or "medicine" refers to a product containing a compound of formula (I) or a form thereof. The present invention includes use of such a medicament for treating a chronic or acute kinase mediated disease, disorder or condition.

The term "pharmaceutically acceptable" refers to molecular entities and compositions that are of sufficient purity and quality for use in the formulation of a pharmaceutical composition, medicine or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a pharmaceutical composition, medicine or medicament for either human or veterinary use.

The term "combination form" refers to the use of a combination product comprising a compound of formula (I) or a form, pharmaceutical composition, medicine or medicament thereof and at least one therapeutic agent for treating a chronic or acute protein kinase mediated disease, disorder or condition.

Advantageously, the effective amount of a combination product for treating a chronic or acute protein kinase mediated disease, disorder or condition may be a reduced amount of either or both the compound or therapeutic agent compared to the effective amount of the compound or therapeutic agent otherwise recommended for treating the disease, disorder or condition. Therefore, it is contemplated that the compound is administered to the subject before, during or after the time the agent is administered.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or a combination thereof.

The term "treating" refers, without limitation, to facilitating the eradication of, inhibiting the progression of or promoting stasis of a chronic or acute kinase mediated disease, disorder or condition.

The term "radiation therapy" refers to a therapy that comprises exposing the subject in need thereof to radiation. The present invention includes a method for administering a compound of formula (I) or a form, pharmaceutical composition, medicine or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

The present invention includes a pharmaceutical composition comprising an admixture of a compound of formula (I) or a form thereof and one or more pharmaceutically acceptable excipients.

The present invention includes a process for making a pharmaceutical composition, medicine or medicament comprising mixing a compound of formula (I) or a form thereof and an optional pharmaceutically acceptable carrier. The present invention includes a pharmaceutical composition, medicine or medicament resulting from the process of mixing a compound of formula (I) or a form thereof and an optional pharmaceutically acceptable carrier. Contemplated processes include both conventional and unconventional pharmaceutical techniques.

Said pharmaceutical composition, medicine or medicament may take a wide variety of forms to effectuate mode of administration, wherein the mode includes, and is not limited to, intravenous (both bolus and infusion), oral, nasal, transdermal, topical with or without occlusion, and via injection intraperitoneally, subcutaneously, intramuscularly, intratumorally, intracerebrally or intracranially. The composition, medicine or medicament may be in a dosage unit such as a tablet, pill, capsule, powder, granule, sterile parenteral solution or suspension, metered aerosol or liquid spray, drop, ampoule, auto-injector device or suppository for such administration modes.

Pharmaceutical compositions, medicines or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the pharmaceutical composition, medicine or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing the pharmaceutical composition, medicine or medicament contains an effective amount of the active ingredient necessary to be therapeutically or prophylactically effective as described above. The pharmaceutical composition, medicine or medicament may contain from about 0.001 mg to about 5000 mg (preferably, from about 0.001 to about 500 mg) of a compound of formula (I) or a form thereof and may be constituted into any form suitable for the mode of administration selected for a subject in need.

An example of a contemplated effective amount for a pharmaceutical composition, medicine or medicament of the present invention may range from about 0.001 mg to about 300 mg/kg of body weight per day. In another example, the range is from about 0.003 to about 100 mg/kg of body weight per day. In another example, the range is from about 0.005 to about 15 mg/kg of body weight per day. The pharmaceutical composition, medicine or medicament may be administered according to a dosage regimen of from about 1 to about 5 times per day.

For oral administration, the pharmaceutical composition, medicine or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of a compound of formula (I) or a form thereof for the symptomatic adjustment of the dosage to the patient to be treated. Optimal dosages will vary depending on factors associated with the particular patient being treated (e.g., age, weight, diet and time of administration), the severity of the condition being treated, the particular compound being used, the mode of administration and the strength of the preparation. The use of either daily administration or post-periodic dosing may be employed.

A representative compound of formula (I) or a form thereof includes a compound selected from the group consisting of:

| Cpd | Name |
|---|---|
| 1 | 4-amino-6-(4-fluoro-2-methyl-1H-indol-5-yloxy)-pyrimidine-5-carbaldehyde O-ethyl-oxime, |
| 2 | 4-amino-6-(2-methyl-1H-indol-5-yloxy)-pyrimidine-5-carbaldehyde O-methyl-oxime, |
| 3 | 4-(1H-indol-5-yloxy)-6-methylamino-pyrimidine-5-carbaldehyde O-methyl-oxime, |
| 4 | 4-(1H-indol-5-yloxy)-6-methoxyamino-pyrimidine-5-carbaldehyde O-methyl-oxime, |
| 5 | 4-amino-6-(quinolin-6-yloxy)-pyrimidine-5-carbaldehyde O-methyl-oxime, |
| 6 | 4-amino-6-(quinolin-7-yloxy)-pyrimidine-5-carbaldehyde O-methyl-oxime, |
| 7 | 4-amino-6-(4-fluoro-1H-indol-5-yloxy)-pyrimidine-5-carbaldehyde O-methyl-oxime, |
| 8 | 4-amino-6-(6-fluoro-1H-indol-5-yloxy)-pyrimidine-5-carbaldehyde O-methyl-oxime, |
| 9 | 4-amino-6-(3-methyl-1H-indol-5-yloxy)-pyrimidine-5-carbaldehyde O-methyl-oxime, |
| 10 | 4-amino-6-(1H-indol-5-yloxy)-pyrimidine-5-carbaldehyde O-methyl-oxime, |
| 11 | 4-amino-6-(1-methyl-1H-indol-5-yloxy)-pyrimidine-5-carbaldehyde O-methyl-oxime, |
| 12 | 4-amino-6-(4-fluoro-2-methyl-1H-indol-5-yloxy)-pyrimidine-5-carbaldehyde O-(2-hydroxy-ethyl)-oxime, |
| 13 | 4-amino-6-(4-fluoro-2-methyl-1H-indol-5-yloxy)-pyrimidine-5-carbaldehyde O-(2-pyrrolidin-1yl-ethyl)-oxime, |
| 14 | 4-amino-6-(4-fluoro-2-methyl-1H-indol-5-yloxy)-pyrimidine-5-carbaldehyde O-(2-morpholin-4-yl-ethyl)-oxime, |
| 15 | 4-amino-6-(4-fluoro-2-methyl-1H-indol-5-yloxy)-pyrimidine-5-carbaldehyde O-(2-dimethylamino-ethyl)-oxime, |
| 16 | 4-amino-6-(4-fluoro-2-methyl-1H-indol-5-yloxy)-pyrimidine-5-carbaldehyde O-(2-methylamino-ethyl)-oxime, |
| 17 | 4-amino-6-(4-fluoro-2-methyl-1H-indol-5-yloxy)-pyrimidine-5-carbaldehyde O-(3-dimethylamino-propyl)-oxime, |

| Cpd | Name |
|---|---|
| 18 | 4-amino-6-(4-fluoro-2-methyl-1H-indol-5-yloxy)-pyrimidine-5-carbaldehyde O-(3-pyrrolidin-1-yl-propyl)-oxime, |
| 19 | 4-amino-6-(4-fluoro-2-methyl-1H-indol-5-yloxy)-pyrimidine-5-carbaldehyde O-(3-morpholin-4-yl-propyl)-oxime, |
| 20 | 4-amino-6-(4-fluoro-2-methyl-1H-indol-5-yloxy)-pyrimidine-5-carbaldehyde O-(3-piperidin-1-yl-propyl)-oxime, |
| 21 | 4-amino-6-(4-fluoro-2-methyl-1H-indol-5-yloxy)-pyrimidine-5-carbaldehyde O-(3-piperazin-1-yl-propyl)-oxime, |
| 22 | 4-amino-6-(4-fluoro-2-methyl-1H-indol-5-yloxy)-pyrimidine-5-carbaldehyde O-[3-(4-methanesulfonyl-piperazin-1-yl)-propyl]-oxime, |
| 23 | 4-amino-6-(4-fluoro-2-methyl-1H-indol-5-yloxy)-pyrimidine-5-carbaldehyde O-[3-(4-acetyl-piperazin-1-yl)-propyl]-oxime, |
| 24 | 4-amino-6-(4-fluoro-2-methyl-1H-indol-5-yloxy)-pyrimidine-5-carbaldehyde O-(4-piperidin-1-yl-butyl)-oxime, |
| 25 | 4-amino-6-(4-fluoro-2-methyl-1H-indol-5-yloxy)-pyrimidine-5-carbaldehyde O-(4-pyrrolidin-1-yl-butyl)-oxime, |
| 26 | 4-amino-6-(4-fluoro-2-methyl-1H-indol-5-yloxy)-pyrimidine-5-carbaldehyde O-(4-morpholin-4-yl-butyl)-oxime, |
| 27 | 4-amino-6-(4-fluoro-2-methyl-1H-indol-5-yloxy)-pyrimidine-5-carbaldehyde oxime, |
| 28 | 4-amino-6-(4-fluoro-2-methyl-1H-indol-5-yloxy)-pyrimidine-5-carbaldehyde O-(2-methoxy-ethyl)-oxime, |
| 29 | 4-amino-6-(4-fluoro-2-methyl-1H-indol-5-yloxy)-pyrimidine-5-carbaldehyde O-(3-hydroxy-propyl)-oxime, |
| 30 | 4-amino-6-(4-fluoro-2-methyl-1H-indol-5-yloxy)-pyrimidine-5-carbaldehyde O-prop-2-ynyl-oxime, |
| 31 | 4-amino-6-(4-fluoro-2-methyl-1H-indol-5-yloxy)-pyrimidine-5-carbaldehyde O-allyl-oxime, |
| 32 | 4-amino-6-(4-fluoro-2-methyl-1H-indol-5-yloxy)-pyrimidine-5-carbaldehyde O-cyclopropylmethyl-oxime, |
| 33 | 4-amino-6-(4-fluoro-2-methyl-1H-indol-5-yloxy)-pyrimidine-5-carbaldehyde O-(3-methoxy-propyl)-oxime, |
| 34 | 4-amino-6-(4-fluoro-2-methyl-1H-indol-5-yloxy)-pyrimidine-5-carbaldehyde O-propyl-oxime, |
| 35 | 4-amino-6-(4-fluoro-2-methyl-1H-indol-5-yloxy)-pyrimidine-5-carbaldehyde O-cyclohexylmethyl-oxime, |
| 36 | 4-amino-6-(4-fluoro-2-methyl-1H-indol-5-yloxy)-pyrimidine-5-carbaldehyde O-benzyl-oxime, |
| 37 | 4-amino-6-(4-fluoro-2-methyl-1H-indol-5-yloxy)-pyrimidine-5-carbaldehyde O-butyl-oxime, |
| 38 | 4-amino-6-(4-fluoro-2-methyl-1H-indol-5-yloxy)-pyrimidine-5-carbaldehyde O-(4-hydroxy-butyl)-oxime, |
| 39 | 5-[6-amino-5-(methoxyimino-methyl)-pyrimidin-4-yloxy]-2-methyl-indole-1-carboxylic acid (2-hydroxy-ethyl)-amide, |
| 40 | 5-[6-amino-5-(methoxyimino-methyl)-pyrimidin-4-yloxy]-2-methyl-indole-1-carboxylic acid (3-hydroxy-propyl)-amide, |
| 41 | 5-[6-amino-5-(methoxyimino-methyl)-pyrimidin-4-yloxy]-2-methyl-indole-1-carboxylic acid (2-dimethylamino-ethyl)-amide, |
| 42 | 5-[6-amino-5-(methoxyimino-methyl)-pyrimidin-4-yloxy]-2-methyl-indole-1-carboxylic acid (4-pyrrolidin-1-yl-butyl)-amide, |
| 43 | 5-[6-amino-5-(methoxyimino-methyl)-pyrimidin-4-yloxy]-4-fluoro-2-methyl-indole-1-carboxylic acid methylamide, |
| 44 | 5-[6-amino-5-(methoxyimino-methyl)-pyrimidin-4-yloxy]-2-methyl-indole-1-carboxylic acid isopropylamide, |
| 45 | 5-[6-amino-5-(methoxyimino-methyl)-pyrimidin-4-yloxy]-2-methyl-indole-1-carboxylic acid prop-2-ynylamide, |
| 46 | 5-[6-amino-5-(methoxyimino-methyl)-pyrimidin-4-yloxy]-2-methyl-indole-1-carboxylic acid cyclopropylamide, |
| 47 | 5-[6-amino-5-(methoxyimino-methyl)-pyrimidin-4-yloxy]-2-methyl-indole-1-carboxylic acid benzylamide, |
| 48 | 5-[6-amino-5-(methoxyimino-methyl)-pyrimidin-4-yloxy]-2-methyl-indole-1-carboxylic acid propylamide, |
| 49 | 5-[6-amino-5-(methoxyimino-methyl)-pyrimidin-4-yloxy]-2-methyl-indole-1-carboxylic acid methylamide, |
| 50 | 1-{4-[6-amino-5-(methoxyimino-methyl)-pyrimidin-4-yloxy]-2-chloro-phenyl}-3-ethyl-urea, |
| 51 | 1-{4-[6-amino-5-(methoxyimino-methyl)-pyrimidin-4-yloxy]-2-chloro-phenyl}-3-methyl-urea, |
| 52 | 1-{4-[6-amino-5-(methoxyimino-methyl)-pyrimidin-4-yloxy]-2-chloro-phenyl}-3-propyl-urea, |
| 53 | 1-allyl-3-{4-[6-amino-5-(methoxyimino-methyl)-pyrimidin-4-yloxy]-2-chloro-phenyl}-urea, |
| 54 | 1-{4-[6-amino-5-(methoxyimino-methyl)-pyrimidin-4-yloxy]-2-chloro-phenyl}-3-phenyl-urea, |
| 55 | 1-{4-[6-amino-5-(methoxyimino-methyl)-pyrimidin-4-yloxy]-2-chloro-phenyl}-3-(2-chloro-phenyl)-urea, |
| 56 | 1-{4-[6-amino-5-(methoxyimino-methyl)-pyrimidin-4-yloxy]-2-chloro-phenyl}-3-(2-fluoro-phenyl)-urea, |

| Cpd | Name |
|---|---|
| 57 | 1-{4-[6-amino-5-(methoxyimino-methyl)-pyrimidin-4-yloxy]-2-chloro-phenyl}-3-(3-fluoro-phenyl)-urea, |
| 58 | 1-{4-[6-amino-5-(methoxyimino-methyl)-pyrimidin-4-yloxy]-2-chloro-phenyl}-3-(2-methoxy-phenyl)-urea, |
| 59 | 1-{4-[6-amino-5-(methoxyimino-methyl)-pyrimidin-4-yloxy]-2-chloro-phenyl}-3-(3-chloro-phenyl)-urea, |
| 60 | 1-{4-[6-amino-5-(methoxyimino-methyl)-pyrimidin-4-yloxy]-2-chloro-phenyl}-3-(4-fluoro-phenyl)-urea, |
| 61 | 1-{4-[6-amino-5-(methoxyimino-methyl)-pyrimidin-4-yloxy]-2-chloro-phenyl}-3-(2,4-difluoro-phenyl)-urea, |
| 62 | 1-{4-[6-amino-5-(methoxyimino-methyl)-pyrimidin-4-yloxy]-2-chloro-phenyl}-3-(4-methoxy-phenyl)-urea, |
| 63 | 1-{4-[6-amino-5-(methoxyimino-methyl)-pyrimidin-4-yloxy]-2-chloro-phenyl}-3-(4-methoxy-phenyl)-urea, |
| 64 | 1-{4-[6-amino-5-(methoxyimino-methyl)-pyrimidin-4-yloxy]-2-chloro-phenyl}-3-butyl-urea, |
| 65 | 1-{4-[6-amino-5-(methoxyimino-methyl)-pyrimidin-4-yloxy]-2-chloro-phenyl}-3-cyclohexyl-urea, |
| 66 | 1-{4-[6-amino-5-(methoxyimino-methyl)-pyrimidin-4-yloxy]-2-methyl-phenyl}-3-ethyl-urea, |
| 67 | 4-amino-6-(4-hydroxy-phenoxy)-pyrimidine-5-carbaldehyde O-methyl-oxime, |
| 68 | 1-{4-[6-amino-5-(methoxyimino-methyl)-pyrimidin-4-yloxy]-phenyl}-3-methyl-urea, |
| 69 | 1-{4-[6-amino-5-(methoxyimino-methyl)-pyrimidin-4-yloxy]-phenyl}-3-ethyl-urea, |
| 70 | 1-{4-[6-amino-5-(methoxyimino-methyl)-pyrimidin-4-yloxy]-3-chloro-phenyl}-3-methyl-urea, |
| 71 | 1-{4-[6-amino-5-(methoxyimino-methyl)-pyrimidin-4-yloxy]-3-chloro-phenyl}-3-ethyl-urea, |
| 72 | 1-{4-[6-amino-5-(methoxyimino-methyl)-pyrimidin-4-yloxy]-2-fluoro-phenyl}-3-methyl-urea, |
| 73 | 1-{4-[6-amino-5-(methoxyimino-methyl)-pyrimidin-4-yloxy]-2-bromo-phenyl}-3-methyl-urea, |
| 74 | 1-{4-[6-amino-5-(methoxyimino-methyl)-pyrimidin-4-yloxy]-2-bromo-phenyl}-3-(4-fluoro-phenyl)-urea, |
| 75 | 1-{4-[6-amino-5-(methoxyimino-methyl)-pyrimidin-4-yloxy]-2-chloro-phenyl}-3-o-tolyl-urea, |
| 76 | 1-{4-[6-amino-5-(methoxyimino-methyl)-pyrimidin-4-yloxy]-2-chloro-phenyl}-3-m-tolyl-urea, |
| 77 | 1-{4-[6-amino-5-(methoxyimino-methyl)-pyrimidin-4-yloxy]-2-chloro-phenyl}-3-p-tolyl-urea, |
| 78 | 1-{4-[6-amino-5-(methoxyimino-methyl)-pyrimidin-4-yloxy]-2-chloro-phenyl}-3-(2,4-difluoro-benzyl)-urea, |
| 79 | 1-{4-[6-amino-5-(methoxyimino-methyl)-pyrimidin-4-yloxy]-2-chloro-phenyl}-3-prop-2-ynyl-urea, |
| 80 | 1-{4-[6-amino-5-(methoxyimino-methyl)-pyrimidin-4-yloxy]-2-chloro-phenyl}-3-isopropyl-urea, |
| 81 | 1-{4-[6-amino-5-(methoxyimino-methyl)-pyrimidin-4-yloxy]-2-chloro-phenyl}-3-(2-hydroxy-ethyl)-urea, |
| 82 | 1-{4-[6-amino-5-(methoxyimino-methyl)-pyrimidin-4-yloxy]-2-chloro-phenyl}-3-(2-dimethylamino-ethyl)-urea, |
| 83 | 1-{4-[6-amino-5-(methoxyimino-methyl)-pyrimidin-4-yloxy]-2-chloro-phenyl}-3-(3-hydroxy-propyl)-urea, |
| 84 | 1-{4-[6-amino-5-(methoxyimino-methyl)-pyrimidin-4-yloxy]-2-chloro-phenyl}-3-(4-pyrrolidin-1-yl-butyl)-urea, |
| 85 | 1-{4-[6-amino-5-(methoxyimino-methyl)-pyrimidin-4-yloxy]-2-chloro-phenyl}-3-cyclopropyl-urea, |
| 86 | 1-{4-[6-amino-5-(methoxyimino-methyl)-pyrimidin-4-yloxy]-2-chloro-phenyl}-3-pyridin-2-yl-urea, |
| 87 | 1-{4-[6-amino-5-(methoxyimino-methyl)-pyrimidin-4-yloxy]-2-chloro-phenyl}-3-pyridin-3-yl-urea, |
| 88 | 1-{4-[6-amino-5-(methoxyimino-methyl)-pyrimidin-4-yloxy]-2-chloro-phenyl}-3-pyridin-4-yl-urea, |
| 89 | 1-{4-[6-amino-5-(methoxyimino-methyl)-pyrimidin-4-yloxy]-2-chloro-phenyl}-3-(4-methyl-thiazol-2-yl)-urea, |
| 90 | 1-{4-[6-amino-5-(methoxyimino-methyl)-pyrimidin-4-yloxy]-2-chloro-phenyl}-3-(5-methyl-thiazol-2-yl)-urea, |
| 91 | 1-{4-[6-amino-5-(methoxyimino-methyl)-pyrimidin-4-yloxy]-2-chloro-phenyl}-3-thiazol-2-yl-urea, |
| 92 | 1-{4-[6-amino-5-(methoxyimino-methyl)-pyrimidin-4-yloxy]-2-chloro-phenyl}-3-(4,5-dimethyl-thiazol-2-yl)-urea, |
| 93 | 1-{4-[6-amino-5-(methoxyimino-methyl)-pyrimidin-4-yloxy]-2-chloro-phenyl}-3-(5-methyl-isoxazol-3-yl)-urea, |
| 94 | N-{4-[6-amino-5-(methoxyimino-methyl)-pyrimidin-4-yloxy]-2-chloro-phenyl}-acetamide, |
| 95 | {4-[6-amino-5-(methoxyimino-methyl)-pyrimidin-4-yloxy]-2-chloro-phenyl}-carbamic acid methyl ester, |

-continued

| Cpd | Name |
|---|---|
| 96 | 2-{4-[6-amino-5-(methoxyimino-methyl)-pyrimidin-4-yloxy]-phenyl}-N-methyl-acetamide, |
| 97 | 2-{4-[6-amino-5-(methoxyimino-methyl)-pyrimidin-4-yloxy]-phenyl}-N-phenyl-acetamide, |
| 98 | 4-[6-amino-5-(methoxyimino-methyl)-pyrimidin-4-yloxy]-N-methyl-benzamide |
| 99 | 2-{4-[6-amino-5-(methoxyimino-methyl)-pyrimidin-4-yloxy]-phenyl}-N-p-tolyl-acetamide, |
| 100 | 2-{4-[6-amino-5-(methoxyimino-methyl)-pyrimidin-4-yloxy]-phenyl}-N-(3-fluoro-phenyl)-acetamide, |
| 101 | 2-{4-[6-amino-5-(methoxyimino-methyl)-pyrimidin-4-yloxy]-phenyl}-N-ethyl-acetamide, |
| 102 | ethyl-carbamic acid 4-[6-amino-5-(methoxyimino-methyl)-pyrimidin-4-yloxy]-phenyl ester, |
| 103 | 1-(4-{6-amino-5-[(2-morpholin-4-yl-ethoxyimino)-methyl]-pyrimidin-4-yloxy}-2-chloro-phenyl)-3-ethyl-urea, |
| 104 | 1-(4-{6-amino-5-[(2-methoxy-ethoxyimino)-methyl]-pyrimidin-4-yloxy}-2-chloro-phenyl)-3-ethyl-urea, |
| 105 | (3-chloro-phenyl)-carbamic acid 4-[6-amino-5-(methoxyimino-methyl)-pyrimidin-4-yloxy]-phenyl ester, |
| 106 | 4-amino-6-(3,5-dimethoxyphenoxy)-5-pyrimidinecarboxaldehyde O-methyloxime, |
| 107 | 5-[{6-amino-5-[(E)-(methoxyimino)methyl]-4-pyrimidinyl}oxy]-2-methyl-1H-indole-3-carboxylic acid ethyl ester, |
| 108 | 4-amino-6-(1,3-benzodioxol-5-yloxy)-5-pyrimidinecarboxaldehyde O-methyloxime, |
| 109 | 4-amino-6-(3-chloro-4-fluorophenoxy)-5-pyrimidinecarboxaldehyde O-methyloxime, |
| 110 | 4-amino-6-[4-(benzyloxy)phenoxy]-5-pyrimidinecarboxaldehyde O-methyloxime, |
| 111 | 4-amino-6-(benzyloxy)-5-pyrimidinecarboxaldehyde O-methyloxime, |
| 112 | 4-amino-6-[(3-fluorophenyl)methoxy]-5-pyrimidinecarboxaldehyde O-methyloxime, |
| 113 | N-[2-{5-[{6-amino-5-[(E)-(methoxyimino)methyl]-4-pyrimidinyl}oxy]-1H-indol-3-yl}ethyl]-acetamide, |
| 114 | 4-amino-6-[(2,6-difluorophenyl)methoxy]-5-pyrimidinecarboxaldehyde O-methyloxime, |
| 115 | 4-amino-6-(2-naphthalenylmethoxy)-5-pyrimidinecarboxaldehyde O-methyloxime, |
| 116 | 4-amino-6-[(2-fluorophenyl)methoxy]-5-pyrimidinecarboxaldehyde O-methyloxime, |
| 117 | 4-amino-6-[(2,4-dichlorophenyl)methoxy]-5-pyrimidinecarboxaldehyde O-methyloxime, |
| 118 | 4-amino-6-[(2,5-dichlorophenyl)methoxy]-5-pyrimidinecarboxaldehyde O-methyloxime, |
| 119 | 4-amino-6-[(3-bromophenyl)methoxy]-5-pyrimidinecarboxaldehyde O-methyloxime, |
| 120 | 4-amino-6-[(3,4-dichlorophenyl)methoxy]-5-pyrimidinecarboxaldehyde O-methyloxime, |
| 121 | 4-amino-6-{[3-(trifluoromethyl)phenyl]methoxy}-5-pyrimidinecarboxaldehyde O-methyloxime, |
| 122 | 4-amino-6-[(3-chlorophenyl)methoxy]-5-pyrimidinecarboxaldehyde O-methyloxime, |
| 123 | 4-amino-6-[(3-methoxyphenyl)methoxy]-5-pyrimidinecarboxaldehyde O-methyloxime, |
| 124 | 4-amino-6-[(3,4-dimethoxyphenyl)methoxy]-5-pyrimidinecarboxaldehyde O-methyloxime, |
| 125 | 4-amino-6-[(4-fluorophenyl)methoxy]-5-pyrimidinecarboxaldehyde O-methyloxime, |
| 126 | 4-amino-6-[(4-chlorophenyl)methoxy]-5-pyrimidinecarboxaldehyde O-methyloxime, |
| 127 | 4-amino-6-[(3,4-difluorophenyl)methoxy]-5-pyrimidinecarboxaldehyde O-methyloxime, |
| 128 | 4-amino-6-[(5-chloro-2-methoxyphenyl)methoxy]-5-pyrimidinecarboxaldehyde O-methyloxime, |
| 129 | 4-amino-6-[(2-chloro-4-fluorophenyl)methoxy]-5-pyrimidinecarboxaldehyde O-methyloxime, |
| 130 | 4-[{[6-amino-5-[(E)-(methoxyimino)methyl]-4-pyrimidinyl]oxy}methyl]-benzonitrile, |
| 131 | 4-amino-6-[(5-bromo-2-chlorophenyl)methoxy]-5-pyrimidinecarboxaldehyde O-methyloxime, |
| 132 | 4-amino-6-[(4-ethynylphenyl)methoxy]-5-pyrimidinecarboxaldehyde O-methyloxime, |
| 133 | 4-amino-6-(2-ethylphenoxy)-5-pyrimidinecarboxaldehyde O-methyloxime, |
| 134 | 4-amino-6-(4-ethylphenoxy)-5-pyrimidinecarboxaldehyde O-methyloxime, |
| 135 | 4-amino-6-[2-methoxy-4-(2-propenyl)phenoxy]-5-pyrimidinecarboxaldehyde O-methyloxime, |
| 136 | 4-amino-6-(3-fluorophenoxy)-5-pyrimidinecarboxaldehyde O-methyloxime, |

-continued

| Cpd | Name |
|---|---|
| 137 | 4-amino-6-(4-fluorophenoxy)-5-pyrimidinecarboxaldehyde O-methyloxime, |
| 138 | 4-amino-6-(4-benzoylphenoxy)-5-pyrimidinecarboxaldehyde O-methyloxime, |
| 139 | 4-[{6-amino-5-[(E)-(methoxyimino)methyl]-4-pyrimidinyl}oxy]-benzeneacetonitrile, |
| 140 | 4-amino-6-[4-(benzyl)phenoxy]-5-pyrimidinecarboxaldehyde O-methyloxime, |
| 141 | 4-amino-6-(5-isoquinolinyloxy)-5-pyrimidinecarboxaldehyde O-methyloxime, |
| 142 | 4-amino-6-{4-[(1Z)-1-(methoxyimino)propyl]phenoxy}-5-pyrimidinecarboxaldehyde O-methyloxime, |
| 143 | 4-amino-6-[(2-methyl-8-quinolinyl)oxy]-5-pyrimidinecarboxaldehyde O-methyloxime, |
| 144 | 4-amino-6-[2-methoxy-4-[(1E)-1-propenyl]phenoxy]-5-pyrimidinecarboxaldehyde O-methyloxime, |
| 145 | 4-amino-6-[(indan-5-yl)oxy]-5-pyrimidinecarboxaldehyde O-methyloxime, |
| 146 | 4-amino-6-(4-methoxyphenoxy)-5-pyrimidinecarboxaldehyde O-methyloxime, |
| 147 | 4-amino-6-[(5,6,7,8-tetrahydro-1-naphthalenyl)oxy]-5-pyrimidinecarboxaldehyde O-methyloxime, |
| 148 | 4-amino-6-(2,4,6-trichlorophenoxy)-5-pyrimidinecarboxaldehyde O-methyloxime, |
| 149 | 4-amino-6-(2,4,6-trimethylphenoxy)-5-pyrimidinecarboxaldehyde O-methyloxime, |
| 150 | 4-amino-6-(2-methoxyphenoxy)-5-pyrimidinecarboxaldehyde O-methyloxime, |
| 151 | 4-[{6-amino-5-[(E)-(methoxyimino)methyl]-4-pyrimidinyl}oxy]-benzoic acid methyl ester, |
| 152 | 4-amino-6-(1-naphthalenyloxy)-5-pyrimidinecarboxaldehyde O-methyloxime, |
| 153 | 4-amino-6-[4-(1H-1,2,4-triazol-1-yl)phenoxy]-5-pyrimidinecarboxaldehyde O-methyloxime, |
| 154 | 4-amino-6-(3,4,5-trimethoxyphenoxy)-5-pyrimidinecarboxaldehyde O-methyloxime, |
| 155 | 4-amino-6-(4-ethyl-2-methoxyphenoxy)-5-pyrimidinecarboxaldehyde O-methyloxime, |
| 156 | 4-amino-6-[2-methoxy-4-(3-oxobutyl)phenoxy]-5-pyrimidinecarboxaldehyde 5-(O-methyloxime), |
| 157 | 4-amino-6-(2-chloro-4,5-dimethylphenoxy)-5-pyrimidinecarboxaldehyde O-methyloxime, |
| 158 | 4-amino-6-[2,5-dimethyl-4-(4-morpholinylmethyl)phenoxy]-5-pyrimidinecarboxaldehyde O-methyloxime, |
| 159 | 4-amino-6-[4-(phenylamino)phenoxy]-5-pyrimidinecarboxaldehyde O-methyloxime, |
| 160 | 4-amino-6-(3-methoxy-5-methylphenoxy)-5-pyrimidinecarboxaldehyde O-methyloxime, |
| 161 | 4-amino-6-[2-methoxy-4-[(1E,3E)-3-(methoxyimino)-1-butenyl]phenoxy]-5-pyrimidinecarboxaldehyde O-methyloxime, |
| 162 | 4-[{6-amino-5-[(E)-(methoxyimino)methyl]-4-pyrimidinyl}oxy]-2-chloro-benzonitrile, |
| 163 | 4-(4-acetyl-3-methylphenoxy)-6-amino-5-pyrimidinecarboxaldehyde O-methyloxime, and |
| 164 | 4-amino-6-{4-[(1Z)-1-(methoxyimino)ethyl]-3-methylphenoxy}-5-pyrimidinecarboxaldehyde O-methyloxime. |

A representative compound of formula (I) or a form thereof includes a compound selected from the group consisting of:

| Cpd | Name |
|---|---|
| 1 | 4-amino-6-(4-fluoro-2-methyl-1H-indol-5-yloxy)-pyrimidine-5-carbaldehyde O-ethyl-oxime, |
| 2 | 4-amino-6-(2-methyl-1H-indol-5-yloxy)-pyrimidine-5-carbaldehyde O-methyl-oxime, |
| 5 | 4-amino-6-(quinolin-6-yloxy)-pyrimidine-5-carbaldehyde O-methyl-oxime, |
| 7 | 4-amino-6-(4-fluoro-1H-indol-5-yloxy)-pyrimidine-5-carbaldehyde O-methyl-oxime, |
| 8 | 4-amino-6-(6-fluoro-1H-indol-5-yloxy)-pyrimidine-5-carbaldehyde O-methyl-oxime, |
| 9 | 4-amino-6-(3-methyl-1H-indol-5-yloxy)-pyrimidine-5-carbaldehyde O-methyl-oxime, |
| 10 | 4-amino-6-(1H-indol-5-yloxy)-pyrimidine-5-carbaldehyde O-methyl-oxime, |
| 12 | 4-amino-6-(4-fluoro-2-methyl-1H-indol-5-yloxy)-pyrimidine-5-carbaldehyde O-(2-hydroxy-ethyl)-oxime, |

-continued

| Cpd | Name |
|---|---|
| 13 | 4-amino-6-(4-fluoro-2-methyl-1H-indol-5-yloxy)-pyrimidine-5-carbaldehyde O-(2-pyrrolidin-1yl-ethyl)-oxime, |
| 14 | 4-amino-6-(4-fluoro-2-methyl-1H-indol-5-yloxy)-pyrimidine-5-carbaldehyde O-(2-morpholin-4-yl-ethyl)-oxime, |
| 15 | 4-amino-6-(4-fluoro-2-methyl-1H-indol-5-yloxy)-pyrimidine-5-carbaldehyde O-(2-dimethylamino-ethyl)-oxime, |
| 16 | 4-amino-6-(4-fluoro-2-methyl-1H-indol-5-yloxy)-pyrimidine-5-carbaldehyde O-(2-methylamino-ethyl)-oxime, |
| 17 | 4-amino-6-(4-fluoro-2-methyl-1H-indol-5-yloxy)-pyrimidine-5-carbaldehyde O-(3-dimethylamino-propyl)-oxime, |
| 18 | 4-amino-6-(4-fluoro-2-methyl-1H-indol-5-yloxy)-pyrimidine-5-carbaldehyde O-(3-pyrrolidin-1-yl-propyl)-oxime, |
| 19 | 4-amino-6-(4-fluoro-2-methyl-1H-indol-5-yloxy)-pyrimidine-5-carbaldehyde O-(3-morpholin-4-yl-propyl)-oxime, |
| 20 | 4-amino-6-(4-fluoro-2-methyl-1H-indol-5-yloxy)-pyrimidine-5-carbaldehyde O-(3-piperidin-1-yl-propyl)-oxime, |
| 21 | 4-amino-6-(4-fluoro-2-methyl-1H-indol-5-yloxy)-pyrimidine-5-carbaldehyde O-(3-piperazin-1-yl-propyl)-oxime, |
| 22 | 4-amino-6-(4-fluoro-2-methyl-1H-indol-5-yloxy)-pyrimidine-5-carbaldehyde O-[3-(4-methanesulfonyl-piperazin-1-yl)-propyl]-oxime, |
| 23 | 4-amino-6-(4-fluoro-2-methyl-1H-indol-5-yloxy)-pyrimidine-5-carbaldehyde O-[3-(4-acetyl-piperazin-1-yl)-propyl]-oxime, |
| 24 | 4-amino-6-(4-fluoro-2-methyl-1H-indol-5-yloxy)-pyrimidine-5-carbaldehyde O-(4-piperidin-1-yl-butyl)-oxime, |
| 25 | 4-amino-6-(4-fluoro-2-methyl-1H-indol-5-yloxy)-pyrimidine-5-carbaldehyde O-(4-pyrrolidin-1-yl-butyl)-oxime, |
| 26 | 4-amino-6-(4-fluoro-2-methyl-1H-indol-5-yloxy)-pyrimidine-5-carbaldehyde O-(4-morpholin-4-yl-butyl)-oxime, |
| 27 | 4-amino-6-(4-fluoro-2-methyl-1H-indol-5-yloxy)-pyrimidine-5-carbaldehyde oxime, |
| 28 | 4-amino-6-(4-fluoro-2-methyl-1H-indol-5-yloxy)-pyrimidine-5-carbaldehyde O-(2-methoxy-ethyl)-oxime, |
| 29 | 4-amino-6-(4-fluoro-2-methyl-1H-indol-5-yloxy)-pyrimidine-5-carbaldehyde O-(3-hydroxy-propyl)-oxime, |
| 30 | 4-amino-6-(4-fluoro-2-methyl-1H-indol-5-yloxy)-pyrimidine-5-carbaldehyde O-prop-2-ynyl-oxime, |
| 31 | 4-amino-6-(4-fluoro-2-methyl-1H-indol-5-yloxy)-pyrimidine-5-carbaldehyde O-allyl-oxime, |
| 32 | 4-amino-6-(4-fluoro-2-methyl-1H-indol-5-yloxy)-pyrimidine-5-carbaldehyde O-cyclopropylmethyl-oxime, |
| 33 | 4-amino-6-(4-fluoro-2-methyl-1H-indol-5-yloxy)-pyrimidine-5-carbaldehyde O-(3-methoxy-propyl)-oxime, |
| 34 | 4-amino-6-(4-fluoro-2-methyl-1H-indol-5-yloxy)-pyrimidine-5-carbaldehyde O-propyl-oxime, |
| 35 | 4-amino-6-(4-fluoro-2-methyl-1H-indol-5-yloxy)-pyrimidine-5-carbaldehyde O-cyclohexylmethyl-oxime, |
| 36 | 4-amino-6-(4-fluoro-2-methyl-1H-indol-5-yloxy)-pyrimidine-5-carbaldehyde O-benzyl-oxime, |
| 37 | 4-amino-6-(4-fluoro-2-methyl-1H-indol-5-yloxy)-pyrimidine-5-carbaldehyde O-butyl-oxime, |
| 38 | 4-amino-6-(4-fluoro-2-methyl-1H-indol-5-yloxy)-pyrimidine-5-carbaldehyde O-(4-hydroxy-butyl)-oxime, |
| 39 | 5-[6-amino-5-(methoxyimino-methyl)-pyrimidin-4-yloxy]-2-methyl-indole-1-carboxylic acid (2-hydroxy-ethyl)-amide, |
| 40 | 5-[6-amino-5-(methoxyimino-methyl)-pyrimidin-4-yloxy]-2-methyl-indole-1-carboxylic acid (3-hydroxy-propyl)-amide, |
| 41 | 5-[6-amino-5-(methoxyimino-methyl)-pyrimidin-4-yloxy]-2-methyl-indole-1-carboxylic acid (2-dimethylamino-ethyl)-amide, |
| 42 | 5-[6-amino-5-(methoxyimino-methyl)-pyrimidin-4-yloxy]-2-methyl-indole-1-carboxylic acid (4-pyrrolidin-1-yl-butyl)-amide, |
| 43 | 5-[6-amino-5-(methoxyimino-methyl)-pyrimidin-4-yloxy]-4-fluoro-2-methyl-indole-1-carboxylic acid methylamide, |
| 44 | 5-[6-amino-5-(methoxyimino-methyl)-pyrimidin-4-yloxy]-2-methyl-indole-1-carboxylic acid isopropylamide, |
| 45 | 5-[6-amino-5-(methoxyimino-methyl)-pyrimidin-4-yloxy]-2-methyl-indole-1-carboxylic acid prop-2-ynylamide, |
| 46 | 5-[6-amino-5-(methoxyimino-methyl)-pyrimidin-4-yloxy]-2-methyl-indole-1-carboxylic acid cyclopropylamide, |
| 48 | 5-[6-amino-5-(methoxyimino-methyl)-pyrimidin-4-yloxy]-2-methyl-indole-1-carboxylic acid propylamide, |
| 49 | 5-[6-amino-5-(methoxyimino-methyl)-pyrimidin-4-yloxy]-2-methyl-indole-1-carboxylic acid methylamide, |
| 50 | 1-{4-[6-amino-5-(methoxyimino-methyl)-pyrimidin-4-yloxy]-2-chloro-phenyl}-3-ethyl-urea, |
| 51 | 1-{4-[6-amino-5-(methoxyimino-methyl)-pyrimidin-4-yloxy]-2-chloro-phenyl}-3-methyl-urea, |
| 52 | 1-{4-[6-amino-5-(methoxyimino-methyl)-pyrimidin-4-yloxy]-2-chloro-phenyl}-3-propyl-urea, |

-continued

| Cpd | Name |
|---|---|
| 53 | 1-allyl-3-{4-[6-amino-5-(methoxyimino-methyl)-pyrimidin-4-yloxy]-2-chloro-phenyl}-urea, |
| 54 | 1-{4-[6-amino-5-(methoxyimino-methyl)-pyrimidin-4-yloxy]-2-chloro-phenyl}-3-phenyl-urea, |
| 55 | 1-{4-[6-amino-5-(methoxyimino-methyl)-pyrimidin-4-yloxy]-2-chloro-phenyl}-3-(2-chloro-phenyl)-urea, |
| 56 | 1-{4-[6-amino-5-(methoxyimino-methyl)-pyrimidin-4-yloxy]-2-chloro-phenyl}-3-(2-fluoro-phenyl)-urea, |
| 57 | 1-{4-[6-amino-5-(methoxyimino-methyl)-pyrimidin-4-yloxy]-2-chloro-phenyl}-3-(3-fluoro-phenyl)-urea, |
| 58 | 1-{4-[6-amino-5-(methoxyimino-methyl)-pyrimidin-4-yloxy]-2-chloro-phenyl}-3-(2-methoxy-phenyl)-urea, |
| 59 | 1-{4-[6-amino-5-(methoxyimino-methyl)-pyrimidin-4-yloxy]-2-chloro-phenyl}-3-(3-chloro-phenyl)-urea, |
| 60 | 1-{4-[6-amino-5-(methoxyimino-methyl)-pyrimidin-4-yloxy]-2-chloro-phenyl}-3-(4-fluoro-phenyl)-urea, |
| 61 | 1-{4-[6-amino-5-(methoxyimino-methyl)-pyrimidin-4-yloxy]-2-chloro-phenyl}-3-(2,4-difluoro-phenyl)-urea, |
| 62 | 1-{4-[6-amino-5-(methoxyimino-methyl)-pyrimidin-4-yloxy]-2-chloro-phenyl}-3-(4-methoxy-phenyl)-urea, |
| 63 | 1-{4-[6-amino-5-(methoxyimino-methyl)-pyrimidin-4-yloxy]-2-chloro-phenyl}-3-(4-methoxy-phenyl)-urea, |
| 64 | 1-{4-[6-amino-5-(methoxyimino-methyl)-pyrimidin-4-yloxy]-2-chloro-phenyl}-3-butyl-urea, |
| 65 | 1-{4-[6-amino-5-(methoxyimino-methyl)-pyrimidin-4-yloxy]-2-chloro-phenyl}-3-cyclohexyl-urea, |
| 66 | 1-{4-[6-amino-5-(methoxyimino-methyl)-pyrimidin-4-yloxy]-2-methyl-phenyl}-3-ethyl-urea, |
| 68 | 1-{4-[6-amino-5-(methoxyimino-methyl)-pyrimidin-4-yloxy-phenyl}-3-methyl-urea, |
| 69 | 1-{4-[6-amino-5-(methoxyimino-methyl)-pyrimidin-4-yloxy-phenyl}-3-ethyl-urea, |
| 70 | 1-{4-[6-amino-5-(methoxyimino-methyl)-pyrimidin-4-yloxy]-3-chloro-phenyl}-3-methyl-urea, |
| 71 | 1-{4-[6-amino-5-(methoxyimino-methyl)-pyrimidin-4-yloxy]-3-chloro-phenyl}-3-ethyl-urea, |
| 72 | 1-{4-[6-amino-5-(methoxyimino-methyl)-pyrimidin-4-yloxy]-2-fluoro-phenyl}-3-methyl-urea, |
| 75 | 1-{4-[6-amino-5-(methoxyimino-methyl)-pyrimidin-4-yloxy]-2-chloro-phenyl}-3-o-tolyl-urea, |
| 76 | 1-{4-[6-amino-5-(methoxyimino-methyl)-pyrimidin-4-yloxy]-2-chloro-phenyl}-3-m-tolyl-urea, |
| 77 | 1-{4-[6-amino-5-(methoxyimino-methyl)-pyrimidin-4-yloxy]-2-chloro-phenyl}-3-p-tolyl-urea, |
| 78 | 1-{4-[6-amino-5-(methoxyimino-methyl)-pyrimidin-4-yloxy]-2-chloro-phenyl}-3-(2,4-difluoro-benzyl)-urea, |
| 79 | 1-{4-[6-amino-5-(methoxyimino-methyl)-pyrimidin-4-yloxy]-2-chloro-phenyl}-3-prop-2-ynyl-urea, |
| 80 | 1-{4-[6-amino-5-(methoxyimino-methyl)-pyrimidin-4-yloxy]-2-chloro-phenyl}-3-isopropyl-urea, |
| 81 | 1-{4-[6-amino-5-(methoxyimino-methyl)-pyrimidin-4-yloxy]-2-chloro-phenyl}-3-(2-hydroxy-ethyl)-urea, |
| 82 | 1-{4-[6-amino-5-(methoxyimino-methyl)-pyrimidin-4-yloxy]-2-chloro-phenyl}-3-(2-dimethylamino-ethyl)-urea, |
| 83 | 1-{4-[6-amino-5-(methoxyimino-methyl)-pyrimidin-4-yloxy]-2-chloro-phenyl}-3-(3-hydroxy-propyl)-urea, |
| 84 | 1-{4-[6-amino-5-(methoxyimino-methyl)-pyrimidin-4-yloxy]-2-chloro-phenyl}-3-(4-pyrrolidin-1-yl-butyl)-urea, |
| 85 | 1-{4-[6-amino-5-(methoxyimino-methyl)-pyrimidin-4-yloxy]-2-chloro-phenyl}-3-cyclopropyl-urea, |
| 86 | 1-{4-[6-amino-5-(methoxyimino-methyl)-pyrimidin-4-yloxy]-2-chloro-phenyl}-3-pyridin-2-yl-urea, |
| 87 | 1-{4-[6-amino-5-(methoxyimino-methyl)-pyrimidin-4-yloxy]-2-chloro-phenyl}-3-pyridin-3-yl-urea, |
| 88 | 1-{4-[6-amino-5-(methoxyimino-methyl)-pyrimidin-4-yloxy]-2-chloro-phenyl}-3-pyridin-4-yl-urea, |
| 89 | 1-{4-[6-amino-5-(methoxyimino-methyl)-pyrimidin-4-yloxy]-2-chloro-phenyl}-3-(4-methyl-thiazol-2-yl)-urea, |
| 90 | 1-{4-[6-amino-5-(methoxyimino-methyl)-pyrimidin-4-yloxy]-2-chloro-phenyl}-3-(5-methyl-thiazol-2-yl)-urea, |
| 91 | 1-{4-[6-amino-5-(methoxyimino-methyl)-pyrimidin-4-yloxy]-2-chloro-phenyl}-3-thiazol-2-yl-urea, |
| 92 | 1-{4-[6-amino-5-(methoxyimino-methyl)-pyrimidin-4-yloxy]-2-chloro-phenyl}-3-(4,5-dimethyl-thiazol-2-yl)-urea, |
| 93 | 1-{4-[6-amino-5-(methoxyimino-methyl)-pyrimidin-4-yloxy]-2-chloro-phenyl}-3-(5-methyl-isoxazol-3-yl)-urea, |
| 95 | {4-[6-amino-5-(methoxyimino-methyl)-pyrimidin-4-yloxy]-2-chloro-phenyl}-carbamic acid methyl ester, |

-continued

| Cpd | Name |
|---|---|
| 97 | 2-{4-[6-amino-5-(methoxyimino-methyl)-pyrimidin-4-yloxy]-phenyl}-N-phenyl-acetamide, |
| 99 | 2-{4-[6-amino-5-(methoxyimino-methyl)-pyrimidin-4-yloxy]-phenyl}-N-p-tolyl-acetamide, |
| 103 | 1-(4-{6-amino-5-[(2-morpholin-4-yl-ethoxyimino)-methyl]-pyrimidin-4-yloxy}-2-chloro-phenyl)-3-ethyl-urea, |
| 104 | 1-(4-{6-amino-5-[(2-methoxy-ethoxyimino)-methyl]-pyrimidin-4-yloxy}-2-chloro-phenyl)-3-ethyl-urea, and |
| 110 | 4-amino-6-[4-(benzyloxy)phenoxy]-5-pyrimidinecarboxaldehyde O-methyloxime. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray ionization mass spectra (MS-ESI) were recorded on a Hewlett Packard 59987A spectrometer. High resolution mass spectra (HRMS) were obtained on a Micromass Autospec. E spectrometer by fast atom bombardment (FAB) technique.

The terms used in describing the invention are commonly used and known to those skilled in the art. As used herein, the following abbreviations and formulas have the indicated meanings:

| Abbreviation | Meaning |
|---|---|
| Cpd | compound |
| DCM | dichloromethane |
| DIC | 2-dimethylaminoisopropyl chloride |
| DMF | N,N-dimethylformamide |
| DMSO | dimethyl sulfoxide |
| HOBT | 1-hydroxybenzotriazole Hydrate |
| min | minute(s) |
| h/hr/hrs | hour(s) |
| Et$_3$N | triethylamine |
| THF | tetrahydrofuran |

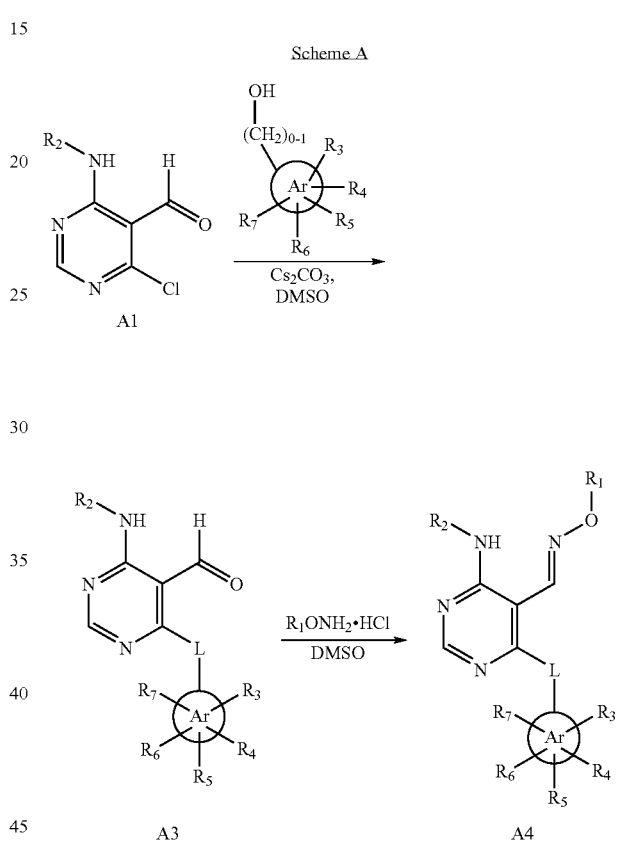

Compound A1 is reacted with Compound A2 and cesium carbonate in DMSO to generate Compound A3, which is then reacted with R$_1$ONH$_2$.HCl to form Compound A4, representative of a compound of formula (I).

The oxime function may be reduced to a cyano substitutent using functional transformations well known to those with skill in the art.

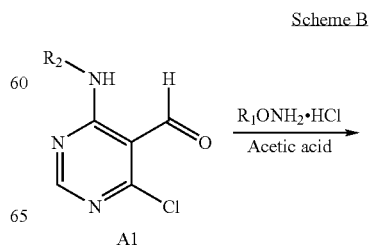

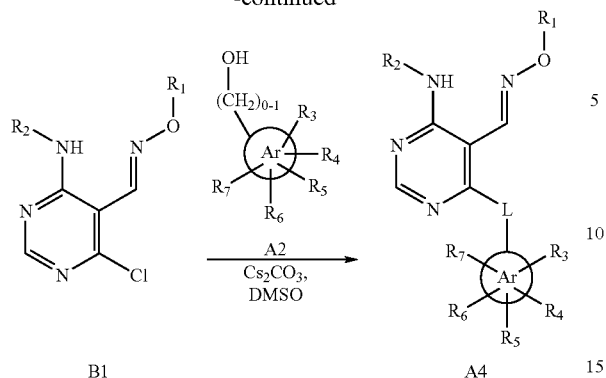

B1 → A4

As an alternative to Scheme A, Compound A1 is reacted with R₁ONH₂.HCl in acetic acid to form Compound B1, which is then reacted with Compound A2 and cesium carbonate in DMSO to generate Compound A4.

Scheme C

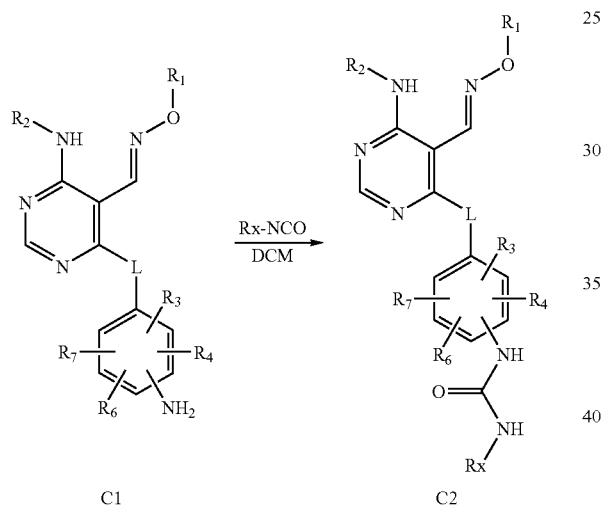

C1 → C2

Compound C1 is reacted with a Rx substituted isocyanate compound in DCM using direct heating to provide Compound C2, representative of a compound of formula (I).

Scheme D

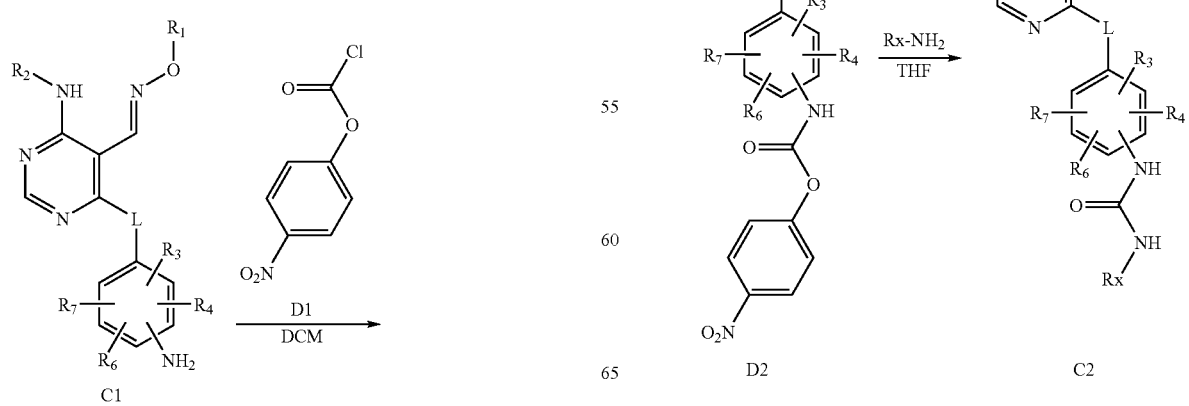

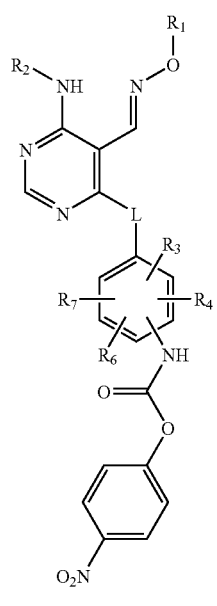

As an alternative to Scheme C, Compound C1 is reacted with 4-nitro-phenyl chloroformate Compound D1 in DCM to provide intermediate Compound D2.

Compound D2 is reacted with a Rx substituted amine compound in THF to provide Compound C2.

EXAMPLE 1

4-amino-6-(4-fluoro-2-methyl-1H-indol-5-yloxy)-pyrimidine-5-carbaldehyde O-ethyl-oxime (Cpd 1)

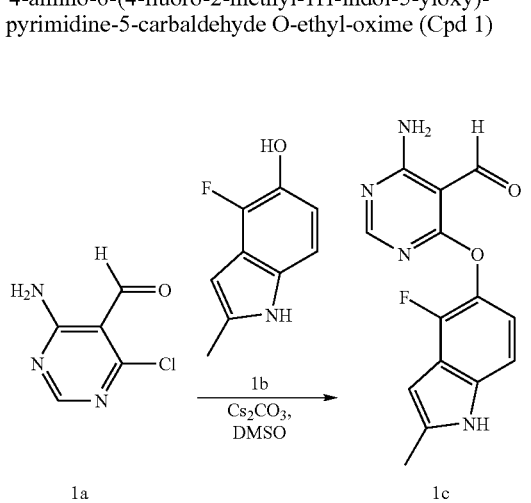

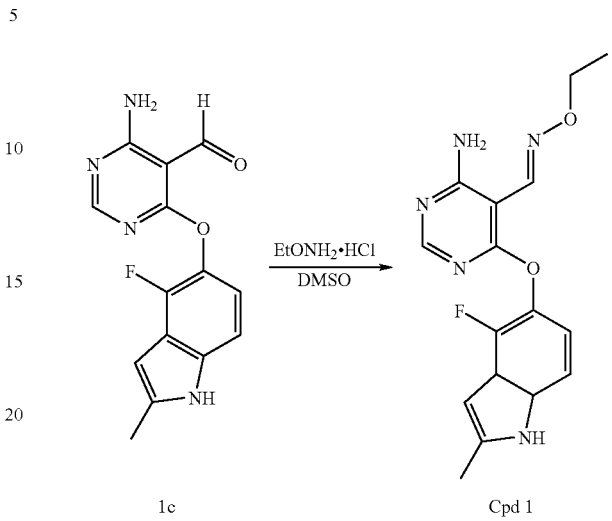

4-amino-6-chloro-pyrimidine-5-carbaldehyde Compound 1a (1.4 g), 4-fluoro-2-methyl-1H-indol-5-ol Compound 1b (1.3 g), Cs$_2$CO$_3$ (5.8 g) and DMSO (10 mL) were added to a flask.

The mixture was stirred at rt for 2 hrs, then poured into water and extracted with EtOAc. The organic layer was separated, dried with MgSO$_4$, then concentrated and the residue was purified by flash chromatography (CH$_2$Cl$_2$:MeOH/9.5:0.5) to afford 4-amino-6-(4-fluoro-2-methyl-1H-indol-5-yloxy)-pyrimidine-5-carbaldehyde Compound 1c (2.2 g, 94%) as a yellow solid. $^1$H NMR (400 MHz, DMSO-d$_6$) δ 11.30 (s, 1H), 10.40 (s, 1H), 8.55 (s, 1H), 8.40 (s, 1H), 8.10 (s, 1H), 7.05 (d, 1H), 6.85 (t, 1H), 6.20 (s, 1H), 2.40 (s, 3H). MS (ESI) m/z: 285 (M+H$^+$).

Compound 1c (0.20 g), O-ethyl-hydroxylamine hydrochloride (0.31 g) and DMSO (10 mL) were added to a flask. The mixture was stirred at rt for 2 hrs, then poured into water and extracted with EtOAc. The organic layer was separated, dried with MgSO$_4$, then concentrated to afford Compound 1 (0.21 g, 96%) as a white solid. $^1$H NMR (300 MHz, CD$_3$OD) δ 8.62 (s, 1H), 8.05 (s, 1H), 7.05 (d, 1H), 6.80 (t, 1H), 6.20 (s, 1H), 4.30 (q, 2H), 2.43 (s, 3H), 1.40 (t, 3H). MS (ESI) m/z: 330 (M+H$^+$).

Using the procedure of Example 1, other compounds representative of the present invention were prepared:

| Cpd | Name and Data |
|---|---|
| 2 | 4-amino-6-(2-methyl-1H-indol-5-yloxy)-pyrimidine-5-carbaldehyde O-methyl-oxime<br>$^1$H NMR(300MHz, DMSO-d$_6$) δ 11.0(s, 1H), 8.60(s, 1H), 8.10(s, 1H), 8.02(s, 1H), 7.55(s, 1H), 7.25(d, 1H), 7.13(s, 1H), 6.75(d, 1H), 6.10(s, 1H), 3.92(s, 3H), 2.38(s, 3H). MS(ESI) m/z: 298(M+H$^+$) |
| 5 | 4-amino-6-(quinolin-6-yloxy)-pyrimidine-5-carbaldehyde O-methyl-oxime<br>$^1$H NMR(300MHz, DMSO-d$_6$) δ 8.90(m, 1H), 8.62(s, 1H), 8.40(d, 1H), 8.25(s, 1H), 8.05(s, 1H), 8.02(d, 1H), 7.75(d, 1H), 7.65(s, 1H), 7.55(dd, 1H), 7.45(dd, 1H), 3.95(s, 3H). MS(ESI) m/z: 296(M+H$^+$) |
| 6 | 4-amino-6-(quinolin-7-yloxy)-pyrimidine-5-carbaldehyde O-methyl-oxime<br>$^1$H NMR(300MHz, DMSO-d$_6$) δ 8.90(m, 1H), 8.62(s, 1H), 8.35(d, 1H), 8.25(s, 1H), 8.05(m, 1H), 8.02(s, 1H), 7.80(m, 1H), 7.60(dd, 1H), 7.55(m, 1H), 3.95(s, 3H). MS(ESI) m/z: 296(M+H$^+$) |
| 7 | 4-amino-6-(4-fluoro-1H-indol-5-yloxy)-pyrimidine-5-carbaldehyde O-methyl-oxime<br>$^1$H NMR(300MHz, DMSO-d$_6$) δ 11.50(s, 1H), 8.60(s, 1H), 8.15(s, 1H), 8.00(s, 1H), 7.55(s, 1H), 7.45(m, 1H), 7.20(d, 1H), 7.00(t, 1H), 6.50(m 1H), 3.95(s, 3H). MS(ESI) m/z: 302(M+H$^+$) |
| 8 | 4-amino-6-(6-fluoro-1H-indol-5-yloxy)-pyrimidine-5-carbaldehyde O-methyl-oxime<br>$^1$H NMR(400MHz, DMSO-d$_6$) δ 11.20(s, 1H), 8.60(s, 1H), 8.15(s, 1H), 8.00(s, 1H), 7.55(s, 1H), 7.42(d, 1H), 7.36(m, 1H), 7.30(d, 1H), 6.40(m, 1H). MS(ESI) m/z: 302(M+H$^+$) |
| 9 | 4-amino-6-(3-methyl-1H-indol-5-yloxy)-pyrimidine-5-carbaldehyde O-methyl-oxime<br>$^1$H NMR(400MHz, DMSO-d$_6$) δ 10.80(s, 1H), 8.60(s, 1H), 8.10(s, 1H), 8.00(s, 1H), 7.55(s, 1H), 7.30(d, 1H), 7.20(s, 1H), 7.15(s, 1H), 6.83(dd, 1H), 3.93(s, 3H), 2.20(s, 3H). MS(ESI) m/z: 299(M+H$^+$) |
| 10 | 4-amino-6-(1H-indol-5-yloxy)-pyrimidine-5-carbaldehyde O-methyl-oxime<br>$^1$H NMR(300MHz, DMSO-d$_6$) δ 11.10(s, 1H), 8.60(s, 1H), 8.10(s, 1H), 8.00(s, 1H), 7.55(s, 1H), 7.40(m, 2H), 7.25(d, 1H), 6.86(dd, 1H), 6.40(m, 1H), 3.95(s, 3H). MS(ESI) m/z: 284(M+H$^+$) |

-continued

| Cpd | Name and Data |
|---|---|
| 12 | 4-amino-6-(4-fluoro-2-methyl-1H-indol-5-yloxy)-pyrimidine-5-carbaldehyde O-(2-hydroxy-ethyl)-oxime<br>¹H NMR(400MHz, CD₃OD) δ 8.75(s, 1H), 7.93(s, 1H), 7.05(d, 1H), 6.80(t, 1H), 6.20(s, 1H), 4.25(t, 2H), 3.85(t, 2H), 2.45(s, 3H). MS(ESI) m/z: 344(M+H⁺) |
| 13 | 4-amino-6-(4-fluoro-2-methyl-1H-indol-5-yloxy)-pyrimidine-5-carbaldehyde O-(2-pyrrolidin-1yl-ethyl)-oxime<br>¹H NMR(300MHz, CDCl₃) δ 8.75(s, 1H), 8.40(s, 1H), 8.12(s, 1H), 7.90(s, 1H), 7.00(d, 1H), 6.85(t, 1H), 6.25(s, 1H), 5.85(s, 1H), 4.35(t, 2H), 2.85(t, 2H), 2.60(m, 4H), 2.40(s, 3H), 1.85(m, 4H). MS(ESI) m/z: 399(M+H⁺) |
| 14 | 4-amino-6-(4-fluoro-2-methyl-1H-indol-5-yloxy)-pyrimidine-5-carbaldehyde O-(2-morpholin-4-yl-ethyl)-oxime<br>¹H NMR(400MHz, THF) δ 10.50(s, 1H), 8.75(s, 1H), 7.96(s, 1H), 7.70(s, 1H), 7.25(s, 1H), 7.00(d, 1H), 6.80(t, 1H), 6.25(s, 1H), 4.25(t, 2H), 3.70(m, 8H), 2.80(t, 2H), 2.40(s, 3H). MS(ESI) m/z: 415(M+H⁺) |
| 15 | 4-amino-6-(4-fluoro-2-methyl-1H-indol-5-yloxy)-pyrimidine-5-carbaldehyde O-(2-dimethylamino-ethyl)-oxime<br>¹H NMR(300MHz, CD₃OD) δ 8.70(s, 1H), 7.90(s, 1H), 7.10(d, 1H), 6.80(t, 1H), 6.20(s, 1H), 4.35(t, 2H), 2.75(t, 2H), 2.40(s, 3H), 2.30(s, 6H). MS(ESI) m/z: 373(M+H⁺) |
| 16 | 4-amino-6-(4-fluoro-2-methyl-1H-indol-5-yloxy)-pyrimidine-5-carbaldehyde O-(2-methylamino-ethyl)-oxime<br>¹H NMR(300MHz, CDCl₃) δ 8.80(s, 1H), 8.30(s, 1H), 8.10(s, 1H), 7.80(s, 1H), 7.00(d, 1H), 6.80(t, 1H), 6.30(s, 1H), 5.75(s, 1H), 4.35(t, 2H), 3.00(t, 3H), 2.50(s, 3H), 2.40(s, 3H). MS(ESI) m/z: 359(M+H⁺) |
| 17 | 4-amino-6-(4-fluoro-2-methyl-1H-indol-5-yloxy)-pyrimidine-5-carbaldehyde O-(3-dimethylamino-propyl)-oxime<br>¹H NMR(300MHz, CDCl₃) δ 8.75(s, 1H), 8.50(s, 1H), 8.10(s, 1H), 7.85(s, 1H), 6.96(d, 1H), 6.85(t, 1H), 6.25(s, 1H), 5.90(s, 1H), 4.25(t, 2H), 2.40(t, 2H), 2.40(s, 3H), 2.30(s, 6H), 1.90(p, 2H). MS(ESI) m/z: 387(M+H⁺) |
| 18 | 4-amino-6-(4-fluoro-2-methyl-1H-indol-5-yloxy)-pyrimidine-5-carbaldehyde O-(3-pyrrolidin-1-yl-propyl)-oxime<br>¹H NMR(300MHz, DMSO-d₆) δ 8.60(s, 1H), 8.15(s, 1H), 8.02(s, 1H), 7.60(s, 1H), 7.05(d, 1H), 6.85(t, 1H), 6.20(s, 1H), 4.20(t, 2H), 2.50(m, 9H), 1.85(t, 2H), 1.70(m, 4H). MS(ESI) m/z: 413(M+H⁺) |
| 19 | 4-amino-6-(4-fluoro-2-methyl-1H-indol-5-yloxy)-pyrimidine-5-carbaldehyde O-(3-morpholin-4-yl-propyl)-oxime<br>¹H NMR(300MHz, DMSO-d₆) δ 11.25(s, 1H), 8.60(s, 1H), 8.15(s, 1H), 8.02(s, 1H), 7.60(s, 1H), 7.10(d, 1H), 6.90(t, 1H), 6.20(s, 1H), 4.20(t, 2H), 3.60(m, 4H), 2.30(m, 9H), 1.82(p, 2H). MS(ESI) m/z: 429(M+H⁺) |
| 20 | 4-amino-6-(4-fluoro-2-methyl-1H-indol-5-yloxy)-pyrimidine-5-carbaldehyde O-(3-piperidin-1-yl-propyl)-oxime<br>¹H NMR(300MHz, DMSO-d₆) δ 11.25(s, 1H), 8.60(s, 1H), 8.10(s, 1H), 8.00(s, 1H), 7.55(s, 1H), 7.06(d, 1H), 6.85(t, 1H), 6.20(s, 1H), 4.20(t, 2H), 2.40(s, 3H), 2.35(m, 6H), 1.80(p, 2H), 1.50(m, 4H), 1.40(m, 2H). MS(ESI) m/z: 427(M+H⁺) |
| 21 | 4-amino-6-(4-fluoro-2-methyl-1H-indol-5-yloxy)-pyrimidine-5-carbaldehyde O-(3-piperazin-1-yl-propyl)-oxime<br>¹H NMR(300MHz, DMSO-d₆) δ 11.25(s, 1H), 8.62(s, 1H), 8.15(s, 1H), 8.00(s, 1H), 7.60(s, 1H), 7.10(d, 1H), 6.85(t, 1H), 6.20(s, 1H), 4.25(t, 2H), 3.35(s, 1H), 2.65(m, 4H), 2.40(s, 3H), 2.30(m, 6H), 1.85(p, 2H). MS(ESI) m/z: 428(M+H⁺) |
| 24 | 4-amino-6-(4-fluoro-2-methyl-1H-indol-5-yloxy)-pyrimidine-5-carbaldehyde O-(4-piperidin-1-yl-butyl)-oxime<br>¹H NMR(400MHz, DMSO-d₆) δ 11.30(s, 1H), 8.60(s, 1H), 8.10(s, 1H), 8.00(s, 1H), 7.60(s, 1H), 7.05(d, 1H), 6.85(t, 1H), 6.20(s, 1H), 4.20(t, 2H), 2.40(s, 3H), 2.25(m, 6H), 1.70(p, 2H), 1.50(m, 6H), 1.35(m, 2H). MS(ESI) m/z: 442(M+H⁺) |
| 25 | 4-amino-6-(4-fluoro-2-methyl-1H-indol-5-yloxy)-pyrimidine-5-carbaldehyde O-(4-pyrrolidin-1-yl-butyl)-oxime<br>¹H NMR(400MHz, DMSO-d₆) δ 11.30(s, 1H), 8.60(s, 1H), 8.15(s, 1H), 8.00(s, 1H), 7.60(s, 1H), 7.10(d, 1H), 6.90(t, 1H), 6.18(s, 1H), 4.20(t, 2H), 3.30(m, 4H), 2.40(m, 5H), 1.70(m, 6H), 1.60(m, 2H). MS(ESI) m/z: 427(M+H⁺) |
| 26 | 4-amino-6-(4-fluoro-2-methyl-1H-indol-5-yloxy)-pyrimidine-5-carbaldehyde O-(4-morpholin-4-yl-butyl)-oxime<br>¹H NMR(400MHz, DMSO-d₆) δ 11.25(s, 1H), 8.60(s, 1H), 8.10(s, 1H), 8.00(s, 1H), 7.60(s, 1H), 7.05(d, 1H), 6.85(t, 1H), 6.20(s, 1H), 4.20(t, 2H), 3.55(t, 4H), 2.40(s, 3H), 2.30(m, 6H), 1.70(p, 2H), 1.55(p, 2H). MS(ESI) m/z: 443(M+H⁺) |
| 27 | 4-amino-6-(4-fluoro-2-methyl-1H-indol-5-yloxy)-pyrimidine-5-carbaldehyde oxime<br>¹H NMR(300MHz, DMSO-d₆) δ 11.50(s, 1H), 11.25(s, 1H), 8.53(s, 1H), 8.05(s, 1H), 8.00(s, 1H), 7.70(s, 1H), 7.05(d, 1H), 6.88(t, 1H), 6.20(s, 1H), 2.40(s, 3H). MS(ESI) m/z: 302(M+H⁺) |
| 48 | 5-[6-amino-5-(methoxyimino-methyl)-pyrimidin-4-yloxy]-2-methyl-indole-1-carboxylic acid propylamide<br>¹H NMR(400MHz, DMSO-d₆) δ 8.58(s, 1H), 8.35(m, 1H), 8.10(s, 1H), 8.00(s, 1H), 7.55(s, 1H), 7.50(d, 1H), 7.20(s, 1H), 6.90(dd, 1H), 3.95(s, 3H), 3.25(q, 2H), 2.50(s, 3H), 1.60(sextet, 2H), 0.95(t, 3H). MS(ESI) m/z: 383(M+H⁺) |
| 49 | 5-[6-amino-5-(methoxyimino-methyl)-pyrimidin-4-yloxy]-2-methyl-indole-1-carboxylic acid methylamide<br>¹H NMR(300MHz, DMSO-d₆) δ 8.60(s, 1H), 8.25(m, 1H), 8.10(s, 1H), 8.00(s, |

| Cpd | Name and Data |
|---|---|
| | 1H), 7.55(s, 1H), 7.53(d, 1H), 7.20(d, 1H), 6.95(dd, 1H), 6.35(s, 1H), 3.95(s, 3H), 2.86(d, 3H), 2.50(s, 3H). MS(ESI) m/z: 355(M+H$^+$) |
| 106 | 4-amino-6-(3,5-dimethoxyphenoxy)-5-pyrimidinecarboxaldehyde O-methyloxime<br>MS(ESI) m/z: 305(M+H$^+$) |
| 107 | 5-[{6-amino-5-[(E)-(methoxyimino)methyl]-4-pyrimidinyl}oxy]-2-methyl-1H-indole-3-carboxylic acid ethyl ester<br>MS(ESI) m/z: 370(M+H$^+$) |
| 108 | 4-amino-6-(1,3-benzodioxol-5-yloxy)-5-pyrimidinecarboxaldehyde O-methyloxime<br>MS(ESI) m/z: 289(M+H$^+$) |
| 109 | 4-amino-6-(3-chloro-4-fluorophenoxy)-5-pyrimidinecarboxaldehyde O-methyloxime<br>MS(ESI) m/z: 297(M+H$^+$) |
| 110 | 4-amino-6-[4-(benzyloxy)phenoxy]-5-pyrimidinecarboxaldehyde O-methyloxime<br>MS(ESI) m/z: 351(M+H$^+$) |
| 111 | 4-amino-6-(benzyloxy)-5-pyrimidinecarboxaldehyde O-methyloxime<br>MS(ESI) m/z: 259(M+H$^+$) |
| 112 | 4-amino-6-[(3-fluorophenyl)methoxy]-5-pyrimidinecarboxaldehyde O-methyloxime<br>MS(ESI) m/z: 277(M+H$^+$) |
| 113 | N-[2-{5-[{6-amino-5-[(E)-(methoxyimino)methyl]-4-pyrimidinyl}oxy]-1H-indol-3-yl}ethyl]-acetamide<br>MS(ESI) m/z: 369(M+H$^+$) |
| 114 | 4-amino-6-[(2,6-difluorophenyl)methoxy]-5-pyrimidinecarboxaldehyde O-methyloxime<br>MS(ESI) m/z: 295(M+H$^+$) |
| 115 | 4-amino-6-(2-naphthalenylmethoxy)-5-pyrimidinecarboxaldehyde O-methyloxime<br>MS(ESI) m/z: 309(M+H$^+$) |
| 116 | 4-amino-6-[(2-fluorophenyl)methoxy]-5-pyrimidinecarboxaldehyde O-methyloxime<br>MS(ESI) m/z: 277(M+H$^+$) |
| 117 | 4-amino-6-[(2,4-dichlorophenyl)methoxy]-5-pyrimidinecarboxaldehyde O-methyloxime<br>MS(ESI) m/z: 327(M+H$^+$) |
| 118 | 4-amino-6-[(2,5-dichlorophenyl)methoxy]-5-pyrimidinecarboxaldehyde O-methyloxime<br>MS(ESI) m/z: 327(M+H$^+$) |
| 119 | 4-amino-6-[(3-bromophenyl)methoxy]-5-pyrimidinecarboxaldehyde O-methyloxime<br>MS(ESI) m/z: 337(M+H$^+$) |
| 120 | 4-amino-6-[(3,4-dichlorophenyl)methoxy]-5-pyrimidinecarboxaldehyde O-methyloxime<br>MS(ESI) m/z: 327(M+H$^+$) |
| 121 | 4-amino-6-{[3-(trifluoromethyl)phenyl]methoxy}-5-pyrimidinecarboxaldehyde O-methyloxime<br>MS(ESI) m/z: 327(M+H$^+$) |
| 122 | 4-amino-6-[(3-chlorophenyl)methoxy]-5-pyrimidinecarboxaldehyde O-methyloxime<br>MS(ESI) m/z: 293(M+H$^+$) |
| 123 | 4-amino-6-[(3-methoxyphenyl)methoxy]-5-pyrimidinecarboxaldehyde O-methyloxime<br>MS(ESI) m/z: 289(M+H$^+$) |
| 124 | 4-amino-6-[(3,4-dimethoxyphenyl)methoxy]-5-pyrimidinecarboxaldehyde O-methyloxime<br>MS(ESI) m/z: 319(M+H$^+$) |
| 125 | 4-amino-6-[(4-fluorophenyl)methoxy]-5-pyrimidinecarboxaldehyde O-methyloxime<br>MS(ESI) m/z: 277(M+H$^+$) |
| 126 | 4-amino-6-[(4-chlorophenyl)methoxy]-5-pyrimidinecarboxaldehyde O-methyloxime<br>MS(ESI) m/z: 293(M+H$^+$) |
| 127 | 4-amino-6-[(3,4-difluorophenyl)methoxy]-5-pyrimidinecarboxaldehyde O-methyloxime<br>MS(ESI) m/z: 295(M+H$^+$) |
| 128 | 4-amino-6-[(5-chloro-2-methoxyphenyl)methoxy]-5-pyrimidinecarboxaldehyde O-methyloxime<br>MS(ESI) m/z: 323(M+H$^+$) |
| 129 | 4-amino-6-[(2-chloro-4-fluorophenyl)methoxy]-5-pyrimidinecarboxaldehyde O-methyloxime<br>MS(ESI) m/z: 311(M+H$^+$) |
| 130 | 4-[{[6-amino-5-[(E)-(methoxyimino)methyl]-4-pyrimidinyl]oxy}methyl]-benzonitrile<br>MS(ESI) m/z: 284(M+H$^+$) |
| 131 | 4-amino-6-[(5-bromo-2-chlorophenyl)methoxy]-5-pyrimidinecarboxaldehyde O-methyloxime<br>MS(ESI) m/z: 371(M+H$^+$) |
| 132 | 4-amino-6-[(4-ethynylphenyl)methoxy]-5-pyrimidinecarboxaldehyde O-methyloxime<br>MS(ESI) m/z: 283(M+H$^+$) |

| Cpd | Name and Data |
|---|---|
| 133 | 4-amino-6-(2-ethylphenoxy)-5-pyrimidinecarboxaldehyde O-methyloxime<br>MS(ESI) m/z: 273(M+H$^+$) |
| 134 | 4-amino-6-(4-ethylphenoxy)-5-pyrimidinecarboxaldehyde O-methyloxime<br>MS(ESI) m/z: 273(M+H$^+$) |
| 135 | 4-amino-6-[2-methoxy-4-(2-propenyl)phenoxy]-5-pyrimidinecarboxaldehyde O-methyloxime<br>MS(ESI) m/z: 315(M+H$^+$) |
| 136 | 4-amino-6-(3-fluorophenoxy)-5-pyrimidinecarboxaldehyde O-methyloxime<br>MS(ESI) m/z: 263(M+H$^+$) |
| 137 | 4-amino-6-(4-fluorophenoxy)-5-pyrimidinecarboxaldehyde O-methyloxime<br>MS(ESI) m/z: 263(M+H$^+$) |
| 138 | 4-amino-6-(4-benzoylphenoxy)-5-pyrimidinecarboxaldehyde O-methyloxime<br>MS(ESI) m/z: 349(M+H$^+$) |
| 139 | 4-[{6-amino-5-[(E)-(methoxyimino)methyl]-4-pyrimidinyl}oxy]-benzeneacetonitrile<br>MS(ESI) m/z: 284(M+H$^+$) |
| 140 | 4-amino-6-[4-(benzyl)phenoxy]-5-pyrimidinecarboxaldehyde O-methyloxime<br>MS(ESI) m/z: 335(M+H$^+$) |
| 141 | 4-amino-6-(5-isoquinolinyloxy)-5-pyrimidinecarboxaldehyde O-methyloxime<br>MS(ESI) m/z: 296(M+H$^+$) |
| 142 | 4-amino-6-{4-[(1Z)-1-(methoxyimino)propyl]phenoxy}-5-pyrimidinecarboxaldehyde O-methyloxime<br>MS(ESI) m/z: 330(M+H$^+$) |
| 143 | 4-amino-6-[(2-methyl-8-quinolinyl)oxy]-5-pyrimidinecarboxaldehyde O-methyloxime<br>MS(ESI) m/z: 310(M+H$^+$) |
| 144 | 4-amino-6-[2-methoxy-4-[(1E)-1-propenyl]phenoxy]-5-pyrimidinecarboxaldehyde O-methyloxime<br>MS(ESI) m/z: 315(M+H$^+$) |
| 145 | 4-amino-6-[(indan-5-yl)oxy]-5-pyrimidinecarboxaldehyde O-methyloxime<br>MS(ESI) m/z: 285(M+H$^+$) |
| 146 | 4-amino-6-(4-methoxyphenoxy)-5-pyrimidinecarboxaldehyde O-methyloxime<br>MS(ESI) m/z: 275(M+H$^+$) |
| 147 | 4-amino-6-[(5,6,7,8-tetrahydro-1-naphthalenyl)oxy]-5-pyrimidinecarboxaldehyde O-methyloxime<br>MS(ESI) m/z: 299(M+H$^+$) |
| 148 | 4-amino-6-(2,4,6-trichlorophenoxy)-5-pyrimidinecarboxaldehyde O-methyloxime<br>MS(ESI) m/z: 347(M+H$^+$) |
| 149 | 4-amino-6-(2,4,6-trimethylphenoxy)-5-pyrimidinecarboxaldehyde O-methyloxime<br>MS(ESI) m/z: 287(M+H$^+$) |
| 150 | 4-amino-6-(2-methoxyphenoxy)-5-pyrimidinecarboxaldehyde O-methyloxime<br>MS(ESI) m/z: 275(M+H$^+$) |
| 151 | 4-[{6-amino-5-[(E)-(methoxyimino)methyl]-4-pyrimidinyl}oxy]-benzoic acid methyl ester<br>MS(ESI) m/z: 303(M+H$^+$) |
| 152 | 4-amino-6-(1-naphthalenyloxy)-5-pyrimidinecarboxaldehyde O-methyloxime<br>MS(ESI) m/z: 295(M+H$^+$) |
| 153 | 4-amino-6-[4-(1H-1,2,4-triazol-1-yl)phenoxy]-5-pyrimidinecarboxaldehyde O-methyloxime<br>MS(ESI) m/z: 312(M+H$^+$) |
| 154 | 4-amino-6-(3,4,5-trimethoxyphenoxy)-5-pyrimidinecarboxaldehyde O-methyloxime<br>MS(ESI) m/z: 335(M+H$^+$) |
| 155 | 4-amino-6-(4-ethyl-2-methoxyphenoxy)-5-pyrimidinecarboxaldehyde O-methyloxime<br>MS(ESI) m/z: 303(M+H$^+$) |
| 156 | 4-amino-6-[2-methoxy-4-(3-oxobutyl)phenoxy]-5-pyrimidinecarboxaldehyde O-methyloxime<br>MS(ESI) m/z: 345(M+H$^+$) |
| 157 | 4-amino-6-(2-chloro-4,5-dimethylphenoxy)-5-pyrimidinecarboxaldehyde O-methyloxime<br>MS(ESI) m/z: 307(M+H$^+$) |
| 158 | 4-amino-6-[2,5-dimethyl-4-(4-morpholinylmethyl)phenoxy]-5-pyrimidinecarboxaldehyde O-methyloxime<br>MS(ESI) m/z: 372(M+H$^+$) |
| 159 | 4-amino-6-[4-(phenylamino)phenoxy]-5-pyrimidinecarboxaldehyde O-methyloxime<br>MS(ESI) m/z: 336(M+H$^+$) |
| 160 | 4-amino-6-(3-methoxy-5-methylphenoxy)-5-pyrimidinecarboxaldehyde O-methyloxime<br>MS(ESI) m/z: 289(M+H$^+$) |
| 161 | 4-amino-6-[2-methoxy-4-[(1E,3E)-3-(methoxyimino)-1-butenyl]phenoxy]-5-pyrimidinecarboxaldehyde O-methyloxime<br>MS(ESI) m/z: 372(M+H$^+$) |
| 162 | 4-[{6-amino-5-[(E)-(methoxyimino)methyl]-4-pyrimidinyl}oxy]-2-chloro-benzonitrile<br>MS(ESI) m/z: 304(M+H$^+$) |

-continued

| Cpd | Name and Data |
|---|---|
| 163 | 4-(4-acetyl-3-methylphenoxy)-6-amino-5-pyrimidinecarboxaldehyde O-methyloxime<br>MS(ESI) m/z: 301(M+H+) |
| 164 | 4-amino-6-{4-[(1Z)-1-(methoxyimino)ethyl]-3-methylphenoxy}-5-pyrimidinecarboxaldehyde O-methyloxime<br>MS(ESI) m/z: 330(M+H+) |

EXAMPLE 2

4-(1H-indol-5-yloxy)-6-methylamino-pyrimidine-5-carbaldehyde O-methyl-oxime (Cpd 3)

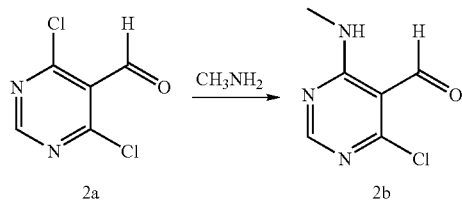

4,6-dichloro-pyrimidine-5-carbaldehyde Compound 2a (0.5 g), methylamine (88 mg) and THF (50 mL) were added to a flask. The mixture was stirred at rt overnight, then concentrated and the residue was purified by flash chromatography (silica gel, hexane:EtOAc/5:5) to afford 4-chloro-6-methylamino-pyrimidine-5-carbaldehyde Compound 2b (0.40 g, 82%). $^1$H NMR (300 MHz, CDCl$_3$) δ 10.38 (s, 1H), 9.15 (s, 1H), 8.45 (s, 1H), 3.15 (d, 3 H). MS (ESI) m/z: 172 (M+H+).

Using the procedure of Example 1, Compound 2b was carried forward in place of Compound 1a to provide Compound 3 (10 mg, 92%). $^1$H NMR (300 MHz, CDCl$_3$) δ 8.70 (s, 1H), 8.20 (s, 2H), 8.00 (s, 1H), 7.25 (m, 2H), 7.10 (m, 1H), 6.80 (m, 1H), 6.42 (m, 1H), 3.90 (s, 3H), 3.10 (d, 3H). MS (ESI) m/z: 298 (M+H+).

EXAMPLE 3

4-(1H-indol-5-yloxy)-6-methoxyamino-pyrimidine-5-carbaldehyde O-methyl-oxime (Cpd 4)

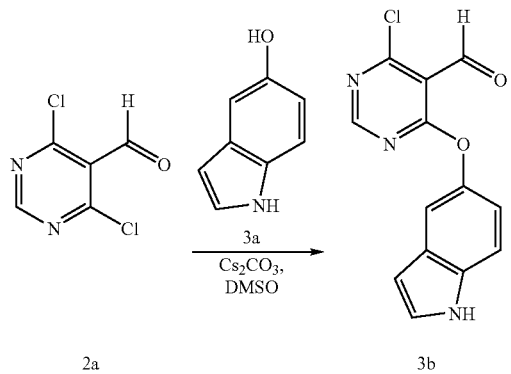

Using the procedure of Example 1, 4,6-dichloro-pyrimidine-5-carbaldehyde Compound 2a (0.10 g) and 5-hydroxyindole Compound 3a (75 mg) were reacted to provide 4-chloro-6-(1H-indol-5-yloxy)-pyrimidine-5-carbaldehyde Compound 3b (15 mg, 10%). $^1$H NMR (400 MHz, CDCl$_3$) δ 10.60 (s, 1H), 8.60 (s, 1H), 8.30 (s, 1H), 7.45 (d, 1H), 7.40 (d, 1H), 7.30 (d, 1H), 6.95 (dd, 1H), 6.55 (d, 1H). MS (ESI) m/z: 306 (M+H+).

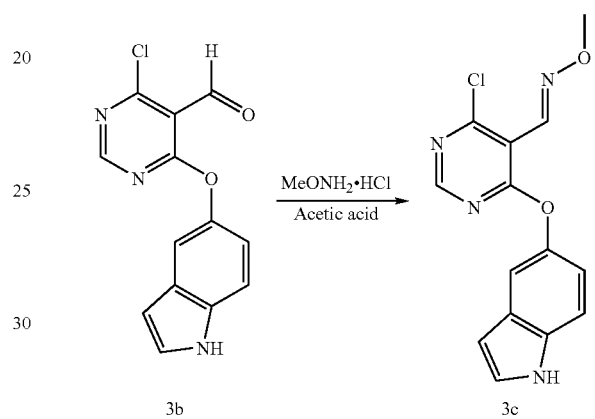

Compound 3b (20 mg), O-methyl-hydroxylamine hydrochloride (12 mg), acetic acid (1 mL) and H$_2$O (0.5 mL) were added to a flask. The mixture was stirred at rt for 1 hr, then poured into H$_2$O and extracted with EtOAc. The organic layer was separated, dried with MgSO$_4$, then concentrated and the residue was purified by flash chromatography (silica gel, hexane:EtOAc/7:3) to afford 4-chloro-6-(1H-indol-5-yloxy)-pyrimidine-5-carbaldehyde O-methyl-oxime Compound 3c (18 mg, 82%). $^1$H NMR (300 MHz, CDCl$_3$) δ 8.47 (s, 1H), 8.44 (s, 1H), 8.30 (s, 1H), 7.42 (d, 1H), 7.40 (d, 1H), 7.30 (d, 1H), 7.00 (dd, 1H), 6.58 (d, 1H), 4.05 (s, 3H). MS (ESI) m/z: 303 (M+H+).

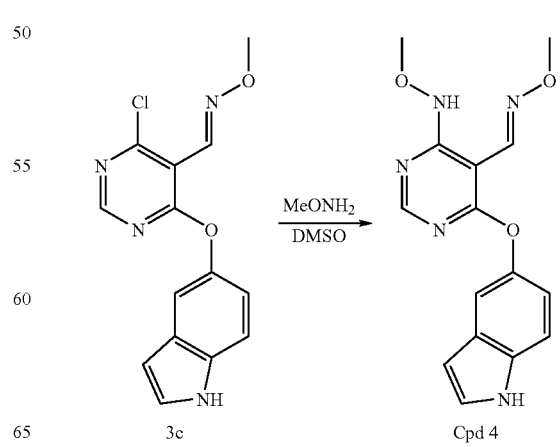

Compound 3c (12 mg), O-methyl-hydroxylamine (5.6 mg), Et$_3$N (12 mg) and DMSO were added to a screw cap tube. The mixture was heated to 85° C. overnight, then poured into water and extracted with EtOAc. The organic layer was separated, dried with MgSO$_4$, then concentrated and the residue was purified by flash chromatography (silica gel, EtOAc: hexane/5:5) to afford Compound 4 (7.7 mg, 62%). $^1$H NMR (400 MHz, CDCl$_3$) δ 10.30 (s, 1H), 8.65 (s, 1H), 8.30 (s, 1H), 8.10 (s, 1H), 7.32 (d, 1H), 7.28 (s, 1H), 7.18 (m, 1H), 6.85 (dd, 1H), 6.50 (m, 1H), 3.95 (s, 3H), 3.90 (s, 3H). MS (ESI) m/z: 312 (M+H$^+$).

EXAMPLE 4

4-amino-6-(1-methyl-1H-indol-5-yloxy)-pyrimidine-5-carbaldehyde O-methyl-oxime (Cpd 11)

Compound 10 (33 mg), methyl iodide (17 mg), cesium carbonate (38 mg) and DMF (2 mL) were added to a flask. The mixture was heated to 50° C. for 2 hrs, then poured into water and extracted with EtOAc. The organic layer was separated, dried with MgSO$_4$, then concentrated and the residue was purified by flash chromatography (silica gel, hexane: EtOAc/5:5) to afford Compound 11 (25 mg, 76%). $^1$H NMR (300 MHz, CD$_3$COCD$_3$) δ 8.65 (s, 1H), 7.95 (s, 1H), 7.75 (s, 1H), 7.40 (d, 1H), 7.35 (d, 1H), 7.28 (d, 1H), 7.10 (dd, 1H), 6.40 (d, 1H), 4.00 (s, 3H), 3.85 (s, 3H). MS (ESI) m/z: 298 (M+H$^+$).

EXAMPLE 5

4-amino-6-(4-fluoro-2-methyl-1H-indol-5-yloxy)-pyrimidine-5-carbaldehyde O-[3-(4-methanesulfonyl-piperazin-1-yl)-propyl]-oxime (Cpd 22)

Compound 21 (15 mg), methanesulfonyl chloride (4 mg), Et$_3$N (4 mg) and THF (1 mL) at 0° C. were added to a flask. After stirring for 30 min, the mixture was poured into H$_2$O and extracted with EtOAc. The organic layer was separated, dried with MgSO$_4$, then concentrated to afford Compound 22 (16 mg, 89%). $^1$H NMR (300 MHz, CD$_3$COCD$_3$) δ 10.40 (s, 1H), 8.70 (s, 1H), 8.00 (s, 1H), 7.80 (s, 1H), 7.18 (s, 1H), 7.15 (d, 1H), 6.90 (t, 1H), 6.25 (s, 1H), 4.35 (t, 2H), 3.40 (m, 4H), 2.85 (m, 1H), 2.50 (s, 3H). MS (ESI) m/z: 506 (M+H$^+$).

EXAMPLE 6

4-amino-6-(4-fluoro-2-methyl-1H-indol-5-yloxy)-pyrimidine-5-carbaldehyde O-[3-(4-acetyl-piperazin-1-yl)-propyl]-oxime (Cpd 23)

Compound 21 (15 mg), acetic anhydride (3.6 mg), pyridine (3 mg) and THF (1 mL) were added to a flask. After stirring for 30 min, the mixture was poured into H$_2$O and extracted with EtOAc. The organic layer was separated, dried with MgSO$_4$, then concentrated to afford Compound 23 (15 mg, 93%). $^1$H NMR (300 MHz, CD$_3$COCD$_3$) δ 10.35 (s, 1H), 8.70 (s, 1H), 8.00 (s, 1H), 7.85 (s, 1H), 7.15 (s, 1H), 7.12 (d, 1H), 6.90 (t, 1H), 6.25 (s, 1H), 4.30 (t, 2H), 3.40 (m, 4H), 2.90 (m, 4H), 2.40 (m, 3H), 2.38 (t, 2H), 1.92 (s, 3H), 1.90 (p, 2H). MS (ESI) m/z: 470 (M+H$^+$).

EXAMPLE 7

4-amino-6-(4-fluoro-2-methyl-1H-indol-5-yloxy)-pyrimidine-5-carbaldehyde O-(2-methoxy-ethyl)-oxime (Cpd 28)

Compound 27 (20 mg), 2-methoxy-ethyl bromide (10 mg), cesium carbonate (22 mg) and DMF (2 mL) were added to a flask. The mixture was heated to 50° C. overnight, then poured into water and extracted with EtOAc. The organic layer was separated, dried with MgSO$_4$, then concentrated and the residue was purified by flash chromatography (silica gel, EtOAc) to afford Compound 28 (22 mg, 92%). $^1$H NMR (300 MHz, CDCl$_3$) δ 8.72 (s, 1H), 8.05 (s, 2H), 7.80 (s, 1H), 6.95 (d, 1H), 6.75 (t, 1H), 6.20 (s, 1H), 4.30 (t, 2H), 3.65 (t, 2H), 3.35 (s, 3H). MS (ESI) m/z: 358 (M+H$^+$).

Using the procedure of Example 7, other compounds representative of the present invention may be prepared:

| Cpd | Name and Data |
| --- | --- |
| 29 | 4-amino-6-(4-fluoro-2-methyl-1H-indol-5-yloxy)-pyrimidine-5-carbaldehyde O-(3-hydroxy-propyl)-oxime<br>$^1$H NMR(300MHz, CDCl$_3$) δ 8.75(s, 1H), 8.15(s, 1H), 8.05(s, 1H), 7.90(s, 1H), 7.05(d, 1H), 6.90(t, 1H), 6.35(s, 1H), 5.80(s, 1H), 4.35(t, 2H), 3.85(t, 2H), 2.45(s, 3H), 2.00(p, 2H). MS(ESI) m/z: 360(M+H$^+$) |
| 30 | 4-amino-6-(4-fluoro-2-methyl-1H-indol-5-yloxy)-pyrimidine-5-carbaldehyde O-prop-2-ynyl-oxime<br>$^1$H NMR(300MHz, DMSO-d$_6$) δ 11.30(s, 1H), 8.62(s, 1H), 8.20(s, 1H), 8.02(s, 1H), 7.55(s, 1H), 7.10(d, 1H), 6.90(t, 1H), 6.20(s, 1H), 4.85(d, 2H), 3.60(t, 1H), 2.40(s, 1H). MS(ESI) m/z: 340(M+H$^+$) |
| 31 | 4-amino-6-(4-fluoro-2-methyl-1H-indol-5-yloxy)-pyrimidine-5-carbaldehyde O-allyl-oxime<br>$^1$H NMR(300MHz, DMSO-d$_6$) δ 11.25(s, 1H), 8.68(s, 1H), 8.15(s, 1H), 8.00(s, 1H), 7.55(s, 1H), 7.10(d, 1H), 6.85(t, 1H), 6.20(s, 1H), 6.00(m, 1H), 5.40(d, 1H), 5.30(d, 1H), 4.70(d, 1H), 2.40(s, 3H). MS(ESI) m/z: 342(M+H$^+$) |
| 32 | 4-amino-6-(4-fluoro-2-methyl-1H-indol-5-yloxy)-pyrimidine-5-carbaldehyde O-cyclopropylmethyl-oxime<br>$^1$H NMR(400MHz, CD$_3$COCD$_3$) δ 10.35(s, 1H), 8.70(s, 1H), 7.95(s, 1H), 7.85(s, 1H), 7.10(d, 1H), 6.90(t, 1H), 6.20(s, 1H), 4.00(d, 2H), 2.42(s, 3H), 1.20(m, 1H), 0.60(m, 2H), 0.30(m, 2H). MS(ESI) m/z: 356(M+H$^+$) |

-continued

| Cpd | Name and Data |
|---|---|
| 33 | 4-amino-6-(4-fluoro-2-methyl-1H-indol-5-yloxy)-pyrimidine-5-carbaldehyde O-(3-methoxy-propyl)-oxime<br>$^1$H NMR(300MHz, DMSO-d$_6$) δ 11.25(s, 1H), 8.60(s, 1H), 8.10(s, 1H), 8.00(s, 1H), 7.55(s, 1H), 7.10(d, 1H), 6.85(t, 1H), 6.20(s, 1H), 4.25(t, 2H), 3.45(t, 2H), 3.25(s, 3H), 2.40(s, 3H), 1.90(m, 2H). MS(ESI) m/z: 374(M+H$^+$) |
| 34 | 4-amino-6-(4-fluoro-2-methyl-1H-indol-5-yloxy)-pyrimidine-5-carbaldehyde O-propyl-oxime<br>$^1$H NMR(300MHz, CD$_3$COCD$_3$) δ 10.40(s, 1H), 8.70(s, 1H), 8.00(s, 1H), 7.85(s, 1H), 7.20(s, 1H), 7.10(d, 1H), 6.90(t, 1H), 6.25(s, 1H), 4.20(t, 2H), 2.50(s, 3H), 1.80(m, 2H), 1.00(t, 2H). MS(ESI) m/z: 344(M+H$^+$) |
| 35 | 4-amino-6-(4-fluoro-2-methyl-1H-indol-5-yloxy)-pyrimidine-5-carbaldehyde O-cyclohexylmethyl-oxime<br>$^1$H NMR(300MHz, CDCl$_3$) δ 8.75(s, 1H), 8.15(s, 1H), 8.00(s, 1H), 7.90(s, 1H), 7.05(d, 1H), 6.85(t, 1H), 6.30(s, 1H), 5.75(s, 1H), 4.00(d, 2H), 2.45(s, 3H), 1.90-1.70(m, 5H), 1.30(m, 6H). MS(ESI) m/z: 398(M+H$^+$) |
| 36 | 4-amino-6-(4-fluoro-2-methyl-1H-indol-5-yloxy)-pyrimidine-5-carbaldehyde O-benzyl-oxime<br>$^1$H NMR(300MHz, CDCl$_3$) δ 8.82(s, 1H), 8.15(s, 1H), 8.05(s, 1H), 7.80(s, 1H), 7.40(m, 5H), 7.05(d, 1H), 6.90(t, 1H), 6.35(s, 1H), 5.70(s, 1H), 2.40(s, 3H). MS(ESI) m/z: 392(M+H$^+$) |
| 37 | 4-amino-6-(4-fluoro-2-methyl-1H-indol-5-yloxy)-pyrimidine-5-carbaldehyde O-butyl-oxime<br>$^1$H NMR(400MHz, CDCl$_3$) δ 8.72(s, 1H), 8.12(s, 1H), 8.00(s, 1H), 7.90(s, 1H), 7.05(d, 1H), 6.85(t, 1H), 6.30(s, 1H), 5.70(s, 1H), 4.15(t, 2H), 2.45(s, 3H), 1.70(p, 2H), 1.45(p, 2H), 1.25(t, 3H). MS(ESI) m/z: 358(M+H$^+$) |
| 38 | 4-amino-6-(4-fluoro-2-methyl-1H-indol-5-yloxy)-pyrimidine-5-carbaldehyde O-(4-hydroxy-butyl)-oxime<br>$^1$H NMR(300MHz, DMSO-d$_6$) δ 11.30(s, 1H), 8.60(s, 1H), 8.10(s, 1H), 7.95(s, 1H), 7.60(s, 1H), 7.05(d, 1H), 6.85(t, 1H), 6.18(s, 1H), 4.45(t, 1H), 4.20(t, 2H), 3.45(q, 2H), 2.38(s, 3H), 1.70(p, 2H), 1.50(p, 2H). MS(ESI) m/z: 374(M+H$^+$) |

EXAMPLE 8

5-[6-amino-5-(methoxyimino-methyl)-pyrimidin-4-yloxy]-2-methyl-indole-1-carboxylic acid (2-hydroxy-ethyl)-amide (Cpd 39)

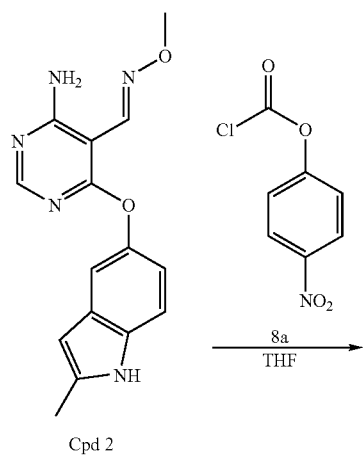

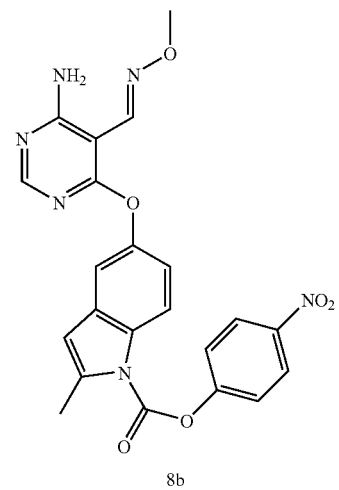

Compound 2 (46 mg in 1 mL THF) was added to a suspension of NaH (7.4 mg) in THF (5 mL) at 0° C. After stirring at 0° C. for 1 hr, the mixture was cannulated to a solution of 4-nitro-phenyl chloroformate Compound 8a (34 mg) in THF (5 mL) at 0° C. After 1 hr, the mixture was filtered and the filtrate was concentrated, then the residue was purified by flash chromatography (silica gel, hexane:EtOAc/5:5) to afford 5-[6-amino-5-(methoxyimino-methyl)-pyrimidin-4-yloxy]-2-methyl-indole-1-carboxylic acid 4-nitro-phenyl ester Compound 8b (8.6 mg, 12%). $^1$H NMR (400 MHz, CDCl$_3$) δ 8.70 (s, 1H), 8.38 (d, 2H), 8.15 (s, 1H), 7.50 (d, 2H), 7.21 (d, 1H), 7.02 (dd, 1H), 6.88 (d, 1H), 6.48 (s, 1H), 4.00 (s, 3H), 2.68 (s, 3H). MS (ESI) m/z: 463 (M+H$^+$).

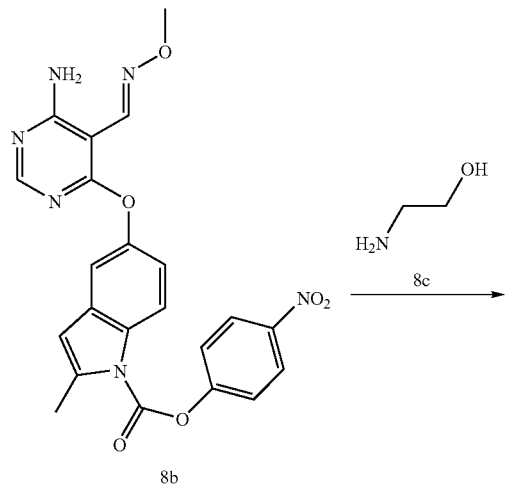

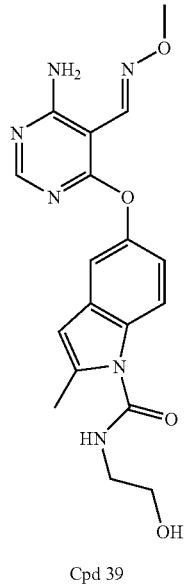

Cpd 39

Compound 8b (6 mg), 2-amino-ethanol Compound 8c (1.6 mg) and THF (1 mL) were added to a flask. The mixture was stirred for 2 hrs, then poured into H$_2$O and extracted with EtOAc. The organic layer was separated, dried with MgSO$_4$, then concentrated and the residue was purified by flash chromatography (silica gel, EtOAc) to afford Compound 39 (40 mg, 86%). $^1$H NMR (300 MHz, CDCl$_3$) δ 8.70 (s, 1H), 8.12 (s, 1H), 7.90 (s, 1H), 7.70 (d, 1H), 7.20 (d, 1H), 6.95 (dd, 1H), 6.30 (s, 1H), 6.10 (t, 1H), 5.80 (s, 1H), 3.90 (m, 2H), 3.65 (q, 2H), 2.60 (s, 3H). MS (ESI) m/z: 386 (M+H$^+$).

Using the procedure of Example 8, other compounds representative of the present invention may be prepared:

| Cpd | Name and Data |
|---|---|
| 40 | 5-[6-amino-5-(methoxyimino-methyl)-pyrimidin-4-yloxy]-2-methyl-indole-1-carboxylic acid(3-hydroxy-propyl)-amide<br>$^1$H NMR(300MHz, CDCl$_3$) δ 8.70(s, 1H), 8.10(s, 1H), 7.69(d, 1H), 7.18(d, 1H), 6.90(dd, 1H), 6.30(s, 1H), 6.25(m, 1H), 4.00(s, 3H), 3.85(m, 2H), 3.65(m, 2H), 2.60(s, 3H), 1.90(m, 2H). MS(ESI) m/z: 399(M+H$^+$) |
| 41 | 5-[6-amino-5-(methoxyimino-methyl)-pyrimidin-4-yloxy]-2-methyl-indole-1-carboxylic acid(2-dimethylamino-ethyl)-amide<br>$^1$H NMR(300MHz, CDCl$_3$) δ 8.70(s, 1H), 8.12(s, 1H), 7.90(s, 1H), 7.75(d, 1H), 7.20(d, 1H), 6.95(dd, 1H), 6.50(s, 1H), 6.30(s, 1H), 5.90(s, 1H), 4.00(s, 3H), 3.60(q, 2H), 2.65(t, 2H), 2.60(s, 3H), 2.30(s, 6H). MS(ESI) m/z: 412(M+H$^+$) |
| 42 | 5-[6-amino-5-(methoxyimino-methyl)-pyrimidin-4-yloxy]-2-methyl-indole-1-carboxylic acid(4-pyrrolidin-1-yl-butyl)-amide<br>$^1$H NMR(300MHz, CDCl$_3$) δ 8.70(s, 1H), 8.11(s, 1H), 7.90(s, 1H), 7.65(d, 1H), 7.40(s, 1H), 7.20(s, 1H), 6.90(dd, 1H), 6.30(s, 1H), 5.70(s, 1H), 4.00(s, 3H), 2.75(m, 4H), 2.60(m, 5H), 2.50(t, 2H), 2.10(m, 4H), 1.90(m, 2H), 1.85(m, 2H). MS(ESI) m/z: 466(M+H$^+$) |

EXAMPLE 9

5-[6-amino-5-(methoxyimino-methyl)-pyrimidin-4-yloxy]-4-fluoro-2-methyl-indole-1-carboxylic acid methylamide (Cpd 43)

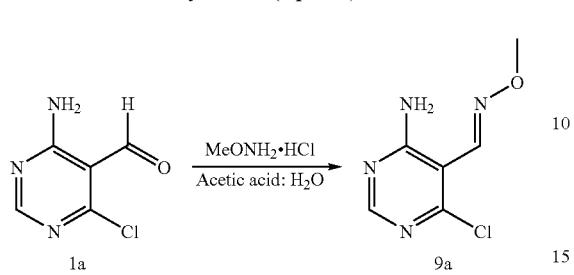

4-amino-6-chloro-pyrimidine-5-carbaldehyde Compound 1a (1.0 g), O-methyl-hydroxylamine hydrochloride (0.94 g) and a mixed solvent of acetic acid (25 mL) and H$_2$O (4 mL) were added to a flask. The mixture was stirred at rt overnight, then concentrated. The residue was suspended in H$_2$O and extracted with EtOAc. The organic layer was separated, dried with MgSO$_4$, then concentrated to afford 4-amino-6-chloro-pyrimidine-5-carbaldehyde O-methyl-oxime Compound 9a (0.97 g, 92%). $^1$H NMR (300 MHz, DMSO-d$_6$) δ 8.55 (s, 1H), 8.50 (s, 1H), 8.25 (s, 1H), 7.70 (s, 1H), 3.98 (s, 3H). MS (ESI) m/z: 188 (M+H$^+$).

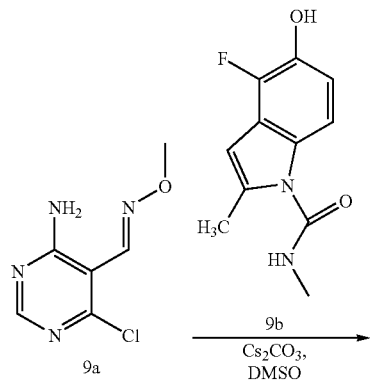

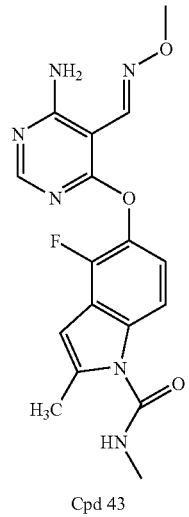

Cpd 43

Compound 9a (9.0 mg), 4-fluoro-5-hydroxy-2-methyl-indole-1-carboxylic acid methylamide Compound 9b (11 mg), cesium carbonate (16 mg) and DMSO (2 mL) were added to a flask. The mixture was stirred for 2 hrs, then poured into water and extracted with EtOAc. The organic layer was separated, dried with MgSO$_4$, then concentrated and the residue was purified by flash chromatography (silica gel, hexane: EtOAc/5:5) to provide Compound 43 (14 mg, 78%). $^1$H NMR (300 MHz, CDCl$_3$) δ 10.30 (s, 1H), 9.25 (s, 1H), 8.70 (s, 1H), 8.28 (s, 1H), 8.05 (s, 1H), 7.05 (d, 1H), 6.88 (t, 1H), 6.30 (s, 1H), 4.10 (s, 3H), 3.00 (d, 3H), 2.45 (s, 3H). MS (ESI) m/z: 374 (M+H$^+$).

Using the procedure of Example 9, other compounds representative of the present invention may be prepared:

| Cpd | Name and Data |
|---|---|
| 44 | 5-[6-amino-5-(methoxyimino-methyl)-pyrimidin-4-yloxy]-2-methyl-indole-1-carboxylic acid isopropylamide<br>$^1$H NMR(300MHz, CD$_3$COCD$_3$) δ 10.15(s, 1H), 10.00(s, 1H), 9.20(s, 1H), 8.67(s, 1H), 8.25(s, 1H), 7.32(d, 1H), 7.20(d, 1H), 6.85(dd, 1H), 6.20(s, 1H), 4.05(s, 3H), 4.00(m, 1H), 2.45(s, 3H), 1.22(d, 6H). MS(ESI) m/z: 381(M+H$^+$) |
| 45 | 5-[6-amino-5-(methoxyimino-methyl)-pyrimidin-4-yloxy]-2-methyl-indole-1-carboxylic acid prop-2-ynylamide<br>$^1$H NMR(300MHz, CD$_3$COCD$_3$) δ 10.15(s, 2H), 9.60(s, 1H), 8.65(s, 1H), 8.25(s, 1H), 7.30(d, 1H), 7.20(d, 1H), 6.85(dd, 1H), 6.20(s, 1H), 4.15(m, 2H), 4.05(s, 3H), 2.70(m, 1H), 2.45(s, 3H). MS(ESI) m/z: 379(M+H$^+$) |
| 46 | 5-[6-amino-5-(methoxyimino-methyl)-pyrimidin-4-yloxy]-2-methyl-indole-1-carboxylic acid cyclopropylamide<br>$^1$H NMR(300MHz, DMSO-d$_6$) δ 11.00(s, 1H), 9.95(s, 1H), 9.30(s, 1H), 8.60(s, 1H), 8.32(s, 1H), 7.25(d, 1H), 7.18(d, 1H), 6.80(dd, 1H), 6.12(s, 1H), 4.00(s, 3H), 2.75(m, 1H), 2.40(s, 3H), 0.75(m, 2H), 0.55(m, 2H). MS(ESI) m/z: 381(M+H$^+$) |

-continued

| Cpd | Name and Data |
|---|---|
| 47 | 5-[6-amino-5-(methoxyimino-methyl)-pyrimidin-4-yloxy]-2-methyl-indole-1-carboxylic acid benzylamide<br>$^1$H NMR(400MHz, CD$_3$COCD$_3$) δ 7.85(s, 1H), 7.60(s, 1H), 7.50(m, 4H), 7.38(m, 3H), 7.30(t, 1H), 6.85(d, 1H), 6.65(dd, 1H), 6.20(s, 1H), 4.55(d, 2H), 2.86(s, 3H), 2.50(s, 3H). MS(ESI) m/z: 431(M+H$^+$) |
| 67 | 4-amino-6-(4-hydroxy-phenoxy)-pyrimidine-5-carbaldehyde O-methyl-oxime<br>$^1$H NMR(400MHz, DMSO-d$_6$) δ 9.38(s, 1H), 8.50(s, 1H), 8.10(s, 1H), 8.00(s, 1H), 7.50(s, 1H), 6.95(d, 2H), 6.72(d, 2H), 3.90(s, 3H). MS(ESI) m/z: 260(M+H$^+$) |

EXAMPLE 10

1-{4-[6-amino-5-(methoxyimino-methyl)-pyrimidin-4-yloxy]-2-chloro-phenyl}-3-ethyl-urea (Cpd 50)

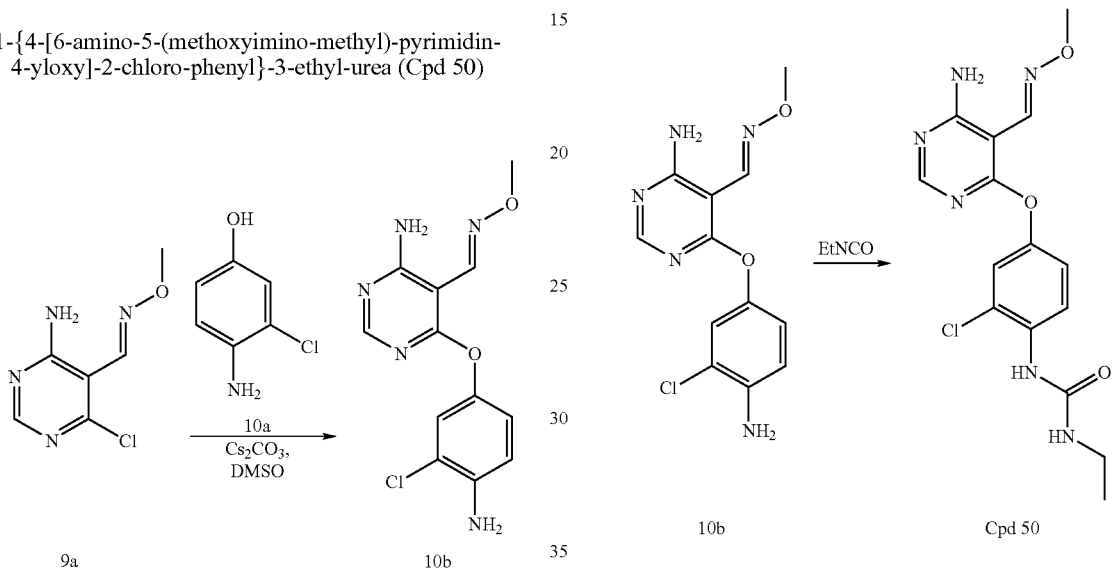

Using the procedure for Example 9, 4-amino-6-chloro-pyrimidine-5-carbaldehyde O-methyl-oxime Compound 9a (0.20 g) and 4-amino-3-chloro-phenol Compound 10a (0.19 g) were reacted to provide 4-amino-6-(4-amino-3-chloro-phenoxy)-pyrimidine-5-carbaldehyde O-methyl-oxime Compound 10b (0.20 g, 65%). $^1$H NMR (400 MHz, DMSO-d$_6$) δ 8.55 (s, 1H), 8.15 (s, 1H), 8.05 (s, 1H), 7.60 (s, 1H), 7.15 (s, 1H), 6.90 (d, 1H), 6.80 (d, 1H), 5.32 (s, 2H), 3.98 (s, 3H). MS (ESI) m/z: 299 (M+H$^+$).

Compound 10b (30 mg), isocyanato-ethane (15 mg) and THF (5 mL) were added to a screw cap tube. The mixture was heated to 50° C. for 4 hrs. The solvent was removed in vacuo and the residue washed with DCM to afford Compound 50 (31 mg, 82%). $^1$H NMR (300 MHz, DMSO-d$_6$) δ 8.50 (s, 1H), 8.15 (s, 1H), 8.08 (d, 1H), 8.06 (s, 1H), 7.95 (s, 1H), 7.60 (s, 1H), 7.30 (d, 1H), 7.10 (dd, 1H), 6.90 (t, 1H), 3.95 (s, 3H), 3.10 (p, 2H), 1.10 (t, 3H). MS (ESI) m/z: 365 (M+H$^+$).

Using the procedure of Example 10, other compounds representative of the present invention may be prepared:

| Cpd | Name and Data |
|---|---|
| 51 | 1-{4-[6-amino-5-(methoxyimino-methyl)-pyrimidin-4-yloxy]-2-chloro-phenyl}-3-methyl-urea<br>$^1$H NMR(400MHz, DMSO-d$_6$) δ 8.50(s, 1H), 8.15(br, 1H), 8.08(d, 1H), 8.05(s, 1H), 8.00(s, 1H), 7.58(br, 1H), 7.31(s, 1H), 7.08(d, 1H), 6.78(m, 1H), 3.95(s, 3H), 2.60(d, 3H). MS(ESI) m/z: 351(M+H$^+$) |
| 52 | 1-{4-[6-amino-5-(methoxyimino-methyl)-pyrimidin-4-yloxy]-2-chloro-phenyl}-3-propyl-urea<br>$^1$H NMR(400MHz, DMSO-d$_6$) δ 8.50(s, 1H), 8.15(br, 1H), 8.10(d, 1H), 8.05(s, 1H), 8.00(s, 1H), 7.58(br, 1H), 7.31(s, 1H), 7.07(d, 1H), 6.94(t, 1H), 3.95(s, 3H), 3.07(q, 2H), 1.45(q, 2H), 0.89(t, 3H). MS(ESI) m/z: 379(M+H$^+$) |
| 53 | 1-allyl-3-{4-[6-amino-5-(methoxyimino-methyl)-pyrimidin-4-yloxy]-2-chloro-phenyl}-urea<br>$^1$H NMR(400MHz, DMSO-d$_6$) δ 8.52(s, 1H), 8.25(br, 1H), 8.07(m, 3H), 7.59(br, 1H), 7.33(s, 1H), 7.07(m, 2H), 5.87(m, 1H), 5.20(d, 1H), 5.10(d, 1H), 3.93(s, 3H), 3.75(t, 2H), 1.45(q, 2H), 0.89(t, 3H). MS(ESI) m/z: 377(M+H$^+$), 399(M+Na$^+$) |
| 54 | 1-{4-[6-amino-5-(methoxyimino-methyl)-pyrimidin-4-yloxy]-2-chloro-phenyl}-3-phenyl-urea |

| Cpd | Name and Data |
|---|---|
|  | ¹H NMR(400MHz, DMSO-d₆) δ 9.36(s, 1H), 8.52(s, 1H), 8.30(s, 1H), 8.15(br, 1H), 8.11(d, 1H), 8.08(s, 1H), 7.58(br, 1H), 7.45(d, 2H), 7.40(s, 1H), 7.29(t, 2H), 7.14(d, 1H), 6.98(t, 1H), 3.95(s, 3H). MS(ESI) m/z: 413(M+H⁺) |
| 55 | 1-{4-[6-amino-5-(methoxyimino-methyl)-pyrimidin-4-yloxy]-2-chloro-phenyl}-3-(2-chloro-phenyl)-urea<br>¹H NMR(400MHz, DMSO-d₆) δ 9.07(s, 1H), 8.98(s, 1H), 8.53(s, 1H), 8.20(br, 1H), 8.10(d, 1H), 8.08(s, 1H), 8.03(d, 1H), 7.60(br, 1H), 7.47(d, 1H), 7.40(s, 1H), 7.30(t, 1H), 7.16(d, 1H), 7.06(t, 1H), 3.95(s, 3H). MS(ESI) m/z: 447(M+H⁺) |
| 56 | 1-{4-[6-amino-5-(methoxyimino-methyl)-pyrimidin-4-yloxy]-2-chloro-phenyl}-3-(2-fluoro-phenyl)-urea<br>¹H NMR(400MHz, DMSO-d₆) δ 9.30(s, 1H), 8.80(s, 1H), 8.53(s, 1H), 8.18(m, 3H), 8.10(s, 1H), 7.60(br, 1H), 7.40(s, 1H), 7.25(t, 1H), 7.18(m, 2H), 7.05(m, 1H), 3.94(s, 3H). MS(ESI) m/z: 431(M+H⁺) |
| 57 | 1-{4-[6-amino-5-(methoxyimino-methyl)-pyrimidin-4-yloxy]-2-chloro-phenyl}-3-(3-fluoro-phenyl)-urea<br>¹H NMR(400MHz, DMSO-d₆) δ 9.57(s, 1H), 8.51(s, 1H), 8.38(s, 1H), 8.18(s, 1H), 8.09(d, 1H), 8.05(s, 1H), 7.60(br, 1H), 7.50(d, 1H), 7.40(s, 1H), 7.30(q, 1H), 7.15(d, 1H), 7.10(d, 1H), 6.80(t, 1H), 3.95(s, 3H). MS(ESI) m/z: 431(M+H⁺) |
| 58 | 1-{4-[6-amino-5-(methoxyimino-methyl)-pyrimidin-4-yloxy]-2-chloro-phenyl}-3-(2-methoxy-phenyl)-urea<br>¹H NMR(400MHz, DMSO-d₆) δ 8.93(d, 2H), 8.51(s, 1H), 8.20(br, 1H), 8.10(m, 2H), 8.05(d, 1H), 7.50(br, 1H), 7.40(s, 1H), 7.15(d, 1H), 7.05(d, 1H), 6.98(t, 1H), 6.90(t, 1H), 3.95(s, 3H), 3.90(s, 3H). MS(ESI) m/z: 443(M+H⁺) |
| 59 | 1-{4-[6-amino-5-(methoxyimino-methyl)-pyrimidin-4-yloxy]-2-chloro-phenyl}-3-(3-chloro-phenyl)-urea<br>¹H NMR(400MHz, DMSO-d₆) δ 9.55(s, 1H), 8.54(s, 1H), 8.40(s, 1H), 8.20(br, 1H), 8.10(m, 2H), 7.75(s, 1H), 7.60(br, 1H), 7.42(s, 1H), 7.33(t, 1H), 7.25(d, 1H), 7.18(d, 1H), 7.05(d, 1H), 3.95(s, 3H). MS(ESI) m/z: 447(M+H⁺) |
| 60 | 1-{4-[6-amino-5-(methoxyimino-methyl)-pyrimidin-4-yloxy]-2-chloro-phenyl}-3-(4-fluoro-phenyl)-urea<br>¹H NMR(400MHz, DMSO-d₆) δ 9.40(s, 1H), 8.54(s, 1H), 8.30(s, 1H), 8.20(br, 1H), 8.10(d, 1H), 8.08(s, 1H), 7.62(br, 1H), 7.49(m, 2H), 7.40(s, 1H), 7.15(m, 3H), 3.95(s, 3H). MS(ESI) m/z: 429(M−H⁻) |
| 61 | 1-{4-[6-amino-5-(methoxyimino-methyl)-pyrimidin-4-yloxy]-2-chloro-phenyl}-3-(2,4-difluoro-phenyl)-urea<br>¹H NMR(400MHz, DMSO-d₆) δ 9.25(s, 1H), 8.75(s, 1H), 8.53(s, 1H), 8.20(br, 1H), 8.10(m, 3H), 7.62(br, 1H), 7.50(s, 1H), 7.40(s, 1H), 7.35(t, 1H), 7.16(d, 1H), 7.05(t, 1H), 3.95(s, 3H). MS(ESI) m/z: 471(M+Na⁺) |
| 62 | 1-{4-[6-amino-5-(methoxyimino-methyl)-pyrimidin-4-yloxy]-2-chloro-phenyl}-3-(4-methoxy-phenyl)-urea<br>¹H NMR(400MHz, DMSO-d₆) δ 9.20(s, 1H), 8.54(s, 1H), 8.25(s, 1H), 8.18(br, 1H), 8.13(d, 1H), 8.08(s, 1H), 7.60(br, 1H), 7.37(m, 3H), 7.15(d, 1H), 6.90(d, 1H), 3.95(s, 3H), 3.73(s, 3H). MS(ESI) m/z: 465(M+Na⁺) |
| 63 | 1-{4-[6-amino-5-(methoxyimino-methyl)-pyrimidin-4-yloxy]-2-chloro-phenyl}-3-(4-methoxy-phenyl)-urea<br>¹H NMR(400MHz, DMSO-d₆) δ 9.48(s, 1H), 8.54(s, 1H), 8.35(s, 1H), 8.12(br, 1H), 8.09(m, 2H), 7.63(br, 1H), 7.51(d, 2H), 7.40(s, 1H), 7.36(d, 2H), 7.16(d, 1H), 3.96(s, 3H), 3.73(s, 3H). MS(ESI) m/z: 469(M+Na⁺) |
| 64 | 1-{4-[6-amino-5-(methoxyimino-methyl)-pyrimidin-4-yloxy]-2-chloro-phenyl}-3-butyl-urea<br>¹H NMR(400MHz, DMSO-d₆) δ 8.52(s, 1H), 8.16(br, 1H), 8.12(d, 1H), 8.08(s, 1H), 7.98(s, 1H), 7.60(br, 1H), 7.33(s, 1H), 7.08(d, 1H), 6.94(t, 1H), 3.95(s, 3H), 3.12(q, 2H), 1.45(m, 2H), 1.35(m, 2H), 0.90(t, 3H). MS(ESI) m/z: 415(M+Na⁺) |
| 65 | 1-{4-[6-amino-5-(methoxyimino-methyl)-pyrimidin-4-yloxy]-2-chloro-phenyl}-3-cyclohexyl-urea<br>¹H NMR(400MHz, DMSO-d₆) δ 8.50(s, 1H), 8.16(br, 1H), 8.12(d, 1H), 8.05(s, 1H), 7.94(s, 1H), 7.58(br, 1H), 7.30(s, 1H), 7.07(d, 1H), 6.93(t, 1H), 3.95(s, 3H), 3.47(m, 1H), 1.71(m, 2H), 1.65(m, 2H), 1.54(m, 1H), 1.38-1.10(m, 5H). MS(ESI) m/z: 419(M+H⁺) 441(M+Na⁺) |
| 69 | 1-{4-[6-amino-5-(methoxyimino-methyl)-pyrimidin-4-yloxy]-phenyl}-3-ethyl-urea<br>¹H NMR(400MHz, DMSO-d₆) δ 8.53(s, 1H), 8.44(s, 1H), 8.11(br, 1H), 8.03(s, 1H), 8.05(s, 1H), 7.55(br, 1H), 7.37(d, 2H), 7.00(d, 2H), 6.07(t, 1H), 3.93(s, 3H), 3.10(m, 2H), 1.05(t, 3H). MS(ESI) m/z: 353(M+Na⁺) |
| 71 | 1-{4-[6-amino-5-(methoxyimino-methyl)-pyrimidin-4-yloxy]-3-chloro-phenyl}-3-ethyl-urea<br>¹H NMR(400MHz, DMSO-d₆) δ 8.66(s, 1H), 8.57(s, 1H), 8.20(br, 1H), 8.05(s, 1H), 7.75(s, 1H), 7.60(br, 1H), 7.20(m, 2H), 6.20(t, 1H), 3.95(s, 3H), 3.15(p, 1H), 1.08(t, 3H). MS(ESI) m/z: 365(M+H⁺) |
| 74 | 1-{4-[6-amino-5-(methoxyimino-methyl)-pyrimidin-4-yloxy]-2-bromo-phenyl}-3-(4-fluoro-phenyl)-urea<br>¹H NMR(400MHz, DMSO-d₆) δ 9.05(s, 1H), 8.60(s, 1H), 8.25(br, 1H), 8.20(s, 1H), 8.15(d, 1H), 8.10(s, 1H), 7.60(br, 1H), 7.42(m, 4H), 7.10(t, 2H), 3.97(s, 3H). MS(ESI) m/z: 497(M+H⁺) |

EXAMPLE 11

1-{4-[6-amino-5-(methoxyimino-methyl)-pyrimidin-4-yloxy]-2-methyl-phenyl}-3-ethyl-urea (Cpd 66)

Using the procedure for Example 9, Compound 9a (0.20 g) and 4-amino-3-methyl-phenol (0.13 g) were reacted to afford 4-amino-6-(4-amino-3-methyl-phenoxy)-pyrimidine-5-carbaldehyde O-methyl-oxime Compound 11a (0.20 g, 68%). $^1$H NMR (400 MHz, DMSO-$d_6$) δ 8.50 (s, 1H), 8.05 (s, 1H), 8.00 (s, 1H), 7.50 (s, 1H), 6.71 (s, 1H), 6.65 (d, 1H), 6.58 (d, 1H), 4.75 (s, 2H), 3.90 (s, 3H), 2.03 (s, 3H). MS (ESI) m/z: 274 (M+H$^+$).

Using the procedure for Example 10, Compound 11a (30 mg) and isocyanato-ethane (15 mg) were reacted to provide Compound 66 (12 mg, 34%). $^1$H NMR (300 MHz, CD$_3$COCD$_3$) δ 8.60 (s, 1H), 7.96 (s, 1H), 7.90 (d, 1H), 7.75 (s, 1H), 7.10 (s, 1H), 6.90 (m, 2H), 5.95 (s, 1H), 3.95 (s, 3H), 3.25 (p, 2H), 2.20 (s, 3H), 1.10 (t, 3H). MS (ESI) m/z: 345 (M+H$^+$).

EXAMPLE 12

1-{4-[6-amino-5-(methoxyimino-methyl)-pyrimidin-4-yloxy]-phenyl}-3-methyl-urea (Cpd 68)

Using the procedure for Example 9, Compound 9a (0.20 g) and 4-amino-phenol (0.16 g) were reacted to provide 4-amino-6-(4-amino-phenoxy)-pyrimidine-5-carbaldehyde O-methyl-oxime Compound 12a (0.17 g, 62%). $^1$H NMR (300 MHz, DMSO-$d_6$) δ 8.50 (s, 1H), 8.10 (s, 1H), 8.00 (s, 1H), 7.50 (s, 1H), 6.80 (d, 2H), 6.55 (d, 2H), 5.00 (s, 2H), 3.90 (s, 3H). MS (ESI) m/z: 260 (M+H$^+$).

Using the procedure for Example 10, Compound 12a (55 mg) and isocyanatomethane (45 mg) were reacted to provide Compound 68 (45 mg, 67%). $^1$H NMR (400 MHz, DMSO-$d_6$) δ 8.52 (s, 2H), 8.10 (br, 1H), 8.05 (s, 1H), 7.58 (br, 1H), 7.38 (d, 2H), 7.00 (d, 2H), 5.99 (m, 1H), 3.93 (s, 3H), 2.61 (d, 3H). MS (ESI) m/z: 317 (M+H$^+$).

EXAMPLE 13

1-{4-[6-amino-5-(methoxyimino-methyl)-pyrimidin-4-yloxy]-3-chloro-phenyl}-3-methyl-urea (Cpd 70)

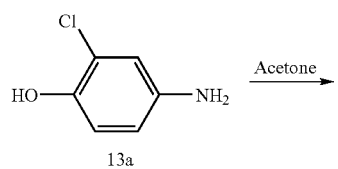

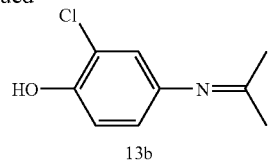

4-amino-2-chloro-phenol Compound 13a was refluxed with acetone to provide 2-chloro-4-isopropylideneamino-phenol Compound 13b in quantitative yield. MS (ESI) m/z: 185 (M+H$^+$).

Using the procedure for Example 9, Compound 9a and Compound 13b were reacted to provide 4-amino-6-(4-amino-2-chloro-phenoxy)-pyrimidine-5-carbaldehyde O-methyl-oxime Compound 13c. MS (ESI) m/z: 294 (M+H$^+$).

Using the procedure for Example 10, Compound 13c (50 mg) and isocyanatomethane (45 mg) were reacted to provide Compound 70 (36 mg, 60%). $^1$H NMR (300 MHz, DMSO-$d_6$) δ 8.76 (s, 1H), 8.57 (s, 1H), 8.20 (br, 1H), 8.05 (s, 1H), 7.75 (s, 1H), 7.60 (br, 1H), 7.25 (d, 1H), 7.18 (d, 1H), 6.12 (m, 1H), 3.95 (s, 3H), 2.65 (d, 3H). MS (ESI) m/z: 351 (M+H$^+$), 373 (M+Na$^+$).

EXAMPLE 14

1-{4-[6-amino-5-(methoxyimino-methyl)-pyrimidin-4-yloxy]-2-fluoro-phenyl}-3-methyl-urea (Cpd 72)

Using the procedure for Example 13, 4-amino-3-fluoro-phenol Compound 14a was refluxed with acetone to provide 3-fluoro-4-isopropylideneamino-phenol Compound 14b in quantitative yield. MS (ESI) m/z: 168 (M+H$^+$).

Using the procedure for Example 9, Compound 9a and Compound 14b were reacted to provide 4-amino-6-(4-amino-3-fluoro-phenoxy)-pyrimidine-5-carbaldehyde O-methyl-oxime Compound 14c. MS (ESI) m/z: 278 (M+H$^+$).

Using the procedure for Example 10, Compound 14c (75 mg) and isocyanatomethane (45 mg) were reacted to provide Compound 72 (7.1 mg, 8%). $^1$H NMR (400 MHz, DMSO-$d_6$) δ 8.54 (s, 1H), 8.30 (s, 1H), 8.18 (br, 1H), 8.05 (m, 2H), 7.60 (br, 1H), 7.15 (d, 1H), 6.94 (d, 1H), 6.42 (t, 1H), 3.95 (s, 3H), 2.65 (t, 3H). MS (ESI) m/z: 335 (M+H$^+$).

EXAMPLE 15

1-{4-[6-amino-5-(methoxyimino-methyl)-pyrimidin-4-yloxy]-2-bromo-phenyl}-3-methyl-urea (Cpd 73)

Using the procedure for Example 9, Compound 9a and 4-amino-3-bromo-phenol Compound 15a were reacted to provide 4-amino-6-(4-amino-3-bromo-phenoxy)-pyrimidine-5-carbaldehyde O-methyl-oxime Compound 15b.

Using the procedure for Example 10, Compound 15b (30 mg) and isocyanatomethane (45 mg) were reacted to provide Compound 73 (16 mg, 46%). $^1$H NMR (400 MHz, DMSO-$d_6$) δ 8.56 (s, 1H), 8.20 (br, 1H), 8.15 (d, 1H), 8.07 (s, 1H), 7.92 (s, 1H), 7.62 (br, 1H), 7.33 (s, 1H), 7.31 (d, 1H), 6.54 (m, 1H), 3.97 (s, 3H), 2.60 (d, 3H).

MS (ESI) m/z: 397 (M+H$^+$).

EXAMPLE 16

1-{4-[6-amino-5-(methoxyimino-methyl)-pyrimidin-4-yloxy]-2-chloro-phenyl}-3-o-tolyl-urea (Cpd 75)

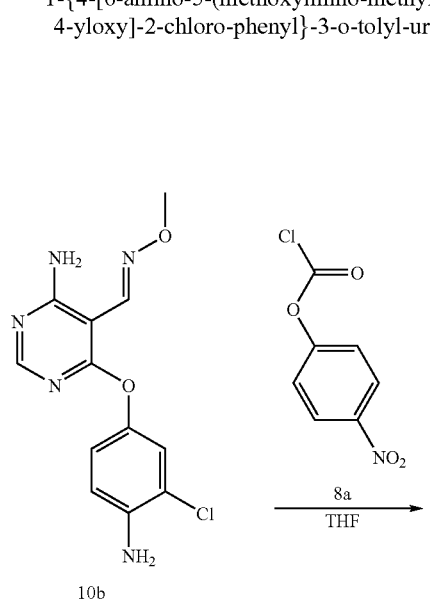

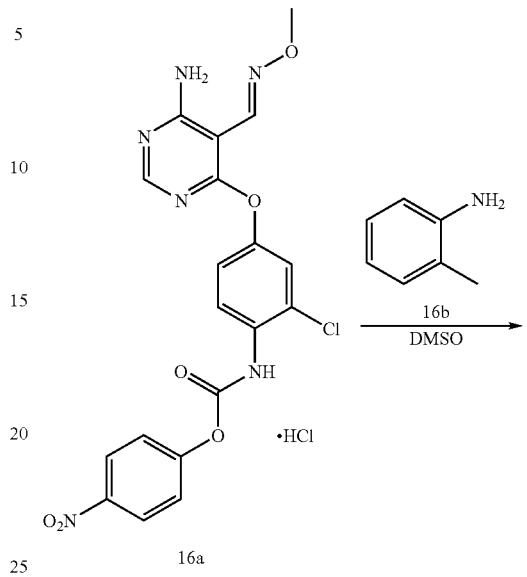

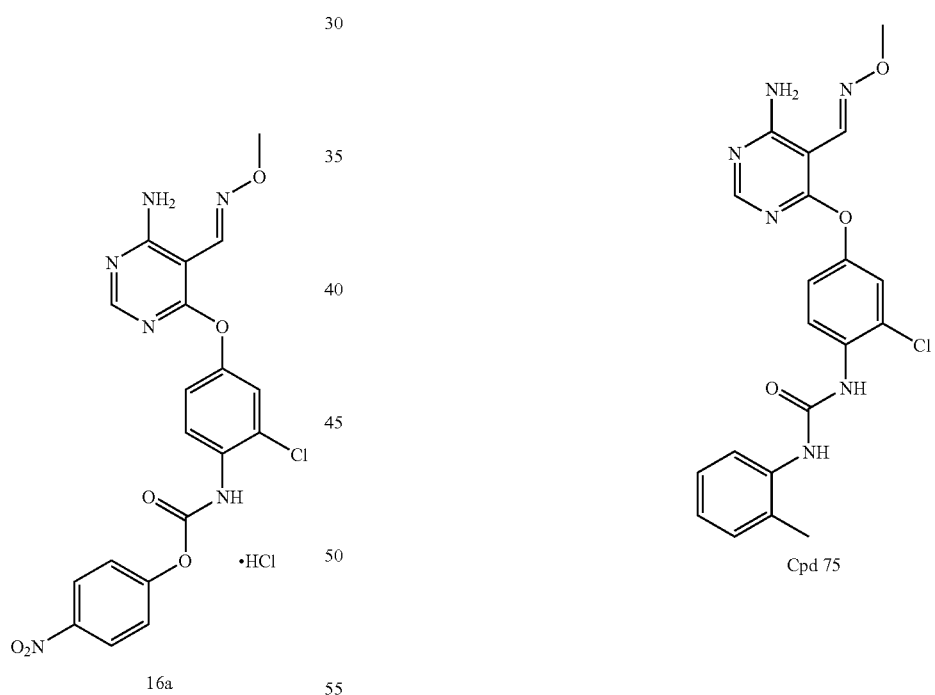

4-amino-6-(4-amino-3-chloro-phenoxy)-pyrimidine-5-carbaldehyde O-methyl-oxime Compound 10b, 4-nitro-phenyl chloroformate Compound 8a and THF were added to a flask. The mixture was stirred at rt for 3 hrs and the product {4-[6-amino-5-(methoxyimino-methyl)-pyrimidin-4-yloxy]-2-chloro-phenyl}-carbamic acid 4-nitro-phenyl ester Compound 16a was collected by filtration, then air dried.

Compound 16a (50 mg), o-tolylamine Compound 16b (48 mg) and DMSO (1 mL) were added to a flask. The mixture was stirred at rt for 1 hr, then poured into water and extracted with EtOAc. The organic layer was separated, dried with $MgSO_4$, then concentrated and the residue washed with organic solvent to afford Compound 75 (29 mg, 67%). $^1$H NMR (400 MHz, DMSO-$d_6$) δ 8.67 (s, 1H), 8.57 (s, 1H), 8.51 (s, 1H), 8.16 (br, 1H), 8.08 (t, 2H), 8.05 (s, 1H), 7.77 (d, 1H), 7.57 (br, 1H), 7.38 (s, 1H), 7.15 (m, 3H), 6.95 (t, 1H), 3.95 (s, 3H), 2.25 (s, 3H). MS (ESI) m/z: 427 (M+H$^+$).

Using the procedure of Example 16, other compounds representative of the present invention may be prepared:

| Cpd | Name and Data |
|---|---|
| 76 | 1-{4-[6-amino-5-(methoxyimino-methyl)-pyrimidin-4-yloxy]-2-chloro-phenyl}-3-m-tolyl-urea
$^1$H NMR(400MHz, DMSO-d$_6$) δ 9.30(s, 1H), 8.52(s, 1H), 8.30(s, 1H), 8.16(br, 1H), 8.11(d, 1H), 8.07(s, 1H), 7.57(br, 1H), 7.38(s, 1H), 7.30(s, 1H), 7.24(d, 1H), 7.15(m, 2H), 6.80(d, 1H), 3.95(s, 3H), 2.28(s, 3H). MS(ESI) m/z: 427(M+H$^+$) |
| 77 | 1-{4-[6-amino-5-(methoxyimino-methyl)-pyrimidin-4-yloxy]-2-chloro-phenyl}-3-p-tolyl-urea
$^1$H NMR(400MHz, DMSO-d$_6$) δ 9.31(s, 1H), 8.53(s, 1H), 8.30(s, 1H), 8.16(br, 1H), 8.11(d, 1H), 8.08(s, 1H), 7.60(br, 1H), 7.35(m, 3H), 7.12(m, 3H), 3.95(s, 3H), 2.25(s, 3H). MS(ESI) m/z: 427(M+H$^+$) |
| 78 | 1-{4-[6-amino-5-(methoxyimino-methyl)-pyrimidin-4-yloxy]-2-chloro-phenyl}-3-(2,4-difluoro-benzyl)-urea
$^1$H NMR(400MHz, DMSO-d$_6$) δ 8.50(s, 1H), 8.15(br, 2H), 8.10(d, 1H), 8.06(s, 1H), 7.57(br, 1H), 7.42(m, 1H), 7.32(s, 1H), 7.25(t, 1H), 7.08(m, 2H), 4.31(d, 2H), 3.93(s, 3H). MS(ESI) m/z: 463(M+H$^+$) |
| 79 | 1-{4-[6-amino-5-(methoxyimino-methyl)-pyrimidin-4-yloxy]-2-chloro-phenyl}-3-prop-2-ynyl-urea
$^1$H NMR(400MHz, DMSO-d$_6$) δ 8.52(s, 1H), 8.15(br, 1H), 8.10(s, 1H), 8.06(s, 1H), 8.02(d, 1H), 7.59(br, 1H), 7.42(s, 1H), 7.25(t, 1H), 7.10(d, 1H), 3.95(s, 3H), 3.93(d, 2H), 3.14(s, 1H). MS(ESI) m/z: 375(M+H$^+$) |
| 80 | 1-{4-[6-amino-5-(methoxyimino-methyl)-pyrimidin-4-yloxy]-2-chloro-phenyl}-3-isopropyl-urea
$^1$H NMR(400MHz, DMSO-d$_6$) δ 8.50(s, 1H), 8.15(br, 1H), 8.12(d, 1H), 8.06(s, 1H), 7.88(s, 1H), 7.58(br, 1H), 7.31(s, 1H), 7.07(d, 1H), 6.87(d, 1H), 3.93(s, 3H), 3.75(m, 1H), 1.10(d, 6H). MS(ESI) m/z: 379(M+H$^+$) |
| 81 | 1-{4-[6-amino-5-(methoxyimino-methyl)-pyrimidin-4-yloxy]-2-chloro-phenyl}-3-(2-hydroxy-ethyl)-urea
$^1$H NMR(400MHz, DMSO-d$_6$) δ 8.52(s, 1H), 8.15(br, 2H), 8.10(d, 1H), 8.07(s, 1H), 7.58(br, 1H), 7.31(s, 1H), 7.07(m, 2H), 4.78(br, 1H), 3.95(s, 3H), 3.47(m, 2H), 3.18(m, 2H). MS(ESI) m/z: 403(M+Na$^+$) |
| 82 | 1-{4-[6-amino-5-(methoxyimino-methyl)-pyrimidin-4-yloxy]-2-chloro-phenyl}-3-(2-dimethylamino-ethyl)-urea
$^1$H NMR(400MHz, DMSO-d$_6$) δ 8.52(s, 1H), 8.20(s, 1H), 8.15(br, 2H), 8.10(d, 1H), 8.07(s, 1H), 7.58(br, 1H), 7.31(s, 1H), 7.07(dm, 1H), 6.97(t, 1H), 3.95(s, 3H), 3.20(q, 2H), 2.32(t, 2H), 2.18(s, 6H). MS(ESI) m/z: 408(M+H$^+$) |
| 83 | 1-{4-[6-amino-5-(methoxyimino-methyl)-pyrimidin-4-yloxy]-2-chloro-phenyl}-3-(3-hydroxy-propyl)-urea
$^1$H NMR(400MHz, DMSO-d$_6$) δ 8.52(s, 1H), 8.15(br, 1H), 8.10(d, 1H), 8.07(s, 1H), 8.01(s, 1H), 7.58(br, 1H), 7.31(s, 1H), 7.07(d, 1H), 6.93(m, 1H), 4.47(br, 1H), 3.93(s, 3H), 3.45(m, 2H), 3.15(m, 2H), 1.58(m, 2H). MS(ESI) m/z: 395(M+H$^+$) |
| 84 | 1-{4-[6-amino-5-(methoxyimino-methyl)-pyrimidin-4-yloxy]-2-chloro-phenyl}-3-(4-pyrrolidin-1-yl-butyl)-urea
$^1$H NMR(400MHz, DMSO-d$_6$) δ 8.52(s, 1H), 8.15(br, 1H), 8.10(d, 1H), 8.07(s, 1H), 8.00(s, 1H), 7.60(br, 1H), 7.32(s, 1H), 7.08(d, 1H), 6.94(t, 1H), 3.95(s, 3H), 3.12(m, 2H), 2.40(m, 6H), 1.58(m, 4H), 1.46(m, 4H). MS(ESI) m/z: 462(M+H$^+$) |
| 85 | 1-{4-[6-amino-5-(methoxyimino-methyl)-pyrimidin-4-yloxy]-2-chloro-phenyl}-3-cyclopropyl-urea
$^1$H NMR(400MHz, DMSO-d$_6$) δ 8.52(s, 1H), 8.15(br, 1H), 8.10(d, 1H), 8.07(s, 1H), 7.88(s, 1H), 7.58(br, 1H), 7.32(s, 1H), 7.10(m, 2H), 3.95(s, 3H), 2.55(m, 1H), 0.65(m, 2H), 0.40(m, 2H). MS(ESI) m/z: 377(M+H$^+$) |
| 86 | 1-{4-[6-amino-5-(methoxyimino-methyl)-pyrimidin-4-yloxy]-2-chloro-phenyl}-3-pyridin-2-yl-urea
$^1$H NMR(400MHz, DMSO-d$_6$) δ 10.01(s, 1H), 8.54(s, 1H), 8.33(s, 1H), 8.31(m, 2H), 8.18(br, 1H), 8.09(s, 1H), 7.79(t, 1H), 7.59(br, 1H), 7.44(s, 1H), 7.25(d, 1H), 7.18(d, 1H), 7.04(t, 1H), 3.93(s, 3H). MS(ESI) m/z: 414(M+H$^+$) |
| 87 | 1-{4-[6-amino-5-(methoxyimino-methyl)-pyrimidin-4-yloxy]-2-chloro-phenyl}-3-pyridin-3-yl-urea
$^1$H NMR(400MHz, DMSO-d$_6$) δ 9.51(s, 1H), 8.62(s, 1H), 8.55(s, 1H), 8.45(s, 1H), 8.22(m, 1H), 8.18(br, 1H), 8.13(d, 1H), 8.09(s, 1H), 7.97(d, 1H), 7.60(br, 1H), 7.44(s, 1H), 7.35(m, 1H), 7.27(d, 1H), 3.95(s, 3H). MS(ESI) m/z: 414(M+H$^+$) |
| 88 | 1-{4-[6-amino-5-(methoxyimino-methyl)-pyrimidin-4-yloxy]-2-chloro-phenyl}-3-pyridin-4-yl-urea
$^1$H NMR(400MHz, DMSO-d$_6$) δ 10.00(s, 1H), 8.60(s, 1H), 8.54(s, 1H), 8.44(m, 2H), 8.20(br, 1H), 8.10(s, 1H), 8.07(d, 1H), 7.62(br, 1H), 7.59(s, 1H), 7.54(d, 1H), 7.45(s, 1H), 7.20(d, 1H), 3.95(s, 3H). MS(ESI) m/z: 414(M+H$^+$) |
| 89 | 1-{4-[6-amino-5-(methoxyimino-methyl)-pyrimidin-4-yloxy]-2-chloro-phenyl}-3-(4-methyl-thiazol-2-yl)-urea
$^1$H NMR(400MHz, DMSO-d$_6$) δ 11.15(s, 1H), 9.20(br, 1H), 8.53(s, 1H), 8.20(br, 1H), 8.13(d, 1H), 8.09(s, 1H), 7.60(br, 1H), 7.45(s, 1H), 7.19(d, 1H), 6.70(s, 1H), 3.95(s, 3H), 2.25(s, 3H). MS(ESI) m/z: 434(M+H$^+$) |
| 90 | 1-{4-[6-amino-5-(methoxyimino-methyl)-pyrimidin-4-yloxy]-2-chloro-phenyl}-3-(5-methyl-thiazol-2-yl)-urea |

| Cpd | Name and Data |
|---|---|
| | $^1$H NMR(400MHz, DMSO-$d_6$) δ 11.46(s, 1H), 9.30(br, 1H), 8.54(s, 1H), 8.22(br, 1H), 8.09(s, 1H), 8.05(d, 1H), 7.60(br, 1H), 7.40(s, 1H), 7.18(d, 1H), 7.05(s, 1H), 3.95(s, 3H), 2.32(s, 3H). MS(ESI) m/z: 434(M+H$^+$) |
| 91 | 1-{4-[6-amino-5-(methoxyimino-methyl)-pyrimidin-4-yloxy]-2-chloro-phenyl}-3-thiazol-2-yl-urea<br>$^1$H NMR(400MHz, DMSO-$d_6$) δ 11.20(s, 1H), 8.75(br, 1H), 8.54(s, 1H), 8.20(br, 1H), 8.15(d, 1H), 8.10(s, 1H), 7.62(br, 1H), 7.47(s, 1H), 7.42(s, 1H), 7.20(d, 1H), 7.15(s, 1H), 3.95(s, 3H). MS(ESI) m/z: 420(M+H$^+$) |
| 92 | 1-{4-[6-amino-5-(methoxyimino-methyl)-pyrimidin-4-yloxy]-2-chloro-phenyl}-3-(4,5-dimethyl-thiazol-2-yl)-urea<br>$^1$H NMR(400MHz, DMSO-$d_6$) δ 10.85(br, 1H), 9.20(br, 1H), 8.54(s, 1H), 8.18(br, 1H), 8.15(d, 1H), 8.08(s, 1H), 7.60(br, 1H), 7.43(s, 1H), 7.18(d, 1H), 3.95(s, 3H), 2.22(s, 3H), 2.14(s, 3H). MS(ESI) m/z: 448(M+H$^+$) |
| 93 | 1-{4-[6-amino-5-(methoxyimino-methyl)-pyrimidin-4-yloxy]-2-chloro-phenyl}-3-(5-methyl-isoxazol-3-yl)-urea<br>$^1$H NMR(400MHz, DMSO-$d_6$) δ 10.10(br, 1H), 8.70(br, 1H), 8.52(s, 1H), 8.18(br, 1H), 8.10(d, 1H), 8.08(s, 1H), 7.58(br, 1H), 7.42(s, 1H), 7.17(d, 1H), 6.50(s, 1H), 3.95(s, 3H), 2.36(s, 3H). MS(ESI) m/z: 418(M+H$^+$) |

EXAMPLE 17

N-{4-[6-amino-5-(methoxyimino-methyl)-pyrimidin-4-yloxy]-2-chloro-phenyl}-acetamide (Cpd 94)

4-amino-6-(4-amino-3-chloro-phenoxy)-pyrimidine-5-carbaldehyde O-methyl-oxime Compound 10b (50 mg), acetyl chloride (26 mg) and triethylamine (34 mg) were reacted to provide Compound 94 (34 mg, 59%). $^1$H NMR (400 MHz, DMSO-$d_6$) δ 9.57 (s, 1H), 8.52 (s, 1H), 8.20 (br, 1H), 8.08 (s, 1H), 7.64 (d, 1H), 7.62 (br, 1H), 7.40 (s, 1H), 7.15 (d, 1H), 3.95 (s, 3H), 2.08 (s, 3H). MS (ESI) m/z: 336 (M+H$^+$).

EXAMPLE 18

{4-[6-amino-5-(methoxyimino-methyl)-pyrimidin-4-yloxy]-2-chloro-phenyl}-carbamic acid methyl ester (Cpd 95)

4-amino-6-(4-amino-3-chloro-phenoxy)-pyrimidine-5-carbaldehyde O-methyl-oxime Compound 10b (50 mg) and methyl chloroformate (30 mg) were reacted to provide Compound 95 (14 mg, 23%). $^1$H NMR (400 MHz, DMSO-$d_6$) δ 9.11 (s, 1H), 8.52 (s, 1H), 8.20 (br, 1H), 8.08 (s, 1H), 7.61 (br, 1H), 7.52 (d, 1H), 7.40 (s, 1H), 7.15 (d, 1H), 3.95 (s, 3H), 3.70 (s, 3H). MS (ESI) m/z: 352 (M+H$^+$).

EXAMPLE 19

2-{4-[6-amino-5-(methoxyimino-methyl)-pyrimidin-4-yloxy]-phenyl}-N-methyl-acetamide (Cpd 96)

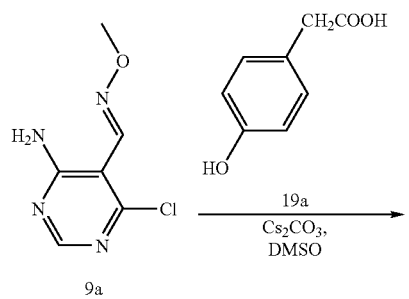

9a

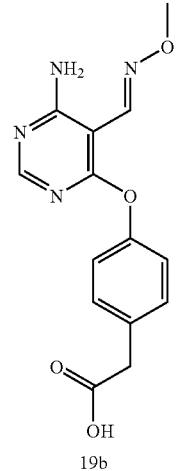

19b

Using the procedure for Example 9, Compound 9a and (4-hydroxy-phenyl)-acetic acid Compound 19a were reacted to provide {4-[6-amino-5-(methoxyimino-methyl)-pyrimidin-4-yloxy]-phenyl}-acetic acid Compound 19b. $^1$H NMR (300 MHz, DMSO-$d_6$) δ 12.38 (br, 1H), 8.53 (s, 1H), 8.18 (s, 1H), 8.15 (br, 1H), 8.07 (s, 1H), 7.58 (br, 1H), 7.27 (d, 2H), 7.08 (d, 2H), 3.93 (s, 3H), 3.59 (s, 2H). MS (ESI) m/z: 303 (M+H$^+$).

Compound 19b (30 mg), methylamine (3.1 mg), HOBT (13 mg) and DIC (13 mg) were reacted to provide Compound 96 (3 mg, 10%). $^1$H NMR (400 MHz, DMSO-$d_6$) δ 8.53 (s, 1H), 8.17 (br, 1H), 8.07 (s, 1H), 8.05 (br, 1H), 7.59 (br, 1H), 7.29 (d, 2H), 7.09 (d, 2H), 3.95 (s, 3H), 3.40 (s, 2H), 2.60 (s, 2H). MS (ESI) m/z: 316 (M+H$^+$).

EXAMPLE 20

2-{4-[6-amino-5-(methoxyimino-methyl)-pyrimidin-4-yloxy]-phenyl}-N-phenyl-acetamide (Cpd 97)

Using the procedure for Example 19, {4-[6-amino-5-(methoxyimino-methyl)-pyrimidin-4-yloxy]-phenyl}-acetic acid Compound 19b (40 mg) and aniline (40 mg) were reacted to provide Compound 97 (1.2 mg, 2%). $^1$H NMR (400 MHz, THF-$d_8$) δ 9.12 (br, 1H), 8.65 (s, 1H), 7.99 (s, 1H), 7.68 (br, 1H), 7.65 (d, 2H), 7.40 (d, 2H), 7.38 (br, 1H), 7.25 (t, 2H), 7.10 (d, 2H), 7.00 (t, 1H), 3.98 (s, 3H), 3.67 (s, 2H). MS (ESI) m/z: 378 (M+H⁺).

EXAMPLE 21

4-[6-amino-5-(methoxyimino-methyl)-pyrimidin-4-yloxy]-N-methyl-benzamide (Cpd 98)

Using the procedure for Example 9, Compound 9a and 4-hydroxy-benzoic acid were reacted to provide 4-[6-amino-5-(methoxyimino-methyl)-pyrimidin-4-yloxy]-benzoic acid Compound 21a. $^1$H NMR (400 MHz, DMSO-d$_6$) δ 12.98 (br, 1H), 8.53 (s, 1H), 8.22 (br, 1H), 8.08 (s, 1H), 7.97 (d, 2H), 7.62 (br, 1H), 7.27 (d, 2H), 3.95 (s, 3H). MS (ESI) m/z: 289 (M+H⁺).

Using the procedure for Example 19, Compound 21a (50 mg) and methylamine (50 mg) were reacted to provide Compound 98 (30 mg, 57%). $^1$H NMR (400 MHz, THF-d$_8$) δ 8.65 (s, 1H), 8.01 (s, 1H), 7.87 (d, 2H), 7.72 (br, 1H), 7.54 (br, 1H), 7.44 (br, 1H), 7.20 (d, 2H), 4.01 (s, 3H), 2.91 (s, 3H). MS (ESI) m/z: 302 (M+H⁺).

EXAMPLE 22

2-{4-[6-amino-5-(methoxyimino-methyl)-pyrimidin-4-yloxy]-phenyl}-N-p-tolyl-acetamide (Cpd 99)

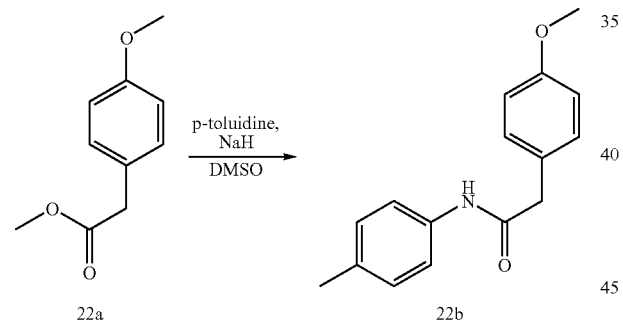

(4-methoxy-phenyl)-acetic acid methyl ester Compound 22a was reacted with p-toluidine and sodium hydride in DMSO at room temperature to provide 2-(4-methoxy-phenyl)-N-p-tolyl-acetamide Compound 22b.

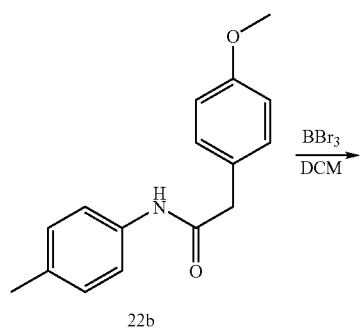

Compound 22b was reacted with borotribromide in dichloromethane to yield 2-(4-hydroxy-phenyl)-N-p-tolyl-acetamide Compound 22c.

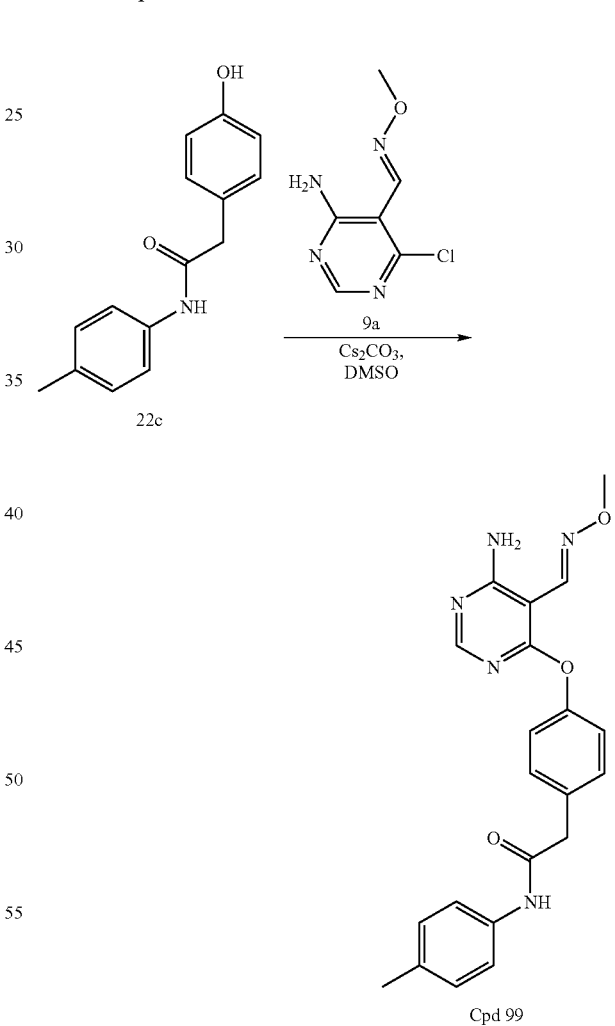

Using the procedure for Example 9, Compound 22c (80 mg) and Compound 9a (72 mg) were reacted to provide Compound 99 (93 mg, 72%). $^1$H NMR (400 MHz, DMSO-d$_6$) δ 10.05 (s, 1H), 8.52 (s, 1H), 8.15 (br, 1H), 8.03 (s, 1H), 7.57 (br, 1H), 7.45 (d, 2H), 7.32 (d, 2H), 7.10 (m, 4H), 3.93 (s, 3H), 3.61 (s, 2H), 2.63 (s, 3H). MS (ESI) m/z: 392 (M+H⁺).

EXAMPLE 23

2-{4-[6-amino-5-(methoxyimino-methyl)-pyrimidin-4-yloxy]-phenyl}-N-(3-fluoro-phenyl)-acetamide (Cpd 100)

Using the procedure for Example 22, (4-methoxy-phenyl)-acetic acid methyl ester Compound 22a was reacted with 3-fluoro-phenylamine and sodium hydride in DMSO at room temperature to provide N-(3-fluoro-phenyl)-2-(4-methoxy-phenyl)-acetamide Compound 23a. Compound 23a was reacted with borotribromide in dichloromethane to yield N-(3-fluoro-phenyl)-2-(4-hydroxy-phenyl)-acetamide Compound 23b.

Using the procedure for Example 9, Compound 23b and Compound 9a were reacted to provide Compound 100. $^1$H NMR (400 MHz, DMSO-$d_6$) δ 10.40 (s, 1H), 8.52 (s, 1H), 8.15 (br, 1H), 8.04 (s, 1H), 7.62 (s, 1H), 7.60 (br, 1H), 7.32 (m, 4H), 7.10 (d, 2H), 6.85 (t, 1H), 3.93 (s, 3H), 3.65 (s, 2H). MS (ESI) m/z: 396 (M+H$^+$).

EXAMPLE 24

2-{4-[6-amino-5-(methoxyimino-methyl)-pyrimidin-4-yloxy]-phenyl}-N-ethyl-acetamide (Cpd 101)

Using the procedure for Example 22, (4-methoxy-phenyl)-acetic acid methyl ester Compound 22a was reacted with ethylamine and sodium hydride in DMSO at room temperature to provide N-ethyl-2-(4-methoxy-phenyl)-acetamide Compound 24a. Compound 24a was reacted with borotribromide in dichloromethane to yield N-ethyl-2-(4-hydroxy-phenyl)-acetamide Compound 24b.

Using the procedure for Example 9, Compound 24b and Compound 9a were reacted to provide Compound 100. $^1$H NMR (300 MHz, DMSO-$d_6$) δ 8.53 (s, 1H), 8.18 (br, 1H), 8.08 (t, 1H), 8.05 (s, 1H), 7.58 (br, 1H), 7.26 (d, 2H), 7.07 (d, 2H), 3.95 (s, 3H), 3.38 (s, 2H), 3.08 (dt, 2H), 1.03 (t, 3H). MS (ESI) m/z: 330 (M+H$^+$), 352 (M+Na$^+$).

EXAMPLE 25 ethyl-carbamic acid 4-[6-amino-5-(methoxyimino-methyl)-pyrimidin-4-yloxy]-phenyl ester (Cpd 102)

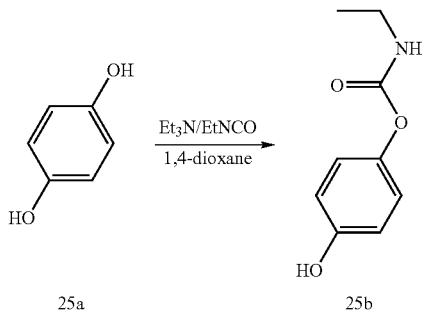

Benzene-1,4-diol Compound 25a was reacted with isocyanato-ethane and a catalytic amount of triethylamine in 1,4-dioxane at room temperature to provide ethyl-carbamic acid 4-hydroxy-phenyl ester Compound 25b.

Using the procedure for Example 9, Compound 25b (200 mg) and Compound 9a (206 mg) were reacted to provide Compound 102 (75 mg, 21%). $^1$H NMR (400 MHz, DMSO-$d_6$) δ 9.92 (s, 1H), 9.47 (s, 1H), 9.21 (t, 1H), 8.55 (s, 1H), 8.40 (s, 1H), 7.00 (d, 2H), 6.78 (d, 2H), 4.00 (s, 3H), 3.28 (dt, 2H), 1.11 (t, 3H). MS (ESI) m/z: 332 (M+H$^+$).

EXAMPLE 26

1-(4-{6-amino-5-[(2-morpholin-4-yl-ethoxyimino)-methyl]-pyrimidin-4-yloxy}-2-chloro-phenyl)-3-ethyl-urea (Cpd 103)

Using the procedure for Example 1, 4-amino-6-chloro-pyrimidine-5-carbaldehyde Compound 1a was reacted with 4-amino-3-chloro-phenol Compound 10a to provide 4-amino-6-(4-amino-3-chloro-phenoxy)-pyrimidine-5-carbaldehyde Compound 26a.

Using the procedure for Example 10, Compound 26a was reacted with isocyanato-ethane to provide 1-[4-(6-amino-5-formyl-pyrimidin-4-yloxy)-2-chloro-phenyl]-3-ethyl-urea Compound 26b.

Using the procedure for Example 1, Compound 26b (50 mg) was reacted with O-(2-morpholin-4-yl-ethyl)-hydroxylamine hydrochloride Compound 26c to provide Compound 103 (31 mg, 45%). $^1$H NMR (400 MHz, DMSO-$d_6$) δ 8.50 (s, 1H), 8.15 (br, 1H), 8.10 (s, 1H), 8.07 (s, 1H), 7.96 (s, 1H), 7.62 (br, 1H), 7.31 (s, 1H), 7.08 (d, 1H), 6.91 (t, 1H), 4.28 (t, 2H), 3.57 (t, 4H), 3.12 (dt, 2H), 2.60 (t, 2H), 2.41 (t, 4H), 1.05 (t, 3H). MS (ESI) m/z: 464 (M+H$^+$).

EXAMPLE 27

1-(4-{6-amino-5-[(2-methoxy-ethoxyimino)-methyl]-pyrimidin-4-yloxy}-2-chloro-phenyl)-3-ethyl-urea (Cpd 104)

Using the procedure for Example 1, 1-[4-(6-amino-5-formyl-pyrimidin-4-yloxy)-2-chloro-phenyl]-3-ethyl-urea Compound 26b was reacted with hydroxy-amine hydrochloride to provide 1-{4-[6-amino-5-(hydroxyimino-methyl)-pyrimidin-4-yloxy]-2-chloro-phenyl}-3-ethyl-urea Compound 27a.

Using the procedure for Example 7, Compound 27a (80 mg) and 1-bromo-2-methoxy-ethane were reacted to provide Compound 104 (20 mg, 22%). $^1$H NMR (400 MHz, DMSO-$d_6$) δ 8.50 (s, 1H), 8.13 (br, 1H), 8.10 (s, 1H), 8.07 (s, 1H), 7.96 (s, 1H), 7.62 (br, 1H), 7.32 (s, 1H), 7.08 (d, 1H), 6.90 (t, 1H), 4.28 (t, 2H), 3.60 (t, 2H), 3.27 (s, 3H), 3.12 (dt, 2H), 1.05 (t, 3H). MS (ESI) m/z: 409 (M+H$^+$), 431 (M+Na$^+$).

EXAMPLE 28

(3-chloro-phenyl)-carbamic acid 4-[6-amino-5-(methoxyimino-methyl)-pyrimidin-4-yloxy]-phenyl ester (Cpd 105)

Benzene-1,4-diol Compound 25a was reacted with 1-chloro-3-isocyanato-benzene Compound 28a and a catalytic amount of triethylamine in 1,4-dioxane at room temperature to provide (3-chloro-phenyl)-carbamic acid 4-hydroxy-phenyl ester Compound 28b.

Using the procedure for Example 1, Compound 28b (200 mg) was reacted with Compound 9a (206 mg) to provide Compound 105 (86 mg, 22%). $^1$H NMR (400 MHz, DMSO-$d_6$) δ 10.20 (s, 1H), 9.50 (s, 1H), 8.60 (s, 1H), 8.55 (s, 1H), 7.80 (m, 1H), 7.55 (d, 1H), 7.40 (t, 1H), 7.15 (d, 1H), 7.05 (d, 2H), 6.80 (d, 2H), 4.05 (s, 3H). MS (ESI) m/z: 414 (M+H$^+$).

BIOLOGICAL EXAMPLES

The ability of the compounds for treating a chronic or acute kinase mediated disease, disorder or condition was determined using the following procedures.

Example 1

CDK1 Screening Assay

A kinase reaction mixture was prepared containing 50 mM Tris-HCl pH=8, 10 mM $MgCl_2$, 0.1 mM $Na_3PO_4$, 1 mM DTT, 10 µM ATP, 0.025 µM biotinylated histone-H1 peptide substrate and 0.2 µCuries per well $^{33}P$-γ-ATP (2000-3000 Ci/mmol). 70 µL of the kinase reaction mixture was dispensed into the well of a streptavidin coated FlashPlate™ (Cat. # SMP103, NEN, Boston, Mass.). Then 1 µL of test compound stock in 100% DMSO was added to the wells resulting in a final concentration of 1% DMSO in the reaction with a 100 µL final reaction volume.

The CDK1:Cyclin-B protein was diluted in 50 mM Tris-HCl pH=8.0, 0.1% BSA at a concentration of 1 ng per µL and 30 µL (30 ng enzyme per test well) was added to each well to initiate the reaction. The reaction was incubated for one hour at 30° C. At the end of the 1 hour incubation, the reaction was terminated by aspirating the mixture from the plate and washing the wells twice with PBS containing 100 mM EDTA. The histone-H1 biotinylated peptide substrate became immobilized on the Flashplate™ and the incorporation of $^{33}P$-γ-ATP was measured by reading the plate on a scintillation counter. Inhibition of the enzymatic activity of CDK1 was measured by observing a reduced amount of $^{33}P$-γ-ATP incorporated into the immobilized peptide.

The CDK1 used was isolated from insect cells expressing both the human CDK1 catalytic subunit and its positive regulatory subunit cyclin B (New England Biolabs, Beverly, Mass., Cat. #6020).

Example 2

VEGF-R2 Screening Assay

The VEGF-R kinase assay was carried out using the CDK kinase assay procedure except that the enzyme was replaced with the VEGF-R2 fusion protein containing a polyhistidine tag at the N-terminus followed by amino acids 786-1343 of the rat VEGF-R2 kinase domain (GenBank Accession #U93306).

Example 3

Aurora-A Screening Assay

The Aurora-A kinase assay was carried out using the CDK kinase assay procedure except that the enzyme was replaced with the full length protein encoding the murine Aurora-A (Accession #GB BC014711) expressed and purified from sf9 insect cells.

Example 4

HER2 Kinase Screening Assay

The HER2 kinase assay was carried out using the CDK kinase assay procedure except that the enzyme was replaced with a HER2 construct containing a polyhistidine tag at the N-terminus followed by 24 additional amino acids and the HER2 cytoplasmic domain beginning at amino acid 676 (Accession #M11730) to the end.

Example 5

RET Kinase Screening Assay

The RET kinase assay was carried out using the CDK kinase assay procedure except that the enzyme was replaced with a construct encoding the RET cytoplasmic domain consisting of the last 492 amino acids of the intracellular domain of the RET tyrosine kinase (Accession #X12949) containing an N-terminal histidine tag was expressed and purified from Hi5 insect cells.

Example 6

KIT Kinase Screening Assay

Compound 50 inhibited the tyrosine kinase KIT having an activity of 500 nM.

Example 7

RAF Kinase Screening Assay

The RAF kinase was assayed at a concentration of 5 nM in kinase reaction buffer (50 mM HEPES (pH 7.4), 100 mM NaCl, 10 mM $MgCl_2$, complete protease inhibitor cocktail (Roche Applied Science, Indianapolis Ind.) used at a dilution of 1:200 when a tablet is dissolved in 1 ml water) and 1 mM NaF). Briefly, Compound 50 was diluted in 30% DMSO and 50 mM HEPES and 10 µl were dispensed into reaction plates. Next, 50 µl of a buffer containing mouse MEK1-GST (100 mM final) and $^{33}P$-ATP (GE Healthcare, Piscataway N.J., 10 µCi/ml final) were added to appropriate wells. Finally, 40 µl of RAF kinase was added. The reaction was incubated for one hour at room temperature. At the end of the 1 hour incubation, the reaction was terminated by the addition of 10 mM ATP in 1% BSA, 50 mM EDTA. The resulting mixture (80 µl) was transferred to 1% BSA-blocked Flashplates (Perkin Elmer, Wellesley Mass.), previously coated overnight with a 1:2500 dilution of anti-GST antibody (GE Healthcare). The plates were incubated 2 hours with shaking at room temperature. Plates were washed three times with PBS, 0.1% triton-X 100 and counted on a Top Count scintillation counter.

Peptide Substrates

| Kinase | Substrate |
|---|---|
| VEGF-R2, HER2 and RET | (Biotin)KHKKLAEGSAYEEV-Amide |
| CDK1 | (Biotin)KTPKKAKKPKTPKKAKKL-Amide |
| Aurora-A | Biotin-GRTGRRNSI-Amide |

Results of assays performed on compounds described above are provided below in Table 1. An $IC_{50}$ listed as >0.1, >1, >10 or >100 means no observed 50% inhibition at the indicated test concentration. An $IC_{50}$ listed as 1, 10 or 100 means approximately 50% inhibition was observed at the indicated test concentration. ND means the compound was not tested in the assay specified.

TABLE 1

| Cpd | $IC_{50}(\mu M)$ CDK1 | $IC_{50}(\mu M)$ VEGF-R2 | $IC_{50}(\mu M)$ HER2 | $IC_{50}(\mu M)$ Aurora-A | $IC_{50}(\mu M)$ Ret |
|---|---|---|---|---|---|
| 1 | >100 | 0.042 | >100 | >100 | >100 |
| 2 | >100 | 0.146 | >1 | ~100 | ~100 |
| 3 | >100 | >100 | >100 | >100 | >100 |
| 4 | >100 | 4.767 | >10 | >100 | ~100 |
| 5 | >100 | 0.700 | >100 | >10 | 2.011 |
| 6 | >100 | 1.588 | >10 | >100 | >10 |

TABLE 1-continued

| Cpd | IC$_{50}$(μM) CDK1 | IC$_{50}$(μM) VEGF-R2 | IC$_{50}$(μM) HER2 | IC$_{50}$(μM) Aurora-A | IC$_{50}$(μM) Ret |
|---|---|---|---|---|---|
| 7 | >100 | 0.117 | 0.653 | >100 | >0.1 |
| 8 | >100 | 0.121 | >1 | >10 | >1 |
| 9 | >100 | 1.038 | 0.208 | >10 | >100 |
| 10 | >100 | 0.276 | 0.697 | >10 | 2.227 |
| 11 | >100 | 1.189 | >10 | >100 | >100 |
| 12 | >100 | 0.044 | 9.590 | ~100 | >10 |
| 13 | >100 | 0.214 | >10 | ~100 | >100 |
| 14 | >100 | 0.0392 | ~10 | >100 | >100 |
| 15 | >100 | 0.187 | 36.07 | >100 | >100 |
| 16 | >100 | 0.093 | 10.880 | >100 | >100 |
| 17 | >100 | 0.101 | ~10 | 33.83 | ~100 |
| 18 | >100 | 0.065 | 1.494 | >10 | 8.110 |
| 19 | >100 | ~0.1 | 1.231 | >100 | 3.58 |
| 20 | >100 | 0.037 | 1.552 | >100 | 4.246 |
| 21 | >100 | 0.036 | 0.767 | >10 | 1.833 |
| 22 | >100 | 0.045 | 1.412 | >100 | 2.765 |
| 23 | >100 | 0.082 | 1.782 | >100 | 8.324 |
| 24 | >100 | 0.085 | 0.2823 | >100 | ND |
| 25 | >100 | 0.13 | 0.5964 | >10 | ND |
| 26 | >100 | 0.048 | 1.015 | >100 | ND |
| 27 | >100 | 0.033 | ~10 | ~10 | >10 |
| 28 | >100 | 0.024 | ~10 | >100 | >100 |
| 29 | >100 | 0.011 | 4.631 | >10 | >10 |
| 30 | >100 | 0.052 | >10 | >100 | ~10 |
| 31 | >100 | 0.052 | >100 | >100 | ~10 |
| 32 | >100 | 0.046 | >100 | >100 | ND |
| 33 | >100 | 0.062 | 3.988 | >10 | ~1 |
| 34 | >100 | 0.043 | >100 | >100 | ~10 |
| 35 | >100 | 0.413 | >100 | >100 | >100 |
| 36 | >100 | 0.201 | >100 | >100 | >100 |
| 37 | >100 | 0.115 | >100 | >100 | >100 |
| 38 | >100 | 0.0577 | 0.8678 | >100 | ND |
| 39 | >100 | 0.1077 | >10 | >100 | ND |
| 40 | 27.97 | 0.0304 | >10 | >100 | ND |
| 41 | >100 | 0.0424 | >10 | ND | >10 |
| 42 | >100 | 0.0542 | >10 | >100 | ND |
| 43 | >100 | ~1 | >10 | >100 | ND |
| 47 | >100 | >100 | >100 | >100 | ND |
| 48 | >100 | 0.0076 | >10 | >100 | ND |
| 49 | >100 | 0.001 | ~100 | >100 | ~10 |
| 50 | >100 | 0.011 | >100 | >100 | 0.212 |
| 51 | >100 | 0.025 | >100 | >100 | ~1 |
| 52 | >100 | 0.0275 | >100 | >100 | ND |
| 53 | >100 | 0.0191 | >10 | >100 | ND |
| 54 | >100 | 0.0030 | >100 | >100 | ND |
| 55 | >100 | 0.0026 | 1.82 | >10 | ND |
| 56 | >100 | 0.0033 | >10 | >100 | ND |
| 57 | >100 | 0.0017 | >10 | >100 | ND |
| 58 | >100 | 0.0025 | 1.697 | >100 | ND |
| 59 | >100 | 0.0030 | >1 | >100 | ND |
| 60 | >100 | 0.0028 | >100 | >10 | ND |
| 61 | >100 | 0.0030 | >100 | >100 | ND |
| 62 | >100 | 0.0016 | >100 | >100 | ND |
| 63 | >100 | 0.0022 | >10 | >100 | ND |
| 64 | >100 | 0.0072 | >100 | >100 | ND |
| 65 | >100 | 0.0065 | >10 | >100 | ND |
| 66 | >100 | 0.180 | >100 | >100 | >10 |
| 67 | >100 | 4.358 | 13.060 | 17.800 | 9.204 |
| 68 | >100 | 0.233 | >100 | >10 | >10 |
| 69 | >100 | 0.142 | >100 | >10 | >10 |
| 70 | >100 | 0.2782 | >100 | >10 | ND |
| 71 | >100 | 0.1794 | >1 | >10 | ND |
| 72 | >100 | 0.1419 | >10 | >100 | ND |
| 73 | >10 | >100 | >1 | >10 | ND |
| 74 | >100 | ~100 | >1 | >10 | ND |
| 75 | >100 | 0.0079 | >100 | >100 | ND |
| 76 | >100 | 0.0020 | >10 | >100 | ND |
| 77 | >100 | 0.0016 | >100 | >100 | ND |
| 78 | >100 | 0.0103 | >100 | >100 | ND |
| 79 | >100 | 0.0275 | >100 | >100 | ND |
| 80 | >100 | 0.0729 | >10 | >10 | ND |
| 81 | >100 | 0.1679 | >100 | >100 | ND |
| 82 | >100 | 0.2846 | >10 | >100 | ND |
| 83 | >100 | 0.4000 | >10 | >100 | ND |
| 84 | >100 | 0.7591 | >10 | >10 | ND |
| 85 | >100 | 0.029 | >100 | >100 | ND |
| 86 | >100 | 0.0340 | >100 | >100 | ND |
| 87 | >100 | 0.0100 | >1 | >100 | ND |
| 88 | >100 | 0.011 | >10 | >10 | ND |
| 89 | >100 | 0.0039 | >1 | >100 | ND |
| 90 | >100 | 0.037 | >1 | >10 | ND |
| 91 | >100 | 0.0034 | >1 | >10 | ND |
| 92 | >100 | 0.002 | >1 | >100 | ND |
| 93 | >100 | 0.002 | >10 | >100 | ND |
| 94 | >100 | 2.2080 | >100 | >100 | ND |
| 95 | >100 | 0.152 | >10 | >100 | ND |
| 96 | >100 | 19.68 | >100 | >10 | ND |
| 97 | >100 | 0.0407 | 1.3080 | >100 | ND |
| 98 | >100 | >100 | >100 | >100 | ND |
| 99 | >100 | 0.008 | 0.2171 | >100 | ND |
| 100 | >100 | ND | 2.801 | >100 | ND |
| 101 | >100 | ND | >100 | >10 | ND |
| 102 | >100 | ND | >100 | >10 | ND |
| 103 | >100 | 0.093 | >100 | >100 | ND |
| 104 | >100 | 0.041 | >100 | >100 | ND |
| 105 | >100 | >100 | >100 | >100 | ND |
| 106 | >100 | >10 | >10 | >100 | ND |
| 107 | >100 | >100 | >100 | >100 | ND |
| 108 | >100 | 3.96 | >10 | >10 | ND |
| 109 | >100 | >100 | >1 | >100 | ND |
| 110 | >100 | ~1 | 0.5552 | >100 | ND |
| 112 | ND | ND | >10 | ND | ND |
| 113 | >100 | >100 | >100 | >100 | ND |
| 115 | ND | >10 | ND | ND | ND |

Discussion of Results for Examples 1-7 Relative to Compound 50

The inhibitory activity of Compound 50 was further determined against a large range of recombinant tyrosine and serine/threonine kinases (data not shown). The kinases with >70% activity at a single dose of 1 μM were further characterized in a 10-point titration IC$_{50}$ determination assay. Compound 50 was determined to be a selective inhibitor of VEGFR-2, confirmed in two independent kinase assays: using recombinant rat VEGFR-2 (Emanuel S., et al. Mol. Pharmacol., 2004, 66:635-647) and in the human VEGFR-2 assay performed at Invitrogen. Compound 50 did not inhibit closely related VEGF receptors (VEGFR-1=4420 nM and VEGFR-3=1100 nM). The activity against RET (183 nM) and KIT (513 nM) has not been confirmed in cells.

Compound 50 and BAY 43-9006 (as a positive control) were tested in a selective Raf kinase assay for activity against C-Raf, B-Raf and the V600E Raf mutant. Inhibition of all the Raf kinases was observed with BAY 43-9006, but there was no activity (tested at 30 μM) observed with Compound 50.

The assays described herein demonstrate that Compound 50 inhibits VEGFR-2 and not other similar tyrosine kinase receptors below 100 nM. Despite potent activity against VEGFR-2 in vitro, Compound 50 did not inhibit the closely related family members, VEGFR-1 and VEGFR-3. Unlike BAY 43-9006 (a dual RAF kinase and VEGFR inhibitor), Compound 50 is not active against B-Raf, C-Raf or the oncogenic V600E Raf kinase.

Example 8

Assay to Measure Inhibition of In Vitro Cell Proliferation

The ability of a test compound to inhibit the proliferation of cell growth was determined by measuring incorporation of $^{14}$C-labelled thymidine into newly synthesized DNA within the cells. This method was used on American Type Culture Collection (ATCC, Virginia) cell lines derived from carcinomas originating from several tissues such as HeLa cervical adenocarcinoma (ATCC Cat. #CCL-2), A375 malignant melanoma (ATCC Cat. #CRL-1619), HCT-116 colon carcinoma (ATCC Cat. #CCL-247). The A431 cell line for epidermoid carcinoma was grown in DMEM containing L-glutamine, sodium pyruvate, 1 g/L glucose+10% FBS.

The carcinoma cells are trypsinized and counted. The cells (3000-8000 count) are added to each well of a 96-well CytoStar tissue culture treated scintillating microplate (Amersham #RPNQ0160) in complete medium (100 μL) and the plate is then incubated in complete medium for 24 hrs at 37° C. in an inert atmosphere containing 5% $CO_2$.

Test compound (1 μL) in 100% DMSO is added to the plate test-wells with DMSO only added to control-wells. The plate is incubated in complete medium for a second 24 hr period at 37° C. in an atmosphere containing 5% $CO_2$.

An aliquot of a solution of Methyl $^{14}$C-thymidine (56 mC/mmol) (NEN #NEC568 or Amersham #CFA532) in complete medium (20 uL to provide 0.2 μCi/well) is then added to each well and the plate is incubated for a third 24 hr period at 37° C. in an atmosphere containing 5% $CO_2$.

The plate contents are then discarded, the plate is washed twice with PBS (200 μL) and then PBS (200 μL) is added to each well. The plate is sealed and the degree of methyl $^{14}$C-thymidine incorporation is quantified on a Packard Top Count.

Cell culture reagents were obtained from Invitrogen (Carlsbad, Calif.) supplemental fetal calf serum was purchased from Hyclone, Logan Utah. Cells were maintained at 37 C plus 5% CO2, and grown as monolayers prior to tumor implantation.

The $IC_{50}$ values for the compounds tested in various cell lines are shown in Table 2.

TABLE 2

| Cpd | $IC_{50}(\mu M)$ HeLa | $IC_{50}(\mu M)$ HCT116 | $IC_{50}(\mu M)$ A375 |
| --- | --- | --- | --- |
| 1 | 0.032 | 0.036 | 0.027 |
| 2 | 0.3888 | 0.3864 | 0.3563 |
| 3 | >10 | >10 | >10 |
| 4 | >10 | 38.28 | >10 |
| 5 | 3.43 | 2.868 | 1.825 |
| 6 | 1.817 | 2.624 | 0.886 |
| 7 | 0.401 | 0.365 | 0.492 |
| 8 | 0.382 | 0.422 | 0.327 |
| 9 | 0.306 | 0.385 | 0.132 |
| 10 | 1.871 | 3.522 | 0.783 |
| 11 | 0.375 | 0.749 | 0.326 |
| 12 | 0.406 | 0.323 | 0.372 |
| 13 | 4.221 | 4.61 | 2.156 |
| 14 | 0.699 | 1.164 | 0.339 |
| 15 | 3.227 | 4.246 | 0.501 |
| 16 | 2.008 | 3.037 | 0.345 |
| 17 | 4.334 | 4.287 | 1.599 |
| 18 | 4.182 | 4.496 | 2.611 |
| 19 | 4.905 | 9.24 | 3.822 |
| 20 | 0.715 | 2.776 | 0.429 |
| 21 | 24.46 | 68.08 | 11.21 |
| 22 | >10 | >10 | >10 |
| 23 | >10 | >10 | >10 |
| 24 | >100 | >100 | >100 |
| 25 | >100 | 0.100 | >100 |
| 26 | >100 | >1 | >100 |
| 27 | 0.472 | 1.136 | 0.492 |
| 28 | 0.308 | 0.387 | 0.233 |
| 29 | 0.362 | 0.452 | 0.336 |
| 30 | 0.028 | 0.028 | 0.030 |
| 31 | 0.042 | 0.040 | 0.021 |
| 32 | 0.324 | 0.333 | 0.070 |
| 33 | 0.346 | 0.438 | 0.300 |
| 34 | 0.040 | 0.030 | 0.028 |
| 35 | 22.66 | 16.06 | 4.924 |
| 36 | 0.266 | 0.311 | 0.062 |
| 37 | 0.607 | 3.004 | 0.446 |
| 38 | 1.828 | 2.34 | 0.618 |
| 39 | 4.368 | 3.425 | 3.772 |
| 40 | 4.244 | 4.536 | 2.589 |
| 41 | >10 | >10 | >1 |
| 42 | >10 | >10 | >1 |
| 47 | >10 | >10 | >10 |
| 48 | 3.367 | 1.219 | 1.154 |
| 49 | 2.981 | 3.138 | 1.385 |
| 50 | 3.574 | 3.704 | 3.912 |
| 51 | 3.751 | 4.208 | 4.090 |
| 52 | >1 | >1 | >1 |
| 53 | >1 | >1 | >1 |
| 54 | >100 | >100 | >100 |
| 55 | >10 | >10 | >10 |
| 56 | >10 | >10 | >10 |
| 57 | >10 | >10 | >10 |
| 58 | 11.94 | 8.187 | 5.056 |
| 59 | >10 | >10 | >10 |
| 60 | >10 | >10 | >10 |
| 61 | >100 | >10 | >100 |
| 62 | >100 | >100 | >100 |
| 63 | >10 | >10 | >10 |
| 64 | >100 | >100 | >100 |
| 65 | >100 | >100 | >100 |
| 66 | >100 | >100 | >100 |
| 67 | 3.991 | 2.946 | 3.222 |
| 68 | >10 | >10 | >10 |
| 69 | >10 | >10 | >10 |
| 70 | 4.060 | 4.86 | 2.547 |
| 71 | 3.975 | 4.794 | 3.090 |
| 72 | >10 | >10 | >10 |
| 73 | >10 | >10 | >10 |
| 74 | >100 | >100 | >10 |
| 75 | >100 | >100 | >100 |
| 76 | >10 | >10 | >10 |
| 77 | >100 | >100 | >100 |
| 78 | >100 | >100 | >100 |
| 79 | 3.582 | 3.721 | 2.20 |
| 80 | >10 | >10 | >1 |
| 81 | 4.27 | 4.058 | 3.906 |
| 82 | >10 | >10 | >10 |
| 83 | 4.18 | 3.782 | 3.944 |
| 84 | >10 | >10 | >1 |
| 85 | >100 | >100 | >10 |
| 86 | >10 | >10 | 6.253 |
| 87 | 4.628 | 4.672 | 3.41 |
| 88 | 7.394 | 4.688 | 4.344 |
| 89 | >10 | >10 | 2.185 |
| 90 | >100 | >10 | >10 |
| 91 | 3.244 | 3.045 | 0.929 |
| 92 | 23.400 | 16.95 | 6.923 |
| 93 | 9.999 | 3.121 | 2.118 |
| 94 | 4.017 | 3.623 | 2.689 |
| 95 | 4.945 | 3.771 | 3.500 |
| 97 | >10 | >10 | >10 |
| 99 | >100 | >100 | >100 |
| 110 | >100 | >100 | >100 |

Discussion of Results for Example 8

When tested in vitro in tumor cell proliferation assays, Compound 50 showed no antiproliferative effects on the HeLa, HCT116 and A375 human cancer cell lines tested at the highest concentration (100 μM).

Example 9

In Vivo Models—Inhibition of Tumor Growth

Female Nu/Nu~nuBR athymic nude mice (obtained from Charles River Laboratories), at the age of 5-6 weeks were feed water and an irradiated standard rodent diet ad libitum, and housed in specific pathogen-free conditions, according to the guidelines of the American Association for Accreditation of Lab Animal Care (AALAC).

Mice were implanted subcutaneously in the right hind flank with the various tumor cell suspensions in HBSS containing 10% FBS: A431 human epidermoid carcinoma ($4\times10^6$ cells/mouse), HCT116 human colorectal carcinoma ($4\times10^6$ cells/mouse) and A375 human skin melanoma ($2\times10^6$ cells/mouse).

The A431 epidermoid carcinoma cell line was chosen due to its ability to secrete VEGF in culture and its dependency on VEGF for angiogenesis and growth in vivo (Viloria-Petit A, Crombet T, Jothy S, et al. (2001) *Cancer Res* 61: 5090-5101). The HCT116 colon carcinoma cell line is dependent on the expression of VEGF to form tumors in nude mice (Okada F, Rak J, St. Croix B, et al. (1998) *Proc Natl Acad Sci USA* 95: 3609-3614). The highly vascularized A375 melanoma model was chosen because it has been shown to respond to VEGF with increased proliferation, is dependent on VEGF, expresses high levels of VEGF and has the unique feature of expressing the VEGFR-2 receptor (Liu B, Earl H. M., Baban D, Shoaibi M, Fabra A, Kerr D J and Seymour L. W. Biochem Biophys Res Commun 1995 217: 721-727).

After the tumors were implanted, Compound 50 (formulated in 0.5% methylcellulose in sterile water) was administered orally once daily at a dose of 10 mg/kg, 50 mg/kg, 100 mg/kg or 200 mg/kg.

In the A431 model and HCT116 models, Compound 50 was administered at 10, 50, 100 and 200 mg/kg, qd. The vehicle-treated group followed the same schedule as the group treated with Compound 50.

In the A375 model, Compound 50 was administered at 100 mg/kg, qd. Treatment ended after 28 days, then tumor growth delay was analyzed to day 60.

The tumors were allowed to establish growth for 10 to 14 days. Tumor size was measured every 3 days. Animals were randomly pair-matched into test groups on day 10 or 11 when their tumors were in the 50-150 mm$^3$ range.

Tumor measurements and body weights were recorded individually (2x/week) during the treatment period of the experiment. Tumors were measured using a digital caliper. Data was recorded/calculated using Study Director software (StudyLog Systems, Inc.) and graphs were created in GraphPad Prizm.

The volume of each tumor in an animal was calculated according to the formula: $(D\times d^2)/2$, where the diameters were determined from two orthogonal measurements on each tumor. The mean tumor volume was determined by averaging all tumor volumes in each group. The mean body weight was determined by averaging all body weights in each group.

The standard deviation was calculated according to the formula (where x was the tumor volume):

$$[\Sigma x^2 - ((\Sigma x)_2/n)]/n-1$$

Percent inhibition was calculated according to the formula (where T=test group, C=control group, O=starting (original) mean tumor volume, E=final (ending) mean tumor volume):

$$1-((T_e-T_o)/(C_e-C_o))\times 100$$

Once dosing ceased, tumor data were collected out to day 60, depending on the model, for any animals remaining on study. Student's t-tests (two-tailed) were used to determine statistical significance of the data (P-values). These values were calculated at the end of the treatment phase using the Study Director software.

The synergistic action or enhancement of conventional chemotherapeutic agent by a test compound can also be determined with this model by comparing animals treated with the standard therapy alone to animals treated with test compound plus the same standard therapy. An additive effect on the delay of tumor growth will be observed if synergistic action due to test compound is occurring.

Discussion of Results for Example 9

In the A431 and HCT116 models, optimum efficacy was achieved from 100 to 200 mg/kg daily. It was observed that <50% inhibition occurred with a dose of 10 mg/kg daily in both these models. The A431 and HCT116 models also showed that the antitumor activity of Compound 50 appeared to be dose-dependent and was statistically significantly at all doses, except at 10 mg/kg in the A431 model, compared to control. Compound 50 treatment was well tolerated, following continuous administration for 24 days, body weights were comparable with control animals.

In the A375 model, statistically significant efficacy was obtained with daily doses of 100 mg/kg Compound 50, a 90% inhibition of growth. At 28 days of continuous dosing, the body weights of treated animals were comparable to the control group. Upon discontinuation of treatment, the tumors did not rapidly regrow. Prolonged tumor growth delay was observed 3-weeks after the last treatment with Compound 50. The delay in tumor growth activity could be correlated with the compound's ability to inhibit the dynamics of tumor blood vessel turnover, similar to SU11248 maintenance therapy (Schueneman A, J. Himmelfarb E., Geng L. et al. Cancer Res 63 4009-4016).

Treatment with Compound 50 resulted in a dose-dependent inhibition of tumor growth after once-a-day oral dosing. Although Compound 50 did not demonstrate antiproliferative effects on cancer cell lines when presented at micromolar levels, it may be delaying tumor growth in xenograft models by other mechanisms unrelated to its anti-VEGFR-2 properties. In fact, plasma levels of 20 µM were achieved under the 100 mg/kg daily dosing schedule used in the in vivo models. When administered at 100 mg/kg on a daily basis, Compound 50 was well-tolerated with no reduction of body weight and no treatment-related deaths occurred after 24-28 days of treatment.

Upon completion of treatment with Compound 50 in the A375 model, tumor growth delay was maintained for 3 weeks. This maintenance significantly delayed regrowth as compared with tumors that were previously treated with vehicle alone. The mechanism of tumor growth delay in the A375 model following Compound 50 treatment might be contributed to its ability to inhibit VEGF. Although Compound 50 treatment had no effect on A375 tumor cell proliferation in vitro, the A375 model is known to express both VEGF and VEGFR-2 and therefore, Compound 50 might be inhibiting the autocrine and paracrine angiogenesis mechanisms necessary for tumor growth. The survival of primitive vessels are believed to be susceptible to VEGF blockade, due to the dependency upon VEGFR-2 mediated signaling (Gerber H-P, McMurtrey A, Kowalski J, et al. (1998) *J Biol Chem* 273: 30336-30343)

These data emphasize that the consequences of inhibiting VEGFR-2 signaling in tumorigenesis may extend beyond simply preventing angiogenesis.

Example 10

C57BL/6J-APC Min-Mouse Model of Human Adenomatous Polyposis Coli

The ability of Compound 50 to inhibit angiogenesis and tumor growth was tested in a spontaneous tumor model. the pre-cancerous polyp formation in the mouse model of human intestinal tumorigenesis. The transgeneic min mouse model has been used to demonstrate anti-angiogenic activity of a number of inhibitors (Kitamura T, Itoh M, Noda T, Matsuura M, Wakabayashi K. (2004) *Int J Cancer* 109: 576-580).

Transgenic C57BL/6J-Apc min mice heterozygous for a dominant nonsense Apc mutation are highly susceptible to spontaneous intestinal adenoma formation (homozygous mice are not viable). One hundred percent of these animals will develop polyps by 12 weeks of age. This model is widely used for studying prevention of intestinal adenoma formation and is well described in the literature (Yang K, Edelmann W, Fan K, et. al. A mouse model of human familial adenomatous polyposis. J Exp Zool. 1997 15; 277(3):245-54).

Female C57BL/6J-Apc$^{Min}$ mice (Jackson Laboratory, MN), 5 weeks of age, were housed (up to 10 mice per group) for a minimum of one week. Animals were then sorted into treatment groups based on body weight such that the mean body weight for the animals in each group was approximately the same. Small cohorts of animals (n=6) were sacrificed at day 1, before treatment to get a baseline number of polyps (mean polyp number at beginning of study).

On Day 1, animals in the negative control group (n=10) were treated with vehicle (0.5% methylcellulose) alone.

Animals in the treated group (n=10) were dosed daily with Compound 50 at 100 mg/kg orally q.d. for one week. At 2 weeks after the first treatment, all animals were sacrificed. The intestine of each mouse was excised, perfused, stained (0.01% Trypan Blue) and polyps were counted under 10× magnification.

Discussion of Results for Example 10

Treatment of C57BL/6J-APC min mice, at 100 mg/kg orally, once-daily with Compound 50 showed statistically significant activity compared to vehicle (0.5% methylcellulose) treated animals (47±7). The activity is clearly demonstrated by the poly counts of animals following 2-week treatment of Compound 50 (27±7) compared to the baseline polyp counts of animals at the beginning of the study (23±4), these groups were not statistically significantly different. The body weights of both JNJ-38158471-treated and vehicle-treated groups were comparable at study end (data not shown).

Example 11

VEGF Mediated Cell Migration Assay

Vascular endothelial growth factor mediated cell migration was measured using the Boyden chamber technique (Boyden S. J., *Exp. Med.*, 1962). The 12-hour endothelial migration assay was measured with the BD Biocoat™ Angiogenesis System (BD Biosciences, Bedford, Mass.).

Human Umbilical Vein Endothelial Cells (HUVEC) (pooled, cryopreserved, lot 3F0409, obtained from Cambrex, Bio Science Walkersville, Inc., Walkersville, Md., Cat. # CC-2519) were supplemented and cultured in EGM™-2 BulletKit (Growth Medium from Cambrex, Cat. # CC-3162). The cells were used at a passage less than 7 and a confluency of 50-90% on 100×20 mm polystyrene tissue culture treated plates (Becton Dickinson Falcon®, Franklin Lakes, N.J., Cat. #253003).

Stock solutions were prepared in DMSO Hybri-Max® (Sigma, Irvine, UK. Cat. # D2650) and in culture media.

The BD Falcon FluoroBloK™ 24-well insert plate 3 µM pore size (cat. #354143) was used. The cells were washed twice with EBM-2™+0.1% BSA (Basal media, Cambrex Cat. # CC-3156) and then starved with basal media for 5 hours in a 37°, 5% $CO^2$ blanket incubator. The cells were harvested by washing the plates with HEPES buffered saline solution (5 mL) (Cambrex cat. # CC-5024) and then trypsinized with trypsin/EDTA (2 mL) (Cambrex cat. # CC-5012) until the cells rounded up. The reaction was stopped using a trypsin neutralizing solution (2 mL) (Cambrex cat. # CC-5002). The cell suspension was centrifuged at 1000 rpm for 5 minutes and the pellet resuspended in 5 mL of EBM-2™+0.1% BSA. Using a hemocytometer, the cell suspension was adjusted to 400,000 cells/ml.

Test compounds were tested at concentrations of 1 µM, 500 nM, 100 nM and 50 nM. The upper Boyden chamber was filled with 500 µL of the cell suspension containing the different compound dilutions. The lower Boyden chambers were filled with 750 µL of EBM-2™ and 0.1% BSA containing VEGF (R&D Systems, Minneapolis, Mn. cat. #293VE) at a concentration of 10 ng/mL. A solution of EBM-2™ and 0.1% BSA was used as a negative control and EGM-2™ alone was used as a positive control. The plate was incubated at 37° under 5% $CO^2$ for 12 hours.

Controls were either unstimulated basal media (no VEGF) or stimulated with VEGF (10 ng/ml). Cells were allowed to migrate for 12-16 hrs during the incubation period.

After the incubation period, the cells were stained using Calcein AM (Molecular Probes, Invitrogen Corporation, Carlsbad, Calif. cat. # C3100MP) at 4 µg/mL. Following incubation for 90 minutes at 37° under 5% $CO^2$, the medium was removed from the upper chambers. The insert plate was transferred into a 24-well polystyrene plate (Falcon cat. #351147) for post cell migration labeling using 500 mL/well of the Calcein AM in Hanks Balanced Salt Solution and DMSO (Cellgro without Ca, Mg and phenol red, Mediatech Inc., Herndon, Va., cat. #21-022-CV). Only the HUVEC cells that had actively migrated were stained. The plate was incubated for 90 minutes at 37°, under 5% $CO^2$. The amount of cells that migrated through the pores were read on the Tecan Safire Multifunction Microplate Reader (Austria GmbH, Grödig/Salzburg, Austria) at an excitation of 485 nm and an emission of 530 nm with a gain of 55.

All groups were set up in triplicates and the assay was performed 3 independent times. VEGF-stimulated migration was set to 100%. Statistical significance was evaluated by comparing the compound-treated groups with the VEGF-induced positive control group.

The graphing was done using GraphPad (GraphPad Prism version 4.0 for Windows, GraphPad Software, San Diego Calif.). Determination of statistical significance was done using the Student's t-test. Test values were considered significantly different from control values at $P<0.05$. The data were shown as a % stimulation of VEGF control (set at 100%).

The % stimulation of cell migration for Compound 50, tested in various concentrations, are shown in Table 3.

TABLE 3

|  | Conc | % Stimulation |
| --- | --- | --- |
| Negative Control | basal media | 38.5% |
| VEGF alone | 10 ng/mL | 100% |
| VEGF/Cpd 50 | 1 µM | 34.5% |
| VEGF/Cpd 50 | 500 nM | 59% |
| VEGF/Cpd 50 | 100 nM | 60% |
| VEGF/Cpd 50 | 50 nM | 82% |

Discussion of Results for Example 11

Consistent with the potent activity shown against VEGF-stimulated VEGFR-2 autophosphorylation in HUVEC, Compound 50 significantly inhibited VEGF-dependent HUVEC migration. Compound 50 prevented the VEGF-induced migration of HUVEC with statistically significant inhibition of cell migration observed at all concentrations tested down to 50 nM. At the highest concentration tested (1 µM), there was complete inhibition of migration, comparable to no VEGF-stimulation.

Example 12

Cell-Based Phospho-VEGFR-2 Inhibition Assay

This assay is extremely sensitive due to the recent development of phospho-specific rabbit monoclonal antibodies against VEGFR-2, that allow direct detection of the activated receptor in whole cell lysates, negating the immunoprecipitation prior to immunoblotting step. This assay and the VEGF mediated cell migration assay (see Example 11) are pharmacodynamic determinants of VEGF function and angiogenesis (Rousseau S, Houle F, Huot J. (2000) *Trends Cardiovasc Med* 10: 321-327).

Human Umbilical Vein Endothelial Cells (HUVEC) were purchased from Cambrex, Bio Science Walkersville, Inc., Walkersville, Md. (cat. #CC-2519, pooled, cryopreserved, lot 3F0409). The cells were supplemented and cultured in EGM™-2 BulletKit (Growth Medium from Cambrex, Cat. # CC-3162). They were used at a passage <7 and a confluency of 50-90% on 100×20 mm polystyrene tissue culture treated plates (Becton Dickinson Falcon®, Franklin Lakes, N.J. cat. #253003).

The HUVEC were seeded (Day 1) at $1.5 \times 10^6$ cells per 10 cm dish in EGM. On Day 2, the media was removed and replaced with EBM+0.1% BSA for 12-16 hours (starvation). On Day 3, either vehicle (DMSO) or Compound 50 (500 nM-1 nM) were added to the media. After 60 minutes at 37° C., the cells were stimulated with 100 ng/ml of VEGF for 5 minutes at 37° C. The cells were directly lysed in SDS-sample buffer and lysates were collected and sonicated on ice for 10 seconds. The lysates were boiled for 4 minutes and those of equal volume (equal cell number) were run on a 10% SDS gel and blotted. The gel was first probed with phospho-VEGFR-2 antibody (Cell Signaling, MA., cat #2478), then stripped and reprobed with an anti-VEGFR-2 antibody (Santa Cruz, Calif., cat C-1158).

The whole cell lysates were subjected to Western analysis to detect phosphorylated (activated) VEGFR-2 or total VEGFR-2. Lane 1 cells were DMSO-treated, without VEGF-stimulation. Lane 2 cells were treated with DMSO, but were stimulated with VEGF. Cells in lanes 3-6 were treated with various concentrations of Compound 50, respectively, and show significant inhibition of VEGFR-2 autophosphorylation. Representative data are shown.

Consistent with its potent in vitro activity against VEGFR-2, Compound 50 inhibited VEGF-induced autophosphorylation of VEGFR-2 in human endothelial cells and blocked VEGF-dependent endothelial migration. Complete inhibition of phospho-VEGFR-2 was observed at 500 nM when compared to basal phospho-VEGFR-2 activity (no VEGF-stimulation). Furthermore, the Compound 50 concentrations required to inhibit VEGF-stimulated signaling (10 nM) are in agreement with concentrations required to inhibit VEGF-stimulated migration (100 nM). The results suggest that Compound 50 targets VEGFR-2 in cells and inhibits VEGF-stimulated VEGFR-2 phosphorylation in HUVEC.

Example 13

Mouse Corneal Micropocket Assay

This method has been described in detail (see Kenyon B, Voest E E, Chen C C, Flynn E, Folkman J and D'Amato R J, A model of angiogenesis in the mouse cornea, Invest. Opthalmol. Vis. Sci., 1996, 37:1625-1632; and, LaMontagne K, Littlewood-E A, Schnell C, O'Reilly T, Wyder L, Sanchez T, Probst B, Butler J, Wood A, Liau G, Billy E, Theuer A, Hla T and Wood J, Antagonism of sphingosine-1-phosphate receptors by FTY720 inhibits angiogenesis and tumor vascularization, Cancer Res., 2006, 66:221-31) and is an in vivo functional assay that provides an important link between biochemical and cellular inhibition (i.e., VEGFR-2 autophosphorylation and VEGF-dependent migration) and functional biological end points (i.e., VEGF-induced angiogenesis in vivo).

Pellets containing the slow-release polymer Hydron® and sucralfate with 180 ng rHuVEGF$_{165}$ were implanted into the cornea of female C57BL/6J mice. Daily oral treatment with either Compound 50 (10 mg/kg or 100 mg/kg) or vehicle (0.5% methylcellulose) was started 24 hours later. The eyes were routinely examined by slit-lamp biomicroscopy (Nikon FS-3V). After sacrifice on day 6, the vascular response was quantified using a linear reticule through the slit lamp. Inhibition was determined by the formula:

Inhibition=[(0.2)(π)(new blood vessel length)(clock hours of neovessels)]

The circumferential zone was measured as clock hours with a 360° reticule (where 30° of arc equals 1 clock hour). The % inhibition of blood vessel growth compared to the vehicle group for Compound 50, tested in various concentrations, is shown in Table 4.

TABLE 4

| Conc | % Inhibition |
|---|---|
| Vehicle | 0% |
| 10 mg/Kg | 15 ± 2% |
| 100 mg/Kg | 83 ± 6% |

Discussion of Results for Example 13

Compared to vehicle control, oral treatment with Compound 50 at 100 mg/kg qd (P<0.001) resulted in a dose-dependent inhibition of VEGF-dependent blood vessel formation versus 10 mg/kg (P=0.01).

Treatment with Compound 50 resulted in a dose-responsive inhibition of VEGF-induced neovascularization in the mouse corneal assay. The 100 mg/kg dose resulted in 83% inhibition, a dose that is efficacious in tumor xenograft models. Consistent with these findings, a dose of 10 mg/kg qd, resulted in 15% inhibition compared to 28-48% inhibition in tumor xenograft models.

The corneal neovascularization data together with the in vitro and VEGFR-2 autophosphorylation inhibition in HUVEC strongly suggests a mechanism-based activity of Compound 50.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. These publications are hereby incorporated by reference in their entirety into this application to describe more fully the state of the art to which this invention pertains.

What is claimed is:

1. A compound of Formula (I):

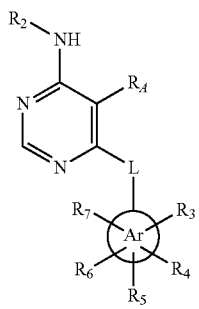

or a salt, stereoisomer, or tautomer thereof, wherein

L is selected from the group consisting of O and O—CH$_2$, wherein the O atom portion of O—CH$_2$ is attached to the pyrimidine ring of formula (I);

Ar is selected from the group consisting of aryl, heteroaryl, benzofused-heterocyclyl and benzofused-C$_{3-12}$cycloalkyl, wherein the benzene ring portion of the benzofused ring system is attached to the L group of formula (I);

R$_A$ is selected from the group consisting of CH=N—O—R$_1$ and cyano;

R$_1$ is selected from the group consisting of hydrogen, C$_{1-8}$alkyl, C$_{2-8}$alkenyl, C$_{2-8}$alkynyl, C$_{1-8}$alkoxy-C$_{1-8}$alkyl, hydroxy-C$_{1-8}$alkyl, amino-C$_{1-8}$alkyl, C$_{1-8}$alkyl-amino-C$_{1-8}$alkyl, C$_{1-8}$alkoxy-C$_{1-8}$alkyl-amino-C$_{1-8}$alkyl, C$_{1-8}$alkyl-sulfonyl-C$_{1-8}$alkyl, C$_{1-8}$alkyl-sulfonyl-oxy-C$_{1-8}$alkyl, C$_{3-12}$cycloalkyl, C$_{3-12}$cycloalkyl-C$_{1-8}$alkyl, aryl, aryl-C$_{1-8}$alkyl, aryl-oxy-C$_{1-8}$alkyl, heterocyclyl, heterocyclyl-C$_{1-8}$alkyl, heterocyclyl-carbonyl-C$_{1-8}$ alkyl, heteroaryl and heteroaryl-C$_{1-8}$alkyl, wherein aryl and aryl-C$_{1-8}$alkyl are each optionally substituted on aryl with one, two, three, four or five substituents each selected from the group consisting of hydroxy, C$_{1-8}$alkyl, C$_{1-8}$alkoxy, amino, C$_{1-8}$alkyl-amino and C$_{1-8}$alkoxy-carbonyl, and wherein heterocyclyl, heterocyclyl-C$_{1-8}$alkyl and heterocyclyl-carbonyl-C$_{1-8}$alkyl are each optionally substituted on heterocyclyl with one, two, three or four substituents each selected from the group consisting of hydroxy, C$_{1-8}$alkyl, C$_{1-8}$alkoxy, amino, C$_{1-8}$alkyl-amino, C$_{1-8}$alkyl-carbonyl, C$_{1-8}$alkoxy-carbonyl, C$_{1-8}$alkyl-sulfonyl and C$_{1-8}$alkyl-sulfonyl-C$_{1-8}$alkyl;

R$_2$ is selected from the group consisting of hydrogen, C$_{1-8}$alkyl and C$_{1-8}$alkoxy; and R$_3$, R$_4$, R$_5$, R$_6$ and R$_7$ is each selected from the group consisting of hydrogen, cyano, halogen, hydroxy, carboxy, C$_{1-8}$alkyl, C$_{1-8}$alkyl-carbonyl, C$_{1-8}$alkyl-carbonyl-C$_{1-8}$alkyl, C$_{1-8}$alkyl-carbonyl-amino, C$_{1-8}$alkyl-carbonyl-amino-C$_{1-8}$alkyl, C$_{1-8}$alkoxy, C$_{1-8}$alkoxy-carbonyl, C$_{1-8}$alkoxy-carbonyl-amino, C$_{1-8}$alkoxy-C$_{1-8}$alkyl, C$_{1-8}$alkoxy-C$_{1-8}$alkyl-carbonyl, C$_{1-8}$alkoxy-C$_{1-8}$alkyl-carbonyl-amino, hydroxy-C$_{1-8}$alkyl, hydroxy-C$_{1-8}$ alkyl-amino-carbonyl, hydroxy-C$_{1-8}$alkyl-amino-carbonyl-amino, halo-C$_{1-8}$alkyl, hydroxy-C$_{1-8}$alkoxy, halo-C$_{1-8}$alkoxy, C$_{2-8}$alkenyl, C$_{2-8}$alkynyl, C$_{1-8}$alkoxy-imino-C$_{1-8}$alkyl, C$_{1-8}$alkoxy-imino-C$_{2-8}$alkenyl, amino, C$_{1-8}$alkyl-amino, amino-carbonyl, C$_{1-8}$alkyl-amino-carbonyl, C$_{2-8}$alkenyl-amino-carbonyl, C$_{2-8}$alkynyl-amino-carbonyl, amino-carbonyl-C$_{1-8}$alkyl C$_{1-8}$alkyl-amino-carbonyl-C$_{1-8}$alkyl, C$_{2-8}$alkenyl-amino-carbonyl-C$_{1-8}$alkyl, C$_{2-8}$alkynyl-amino-carbonyl-C$_{1-8}$ alkyl, C$_{1-8}$alkyl-amino-carbonyl-amino, C$_{2-8}$alkenyl-amino-carbonyl-amino, C$_{2-8}$alkynyl-amino-carbonyl-amino, C$_{1-8}$alkyl-amino-carbonyl-oxy, C$_{2-8}$alkenyl-amino-carbonyl-oxy, C$_{2-8}$alkynyl-amino-carbonyl-oxy, amino-C$_{1-8}$alkyl, C$_{1-8}$alkyl-amino-C$_{1-8}$alkyl, amino-C$_{1-8}$alkyl-amino-carbonyl, C$_{1-8}$alkyl-amino-C$_{1-8}$alkyl-amino-carbonyl, amino-C$_{1-8}$alkyl-amino-carbonyl-amino, C$_{1-8}$alkyl-amino-C$_{1-8}$alkyl-amino-carbonyl-amino, C$_{3-12}$cycloalkyl, C$_{3-12}$cycloalkyl-C$_{1-8}$alkyl, C$_{3-12}$cycloalkyl-C$_{1-8}$alkoxy, C$_{3-12}$cycloalkyl-amino-carbonyl, C$_{3-12}$cycloalkyl-amino-carbonyl-amino, C$_{3-12}$cycloalkyl-C$_{1-8}$alkyl-amino-carbonyl, C$_{3-12}$cycloalkyl-C$_{1-8}$alkyl-amino-carbonyl-amino, C$_{3-12}$cycloalkyl-amino-carbonyl-C$_{1-8}$alkyl, aryl, aryl-oxy, aryl-C$_{1-8}$alkyl, aryl-C$_{1-8}$alkoxy, aryl-carbonyl, aryl-amino, aryl-amino-carbonyl, aryl-amino-carbonyl-amino, aryl-C$_{1-8}$alkyl-amino-carbonyl, aryl-C$_{1-8}$alkyl-amino-carbonyl-amino, aryl-amino-carbonyl-C$_{1-8}$alkyl, aryl-amino-carbonyl-oxy, heteroaryl, heteroaryl-oxy, heteroaryl-C$_{1-8}$alkoxy, heteroaryl-amino-carbonyl, heteroaryl-amino-carbonyl-amino, heteroaryl-C$_{1-8}$alkyl-amino-carbonyl, heteroaryl-C$_{1-8}$alkyl-amino-carbonyl-amino, heteroaryl-amino-carbonyl-C$_{1-8}$alkyl, heterocyclyl, heterocyclyl-C$_{1-8}$alkyl, heterocyclyl-C$_{1-8}$alkyl-amino-carbonyl, heterocyclyl-C$_{1-8}$alkyl-amino-carbonyl-amino and heterocyclyl-amino-carbonyl-C$_{1-8}$alkyl, wherein aryl, aryl-oxy, aryl-C$_{1-8}$alkyl, aryl-C$_{1-8}$alkoxy, aryl-carbonyl, aryl-amino, aryl-amino-carbonyl-amino, aryl-C$_{1-8}$alkyl-amino-carbonyl, aryl-C$_{1-8}$alkyl-amino-carbonyl-amino, aryl-amino-carbonyl-C$_{1-8}$alkyl, aryl-amino-carbonyl-oxy, heteroaryl and heteroaryl-amino-carbonyl-amino are each optionally substituted on aryl and heteroaryl with one, two, three, four or five substituents each selected from the group consisting of cyano, halogen, hydroxy, C$_{1-8}$alkyl, C$_{1-8}$alkoxy, amino, C$_{1-8}$alkyl-amino, amino-C$_{1-8}$alkyl, C$_{1-8}$alkyl-amino-C$_{1-8}$alkyl and C$_{1-8}$alkoxy-carbonyl.

2. The compound of claim 1, wherein Ar is selected from the group consisting of aryl and heteroaryl.

3. The compound of claim 1, wherein Ar is selected from the group consisting of benzofused-heterocyclyl and benzofused-C$_{3-12}$cycloalkyl, wherein the benzene ring portion of the benzofused ring system is attached to the L group.

4. The compound of claim 1, wherein Ar is selected from the group consisting of phenyl, naphthalenyl, indolyl, quinolinyl, isoquinolinyl, benzo[1,3]dioxolyl, indanyl and 5,6,7,8-tetrahydro-naphthalenyl.

5. The compound of claim 1, wherein R$_A$ is CH=N—O—R$_1$.

6. The compound of claim 1, wherein R$_1$ is selected from the group consisting of hydrogen, C$_{1-8}$alkyl, C$_{2-8}$alkenyl, C$_{2-8}$alkynyl, C$_{1-8}$alkoxy-C$_{1-8}$alkyl, hydroxy-C$_{1-8}$alkyl, amino-C$_{1-8}$alkyl, C$_{1-8}$alkyl-amino-C$_{1-8}$alkyl, C$_{3-12}$cycloalkyl, C$_{3-12}$cycloalkyl-C$_{1-8}$alkyl, aryl, aryl-C$_{1-8}$alkyl, heterocyclyl, heterocyclyl-C$_{1-8}$alkyl, heteroaryl and heteroaryl-C$_{1-8}$alkyl, wherein heterocyclyl and heterocyclyl-C$_{1-8}$alkyl are each optionally substituted on heterocyclyl with one, two, three or four substituents each selected from the group consisting of hydroxy, C$_{1-8}$alkyl, C$_{1-8}$alkoxy, amino, C$_{1-8}$alkyl-amino, C$_{1-8}$alkyl-carbonyl, C$_{1-8}$alkoxy-carbonyl and C$_{1-8}$alkyl-sulfonyl.

7. The compound of claim 1, wherein R$_1$ is selected from the group consisting of hydrogen, C$_{1-8}$alkyl, C$_{2-8}$alkenyl, C$_{2-8}$alkynyl, C$_{1-8}$alkoxy-C$_{1-8}$alkyl, hydroxy-C$_{1-8}$alkyl, $C_{1-8}$alkyl-amino-$C_{1-8}$alkyl, $C_{3-12}$cycloalkyl-$C_{1-8}$alkyl, aryl-$C_{1-8}$alkyl and heterocyclyl-$C_{1-8}$alkyl, wherein heterocyclyl-$C_{1-8}$alkyl is optionally substituted on heterocyclyl with $C_{1-8}$alkyl-carbonyl or $C_{1-8}$alkyl-sulfonyl.

8. The compound of claim 1, wherein $R_1$ is selected from the group consisting of hydrogen, $C_{1-8}$alkyl, $C_{2-8}$alkenyl, $C_{2-8}$alkynyl, $C_{1-8}$alkoxy-$C_{1-8}$alkyl, hydroxy-$C_{1-8}$alkyl, $C_{1-8}$alkyl-amino-$C_{1-8}$alkyl, cyclopropyl-$C_{1-8}$alkyl, cyclohexyl-$C_{1-8}$alkyl, phenyl-$C_{1-8}$alkyl, pyrrolidinyl-$C_{1-8}$alkyl, morpholinyl-$C_{1-8}$alkyl, piperidinyl-$C_{1-8}$alkyl and piperazinyl-$C_{1-8}$alkyl, wherein piperazinyl-$C_{1-8}$alkyl is optionally substituted on piperazinyl with $C_{1-8}$alkyl-carbonyl or $C_{1-8}$alkyl-sulfonyl.

9. The compound of claim 1, wherein $R_2$ is hydrogen.

10. The compound of claim 1, wherein $R_2$ is $C_{1-8}$alkyl.

11. The compound of claim 1, wherein $R_2$ is $C_{1-8}$alkoxy.

12. The compound of claim 1, wherein $R_3$, $R_4$, $R_5$, $R_6$ and $R_7$ is each selected from the group consisting of hydrogen, cyano, halogen, hydroxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$alkyl, $C_{1-8}$alkoxy, $C_{1-8}$alkoxy-carbonyl, $C_{1-8}$alkoxy-carbonyl-amino, $C_{1-8}$alkoxy-$C_{1-8}$alkyl, hydroxy-$C_{1-8}$alkyl, hydroxy-$C_{1-8}$alkyl-amino-carbonyl, hydroxy-$C_{1-8}$alkyl-amino-carbonyl-amino, halo-$C_{1-8}$alkyl, hydroxy-$C_{1-8}$alkoxy, halo-$C_{1-8}$alkoxy, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, amino, $C_{1-8}$alkyl-amino, amino-carbonyl, $C_{1-8}$alkyl-amino-carbonyl, $C_{2-8}$alkenyl-amino-carbonyl, $C_{2-8}$alkynyl-amino-carbonyl, amino-carbonyl-$C_{1-8}$alkyl, $C_{1-8}$alkyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, amino-$C_{1-8}$alkyl, $C_{1-8}$alkyl-amino-$C_{1-8}$alkyl, amino-$C_{1-8}$alkyl-amino-carbonyl, $C_{1-8}$alkyl-amino-$C_{1-8}$alkyl-amino-carbonyl, amino-$C_{1-8}$alkyl-amino-carbonyl-amino, $C_{1-8}$alkyl-amino-$C_{1-8}$alkyl-amino-carbonyl-amino, $C_{3-12}$cycloalkyl, $C_{3-12}$cycloalkyl-amino-carbonyl, $C_{3-12}$cycloalkyl-amino-carbonyl-amino, $C_{3-12}$cycloalkyl-$C_{1-8}$alkyl-amino-carbonyl, $C_{3-12}$cycloalkyl-$C_{1-8}$alkyl-amino-carbonyl-amino, $C_{3-12}$cycloalkyl-amino-carbonyl-$C_{1-8}$alkyl, aryl, aryl-$C_{1-8}$alkyl, aryl-$C_{1-8}$alkoxy, aryl-carbonyl, aryl-amino, aryl-amino-carbonyl, aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy, heteroaryl, heteroaryl-amino-carbonyl, heteroaryl-amino-carbonyl-amino, heteroaryl-$C_{1-8}$alkyl-amino-carbonyl, heteroaryl-$C_{1-8}$alkyl-amino-carbonyl-amino, heteroaryl-amino-carbonyl-$C_{1-8}$alkyl, heterocyclyl, heterocyclyl-$C_{1-8}$alkyl, heterocyclyl-$C_{1-8}$alkyl-amino-carbonyl, heterocyclyl-$C_{1-8}$alkyl-amino-carbonyl-amino and heterocyclyl-amino-carbonyl-$C_{1-8}$alkyl, wherein aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy and heteroaryl-amino-carbonyl-amino are each optionally substituted on aryl and heteroaryl with one, two, three, four or five substituents each selected from the group consisting of cyano, halogen, hydroxy, $C_{1-8}$alkyl, $C_{1-8}$alkoxy, amino, $C_{1-8}$alkyl-amino, amino-$C_{1-8}$alkyl, $C_{1-8}$alkyl-amino-$C_{1-8}$alkyl and $C_{1-8}$alkoxy-carbonyl.

13. The compound of claim 1, wherein $R_3$, $R_4$, $R_5$, $R_6$ and $R_7$ is each selected from the group consisting of hydrogen, cyano, halogen, hydroxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$alkyl, $C_{1-8}$alkoxy, $C_{1-8}$alkoxy-carbonyl, $C_{1-8}$alkoxy-carbonyl-amino, hydroxy-$C_{1-8}$alkyl-amino-carbonyl, hydroxy-$C_{1-8}$alkyl-amino-carbonyl-amino, halo-$C_{1-8}$alkyl, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, $C_{1-8}$alkyl-amino-carbonyl, $C_{2-8}$alkynyl-amino-carbonyl, $C_{1-8}$alkyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, $C_{1-8}$alkyl-amino-$C_{1-8}$alkyl-amino-carbonyl, $C_{1-8}$alkyl-amino-$C_{1-8}$alkyl-amino-carbonyl-amino, $C_{3-12}$cycloalkyl-amino-carbonyl, $C_{3-12}$cycloalkyl-amino-carbonyl-amino, aryl-$C_{1-8}$alkyl, aryl-$C_{1-8}$alkoxy, aryl-carbonyl, aryl-amino, aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy, heteroaryl, heteroaryl-amino-carbonyl-amino, heterocyclyl-$C_{1-8}$alkyl, heterocyclyl-$C_{1-8}$alkyl-amino-carbonyl and heterocyclyl-$C_{1-8}$alkyl-amino-carbonyl-amino, wherein aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy and heteroaryl-amino-carbonyl-amino are each optionally substituted on aryl and heteroaryl with one or two substituents each selected from the group consisting of halogen, $C_{1-8}$alkyl and $C_{1-8}$alkoxy.

14. The compound of claim 1, wherein $R_3$, $R_4$, $R_5$, $R_6$ and $R_7$ is each selected from the group consisting of hydrogen, cyano, halogen, hydroxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$alkyl, $C_{1-8}$alkoxy, $C_{1-8}$alkoxy-carbonyl, $C_{1-8}$alkoxy-carbonyl-amino, hydroxy-$C_{1-8}$alkyl-amino-carbonyl, hydroxy-$C_{1-8}$alkyl-amino-carbonyl-amino, halo-$C_{1-8}$alkyl, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, $C_{1-8}$alkyl-amino-carbonyl, $C_{2-8}$alkynyl-amino-carbonyl, $C_{1-8}$alkyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, $C_{1-8}$alkyl-amino-$C_{1-8}$alkyl-amino-carbonyl, $C_{1-8}$alkyl-amino-$C_{1-8}$alkyl-amino-carbonyl-amino, cyclopropyl-amino-carbonyl, cyclohexyl-amino-carbonyl-amino, cyclopropyl-amino-carbonyl-amino, phenyl-$C_{1-8}$alkyl, phenyl-$C_{1-8}$alkoxy, phenyl-carbonyl, phenyl-amino, phenyl-amino-carbonyl-amino, phenyl-$C_{1-8}$alkyl-amino-carbonyl, phenyl-$C_{1-8}$alkyl-amino-carbonyl-amino, phenyl-amino-carbonyl-$C_{1-8}$alkyl, phenyl-amino-carbonyl-oxy, [1,2,4]triazolyl, pyridinyl-amino-carbonyl-amino, thiazolyl-amino-carbonyl-amino, isoxazolyl-amino-carbonyl-amino, morpholinyl-$C_{1-8}$alkyl, pyrrolidinyl-$C_{1-8}$alkyl-amino-carbonyl and pyrrolidinyl-$C_{1-8}$alkyl-amino-carbonyl-amino, wherein phenyl-amino-carbonyl-amino, phenyl-$C_{1-8}$alkyl-amino-carbonyl, phenyl-$C_{1-8}$alkyl-amino-carbonyl-amino, phenyl-amino-carbonyl-$C_{1-8}$alkyl, phenyl-amino-carbonyl-oxy and thiazolyl-amino-carbonyl-amino isoxazolyl-amino-carbonyl-amino is each optionally substituted on phenyl, thiazolyl and isoxazolyl with one or two substituents each selected from the group consisting of halogen, $C_{1-8}$alkyl and $C_{1-8}$alkoxy.

15. The compound of claim 1, wherein

L is selected from the group consisting of O and O—$CH_2$, wherein the O atom portion of O—$CH_2$ is attached to the pyrimidine ring of formula (I);

Ar is selected from the group consisting of aryl, heteroaryl, benzofused-heterocyclyl and benzofused-$C_{3-12}$cycloalkyl, wherein the benzene ring portion of the benzofused ring system is attached to the L group of formula (I);

$R_A$ is CH=N—O—$R_1$;

$R_1$ is selected from the group consisting of hydrogen, $C_{1-8}$alkyl, $C_{2-8}$alkenyl, $C_{2-8}$alkynyl, $C_{1-8}$alkoxy-$C_{1-8}$alkyl, hydroxy-$C_{1-8}$alkyl, $C_{1-8}$alkyl-amino-$C_{1-8}$alkyl, $C_{3-12}$cycloalkyl-$C_{1-8}$alkyl, aryl-$C_{1-8}$alkyl and heterocyclyl-$C_{1-8}$alkyl, wherein heterocyclyl-$C_{1-8}$alkyl is optionally substituted on heterocyclyl with $C_{1-8}$alkyl-carbonyl or $C_{1-8}$alkyl-sulfonyl;

$R_2$ is selected from the group consisting of hydrogen, $C_{1-8}$alkyl and $C_{1-8}$alkoxy; and $R_3$, $R_4$, $R_5$, $R_6$ and $R_7$ is each selected from the group consisting of hydrogen, cyano, halogen, hydroxy, $C_{1-8}$alkyl, $C_{1-8}$alkyl-carbonyl, $C_{1-8}$alkyl-carbonyl-$C_{1-8}$alkyl, $C_{1-8}$alkyl-carbonyl-amino, $C_{1-8}$alkyl-carbonyl-amino-$C_{1-8}$alkyl, $C_{1-8}$alkoxy, $C_{1-8}$alkoxy-carbonyl, $C_{1-8}$alkoxy-carbonyl-amino, hydroxy-$C_{1-8}$alkyl-amino-carbonyl, hydroxy-$C_{1-8}$alkyl-amino-carbonyl-amino, halo-$C_{1-8}$alkyl, $C_{2-8}$alkenyl, $C_{2-8}$alkynyl, $C_{1-8}$alkoxy-imino-$C_{1-8}$alkyl, $C_{1-8}$alkoxy-imino-$C_{2-8}$alkenyl, $C_{1-8}$alkyl-amino-carbonyl, $C_{2-8}$alkynyl-amino-carbonyl, $C_{1-8}$alkyl-amino-carbonyl-$C_{1-8}$alkyl, $C_{1-8}$alkyl-amino-carbonyl-amino, $C_{2-8}$alkenyl-amino-carbonyl-amino, $C_{2-8}$alkynyl-amino-carbonyl-amino, $C_{1-8}$alkyl-amino-carbonyl-oxy, $C_{1-8}$alkyl-amino-$C_{1-8}$alkyl-amino-carbonyl, $C_{1-8}$alkyl-amino-$C_{1-8}$alkyl-amino-carbonyl-amino, $C_{3-12}$cycloalkyl-amino-carbonyl, $C_{3-12}$cycloalkyl-amino-carbonyl-amino, aryl-$C_{1-8}$alkyl, aryl-$C_{1-8}$alkoxy, aryl-carbonyl, aryl-amino, aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy, heteroaryl, heteroaryl-amino-carbonyl-amino, heterocyclyl-$C_{1-8}$alkyl, heterocyclyl-$C_{1-8}$alkyl-amino-carbonyl and heterocyclyl-$C_{1-8}$alkyl-amino-carbonyl-amino, wherein aryl-amino-carbonyl-amino, aryl-$C_{1-8}$alkyl-amino-carbonyl, aryl-$C_{1-8}$alkyl-amino-carbonyl-amino, aryl-amino-carbonyl-$C_{1-8}$alkyl, aryl-amino-carbonyl-oxy and heteroaryl-amino-carbonyl-amino are each optionally substituted on aryl and heteroaryl with one or two substituents each selected from the group consisting of halogen, $C_{1-8}$alkyl and $C_{1-8}$alkoxy.

16. The compound of claim 1, wherein the compound is selected from the group consisting of:

4-amino-6-(4-fluoro-2-methyl-1H-indol-5-yloxy)-pyrimidine-5-carbaldehyde O-ethyl-oxime, 4-amino-6-(2-methyl-1H-indol-5-yloxy)-pyrimidine-5-carbaldehyde O-methyl-oxime, 4-(1H-indol-5-yloxy)-6-methylamino-pyrimidine-5-carbaldehyde O-methyl-oxime, 4-(1H-indol-5-yloxy)-6-methoxyamino-pyrimidine-5-carbaldehyde O-methyl-oxime, 4-amino-6-(quinolin-6-yloxy)-pyrimidine-5-carbaldehyde O-methyl-oxime, 4-amino-6-(quinolin-7-yloxy)-pyrimidine-5-carbaldehyde O-methyl-oxime, 4-amino-6-(4-fluoro-1H-indol-5-yloxy)-pyrimidine-5-carbaldehyde O-methyl-oxime, 4-amino-6-(6-fluoro-1H-indol-5-yloxy)-pyrimidine-5-carbaldehyde O-methyl-oxime, 4-amino-6-(3-methyl-1H-indol-5-yloxy)-pyrimidine-5-carbaldehyde O-methyl-oxime, 4-amino-6-(1H-indol-5-yloxy)-pyrimidine-5-carbaldehyde O-methyl-oxime, 4-amino-6-(1-methyl-1H-indol-5-yloxy)-pyrimidine-5-carbaldehyde O-methyl-oxime, 4-amino-6-(4-fluoro-2-methyl-1H-indol-5-yloxy)-pyrimidine-5-carbaldehyde O-(2-hydroxy-ethyl)-oxime, 4-amino-6-(4-fluoro-2-methyl-1H-indol-5-yloxy)-pyrimidine-5-carbaldehyde O-(2-pyrrolidin-lyl-ethyl)-oxime, 4-amino-6-(4-fluoro-2-methyl-1H-indol-5-yloxy)-pyrimidine-5-carbaldehyde O-(2-morpholin-4-yl-ethyl)-oxime, 4-amino-6-(4-fluoro-2-methyl-1H-indol-5-yloxy)-pyrimidine-5-carbaldehyde O-(2-dimethylamino-ethyl)-oxime, 4-amino-6-(4-fluoro-2-methyl-1H-indol-5-yloxy)-pyrimidine-5-carbaldehyde O-(2-methylamino-ethyl)-oxime, 4-amino-6-(4-fluoro-2-methyl-1H-indol-5-yloxy)-pyrimidine-5-carbaldehyde O-(3-dimethylamino-propyl)-oxime, 4-amino-6-(4-fluoro-2-methyl-1H-indol-5-yloxy)-pyrimidine-5-carbaldehyde O-(3-pyrrolidin-1-yl-propyl)-oxime, 4-amino-6-(4-fluoro-2-methyl-1H-indol-5-yloxy)-pyrimidine-5-carbaldehyde O-(3-morpholin-4-yl-propyl)-oxime, 4-amino-6-(4-fluoro-2-methyl-1H-indol-5-yloxy)-pyrimidine-5-carbaldehyde O-(3-piperidin-1-yl-propyl)-oxime, 4-amino-6-(4-fluoro-2-methyl-1H-indol-5-yloxy)-pyrimidine-5-carbaldehyde O-(3-piperazin-1-yl-propyl)-oxime, 4-amino-6-(4-fluoro-2-methyl-1H-indol-5-yloxy)-pyrimidine-5-carbaldehyde O-[3-(4-methanesulfonyl-piperazin-1-yl)-propyl]-oxime, 4-amino-6-(4-fluoro-2-methyl-1H-indol-5-yloxy)-pyrimidine-5-carbaldehyde O-[3-(4-acetyl-piperazin-1-yl)-propy]-oxime, 4-amino-6-(4-fluoro-2-methyl-1H-indol-5-yloxy)-pyrimidine-5-carbaldehyde O-(4-piperidin-1-yl-butyl)-oxime, 4-amino-6-(4-fluoro-2-methyl-1H-indol-5-yloxy)-pyrimidine-5-carbaldehyde O-(4-pyrrolidin-1-yl-butyl)-oxime, 4-amino-6-(4-fluoro-2-methyl-1H-indol-5-yloxy)-pyrimidine-5-carbaldehyde O-(4-morpholin-4-yl-butyl)-oxime, 4-amino-6-(4-fluoro-2-methyl-1H-indol-5-yloxy)-pyrimidine-5-carbaldehyde oxime, 4-amino-6-(4-fluoro-2-methyl-1H-indol-5-yloxy)-pyrimidine-5-carbaldehyde O-(2-methoxy-ethyl)-oxime, 4-amino-6-(4-fluoro-2-methyl-1H-indol-5-yloxy)-pyrimidine-5-carbaldehyde O-(3-hydroxy-propyl)-oxime, 4-amino-6-(4-fluoro-2-methyl-1H-indol-5-yloxy)-pyrimidine-5-carbaldehyde O-prop-2-ynyl-oxime, 4-amino-6-(4-fluoro-2-methyl-1H-indol-5-yloxy)-pyrimidine-5-carbaldehyde O-allyl-oxime, 4-amino-6-(4-fluoro-2-methyl-1H-indol-5-yloxy)-pyrimidine-5-carbaldehyde O-cyclopropylmethyl-oxime, 4-amino-6-(4-fluoro-2-methyl-1H-indol-5-yloxy)-pyrimidine-5-carbaldehyde O-(3-methoxy-propyl)-oxime,
4-amino-6-(4-fluoro-2-methyl-1H-indol-5-yloxy)-pyrimidine-5-carbaldehyde O-propyl-oxime,
4-amino-6-(4-fluoro-2-methyl-1H-indol-5-yloxy)-pyrimidine-5-carbaldehyde O-cyclohexylmethyl-oxime,
4-amino-6-(4-fluoro-2-methyl-1H-indol-5-yloxy)-pyrimidine-5-carbaldehyde O-benzyl-oxime,
4-amino-6-(4-fluoro-2-methyl-1H-indol-5-yloxy)-pyrimidine-5-carbaldehyde O-butyl-oxime,
4-amino-6-(4-fluoro-2-methyl-1H-indol-5-yloxy)-pyrimidine-5-carbaldehyde O-(4-hydroxy-butyl)-oxime,
5-[6-amino-5-(methoxyimino-methyl)-pyrimidin-4-yloxy]-2-methyl-indole-1-carboxylic acid (2-hydroxy-ethyl)-amide,
5-[6-amino-5-(methoxyimino-methyl)-pyrimidin-4-yloxy]-2-methyl-indole-1-carboxylic acid (3-hydroxy-propyl)-amide,
5-[6-amino-5-(methoxyimino-methyl)-pyrimidin-4-yloxy]-2-methyl-indole-1-carboxylic acid (2-dimethylamino-ethyl)-amide,
5-[6-amino-5-(methoxyimino-methyl)-pyrimidin-4-yloxy]-2-methyl-indole-1-carboxylic acid (4-pyrrolidin-1-yl-butyl)-amide,
5-[6-amino-5-(methoxyimino-methyl)-pyrimidin-4-yloxy]-4-fluoro-2-methyl-indole-1-carboxylic acid methylamide,
5-[6-amino-5-(methoxyimino-methyl)-pyrimidin-4-yloxy]-2-methyl-indole-1-carboxylic acid isopropylamide,
5-[6-amino-5-(methoxyimino-methyl)-pyrimidin-4-yloxy]-2-methyl-indole-1-carboxylic acid prop-2-ynylamide,
5-[6-amino-5-(methoxyimino-methyl)-pyrimidin-4-yloxy]-2-methyl-indole-1-carboxylic acid cyclopropylamide,
5-[6-amino-5-(methoxyimino-methyl)-pyrimidin-4-yloxy]-2-methyl-indole-1-carboxylic acid benzylamide,
5-[6-amino-5-(methoxyimino-methyl)-pyrimidin-4-yloxy]-2-methyl-indole-1-carboxylic acid propylamide,
5-[6-amino-5-(methoxyimino-methyl)-pyrimidin-4-yloxy]-2-methyl-indole-1-carboxylic acid methylamide,
1-{4-[6-amino-5-(methoxyimino-methyl)-pyrimidin-4-yloxy]-2-chloro-phenyl}-3-ethyl-urea,
1-{4-[6-amino-5-(methoxyimino-methyl)-pyrimidin-4-yloxy]-2-chloro-phenyl}-3-methyl-urea,
1-{4-[6-amino-5-(methoxyimino-methyl)-pyrimidin-4-yloxy]-2-chloro-phenyl}-3-propyl-urea,
1-allyl-3-{4-[6-amino-5-(methoxyimino-methyl)-pyrimidin-4-yloxy]-2-chloro-phenyl}-urea,
1-{4-[6-amino-5-(methoxyimino-methyl)-pyrimidin-4-yloxy]-2-chloro-phenyl}-3-phenyl-urea,
1-{4-[6-amino-5-(methoxyimino-methyl)-pyrimidin-4-yloxy]-2-chloro-phenyl}-3-(2-chloro-phenyl)-urea,
1-{4-[6-amino-5-(methoxyimino-methyl)-pyrimidin-4-yloxy]-2-chloro-phenyl}-3-(2-fluoro-phenyl)-urea,
1-{4-[6-amino-5-(methoxyimino-methyl)-pyrimidin-4-yloxy]-2-chloro-phenyl}-3-(3-fluoro-phenyl)-urea,
1-{4-[6-amino-5-(methoxyimino-methyl)-pyrimidin-4-yloxy]-2-chloro-phenyl}-3-(2-methoxy-phenyl)-urea,
1-{4-[6-amino-5-(methoxyimino-methyl)-pyrimidin-4-yloxy]-2-chloro-phenyl}-3-(3-chloro-phenyl)-urea,
1-{4-[6-amino-5-(methoxyimino-methyl)-pyrimidin-4-yloxy]-2-chloro-phenyl}-3-(4-fluoro-phenyl)-urea,
1-{4-[6-amino-5-(methoxyimino-methyl)-pyrimidin-4-yloxy]-2-chloro-phenyl}-3-(2,4-difluoro-phenyl)-urea,
1-{4-[6-amino-5-(methoxyimino-methyl)-pyrimidin-4-yloxy]-2-chloro-phenyl}-3-(4-methoxy-phenyl)-urea,
1-{4-[6-amino-5-(methoxyimino-methyl)-pyrimidin-4-yloxy]-2-chloro-phenyl}-3-(4-methoxy-phenyl)-urea,
1-{4-[6-amino-5-(methoxyimino-methyl)-pyrimidin-4-yloxy]-2-chloro-phenyl}-3-butyl-urea,
1-{4-[6-amino-5-(methoxyimino-methyl)-pyrimidin-4-yloxy]-2-chloro-phenyl}-3-cyclohexyl-urea,
1-{4-[6-amino-5-(methoxyimino-methyl)-pyrimidin-4-yloxy]-2-methyl-phenyl}-3-ethyl-urea,
4-amino-6-(4-hydroxy-phenoxy)-pyrimidine-5-carbaldehyde O-methyl-oxime,
1-{4-[6-amino-5-(methoxyimino-methyl)-pyrimidin-4-yloxy]-phenyl}-3-methyl-urea,
1-{4-[6-amino-5-(methoxyimino-methyl)-pyrimidin-4-yloxy]-phenyl}-3-ethyl-urea,
1-{4-[6-amino-5-(methoxyimino-methyl)-pyrimidin-4-yloxy]-3-chloro-phenyl}-3-methyl-urea,
1-{4-[6-amino-5-(methoxyimino-methyl)-pyrimidin-4-yloxy]-3-chloro-phenyl}-3-ethyl-urea,
1-{4-[6-amino-5-(methoxyimino-methyl)-pyrimidin-4-yloxy]-2-fluoro-phenyl}-3-methyl-urea,
1-{4-[6-amino-5-(methoxyimino-methyl)-pyrimidin-4-yloxy]-2-bromo-phenyl}-3-methyl-urea,
1-{4-[6-amino-5-(methoxyimino-methyl)-pyrimidin-4-yloxy]-2-bromo-phenyl}-3-(4-fluoro-phenyl)-urea,
1-{4-[6-amino-5-(methoxyimino-methyl)-pyrimidin-4-yloxy]-2-chloro-phenyl}-3-o-tolyl-urea,
1-{4-[6-amino-5-(methoxyimino-methyl)-pyrimidin-4-yloxy]-2-chloro-phenyl}-3-m-tolyl-urea,
1-{4-[6-amino-5-(methoxyimino-methyl)-pyrimidin-4-yloxy]-2-chloro-phenyl}-3-p-tolyl-urea,
1-{4-[6-amino-5-(methoxyimino-methyl)-pyrimidin-4-yloxy]-2-chloro-phenyl}-3-(2,4-difluoro-benzyl)-urea,
1-{4-[6-amino-5-(methoxyimino-methyl)-pyrimidin-4-yloxy]-2-chloro-phenyl}-3prop-2-ynyl-urea,
1-{4-[6-amino-5-(methoxyimino-methyl)-pyrimidin-4-yloxy]-2-chloro-phenyl}-3-isopropyl-urea,
1-{4-[6-amino-5-(methoxyimino-methyl)-pyrimidin-4-yloxy]-2-chloro-phenyl}-3-(2-hydroxy-ethyl)-urea,
1-{4-[6-amino-5-(methoxyimino-methyl)-pyrimidin-4-yloxy]-2-chloro-phenyl}-3-(2-dimethylamino-ethyl)-urea,
1-{4-[6-amino-5-(methoxyimino-methyl)-pyrimidin-4-yloxy]-2-chloro-phenyl}-3-(3-hydroxy-propyl)-urea,
1-{4-[6-amino-5-(methoxyimino-methyl)-pyrimidin-4-yloxy]-2-chloro-phenyl}-3-(4-pyrrolidin-1-yl-butyl)-urea,
1-{4-[6-amino-5-(methoxyimino-methyl)-pyrimidin-4-yloxy]-2-chloro-phenyl}-3-cyclopropyl-urea,
1-{4-[6-amino-5-(methoxyimino-methyl)-pyrimidin-4-yloxy]-2-chloro-phenyl}-3-pyridin-2-yl-urea,
1-{4-[6-amino-5-(methoxyimino-methyl)-pyrimidin-4-yloxy]-2-chloro-phenyl}-3-pyridin-3-yl-urea,
1-{4-[6-amino-5-(methoxyimino-methyl)-pyrimidin-4-yloxy]-2-chloro-phenyl}-3-pyridin-4-yl-urea,
1-{4-[6-amino-5-(methoxyimino-methyl)-pyrimidin-4-yloxy]-2-chloro-phenyl}-3-(4-methyl-thiazol-2-yl)-urea,
1-{4-[6-amino-5-(methoxyimino-methyl)-pyrimidin-4-yloxy]-2-chloro-phenyl}-3-(5-methyl-thiazol-2-yl)-urea,
1-{4-[6-amino-5-(methoxyimino-methyl)-pyrimidin-4-yloxy]-2-chloro-phenyl}-3-thiazol-2-yl-urea, 1-{4-[6-amino-5-(methoxyimino-methyl)-pyrimidin-4-yloxy]-2-chloro-phenyl}-3-(4,5-dimethyl-thiazol-2-yl)-urea,
1-{4-[6-amino-5-(methoxyimino-methyl)-pyrimidin-4-yloxy]-2-chloro-phenyl}-3-(5-methyl-isoxazol-3-yl)-urea,
N-{4-[6-amino-5-(methoxyimino-methyl)-pyrimidin-4-yloxy]-2-chloro-phenyl}-acetamide,
{4-[6-amino-5-(methoxyimino-methyl)-pyrimidin-4-yloxy]-2-chloro-phenyl}-carbamic acid methyl ester,
2-{4-[6-amino-5-(methoxyimino-methyl)-pyrimidin-4-yloxy]-phenyl}-N-methyl-acetamide,
2-{4-[6-amino-5-(methoxyimino-methyl)-pyrimidin-4-yloxy]-phenyl}-N-phenyl-acetamide,
4-[6-amino-5-(methoxyimino-methyl)-pyrimidin-4-yloxy]-N-methyl-benzamide
2-{4-[6-amino-5-(methoxyimino-methyl)-pyrimidin-4-yloxy]-phenyl}-N-p-tolyl-acetamide,
2-{4-[6-amino-5-(methoxyimino-methyl)-pyrimidin-4-yloxy]-phenyl}-N-(3-fluoro-phenyl)-acetamide,
2-{4-[6-amino-5-(methoxyimino-methyl)-pyrimidin-4-yloxy]-phenyl}-N-ethyl-acetamide,
ethyl-carbamic acid 4-[6-amino-5-(methoxyimino-methyl)-pyrimidin-4-yloxy]-phenyl ester,
1-(4-{6-amino-5-[(2-morpholin-4-yl-ethoxyimino)-methyl]-pyrimidin-4-yloxy}-2-chloro-phenyl)-3-ethyl-urea,
1-(4-{6-amino-5-[(2-methoxy-ethoxyimino)-methyl]-pyrimidin-4-yloxy}-2-chloro-phenyl)-3-ethyl-urea,
(3-chloro-phenyl)-carbamic acid 4-[6-amino-5-(methoxy-imino-methyl)-pyrimidin-4-yloxy]-phenyl ester,
4-amino-6-(3,5-dimethoxyphenoxy)-5-pyrimidinecarboxaldehyde O-methyloxime,
5-[{6-amino-5-[(E)-(methoxyimino)methyl]-4-pyrimidinyl}oxy]-2-methyl-1H-indole-3-carboxylic acid ethyl ester,
4-amino-6-(1,3-benzodioxol-5-yloxy)-5-pyrimidinecarboxaldehyde O-methyloxime,
4-amino-6-(3-chloro-4-fluorophenoxy)-5-pyrimidinecarboxaldehyde O-methyloxime,
4-amino-6-[4-(benzyloxy)phenoxy]-5-pyrimidinecarboxaldehyde O-methyloxime,
4-amino-6-(benzyloxy)-5-pyrimidinecarboxaldehyde O-methyloxime,
4-amino-6-[(3-fluorophenylmethoxy]-5-pyrimidinecarboxaldehyde O-methyloxime,
N-[2-{5-[{6-amino-5-[(E)-(methoxyimino)methyl]-4-pyrimidinyl}oxy]-1H-indol-3-yl}ethyl]-acetamide,
4-amino-6-[(2,6-difluorophenyl)methoxy]-5-pyrimidinecarboxaldehyde O-methyloxime,
4-amino-6-(2-naphthalenylmethoxy)-5-pyrimidinecarboxaldehyde O-methyloxime,
4-amino-6-[(2-fluorophenyl)methoxy]-5-pyrimidinecarboxaldehyde O-methyloxime,
4-amino-6-[(2,4-dichlorophenyl)methoxy]-5-pyrimidinecarboxaldehyde O-methyloxime,
4-amino-6-[(2,5-dichlorophenyl)methoxy]-5-pyrimidinecarboxaldehyde O-methyloxime,
4-amino-6-[(3-bromophenyl)methoxy]-5-pyrimidinecarboxaldehyde O-methyloxime,
4-amino-6-[(3,4-dichlorophenyl)methoxy]-5-pyrimidinecarboxaldehyde O-methyloxime,
4-amino-6-{[3-(trifluoromethyl)phenyl]methoxy}-5-pyrimidinecarboxaldehyde O-methyloxime,
4-amino-6-[(3-chlorophenyl)methoxy]-5-pyrimidinecarboxaldehyde O-methyloxime,
4-amino-6-[(3-methoxyphenyemethoxy]-5-pyrimidinecarboxaldehyde O-methyloxime,
4-amino-6-[(3,4-dimethoxyphenyl)methoxy]-5-pyrimidinecarboxaldehyde O-methyloxime,
4-amino-6-[(4-fluorophenyl)methoxy]-5-pyrimidinecarboxaldehyde O-methyloxime,
4-amino-6-[(4-chlorophenyl)methoxy]-5-pyrimidinecarboxaldehyde O-methyloxime,
4-amino-6-[(3,4-difluorophenyl)methoxy]-5-pyrimidinecarboxaldehyde O-methyloxime,
4-amino-6-[(5-chloro-2-methoxyphenyl)methoxy]-5-pyrimidinecarboxaldehyde O-methyloxime,
4-amino-6-[(2-chloro-4-fluorophenyl)methoxy]-5-pyrimidinecarboxaldehyde O-methyloxime,
4-[{[6-amino-5-[(E)-(methoxyimino)methyl]-4-pyrimidinyl]oxy}methyl]-benzonitrile,
4-amino-6-[(5-bromo-2-chlorophenyl)methoxy]-5-pyrimidinecarboxaldehyde O-methyloxime,
4-amino-6-[(4-ethynylphenyl)methoxy]-5-pyrimidinecarboxaldehyde O-methyloxime,
4-amino-6-(2-ethylphenoxy)-5-pyrimidinecarboxaldehyde O-methyloxime,
4-amino-6-(4-ethylphenoxy)-5-pyrimidinecarboxaldehyde O-methyloxime,
4-amino-6-[2-methoxy-4-(2-propenyl)phenoxy]-5-pyrimidinecarboxaldehyde O-methyloxime,
4-amino-6-(3-fluorophenoxy)-5-pyrimidinecarboxaldehyde O-methyloxime,
4-amino-6-(4-fluorophenoxy)-5-pyrimidinecarboxaldehyde O-methyloxime,
4-amino-6-(4-benzoylphenoxy)-5-pyrimidinecarboxaldehyde O-methyloxime,
4-[{6-amino-5-[(E)-(methoxyimino)methyl]-4-pyrimidinyl}oxy]-benzeneacetonitrile,
4-amino-6-[4-(benzyl)phenoxy]-5-pyrimidinecarboxaldehyde O-methyloxime,
4-amino-6-(5-isoquinolinyloxy)-5-pyrimidinecarboxaldehyde O-methyloxime,
4-amino-6-{4-[(1Z)-1-(methoxyimino)propyl]phenoxy}-5-pyrimidinecarboxaldehyde O-methyloxime,
4-amino-6-[(2-methyl-8-quinolinyl)oxy]-5-pyrimidinecarboxaldehyde O-methyloxime,
4-amino-6-[2-methoxy-4-[(1E)-1-propenyl]phenoxy]-5-pyrimidinecarboxaldehyde O-methyloxime,
4-amino-6-[(indan-5-yl)oxy]-5-pyrimidinecarboxaldehyde O-methyloxime,
4-amino-6-(4-methoxyphenoxy)-5-pyrimidinecarboxaldehyde O-methyloxime,
4-amino-6-[(5,6,7,8-tetrahydro-1-naphthalenyl)oxy]-5-pyrimidinecarboxaldehyde O-methyloxime,
4-amino-6-(2,4,6-trichlorophenoxy)-5-pyrimidinecarboxaldehyde O-methyloxime,
4-amino-6-(2,4,6-trimethylphenoxy)-5-pyrimidinecarboxaldehyde O-methyloxime,
4-amino-6-(2-methoxyphenoxy)-5-pyrimidinecarboxaldehyde O-methyloxime,
4-[{6-amino-5-[(E)-(methoxyimino)methyl]-4-pyrimidinyl}oxy]-benzoic acid methyl ester,
4-amino-6-(1-naphthalenyloxy)-5-pyrimidinecarboxaldehyde O-methyloxime,
4-amino-6-[4-(1H-1,2,4-triazol-1-yl)phenoxy]-5-pyrimidinecarboxaldehyde O-methyloxime,
4-amino-6-(3,4,5-trimethoxyphenoxy)-5-pyrimidinecarboxaldehyde O-methyloxime,
4-amino-6-(4-ethyl-2-methoxyphenoxy)-5-pyrimidinecarboxaldehyde O-methyloxime, 4-amino-6-[2-methoxy-4-(3-oxobutyl)phenoxy]-5-pyrimidinecarboxaldehyde 5-(O-methyloxime),
4-amino-6-(2-chloro-4,5-dimethylphenoxy)-5-pyrimidinecarboxaldehyde O-methyloxime,
4-amino-6-[2,5-dimethyl-4-(4-morpholinylmethyl)phenoxy]-5-pyrimidinecarboxaldehyde O-methyloxime,
4-amino-6-[4-(phenylamino)phenoxy]-5-pyrimidinecarboxaldehyde O-methyloxime,
4-amino-6-(3-methoxy-5-methylphenoxy)-5-pyrimidinecarboxaldehyde O-methyloxime,
4-amino-6-[2-methoxy-4-[(1E,3E)-3-(methoxyimino)-1-butenyl]phenoxy]-5-pyrimidinecarboxaldehyde O-methyloxime,
4-[{6-amino-5-[(E)-(methoxyimino)methyl]-4-pyrimidinyl}oxy]-2-chloro-benzonitrile,
4-(4-acetyl-3-methylphenoxy)-6-amino-5-pyrimidinecarboxaldehyde O-methyloxime,
4-amino-6-{4-[(1Z)-1-(methoxyimino)ethyl]-3-methylphenoxy}-5-pyrimidinecarboxaldehyde O-methyloxime, the stereoisomeric forms thereof, and the pharmaceutically acceptable salts thereof.

17. The compound of claim 16, wherein the compound is selected from the group consisting of:
4-amino-6-(4-fluoro-2-methyl-1H-indol-5-yloxy)-pyrimidine-5-carbaldehyde O-ethyl-oxime,
4-amino-6-(2-methyl-1H-indol-5-yloxy)-pyrimidine-5-carbaldehyde O-methyl-oxime,
4-amino-6-(quinolin-6-yloxy)-pyrimidine-5-carbaldehyde O-methyl-oxime,
4-amino-6-(4-fluoro-1H-indol-5-yloxy)-pyrimidine-5-carbaldehyde O-methyl-oxime,
4-amino-6-(6-fluoro-1H-indol-5-yloxy)-pyrimidine-5-carbaldehyde O-methyl-oxime,
4-amino-6-(3-methyl-1H-indol-5-yloxy)-pyrimidine-5-carbaldehyde O-methyl-oxime,
4-amino-6-(1H-indol-5-yloxy)-pyrimidine-5-carbaldehyde O-methyl-oxime,
4-amino-6-(4-fluoro-2-methyl-1H-indol-5-yloxy)-pyrimidine-5-carbaldehyde O-(2-hydroxy-ethyl)-oxime,
4-amino-6-(4-fluoro-2-methyl-1H-indol-5-yloxy)-pyrimidine-5-carbaldehyde O-(2-pyrrolidin-1yl-ethyl)-oxime,
4-amino-6-(4-fluoro-2-methyl-1H-indol-5-yloxy)-pyrimidine-5-carbaldehyde O-(2-morpholin-4-yl-ethyl)-oxime,
4-amino-6-(4-fluoro-2-methyl-1H-indol-5-yloxy)-pyrimidine-5-carbaldehyde O-(2-dimethylamino-ethyl)-oxime,
4-amino-6-(4-fluoro-2-methyl-1H-indol-5-yloxy)-pyrimidine-5-carbaldehyde O-(2-methylamino-ethyl)-oxime,
4-amino-6-(4-fluoro-2-methyl-1H-indol-5-yloxy)-pyrimidine-5-carbaldehyde O-(3-dimethylamino-propyl)-oxime,
4-amino-6-(4-fluoro-2-methyl-1H-indol-5-yloxy)-pyrimidine-5-carbaldehyde O-(3-pyrrolidin-1-yl-propyl)-oxime,
4-amino-6-(4-fluoro-2-methyl-1H-indol-5-yloxy)-pyrimidine-5-carbaldehyde O-(3-morpholin-4-yl-propyl)-oxime,
4-amino-6-(4-fluoro-2-methyl-1H-indol-5-yloxy)-pyrimidine-5-carbaldehyde O-(3-piperidin-1-yl-propyl)-oxime,
4-amino-6-(4-fluoro-2-methyl-1H-indol-5-yloxy)-pyrimidine-5-carbaldehyde O-(3-piperazin-1-yl-propyl)-oxime,
4-amino-6-(4-fluoro-2-methyl-1H-indol-5-yloxy)-pyrimidine-5-carbaldehyde O-[3-(4-methanesulfonyl-piperazin-1-yl)-propyl]-oxime,
4-amino-6-(4-fluoro-2-methyl-1H-indol-5-yloxy)-pyrimidine-5-carbaldehyde O-[3-(4-acetyl-piperazin-1-yl)-propyl]-oxime,
4-amino-6-(4-fluoro-2-methyl-1H-indol-5-yloxy)-pyrimidine-5-carbaldehyde O-(4-piperidin-1-yl-butyl)-oxime,
4-amino-6-(4-fluoro-2-methyl-1H-indol-5-yloxy)-pyrimidine-5-carbaldehyde O-(4-pyrrolidin-1-yl-butyl)-oxime,
4-amino-6-(4-fluoro-2-methyl-1H-indol-5-yloxy)-pyrimidine-5-carbaldehyde O-(4-morpholin-4-yl-butyl)-oxime,
4-amino-6-(4-fluoro-2-methyl-1H-indol-5-yloxy)-pyrimidine-5-carbaldehyde oxime,
4-amino-6-(4-fluoro-2-methyl-1H-indol-5-yloxy)-pyrimidine-5-carbaldehyde O-(2-methoxy-ethyl)-oxime,
4-amino-6-(4-fluoro-2-methyl-1H-indol-5-yloxy)-pyrimidine-5-carbaldehyde O-(3-hydroxy-propyl)-oxime,
4-amino-6-(4-fluoro-2-methyl-1H-indol-5-yloxy)-pyrimidine-5-carbaldehyde O-prop-2-ynyl-oxime,
4-amino-6-(4-fluoro-2-methyl-1H-indol-5-yloxy)-pyrimidine-5-carbaldehyde O-allyl-oxime,
4-amino-6-(4-fluoro-2-methyl-1H-indol-5-yloxy)-pyrimidine-5-carbaldehyde O-cyclopropylmethyl-oxime,
4-amino-6-(4-fluoro-2-methyl-1H-indol-5-yloxy)-pyrimidine-5-carbaldehyde O-(3-methoxy-propyl)-oxime,
4-amino-6-(4-fluoro-2-methyl-1H-indol-5-yloxy)-pyrimidine-5-carbaldehyde O-propyl-oxime,
4-amino-6-(4-fluoro-2-methyl-1H-indol-5-yloxy)-pyrimidine-5-carbaldehyde O-cyclohexylmethyl-oxime,
4-amino-6-(4-fluoro-2-methyl-1H-indol-5-yloxy)-pyrimidine-5-carbaldehyde O-benzyl-oxime,
4-amino-6-(4-fluoro-2-methyl-1H-indol-5-yloxy)-pyrimidine-5-carbaldehyde O-butyl-oxime,
4-amino-6-(4-fluoro-2-methyl-1H-indol-5-yloxy)-pyrimidine-5-carbaldehyde O-(4-hydroxy-butyl)-oxime,
5-[6-amino-5-(methoxyimino-methyl)-pyrimidin-4-yloxy]-2-methyl-indole-1-carboxylic acid (2-hydroxy-ethyl)-amide,
5-[6-amino-5-(methoxyimino-methyl)-pyrimidin-4-yloxy]-2-methyl-indole-1-carboxylic acid (3-hydroxy-propyl)-amide,
5-[6-amino-5-(methoxyimino-methyl)-pyrimidin-4-yloxy]-2-methyl-indole-1-carboxylic acid (2-dimethylamino-ethyl)-amide,
5-[6-amino-5-(methoxyimino-methyl)-pyrimidin-4-yloxy]-2-methyl-indole-1-carboxylic acid (4-pyrrolidin-1-yl-butyl)-amide,
5-[6-amino-5-(methoxyimino-methyl)-pyrimidin-4-yloxy]-4-fluoro-2-methyl-indole-1-carboxylic acid methylamide,
5-[6-amino-5-(methoxyimino-methyl)-pyrimidin-4-yloxy]-2-methyl-indole-1-carboxylic acid isopropylamide,
5-[6-amino-5-(methoxyimino-methyl)-pyrimidin-4-yloxy]-2-methyl-indole-1-carboxylic acid prop-2-ynylamide,
5-[6-amino-5-(methoxyimino-methyl)-pyrimidin-4-yloxy]-2-methyl-indole-1-carboxylic acid cyclopropylamide,
5-[6-amino-5-(methoxyimino-methyl)-pyrimidin-4-yloxy]-2-methyl-indole-1-carboxylic acid propylamide, 5-[6-amino-5-(methoxyimino-methyl)-pyrimidin-4-yloxy]-2-methyl-indole-1-carboxylic acid methylamide,
1-{4-[6-amino-5-(methoxyimino-methyl)-pyrimidin-4-yloxy]-2-chloro-phenyl}-3-ethyl-urea,
1-{4-[6-amino-5-(methoxyimino-methyl)-pyrimidin-4-yloxy]-2-chloro-phenyl}-3-methyl-urea,
1-{4-[6-amino-5-(methoxyimino-methyl)-pyrimidin-4-yloxy]-2-chloro-phenyl}-3-propyl-urea,
1-allyl-3-{4-[6-amino-5-(methoxyimino-methyl)-pyrimidin-4-yloxy]-2-chloro-phenyl}-urea,
1-{4-[6-amino-5-(methoxyimino-methyl)-pyrimidin-4-yloxy]-2-chloro-phenyl}-3-phenyl-urea,
1-{4-[6-amino-5-(methoxyimino-methyl)-pyrimidin-4-yloxy]-2-chloro-phenyl}-3-(2-chloro-phenyl)-urea,
1-{4-[6-amino-5-(methoxyimino-methyl)-pyrimidin-4-yloxy]-2-chloro-phenyl}-3-(2-fluoro-phenyl)-urea,
1-{4-[6-amino-5-(methoxyimino-methyl)-pyrimidin-4-yloxy]-2-chloro-phenyl}-3-(3-fluoro-phenyl)-urea,
1-{4-[6-amino-5-(methoxyimino-methyl)-pyrimidin-4-yloxy]-2-chloro-phenyl}-3-(2-methoxy-phenyl)-urea,
1-{4-[6-amino-5-(methoxyimino-methyl)-pyrimidin-4-yloxy]-2-chloro-phenyl}-3-(3-chloro-phenyl)-urea,
1-{4-[6-amino-5-(methoxyimino-methyl)-pyrimidin-4-yloxy]-2-chloro-phenyl}-3-(4-fluoro-phenyl)-urea,
1-{4-[6-amino-5-(methoxyimino-methyl)-pyrimidin-4-yloxy]-2-chloro-phenyl}-3-(2,4-difluoro-phenyl)-urea,
1-{4-[6-amino-5-(methoxyimino-methyl)-pyrimidin-4-yloxy]-2-chloro-phenyl}-3-(4-methoxy-phenyl)-urea,
1-{4-[6-amino-5-(methoxyimino-methyl)-pyrimidin-4-yloxy]-2-chloro-phenyl}-3-(4-methoxy-phenyl)-urea,
1-{4-[6-amino-5-(methoxyimino-methyl)-pyrimidin-4-yloxy]-2-chloro-phenyl}-3-butyl-urea,
1-{4-[6-amino-5-(methoxyimino-methyl)-pyrimidin-4-yloxy]-2-chloro-phenyl}-3-cyclohexyl-urea,
1-{4-[6-amino-5-(methoxyimino-methyl)-pyrimidin-4-yloxy]-2-methyl-phenyl}-3-ethyl-urea,
1-{4-[6-amino-5-(methoxyimino-methyl)-pyrimidin-4-yloxy]-phenyl}-3-methyl-urea,
1-{4-[6-amino-5-(methoxyimino-methyl)-pyrimidin-4-yloxy]-phenyl}-3-ethyl-urea,
1-{4-[6-amino-5-(methoxyimino-methyl)-pyrimidin-4-yloxy]-3-chloro-phenyl}-3-methyl-urea,
1-{4-[6-amino-5-(methoxyimino-methyl)-pyrimidin-4-yloxy]-3-chloro-phenyl}-3-ethyl-urea,
1-{4-[6-amino-5-(methoxyimino-methyl)-pyrimidin-4-yloxy]-2-fluoro-phenyl}-3-methyl-urea,
1-{4-[6-amino-5-(methoxyimino-methyl)-pyrimidin-4-yloxy]-2-chloro-phenyl}-3-o-tolyl-urea,
1-{4-[6-amino-5-(methoxyimino-methyl)-pyrimidin-4-yloxy]-2-chloro-phenyl}-3-m-tolyl-urea,
1-{4-[6-amino-5-(methoxyimino-methyl)-pyrimidin-4-yloxy]-2-chloro-phenyl}-3-p-tolyl-urea,
1-{4-[6-amino-5-(methoxyimino-methyl)-pyrimidin-4-yloxy]-2-chloro-phenyl}-3-(2,4-difluoro-benzyl)-urea,
1-{4-[6-amino-5-(methoxyimino-methyl)-pyrimidin-4-yloxy]-2-chloro-phenyl}-3-prop-2-ynyl-urea,
1-{4-[6-amino-5-(methoxyimino-methyl)-pyrimidin-4-yloxy]-2-chloro-phenyl}-3-isopropyl-urea,
1-{4-[6-amino-5-(methoxyimino-methyl)-pyrimidin-4-yloxy]-2-chloro-phenyl}-3-(2-hydroxy-ethyl)-urea,
1-{4-[6-amino-5-(methoxyimino-methyl)-pyrimidin-4-yloxy]-2-chloro-phenyl}-3-(2-dimethylamino-ethyl)-urea,
1-{4-[6-amino-5-(methoxyimino-methyl)-pyrimidin-4-yloxy]-2-chloro-phenyl}-3-(3-hydroxy-propyl)-urea,
1-{4-[6-amino-5-(methoxyimino-methyl)-pyrimidin-4-yloxy]-2-chloro-phenyl}-3-(4-pyrrolidin-1-yl-butyl)-urea,
1-{4-[6-amino-5-(methoxyimino-methyl)-pyrimidin-4-yloxy]-2-chloro-phenyl}-3-cyclopropyl-urea,
1-{4-[6-amino-5-(methoxyimino-methyl)-pyrimidin-4-yloxy]-2-chloro-phenyl}-3-pyridin-2-yl-urea,
1-{4-[6-amino-5-(methoxyimino-methyl)-pyrimidin-4-yloxy]-2-chloro-phenyl}-3-pyridin-3-yl-urea,
1-{4-[6-amino-5-(methoxyimino-methyl)-pyrimidin-4-yloxy]-2-chloro-phenyl}-3-pyridin-4-yl-urea,
1-{4-[6-amino-5-(methoxyimino-methyl)-pyrimidin-4-yloxy]-2-chloro-phenyl}-3-(4-methyl-thiazol-2-yl)-urea,
1-{4-[6-amino-5-(methoxyimino-methyl)-pyrimidin-4-yloxy]-2-chloro-phenyl}-3-(5-methyl-thiazol-2-yl)-urea,
1-{4-[6-amino-5-(methoxyimino-methyl)-pyrimidin-4-yloxy]-2-chloro-phenyl}-3-thiazol-2-yl-urea,
1-{4-[6-amino-5-(methoxyimino-methyl)-pyrimidin-4-yloxy]-2-chloro-phenyl}-3-(4,5-dimethyl-thiazol-2-yl)-urea,
1-{4-[6-amino-5-(methoxyimino-methyl)-pyrimidin-4-yloxy]-2-chloro-phenyl}-3-(5-methyl-isoxazol-3-yl)-urea,
{4-[6-amino-5-(methoxyimino-methyl)-pyrimidin-4-yloxy]-2-chloro-phenyl}-carbamic acid methyl ester,
2-{4-[6-amino-5-(methoxyimino-methyl)-pyrimidin-4-yloxy]-phenyl}-N-phenyl-acetamide,
2-{4-[6-amino-5-(methoxyimino-methyl)-pyrimidin-4-yloxy]-phenyl}-N-p-tolyl-acetamide,
1-(4-{6-amino-5-[(2-morpholin-4-yl-ethoxyimino)-methyl]-pyrimidin-4-yloxy}-2-chloro-phenyl)-3-ethyl-urea,
1-(4-{6-amino-5-[(2-methoxy-ethoxyimino)-methyl]-pyrimidin-4-yloxy}-2-chloro-phenyl)-3-ethyl-urea,
4-amino-6-[4-(benzyloxy)phenoxy]-5-pyrimidinecarboxaldehyde O-methyloxime, the stereoisomeric forms thereof,
and the pharmaceutically acceptable salts thereof.

18. A process for preparing a pharmaceutical composition comprising the step of admixing the compound of claim 1 and a pharmaceutically acceptable carrier.

* * * * *